(12) United States Patent
Bur et al.

(10) Patent No.: US 10,189,839 B2
(45) Date of Patent: *Jan. 29, 2019

(54) TRICYCLIC IMIDAZOLE COMPOUNDS AS INHIBITORS OF TRYPTOPHAN HYDROXYLASE

(71) Applicant: ACTELION PHARMACEUTICALS LTD, Allschwil (CH)

(72) Inventors: Daniel Bur, Allschwil (CH); Corinna Grisostomi, Allschwil (CH); Oliver Nayler, Allschwil (CH); Lubos Remen, Allschwil (CH); Magali Vercauteren, Allschwil (CH); Richard Welford, Allschwil (CH)

(73) Assignee: ACTELION PHARMACEUTICALS LTD, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/038,015

(22) PCT Filed: Nov. 18, 2014

(86) PCT No.: PCT/EP2014/074887
§ 371 (c)(1),
(2) Date: May 19, 2016

(87) PCT Pub. No.: WO2015/075025
PCT Pub. Date: May 28, 2015

(65) Prior Publication Data
US 2016/0289232 A1    Oct. 6, 2016

(30) Foreign Application Priority Data
Nov. 19, 2013  (WO) .................. PCT/IB2013/060243

(51) Int. Cl.
C07D 471/04    (2006.01)
C07D 498/12    (2006.01)
C07D 513/14    (2006.01)
C07D 471/14    (2006.01)

(52) U.S. Cl.
CPC ......... *C07D 471/14* (2013.01); *C07D 471/04* (2013.01); *C07D 498/12* (2013.01); *C07D 513/14* (2013.01)

(58) Field of Classification Search
CPC ... C07D 471/04; C07D 498/12; C07D 513/14
See application file for complete search history.

(56) References Cited

FOREIGN PATENT DOCUMENTS

| WO | WO 02/38153 A1 | 5/2002 |
| WO | WO 2007/089335 A2 | 8/2007 |
| WO | WO 2008/073933 A2 | 6/2008 |
| WO | WO 2014/195847 A2 | 12/2014 |
| WO | WO 2015/075023 A1 | 5/2015 |
| WO | WO 2016/177690 A1 | 11/2016 |

OTHER PUBLICATIONS

A. Elizabeth Linder et al., "Body Distribution of Infused Serotonin in Rats," Clinical and Experimental Pharmacology and Physiology, 2009, vol. 36, pp. 599-601.
Carla M. R. Lacerda et al., "Local serotonin mediates cyclic strain-induced phenotype transformation, matrix degradation, and glycosaminoglycan synthesis in cultured sheep mitral valves," Am J Physiol Heart Circ Physiol, 2012, vol. 302, pp. H1983-H1990.
Clara Dees et al., "Platelet-derived serotonin links vascular disease and tissue fibrosis," The Journal of Experimental Medicine, 2011, vol. 208, pp. 961-972.
Diego J. Walther et al., "A unique central tryptophan hydroxylase isoform," Biochemical Pharmacology, 2003, vol. 66, pp. 1673-1680.
Diego J. Walther et al., "Synthesis of Serotonin by a Second Tryptophan Hydroxylase Isoform," Science, 2003, vol. 299, p. 76.
Elizabeth C. Nowak et al., "Tryptophan Hydroxylase-1 regulates immune tolerance and inflammation," The Journal of Experimental Medicine, 2012, vol. 11, pp. 2127-2135.
Gianfranco Alpini et al., "Serotonin Metabolism Is Dysregulated in Cholangiocarcinoma which Has Implications for Tumor Growth," Cancer Res, 2008, vol. 68, pp. 9184-9193.
Jean-Eric Ghia et al., "Serotonin Has a Key Role in Pathogenesis of Experimental Colitis," Gastroenterology, 2009, vol. 137, pp. 1649-1660.
Johan Wouters et al., Pharmaceutical Salts and Co-Crystals, 2012, pp. 1-10.
Karl Engelman, M.D. et al., "Inhibition of Serotonin Synthesis by Para-Chlorophenylalanine in Patients With the Carcinoid Syndrome," The New England Journal of Medicine, Nov. 1967 vol. 277, pp. 1103-1108.
Lavern J. Weber, "p-chlorophenylalanine depletion of gastrointestinal 5-hydroxytryptamine," Biochemical Pharmacology, 1970, vol. 19, pp. 2169-2172.

(Continued)

*Primary Examiner* — Samira J Jean-Louis
(74) *Attorney, Agent, or Firm* — Hoxie & Associates LLC

(57) ABSTRACT

The present invention relates to compounds of the formula (I)

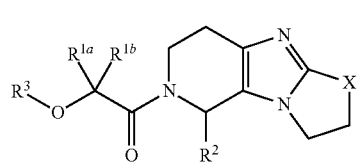

Formula (I)

wherein $R^{1a}$, $R^{1b}$, $R^2$, $R^3$, and X are as described in the description, to their preparation, to pharmaceutically acceptable salts thereof, and to their use as pharmaceuticals, to pharmaceutical compositions containing one or more compounds of formula (I), to methods for the preparation of such compounds of formula (I), and especially to their use as TPH modulators.

16 Claims, No Drawings

(56) References Cited

OTHER PUBLICATIONS

Loredana Ciuclan et al., "Imatinib Attenuates Hypoxia-induced Pulmonary Arterial Hypertension Pathology via Reduction in 5-Hypertension Pathology via Reduction in 5-Hydroxytryptamine through Inhibition of Tryptophan Hydroxylase 1 Expression," American Journal of Respiratory and Critical Care Medicine 2013 vol. 187 pp. 78-89.

M.T. Hyyppa et al., "Rapid Accumulation of H3-Serotonin in Brains of Rats Receiving Intraperitoneal H3-Trptophan: Effects of 5, 6,-Dihydroxytryptamine or Female Sex Hormones," Journal of Neural Transmission, 1973, vol. 34, pp. 111-124.

Melanie Konigshoff et al., "Increased expression of 5-hydroxytryptamine 2A/B receptors in idiopathic pulmonary fibrosis: a rationale for therapeutic intervention," Thorax, 2010, vol. 6, pp. 949-955.

Mirko Diksic, PhD., "Labelled •-methyl-L-tryptophan as a tracer for the study of the brain serotonergic system," Journal of Psychiatry & Neuroscience, 2001, vol. 26, pp. 293-303.

Mirko Diksic, PhD., et al., "Study of the brain serotonergic system with labeled •-methyl-L-tryptophan," Journal of Neurochemistry, 2001, vol. 78, pp. 1185-1200.

P. Heinrich Stahl et al., Handbook of Pharmaceutical Salts Properties, Selection and Use, 2008, pp. 1-24.

Paul P. Bertrand et al., "Serotonin release and uptake in the gastrointestinal tract," Autonomic Neuroscience: Basic and Clinical. 2010, vol. 153, pp. 47-57.

Philip M. Brown et al., "The Tryptophan Hydroxylase Inhibitor LX1031 Shows Clinical Benefit in Patients With Nonconstipating Irritable Bowel Syndrome," Gastroenterology, 2011, vol. 141, pp. 507-516.

Qingyun Liu et al., "Discovery and Characterization of Novel Tryptophan Hydroxylase Inhibitors That Selectively Inhibit Serotonin Synthesis in the Gastrointestinal Tract," The Journal of Pharmacology and Experimental Therapeutics, 2008, vol. 325, pp. 47-55.

R.J. Hicks, "Use of molecular targeted agents for the diagnosis, staging and therapy of neuroendocrine malignancy," Cancer Imagine, 2010, vol. 10, pp. S83-S91.

Remington (2005) The Science and Practice of Pharmacy, 21st Edition, Part 5, "Pharmaceutical Manufacturing."

Theodora W. Greene et al., Protective Groups in Organic Synthesis, Third Edition, 1999, pp. 1-52.

Thorsten Durk et al., "Production of Serotonin by Tryptophan Hydroxylase 1 and Release via Platelets Contributes to Allergic Airway Inflammation," American Journal of Respiratory and Critical Care Medicine, 2013, vol. 187, pp. 476-485.

Toshiaki Shinka et al., "Serotonin synthesis and metabolism-related molecules in a human prostate cancer cell line," Oncology Letters, 2011, vol. 2, pp. 211-215.

Vaibhav P Pai et al., "Altered serotonin physiology in human breast cancers favors paradoxical growth and cell survival," Breast Cancer Res., 2009, vol. 11, pp. 1-17.

Vijay K. Yadav et al., "Pharmacological inhibition of gut-derived serotonin synthesis is a potential bone anabolic treatment for osteoporosis," Nature Medicine, 2010, vol. 16, pp. 308-312.

William L. Hasler, MD, "Serotonin and the GI Tract," Curr Gastroenterol Rep, 2009, vol. 11, pp. 383-391.

Co-Pending U.S. Appl. No. 15/571,700, filed Nov. 3, 2017.

TRICYCLIC IMIDAZOLE COMPOUNDS AS INHIBITORS OF TRYPTOPHAN HYDROXYLASE

CROSS REFERENCE TO RELATED APPLICATION

This application is a 35 U.S.C. 371 National Phase of PCT Application No. PCT/EP2014/074887 filed Nov. 18, 2014, which claims priority to PCT Application No. PCT/IB2013/060243 filed Nov. 19, 2013, the disclosure of these prior applications are hereby incorporated in their entirety by reference.

The present invention relates to novel tricyclic imidazole derivatives of Formula (I), and their use as pharmaceuticals. The invention also concerns related aspects including processes for the preparation of the compounds, pharmaceutical compositions containing one or more compounds of Formula (I), and especially their use as TPH inhibitors.

The biogenic amine serotonin (5HT) is a biochemical messenger and regulator that signals through 13 receptors which are distributed throughout the nervous system and peripheral organs. 5HT is synthesized in 2 steps from the dietary amino acid L-tryptophan (L-Tryp). The first and rate limiting step in the tryptophan-serotonin metabolism is the hydroxylation of L-Tryp by the non-heme pterin dependent oxygenase tryptophan hydroxylase (TPH).

such as lung fibrosis (Konigshoff, M. et al. (2010) "Increased expression of 5-hydroxytryptamine2A/B receptors in idiopathic pulmonary fibrosis: a rationale for therapeutic intervention." *Thorax* 65(11): 949-955.), pulmonary hypertension (Ciuclan, L. et al. (2013) "Imatinib attenuates hypoxia-induced pulmonary arterial hypertension pathology via reduction in 5-hydroxytryptamine through inhibition of tryptophan hydroxylase 1 expression." *Am J Respir Crit Care Med* 187(1): 78-89), radiation pneumonitis (including that giving rise to or contributing to pulmonary hypertension), asthma (Durk, T. et al. (2013). "Production of serotonin by tryptophan hydroxylase 1 and release via platelets contribute to allergic airway inflammation." *Am J Respir Crit Care Med* 187(5): 476-485), adult respiratory distress syndrome (ARDS); osteoporosis (Yadav, V. K. et al. (2010) "Pharmacological inhibition of gut-derived serotonin synthesis is a potential bone anabolic treatment for osteoporosis." *Nat Med* 16, 308-312); gastrointestinal disorders including inflammatory bowel disease, ulcerative colitis (Ghia, J. E. et al. (2009) "Serotonin has a key role in pathogenesis of experimental colitis." *Gastroenterology* 137 (5): 1649-1660), postinfectious irritable bowel syndrome, coeliac disease, idiopathic constipation, irritable bowel syndrome (Brown, P. M. et al. (2011) "The tryptophan hydroxylase inhibitor LX1031 shows clinical benefit in patients with nonconstipating irritable bowel syndrome", *Gastroenterology* 141, 507-516), and carcinoid syndrome (Engelman, K., Scheme 1:
The tryptophan-serotonin metabolism and the major detectable metabolites thereof: serotonin (5HT) and 5-hydroxyindole acetic acid (5HIAA)

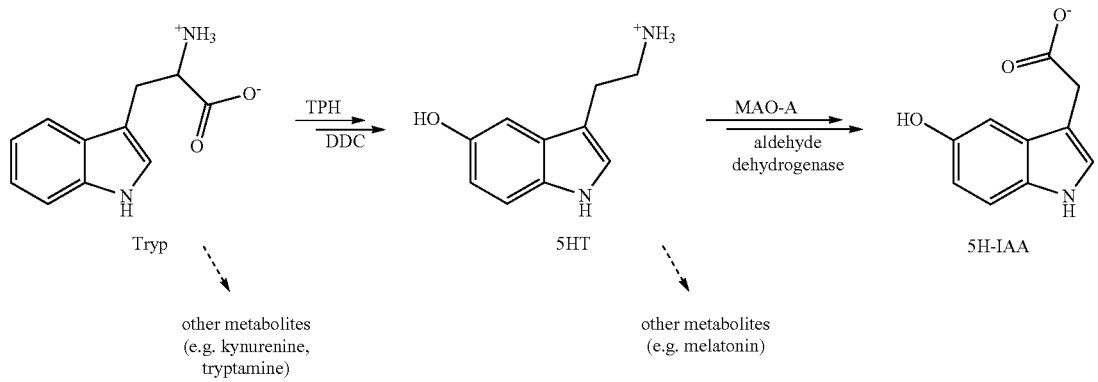

This is followed by rapid decarboxylation of 5-hydroxytryptophan by the enzyme aromatic amino acid decarboxylase (DDC). 5HT is further metabolized to 5-hydroxyindole acetic acid (5HIAA) by a combination of monoamine oxidase-A (MAO-A) and, subsequently, an aldehyde dehydrogenase. 5HIAA is excreted in the urine. An additional 5HT metabolic pathway in the pineal gland leads to production of melatonin which is involved in the circadian regulation of the sleep-wake cycle.

TPH comprises two isoforms: TPH2 is mainly expressed in neuronal cell types in the central nervous system (CNS), while TPH1 is mainly expressed in peripheral tissues, including the entrochromaffin cells (EC) in the gut, where it is responsible for synthesizing 5HT that is stored in circulating blood platelets. TPH1 and thus altered tryptophan-serotonin metabolism has been implicated as a potential drug target in a number of pathophysiologies such as lung diseases including e.g. chronic obstructive pulmonary disease (COPD), pulmonary embolism, interstitial lung disease et al. (1967). "Inhibition of serotonin synthesis by parachlorophenylalanine in patients with the carcinoid syndrome." *N Engl J Med* 277(21): 1103-1108). Further examples are myxomatous valve disease (Lacerda, C. M. et al. (2012) "Local serotonin mediates cyclic strain-induced phenotype transformation, matrix degradation, and glycosaminoglycan synthesis in cultured sheep mitral valves." *Am J Physiol Heart Circ Physiol* 302(10): H1983-1990); thrombosis; sleep disorders; pain; type1 and type 2 diabetes; liver disease including e.g. (viral-induced) hepatitis, fibrosis, transplantation, regeneration; acute and chronic hypertension; aortic and coronary artery disease; cancer, including e.g breast cancer (Pai V P et al. (2009) "Altered serotonin physiology in human breast cancers favors paradoxical growth and cell survival." *Breast Cancer Res.* 11(6)), prostate cancer (Shinka T et al. (2011) "Serotonin synthesis and metabolism-related molecules in a human prostate cancer cell line." *Oncol Lett. March;* 2(2):211-215) and neuroendocrine tumors (Hicks R J. (2010) "Use of molecular targeted agents for the diagnosis, staging and therapy of neuroendocrine malignancy." *Cancer Imaging*. October 4; 10 Spec no S83-91); subarachnoid hemorrhage; abdominal migraine; CREST syndrome (calcinosis, Raynaud's phenomenon, esophageal dysfunction, sclerodactyly, telangiectasia); Gilbert's syndrome; nausea; serotonin syndrome; functional anorectal disorders; functional bloating; immune tolerance and inflammatory diseases including e.g. multiple sclerosis and systemic sclerosis (Nowak E C et al. (2012) "Tryptophan hydroxylase-1 regulates immune tolerance and inflammation." *J Exp Med*. October 22; 209(11):2127-35; Dees C et al (2011) Platelet-derived serotonin links vascular disease and tissue fibrosis. *J Exp Med. May* 9; 208(5):961-72.).

TPH2 has been implicated as a potential drug target in a number of neurological health disorders including depression; anxiety including generalized anxiety disorder and social phobia; emetic disorders; migraine; substance abuse; attention deficit disorder (ADD); attention deficit hyperactivity disorder (ADHD); bipolar disorder; suicidal behavior; behavioral disorder; schizophrenia; Parkinson's disease; Huntigton's disease; autism; dyskinesia; eating disorders; type 2 diabetes; pain; Alzheimer's disease; sexual dysfunction; and brain tumors.

The role of 5HT in the brain as a neurotransmitter is well characterized. Brain 5HT is produced rapidly after uptake of circulating L-Tryp from the plasma (Hyyppa, M. T., et al. (1973) "Rapid accumulation of H3-serotonin in brains of rats receiving intraperitoneal H3-tryptophan: effects of 5,6-dihydroxytryptamine or female sex hormones", *J Neural Transm* 34, 111-124). The production of brain 5HT was extensively probed in the 1990s and 2000s, with the most prominent tool being intra venous (i.v.) administration of $^{14}$C-1-methyl-tryptophan which is taken-up into the brain (Diksic, M. (2001) "Labelled alpha-methyl-L-tryptophan as a tracer for the study of the brain serotonergic system", *J Psychiatry Neurosci* 26, 293-303; Diksic, M., and Young, S. N. (2001) "Study of the brain serotonergic system with labeled alpha-methyl-L-tryptophan", *J Neurochem* 78, 1185-1200). A frequently noted advantage of this approach is that the produced $^{14}$C-1-methyl 5HT is not further metabolized and builds up in the brain. However, this and possible other disruptions of metabolism could equally lead to unwanted perturbations in the 5HT synthesis system caused simply by the additional methyl appendage.

In the periphery, 5HT is predominantly produced by TPH1 in a number of organs. The gut enterochromaffin cells are often cited to be the primary peripheral site of 5HT synthesis, where it plays roles amongst others in gut motor activity, visceral sensation and intestinal secretion (Bertrand, P. P., and Bertrand, R. L. (2010) "Serotonin release and uptake in the gastrointestinal tract", *Auton Neurosci* 153, 47-57; Hasier, W. L. (2009) "Serotonin and the GI tract", *Curr Gastroenterol Rep* 11, 383-391). Serotonin secreted from the EC eventually finds its way out of the tissue into the blood. There, 5HT is actively taken up by blood platelets, where it is stored. Activated platelets disgorge 5HT and it subsequently serves as a vasoconstrictor and helps to regulate hemostatis and blood clotting. Linder et al. (2009) recently characterized 5HT concentrations in a number of organs in the rat (Linder, A. E., et al. (2009) "Body distribution of infused serotonin in rats", *Clin Exp Pharmacol Physiol* 36, 599-601). Notably the lung was found to have a similar 5HT concentration to the gut. Other researchers have measured TPH1 gene expression by qPCR and the results suggest that TPH1 is probably active in other organs including the thymus and the spleen (Walther, D. J. and M. Bader (2003). "A unique central tryptophan hydroxylase isoform." *Biochem Pharmacol* 66(9): 1673-1680). Furthermore, significantly elevated 5HT concentrations are thought to be responsible for certain conditions associated with carcinoid tumors (known as carcinoid syndrome).

The earliest reported TPH inhibitor used in vivo was p-chlorophenylalanine (PCA). PCA was demonstrated to lower 5HT in both the gut (~50% original) and the brain (~20% original) after dosing of 200 mg/kg intra peritonial (i.p.) four times a day (qid) for 3 days (Weber, L. J. (1970) "p-Chlorophenylalanine depletion of gastrointestinal 5-hydroxytryptamine", *Biochem Pharmacol* 19, 2169-2172). PCA has also shown utility in a xenograft model of cholangiocarcinoma, where a dramatic reduction in tumor volume was observed (Alpini, G., et al. (2008) "Serotonin metabolism is dysregulated in cholangiocarcinoma, which has implications for tumor growth", *Cancer Res* 68, 9184-9193). Following the discovery of the peripheral TPH1 enzyme (Walther, D. J., et al. (2003) "Synthesis of serotonin by a second tryptophan hydroxylase isoform", *Science* 299, 76), a number of studies indicating roles for peripheral 5HT in disease revealed the potential of TPH1 as a drug target. The company Lexicon Pharmaceuticals Ltd has synthesized and characterized a number of small molecule inhibitors of TPH1. LP533401 was demonstrated to lower gut 5HT in mice without effecting brain concentrations (Liu, Q., et al. (2008) "Discovery and characterization of novel tryptophan hydroxylase inhibitors that selectively inhibit serotonin synthesis in the gastrointestinal tract", *J Pharmacol Exp Ther* 325, 47-55). LP533401 has been further characterized in both mouse and rat models of osteoporosis (Yadav, V. K., et al. (2010) "Pharmacological inhibition of gut-derived serotonin synthesis is a potential bone anabolic treatment for osteoporosis", *Nat Med* 16, 308-312). LX1031 ((S)-2-Amino-3-(4-{2-amino-6-[(R)-2,2,2-trifluoro-1-(3'-methoxy-biphenyl-4-yl)-ethoxy]-pyrimidin-4-yl}-phenyl)-propionic acid, WO2007/089335) was the first TPH inhibitor from Lexicon Pharmaceuticals Ltd to enter clinical trials and similar to LP533401 lowers 5HT in the jejunum, with only a minor reduction observed in the colon and no effect on brain 5HT. In a phase IIA study LX1031 qid did not affect blood 5HT and had very modest effects on urinary 5HIAA (up to 30% reduction) (Brown, P. M., et al. (2011) "The tryptophan hydroxylase inhibitor LX1031 shows clinical benefit in patients with nonconstipating irritable bowel syndrome", *Gastroenterology* 141, 507-516). A further small molecule inhibitor of TPH1 is LX1032 ((S)-2-Amino-3-[4-(2-amino-6-{(R)-1-[4-chloro-2-(3-methyl-pyrazol-1-yl)-phenyl]-2,2,2-trifluoro-ethoxy}-pyrimidin-4-yl)-phenyl]-propionic acid ethyl ester, WO2008/073933), which is disclosed to be in clinical studies for carcinoid syndrome.

The present invention, thus, provides novel tricyclic imidazole derivatives of formula (I) which are non-peptide inhibitors of human TPH potentially useful in the treatment of disorders relating to disease or disorder characterized by an altered rate of the tryptophan-serotonin metabolism, comprising especially lung fibrosis; pulmonary hypertension including pulmonary arterial hypertension; asthma; osteoporosis; ulcerative colitis; irritable bowel syndrome; carcinoid syndrome; cancer including breast cancer, prostate cancer, and neuroendocrine tumors with elevated serotonin secretion (e.g carcinoid tumors); and inflammatory diseases including multiple sclerosis and systemic sclerosis.

1) In a first embodiment, the present invention relates to compounds of Formula (I)

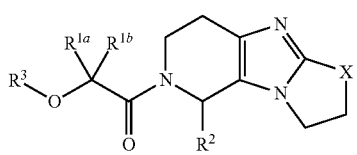

Formula (I)

wherein

X represents —CH$_2$—, —CH$_2$—CH$_2$—, —CH$_2$—CH$_2$—CH$_2$—, —S—, *—CH$_2$—O—, or *—CH$_2$—NR$^x$— wherein R$^x$ represents hydrogen, —CO—(C$_{1-4}$)alkyl, —(C$_{1-3}$)alkyl-(C$_{3-6}$)cycloalkyl, (C$_{3-6}$)cycloalkyl, or —CO—(C$_{1-4}$)alkoxy; wherein the asterisks indicate the bond attached to the imidazole ring;

R$^{1a}$ and R$^{1b}$ independently represent hydrogen, methyl, ethyl; or R$^{1a}$ and R$^{1b}$ together with the carbon atom to which they are attached to form a cyclopropyl ring;

R$^2$ represents aryl (especially phenyl), or heteroaryl (notably 5- or 6-membered heteroaryl, especially pyridinyl, thiazolyl, thiophenyl, oxadiazolyl), wherein said aryl or heteroaryl independently is unsubstituted, or mono-, di-, or tri-substituted, wherein the substituents are independently selected from:

(C$_{1-4}$)alkyl;
(C$_{1-4}$)alkoxy;
(C$_{3-6}$)cycloalkyl;
(C$_{1-3}$)fluoroalkyl;
(C$_{1-3}$)fluoroalkoxy;
halogen;
cyano;
—(CH$_2$)$_n$—NR$^{21}$R$^{22}$; wherein n represents the integer 0 or 1; and
  R$^{21}$ and R$^{22}$ independently represent hydrogen or (C$_{1-4}$)alkyl; or
  R$^{21}$ and R$^{22}$ together with the nitrogen atom to which they are attached to form a 4- to 7-membered saturated ring, wherein said ring optionally contains one ring oxygen atom;
—CO—NR$^{23}$R$^{24}$, wherein R$^{23}$ and R$^{24}$ independently represent hydrogen or (C$_{1-4}$)alkyl;
—CO—NH—CN;
—NR$^{25}$—CO—NR$^{26}$R$^{27}$, wherein R$^{25}$, R$^{26}$ and R$^{27}$ independently represent hydrogen or (C$_{1-4}$)alkyl;
—CO—(C$_{1-4}$)alkoxy;
phenyl;
hydroxy-(C$_{1-4}$)alkyl;
(C$_{1-3}$)alkoxy-(C$_{1-4}$)alkyl;
hydroxy-(C$_{2-4}$)alkoxy; or
(C$_{1-3}$)alkoxy-(C$_{2-4}$)alkoxy;

R$^3$ represents aryl (especially phenyl), or heteroaryl (notably 5- or 6-membered heteroaryl, especially pyridinyl or pyrimidinyl), wherein said aryl or heteroaryl independently is unsubstituted, or mono-, di-, or tri-substituted (especially mono- or di-substituted), wherein the substituents are independently selected from:

—NR$^4$—SO$_2$—Y—R$^5$, wherein
  R$^4$ represents hydrogen or (C$_{1-3}$)alkyl; Y represents a direct bond; and R$^5$ represents (C$_{1-4}$)alkyl (especially methyl), or (C$_{3-6}$)cycloalkyl (especially cyclopropyl); or
  R$^4$ represents hydrogen or (C$_{1-3}$)alkyl; Y represents —NR$^Y$— wherein R$^Y$ represents (C$_{1-3}$)alkyl; and R$^5$ represents (C$_{1-4}$)alkyl (especially R$^4$ represents hydrogen, Y represents —N(CH$_3$)— and R$^5$ represents (C$_{1-4}$)alkyl); or R$^4$ and R$^5$ together with the nitrogen and the —SO$_2$—Y-group to which they are attached to form a 5-, 6-, or 7-membered ring, wherein Y represents a direct bond or —NR$^Y$— wherein R$^Y$ represents (C$_{1-3}$)alkyl (especially such ring is 5-methyl-1,1-dioxido-1,2,5-thiadiazolidin-2-yl or 1,1-dioxidoisothiazolidin-2-yl);

—CO—NR$^6$R$^7$, wherein R$^6$ and R$^7$ independently represent hydrogen, (C$_{1-4}$)alkyl, or (C$_{3-6}$)cycloalkyl (especially one of R$^6$ and R$^7$ represents hydrogen or methyl, and the other of R$^6$ and R$^7$ represents (C$_{1-4}$)alkyl, or (C$_{3-6}$)cycloalkyl);

—SO$_2$—R$^8$ wherein R$^8$ represents (C$_{1-5}$)alkyl, or —NR$^{81}$R$^{82}$, wherein R$^{81}$ and R$^{82}$ independently represent hydrogen or (C$_{1-4}$)alkyl;

—(CH$_2$)$_m$—NR$^9$R$^{10}$; wherein m represents the integer 0 or 1; and
  R$^9$ and R$^{10}$ independently represent hydrogen, (C$_{1-4}$)alkyl, (C$_{2-3}$)fluoroalkyl, hydroxy-(C$_{2-4}$)alkyl, (C$_{1-4}$)alkoxy-(C$_{2-4}$)alkyl; or
  R$^9$ and R$^{10}$ together with the nitrogen to which they are attached to form a 4- to 7-membered ring optionally containing an oxygen ring atom or a group —NR$^{11}$— wherein R$^{11}$ represents (C$_{1-4}$)alkyl, and wherein said ring is optionally substituted with one or two fluorine substituents (notably such ring is morpholin-4-yl, 3,3-difluoro-azetidin-1-yl, or 1-methyl-piperazin-4-yl);

(C$_{1-4}$)alkyl;
(C$_{3-6}$)cycloalkyl;
(C$_{1-4}$)alkoxy;
(C$_{1-3}$)fluoroalkyl;
(C$_{1-3}$)fluoroalkoxy;
halogen;
cyano; or
5-membered heteroaryl (notably oxazolyl, especially oxazol-2-yl).

The compounds of Formula (I) contain at least one and possibly more stereogenic or asymmetric centers, such as one or more asymmetric carbon atoms. The compounds of Formula (I) may thus be present as mixtures of stereoisomers or in stereoisomerically enriched form, preferably as pure stereoisomers. Mixtures of stereoisomers may be separated in a manner known to a person skilled in the art.

The term "enriched", for example when used in the context of enantiomers is understood in the context of the present invention to mean especially that the respective enantiomer is present in a ratio (mutatis mutandis:purity) of at least 70:30, and notably of at least 90:10 (mutatis mutandis: purity of 70%/90%) with respect to the respective other enantiomer. Preferably the term refers to the respective essentially pure enantiomer. The term "essentially", for example when used in a term such as "essentially pure" is understood in the context of the present invention to mean especially that the respective stereoisomer/composition/compound etc. consists in an amount of at least 90, especially of at least 95, and notably of at least 99 percent by weight of the respective pure stereoisomer/composition/compound etc. . . . . .

In some instances, the compounds of formula (I) may contain tautomeric forms. Such tautomeric forms are encompassed in the scope of the present invention.

Where the plural form is used for compounds, salts, pharmaceutical compositions, diseases or the like, this is intended to mean also a single compound, salt, disease or the like.

Any reference to a compound of Formula (I) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Phramaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

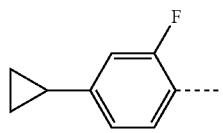

is the 2-fluoro-4-cyclopropyl-phenyl group.

Definitions provided herein are intended to apply uniformly to the compounds of formulae (I), (II), (Ill), (IV) and (I$_E$) as defined in any one of embodiments 1) to 32), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, bromine or iodine, preferably fluorine or chlorine.

The term "alkyl", used alone or in combination, refers to a straight or branched saturated hydrocarbon chain containing one to six carbon atoms. The term "$(C_{x-y})$alkyl" (x and y each being an integer), refers to an alkyl group as defined before containing x to y carbon atoms. For example a $(C_{1-4})$alkyl group contains from one to four carbon atoms. Examples of $(C_{1-4})$alkyl groups are methyl, ethyl, propyl, isopropyl, n-butyl, isobutyl, sec.-butyl and tert-butyl. Preferred are methyl and ethyl. Most preferred is methyl.

The term "alkoxy", used alone or in combination, refers to an alkyl-O— group wherein the alkyl refers to a straight or branched saturated hydrocarbon chain containing one to six carbon atoms. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of $(C_{1-4})$alkoxy groups are methoxy, ethoxy, n-propoxy, isopropoxy, n-butoxy, isobutoxy, sec.-butoxy and tert-butoxy. Preferred is methoxy.

The term "$(C_{1-3})$fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of $(C_{1-3})$ fluoroalkyl groups include trifluoromethyl, difluoromethyl, fluoromethyl, 2-fluoroethyl, 2,2-difluoroethyl, and 2,2,2-trifluoroethyl. Preferred are $(C_1)$fluoroalkyl groups such as trifluoromethyl or difluoromethyl.

The term "$(C_{1-3})$fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of $(C_{1-3})$fluoroalkoxy groups include trifluoromethoxy, difluoromethoxy and 2,2,2-trifluoroethoxy. Preferred are $(C_1)$ fluoroalkoxy groups such as trifluoromethoxy and difluoromethoxy.

The term "cycloalkyl", used alone or in combination, refers to a saturated carbocyclic ring containing three to seven carbon atoms. The term "$(C_{x-y})$cycloalkyl" (x and y each being an integer), refers to a cycloalkyl group as defined before containing x to y carbon atoms. For example a $(C_{3-7})$cycloalkyl group contains from three to seven carbon atoms. Examples of cycloalkyl groups are cyclopropyl, cyclobutyl, cyclopentyl, cyclohexyl, and cycloheptyl. Preferred is cyclopropyl.

The term "aryl", used alone or in combination, means phenyl or naphthyl, preferably phenyl. The above-mentioned aryl groups are unsubstituted or substituted as explicitly defined. For the substituent "R$^2$" representing aryl, the term especially means phenyl. The aryl group as used for the substituent "R$^2$" is unsubstituted, or mono-, di-, or tri-substituted as explicitly defined; especially mono-, di-, or tri-substituted. The substituents of such aryl groups as used for the substituent "R$^2$" are independently selected from $(C_{1-4})$alkyl; $(C_{1-4})$alkoxy; $(C_{3-6})$cycloalkyl; $(C_{1-3})$fluoroalkyl; $(C_{1-3})$fluoroalkoxy; halogen; cyano; —$(CH_2)_n$—NR$^{21}$R$^{22}$; wherein n and R$^{21}$ and R$^{22}$ are as explicitly defined; —CO—NR$^{23}$R$^{24}$, wherein R$^{23}$ and R$^{24}$ independently represent hydrogen or $(C_{1-4})$alkyl; —CO—NH—CN; —NR$^{25}$—CO—NR$^{26}$R$^{27}$, wherein R$^{25}$, R$^{26}$ and R$^{27}$ independently represent hydrogen or $(C_{1-4})$alkyl; —CO—$(C_{1-4})$ alkoxy; or phenyl; or, in addition to the above listed:

hydroxy-$(C_{1-4})$alkyl; hydroxy-$(C_{2-4})$alkoxy; $(C_{1-3})$alkoxy-$(C_{1-4})$alkyl; or $(C_{1-3})$alkoxy-$(C_{2-4})$alkoxy. Notably, the substituents of groups $R^2$ representing phenyl are independently selected from $(C_{1-4})$alkyl; $(C_{3-6})$cycloalkyl; $(C_{1-3})$fluoroalkoxy; halogen; cyano; hydroxy-$(C_{1-4})$alkyl; hydroxy-$(C_{2-4})$alkoxy; $(C_{1-3})$alkoxy-$(C_{1-4})$alkyl; or $(C_{1-3})$alkoxy-$(C_{2-4})$alkoxy; especially from $(C_{1-4})$alkyl; $(C_{3-6})$cycloalkyl; or halogen. Particular substituents are independently selected from from methyl, methoxy, cyclopropyl, trifluoromethoxy, fluoro, chloro, cyano, methoxymethyl, methoxycarbonyl, 2-hydroxy-ethoxy, 2-hydroxypropan-2-yl, 2-methoxy-ethoxy, or 2-methoxypropan-2-yl; especially from methyl, cyclopropyl, fluoro, or chloro. Particular examples of such aryl groups as used for "$R^2$" are 2-fluoro-4-methyl-phenyl, 4-chloro-2-fluoro-phenyl, 2,3-difluoro-4-methyl-phenyl, 2,5-difluoro-4-methyl-phenyl, and 4-cyclopropyl-2-fluoro-phenyl. In addition, further particular examples of such aryl groups as used for "$R^2$" are 2-fluoro-4-methoxy-phenyl, 2-fluoro-4-cyano-phenyl, 2-fluoro-4-methoxymethyl-phenyl, 2-fluoro-4-methoxycarbonyl-phenyl, 2-fluoro-4-(2-hydroxyethoxy)-phenyl, 2-fluoro-4-(2-methoxyethoxy)-phenyl, 2-fluoro-4-(2-hydroxy-propan-2-yl)-phenyl, 2-fluoro-4-(2-methoxy-propan-2-yl)-phenyl, and 2-fluoro-4-trifluoromethoxy-phenyl. For the substituent "$R^3$" representing aryl, the term especially means phenyl. The aryl group as used for the substituent "$R^3$" is unsubstituted, or mono-, di-, or tri-substituted as explicitly defined; notably it is mono-, di-, or tri-substituted; escpecially di-substituted wherein one substituent is attached in para position with regard to the point of attachment to the rest of the molecule. Particular examples of such aryl groups as used for "$R^3$" are 4-chloro-2-ethyl-phenyl, 2-ethyl-4-fluoro-phenyl, 4-chloro-2-cyano-phenyl, 2-chloro-4-cyano-phenyl, 2-chloro-4-trifluoromethyl-phenyl, 2-chloro-4-(dimethyl-carbamoyl)-phenyl, 2-chloro-4-(morpholin-4-yl)-phenyl, and 2-chloro-4-(morpholin-4-yl-methyl)-phenyl.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl; 6-membered heteroaryl groups such as pyridinyl, pyrimidinyl, pyridazinyl, pyrazinyl; and 8- to 10-membered bicyclic heteroaryl groups such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, thienopyridinyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined.

In case "$R^2$" represents "heteroaryl", the term means heteroaryl groups, notably 5- or 6-membered heteroaryl groups, as defined before. In one embodiment, the term especially refers to thiophenyl, thiazolyl, oxadiazolyl, and pyridinyl. The above-mentioned heteroaryl groups as used for the substituent "$R^2$" are unsubstituted or substituted as explicitly defined. In particular, the above-mentioned heteroaryl groups are mono-, or di-substituted, wherein the substituents are independently selected from $(C_{1-4})$alkyl; $(C_{3-6})$cycloalkyl; $(C_{1-3})$fluoroalkyl; halogen; —$NR^{21}R^{22}$; wherein $R^{21}$ and $R^{22}$ independently represent $(C_{1-4})$alkyl; —CO—$NR^{23}R^{24}$, wherein $R^{23}$ and $R^{24}$ independently represent hydrogen or $(C_{1-4})$alkyl; —$NR^{25}$—CO—$NR^{26}R^{27}$, wherein $R^{25}$, $R^{26}$ and $R^{27}$ independently represent hydrogen or $(C_{1-4})$alkyl (especially one of $R^{26}$ and $R^{27}$ represents $(C_{1-4})$alkyl, and the remaining of $R^{25}$, $R^{26}$ and $R^{27}$ represent hydrogen); —CO—$(C_{1-4})$alkoxy; or phenyl; or, in addition to the above listed: hydroxy-$(C_{1-4})$alkyl; hydroxy-$(C_{2-4})$alkoxy; $(C_{1-3})$alkoxy-$(C_{1-4})$alkyl; or $(C_{1-3})$alkoxy-$(C_{2-4})$alkoxy. In a sub-embodiment, substituents are especially selected from $(C_{1-4})$alkyl; $(C_{3-6})$cycloalkyl; $(C_{1-3})$fluoroalkyl; or halogen. Particular examples of heteroaryl groups as used for the substitutent "$R^2$" are 3-fluoro-thiophen-2-yl, 4-(dimethyl-carbamoyl)-thiophen-2-yl, 5-(dimethyl-carbamoyl)-3-fluoro-thiophen-2-yl, 4-(methoxy-carbonyl)-thiophen-2-yl, 4-(cyano-carbamoyl)-thiophen-2-yl, 4-methyl-thiazol-5-yl, 2-methyl-thiazol-5-yl, 2,4-dimethyl-thiazol-5-yl, 2-ethyl-4-methyl-thiazol-5-yl, 2-isopropyl-4-methyl-thiazol-5-yl, 4-methyl-2-trifluoromethyl-thiazol-5-yl, 2-dimethylamino-thiazol-5-yl, 4-(methyl-carbamoyl)-thiazol-2-yl, 4-(ethoxy-carbonyl)-thiazol-2-yl, 2-(3-ethylureido))-thiazol-4-yl, 2-phenyl-thiazol-5-yl, 3-phenyl-[1,2,4]oxadiazol-5-yl, 5-chloro-pyridin-2-yl, 4-chloro-pyridin-2-yl, 3-fluoro-pyridin-2-yl, 5-fluoro-3-methyl-pyridin-2-yl, 3-fluoro-5-methyl-pyridin-2-yl, 5-chloro-3-fluoro-pyridin-2-yl, 5-cyclopropyl-3-fluoro-pyridin-2-yl.

In case "$R^3$" represents "heteroaryl", the term means heteroaryl groups, notably 5- or 6-membered heteroaryl groups (especially 6-membered heteroaryl groups containing one or two nitrogen atoms) as defined before. In one embodiment, the term especially refers to pyridinyl or pyrimidinyl, in particular pyridinyl which is attached to the rest of the molecule in position 3 or pyrimidinyl which is attached to the rest of the molecule in position 5. The above-mentioned heteroaryl groups as used for the substitutent "$R^3$" are unsubstituted or mono-, di-, or tri-substituted as explicitly defined; notably mono-, di-, or tri-substituted; especially di-substituted wherein one substituent is attached in para position with regard to the point of attachment to the rest of the molecule. Particular examples of heteroaryl groups as used for the substitutent "$R^3$" are 2-ethyl-6-methyl-pyridin-3-yl, 2-chloro-6-cyano-pyridin-3-yl, 2-chloro-6-cyclopropyl-pyridin-3-yl, 2-ethyl-6-cyclopropyl-pyridin-3-yl, 2-chloro-6-trifluoromethyl-pyridin-3-yl, 2-chloro-6-oxazol-2-yl-pyridin-3-yl, 2-chloro-6-(3,3-difluoro-azetidin-1-yl)-pyridin-3-yl, 2-chloro-6-(morpholin-4-yl)-pyridin-3-yl, 2-chloro-6-(4-methyl-piperazin-1-yl)-pyridin-3-yl, 2-chloro-5-fluoro-pyridin-3-yl, 2-chloro-pyridin-3-yl, 2-trifluoromethyl-pyridin-3-yl, 2-chloro-4-ethyl-pyrimidin-5-yl, 2-chloro-6-(methyl-carbamoyl)-pyridin-3-yl, 2-chloro-6-(dimethyl-carbamoyl)-pyridin-3-yl, 2-chloro-6-(ethyl-(methyl)-carbamoyl)-pyridin-3-yl, 2-chloro-6-(cyclopropyl-carbamoyl)-pyridin-3-yl, 2-chloro-6-(cyclopropyl-(methyl)-carbamoyl)-pyridin-3-yl, 6-(cyclopropyl-carbamoyl)-2-ethyl-pyridin-3-yl, 2-chloro-6-(isopropyl-(methyl)-carbamoyl)-pyridin-3-yl, 2-chloro-6-(methylsulfonamido)-pyridin-3-yl, 2-chloro-6-(N-methyl-methylsulfonamido)-pyridin-3-yl, 2-ethyl-6-(methylsulfonamido)-pyridin-3-yl, 2-methoxy-6-(methylsulfonamido)-pyridin-3-yl, 2-chloro-6-(1,1-dioxo-isothiazolidin-2-yl)-pyridin-3-yl, 6-(1,1-dioxo-isothiazolidin-2-yl)-2-ethyl-pyridin-3-yl, 2-chloro-6-(5-methyl-1,1-dioxo-[1,2,5]thiadiazolidin-2-yl)-pyridin-3-yl, 2-ethyl-6-((N,N-dim ethylsulfamoyl)amino)-pyridin-3-yl, 4-ethyl-2-(methylsulfonamido)-pyrimidin-5-yl. In addition, further particular examples of heteroaryl groups as used for the substitutent "$R^3$" are 2-chloro-6-(dimethylamino)-pyridin-3-yl, 2-chloro-6-(methylsulfonyl)pyridin-3-yl, 2-chloro-6-[(2-hydroxyethyl)-methylamino)pyridin-3-yl, 2-chloro-6-[(2-methoxyethyl)-methylamino] pyridin-3-yl, 2-chloro-6-(N,N-dimethylsulfamoyl)pyridin-3-yl, 2-chloro-6-[(2,2,2-trifluoroethyl)-methylamino]pyridin-3-yl, 6-(cyclopropyl-carbamoyl)-2-cyclopropyl-pyridin-3-yl, and 2-cyclopropyl-6-(methylsulfonamido)-pyridin-3-yl.

The term "cyano" refers to a group —CN.

An example of a group "—$(CH_2)_n$—$NR^{21}R^{22}$" as used for substituents of the group $R^2$ is dimethylamino.

Examples of groups "—CO—$NR^{23}R^{24}$" as used for substituents of the group $R^2$ are methyl-carbamoyl, and dimethyl-carbamoyl.

An example of a group "—$NR^{25}$—CO—$NR^{26}R^{27}$" as used for substituents of the group $R^2$ is 3-ethylureido.

Examples of groups "—$(CH_2)_m$—$NR^9R^{10}$, wherein $R^9$ and $R^{10}$ together with the nitrogen to which they are attached to form a 4-, 5-, or 6-membered ring optionally containing an oxygen ring atom or a group —$NR^{11}$— wherein $R^{11}$ represents $(C_{1-4})$alkyl, and wherein said ring is optionally substituted with one or two fluorine substituents" as used for substituents of the group $R^3$, respectively, as used for the substituent $R^{3a}$, are especially those where $R^9$ and $R^{10}$ together with the nitrogen to which they are attached to form a 4-, 5-, or 6-membered ring, wherein said ring either optionally contains an oxygen ring atom or a group —$NR^{11}$— wherein $R^{11}$ represents $(C_{1-4})$alkyl; or wherein said ring is optionally substituted with one or two fluorine substituents. Examples of such groups "—$(CH_2)_m$—$NR^9R^{10}$" are morpholin-4-yl, (morpholin-4-yl)-methyl, 3,3-difluoro-azetidin-1-yl, and 1-methyl-piperazin-4-yl.

It is understood that in groups "—$NR^4$—$SO_2$—Y—$R^5$, wherein $R^4$ and $R^5$ together with the nitrogen and the —$SO_2$—Y-group to which they are attached to form a 5-, 6-, or 7-membered ring" as used for substituents of the group $R^3$, respectively, as used for the substituent $R^{3a}$, the ring fragment formed by $R^4$ and $R^5$ is carbocyclic and does not contain further heteroatoms (in addition to the —N—$SO_2$—Y— fragment which is part of the ring). The same applies mutatis mutandis for the groups "—$NR^{43}$—$SO_2$—$R^{53}$" and "—$NR^{44}$—$SO_2$—$NR^{Y4}$—$R^{54}$". Examples of groups "—$NR^4$—$SO_2$—Y—$R^5$" are methylsulfonamido, N-methyl-methylsulfonamido, and 1,1-dioxo-isothiazolidin-2-yl; as well as (N,N-dimethylsulfamoyl)-amino, and 5-methyl-1,1-dioxo-[1,2,5]thiadiazolidin-2-yl.

Examples of groups "—CO—$NR^6R^7$" as used for substituents of the group $R^3$, respectively, as used for the substituent $R^{3a}$, are methyl-carbamoyl, dimethyl-carbamoyl, ethyl-(methyl)-carbamoyl, cyclopropyl-carbamoyl, cyclopropyl-(methyl)-carbamoyl, isopropyl-(methyl)-carbamoyl.

Examples of a group "—$SO_2$—$R^8$" as used for substituents of the group $R^3$, respectively, as used for the substituent $R^{3a}$, are methylsulfonyl, sulfamoyl, N-methylsulfamoyl, and N,N-dimethylsulfamoyl.

Examples of "hydroxy-$(C_{1-4})$alkyl" groups as used for substituents of the group $R^2$ are hydroxymethyl, and 2-hydroxypropan-2-yl.

Examples of "$(C_{1-3})$alkoxy-$(C_{1-4})$alkyl" groups as used for substituents of the group $R^2$ are methoxymethyl, and 2-methoxypropan-2-yl.

An example of a "hydroxy-$(C_{2-4})$alkoxy" group as used for substituents of the group $R^2$ is 2-hydroxy-ethoxy.

An example of a "$(C_{1-3})$alkoxy-$(C_{2-4})$alkoxy group as used for substituents of the group $R^2$ is 2-methoxy-ethoxy.

An example of a "—CO—$(C_{1-4})$alkoxy" group as used for substituents of the group $R^2$ is methoxy-carbonyl.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of 25° C.

Further embodiments of the invention are presented hereinafter.

2) A second aspect of the invention relates to compounds of Formula (I) according to embodiment 1), wherein the absolute configuration of the carbon atom carrying the substituent $R^2$ is as depicted in Formula ($I_E$):

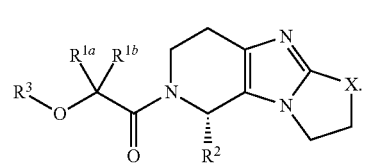

Formula ($I_E$)

3) A further embodiment relates to compounds according to embodiments 1) or 2) wherein $R^{1a}$ and $R^{1b}$ both represent hydrogen.

4) A further embodiment relates to compounds according to any one of embodiments 1) to 3), wherein X represents —$CH_2$—, —$CH_2$—$CH_2$—, —$CH_2$—$CH_2$—$CH_2$—, —S—, *—$CH_2$—O—, or *—$CH_2$—$NR^x$—wherein $R^x$ represents hydrogen, —CO—$CH_3$, —$(CH_2)$cyclopropyl, cyclopropyl, or —CO—O— tert-butyl; wherein the asterisks indicate the bond attached to the imidazole ring.

5) A further embodiment relates to compounds according to any one of embodiments 1) to 3), wherein X represents —$CH_2$—, —$CH_2$—$CH_2$—, or —S— (especially —$CH_2$—$CH_2$—, or —S—).

6) A further embodiment relates to compounds according to any one of embodiments 1) to 3), wherein X represents —$CH_2$—, or —$CH_2$—$CH_2$— (especially —$CH_2$—$CH_2$—).

7) A further embodiment relates to compounds according to any one of embodiments 1) to 3), wherein X represents —S—.

8) A further embodiment relates to compounds according to any one of embodiments 1) to 7), wherein $R^2$ represents phenyl, or 5- or 6-membered heteroaryl (notably pyridinyl, thiazolyl, thiophenyl, oxadiazolyl), wherein said phenyl or heteroaryl independently is mono-, di-, or tri-substituted, wherein the substituents are independently selected from:
  $(C_{1-4})$alkyl;
  $(C_{1-4})$alkoxy;
  $(C_{3-6})$cycloalkyl;
  $(C_{1-3})$fluoroalkyl;
  $(C_{1-3})$fluoroalkoxy;
  halogen;
  cyano;

—NR$^{21}$R$^{22}$; wherein
R$^{21}$ and R$^{22}$ independently represent hydrogen or (C$_{1-4}$)alkyl; or
R$^{21}$ and R$^{22}$ together with the nitrogen atom to which they are attached to form a 4- to 7-membered saturated ring, wherein said ring optionally contains one ring oxygen atom;
—CO—NR$^{23}$R$^{24}$, wherein R$^{23}$ and R$^{24}$ independently represent hydrogen or (C$_{1-4}$)alkyl;
—NR$^{25}$—CO—NR$^{26}$R$^{27}$, wherein R$^{25}$, R$^{26}$ and R$^{27}$ independently represent hydrogen or (C$_{1-4}$)alkyl;
—CO—(C$_{1-4}$)alkoxy;
phenyl;
hydroxy-(C$_{1-4}$)alkyl;
(C$_{1-3}$)alkoxy-(C$_{1-4}$)alkyl;
hydroxy-(C$_{2-4}$)alkoxy; or
(C$_{1-3}$)alkoxy-(C$_{2-4}$)alkoxy.

9) A further embodiment relates to compounds according to any one of embodiments 1) to 7), wherein R$^2$ represents phenyl, or 5- or 6-membered heteroaryl (notably pyridinyl, thiazolyl, thiophenyl, or oxadiazolyl), wherein said phenyl or heteroaryl independently is mono-, di-, or tri-substituted, wherein the substituents are independently selected from:
(C$_{1-4}$)alkyl;
(C$_{3-6}$)cycloalkyl;
(C$_{1-3}$)fluoroalkyl;
halogen;
cyano;
—NR$^{21}$R$^{22}$; wherein R$^{21}$ and R$^{22}$ independently represent (C$_{1-4}$)alkyl;
—CO—NR$^{23}$R$^{24}$, wherein R$^{23}$ and R$^{24}$ independently represent hydrogen or (C$_{1-4}$)alkyl;
—NR$^{25}$—CO—NR$^{26}$R$^{27}$, wherein R$^{25}$, R$^{26}$ and R$^{27}$ independently represent hydrogen or (C$_{1-4}$)alkyl;
—CO—(C$_{1-4}$)alkoxy;
phenyl.

10) A further embodiment relates to compounds according to any one of embodiments 1) to 7), wherein R$^2$ represents a phenyl, pyridinyl, thiazolyl, thiophenyl, or oxadiazolyl group, wherein said group independently is mono-, di-, or tri-substituted, wherein the substituents are independently selected from:
(C$_{1-4}$)alkyl;
(C$_{3-6}$)cycloalkyl;
(C$_{1-3}$)fluoroalkyl;
halogen;
cyano;
—NR$^{21}$R$^{22}$; wherein R$^{21}$ and R$^{22}$ independently represent (C$_{1-4}$)alkyl;
—CO—NR$^{23}$R$^{24}$, wherein R$^{23}$ and R$^{24}$ independently represent hydrogen or (C$_{1-4}$)alkyl;
—NR$^{25}$—CO—NR$^{26}$R$^{27}$, wherein R$^{25}$, R$^{26}$ and R$^{27}$ independently represent hydrogen or (C$_{1-4}$)alkyl;
—CO—(C$_{1-4}$)alkoxy; or
phenyl.

11) A further embodiment relates to compounds according to any one of embodiments 1) to 7), wherein
R$^2$ represents phenyl, wherein said phenyl is mono-, di-, or tri-substituted, wherein the substituents are independently selected from:
(C$_{1-4}$)alkyl;
(C$_{3-6}$)cycloalkyl;
(C$_{1-3}$)fluoroalkyl;
halogen;
cyano;
hydroxy-(C$_{1-4}$)alkyl;
(C$_{1-3}$)alkoxy-(C$_{1-4}$)alkyl;
hydroxy-(C$_{2-4}$)alkoxy; or
(C$_{1-3}$)alkoxy-(C$_{2-4}$)alkoxy.
or R$^2$ represents 5- or 6-membered heteroaryl (notably pyridinyl, thiazolyl, thiophenyl, or oxadiazolyl), wherein said heteroaryl is mono-, or di-substituted, wherein the substituents are independently selected from:
(C$_{1-4}$)alkyl;
(C$_{3-6}$)cycloalkyl;
(C$_{1-3}$)fluoroalkyl;
halogen;
—NR$^{21}$R$^{22}$; wherein R$^{21}$ and R$^{22}$ independently represent (C$_{1-4}$)alkyl;
—CO—NR$^{23}$R$^{24}$, wherein R$^{23}$ and R$^{24}$ independently represent hydrogen or (C$_{1-4}$)alkyl;
—NR$^{25}$—CO—NR$^{26}$R$^{27}$, wherein R$^{25}$, R$^{26}$ and R$^{27}$ independently represent hydrogen or (C$_{1-4}$)alkyl (especially one of R$^{26}$ and R$^{27}$ represents (C$_{1-4}$)alkyl, and the remaining of R$^{25}$, R$^{26}$ and R$^{27}$ represent hydrogen);
—CO—(C$_{1-4}$)alkoxy; or
phenyl.

12) A further embodiment relates to compounds according to any one of embodiments 1) to 7), wherein
R$^2$ represents phenyl, wherein said phenyl is mono-, di-, or tri-substituted, wherein the substituents are independently selected from:
(C$_{1-4}$)alkyl;
(C$_{3-6}$)cycloalkyl; or
halogen;
or R$^2$ represents 5- or 6-membered heteroaryl (notably pyridinyl, thiazolyl, or thiophenyl, especially pyridinyl or thiazolyl), wherein said heteroaryl is mono-, or di-substituted, wherein the substituents are independently selected from:
(C$_{1-4}$)alkyl;
(C$_{3-6}$)cycloalkyl;
(C$_{1-3}$)fluoroalkyl; or
halogen.

13) A further embodiment relates to compounds according to any one of embodiments 1) to 7), wherein
R$^2$ represents 2-fluoro-4-methyl-phenyl, 4-chloro-2-fluoro-phenyl, 2,3-difluoro-4-methyl-phenyl, 2,5-difluoro-4-methyl-phenyl, or 4-cyclopropyl-2-fluoro-phenyl; or
or R$^2$ represents 3-fluoro-thiophen-2-yl, 4-(dimethyl-carbamoyl)-thiophen-2-yl, 5-(dimethyl-carbamoyl)-3-fluoro-thiophen-2-yl, 4-(methoxy-carbonyl)-thiophen-2-yl, 4-(cyano-carbamoyl)-thiophen-2-yl, 4-methyl-thiazol-5-yl, 2-methyl-thiazol-5-yl, 2,4-dimethyl-thiazol-5-yl, 2-ethyl-4-methyl-thiazol-5-yl, 2-isopropyl-4-methyl-thiazol-5-yl, 4-methyl-2-trifluoromethyl-thiazol-5-yl, 2-dimethylamino-thiazol-5-yl, 4-(methyl-carbamoyl)-thiazol-2-yl, 4-(ethoxy-carbonyl)-thiazol-2-yl, 2-(3-ethylureido))-thiazol-4-yl, 2-phenyl-thiazol-5-yl, 3-phenyl-[1,2,4]oxadiazol-5-yl, 5-chloro-pyridin-2-yl, 4-chloro-pyridin-2-yl, 3-fluoro-pyridin-2-yl, 5-fluoro-3-methyl-pyridin-2-yl, 3-fluoro-5-methyl-pyridin-2-yl, 5-chloro-3-fluoro-pyridin-2-yl, or 5-cyclopropyl-3-fluoro-pyridin-2-yl;
or R$^2$ represents 2-fluoro-4-methoxy-phenyl, 2-fluoro-4-cyano-phenyl, 2-fluoro-4-methoxymethyl-phenyl, 2-fluoro-4-methoxycarbonyl-phenyl, 2-fluoro-4-(2-hydroxyethoxy)-phenyl, 2-fluoro-4-(2-methoxyethoxy)-phenyl, 2-fluoro-4-(2-hydroxy-propan-2-yl)-phenyl, 2-fluoro-4-(2-methoxy-propan-2-yl)-phenyl, and 2-fluoro-4-trifluoromethoxy-phenyl.

14) A further embodiment relates to compounds according to any one of embodiments 1) to 13), wherein $R^3$ represents phenyl, or pyridinyl, or pyrimidinyl, wherein said phenyl or pyridinyl or pyrimidinyl independently is mono-, di-, or tri-substituted (especially mono- or di-substituted), wherein the substituents are independently selected from:

—$NR^4$—$SO_2$—Y—$R^5$, wherein
  $R^4$ represents hydrogen or $(C_{1-3})$alkyl; Y represents a direct bond; and $R^5$ represents $(C_{1-4})$alkyl (especially methyl), or $(C_{3-6})$cycloalkyl (especially cyclopropyl); or
  $R^4$ represents hydrogen or $(C_{1-3})$alkyl; Y represents —$NR^Y$— wherein $R^Y$ represents $(C_{1-3})$alkyl; and $R^5$ represents $(C_{1-4})$alkyl (especially $R^4$ represents hydrogen, Y represents —$N(CH_3)$— and $R^5$ represents $(C_{1-4})$alkyl); or
  $R^4$ and $R^5$ together with the nitrogen and the —$SO_2$—Y-group to which they are attached to form a 5-, 6-, or 7-membered ring, wherein Y represents a direct bond or —$NR^Y$— wherein $R^Y$ represents $(C_{1-3})$alkyl (especially such ring is 5-methyl-1,1-dioxido-1,2,5-thiadiazolidin-2-yl or 1,1-dioxidoisothiazolidin-2-yl);
—CO—$NR^6R^7$, wherein $R^6$ and $R^7$ independently represent hydrogen, $(C_{1-4})$alkyl, or $(C_{3-6})$cycloalkyl [especially one of $R^6$ and $R^7$ represents hydrogen or methyl, and the other of $R^6$ and $R^7$ represents $(C_{1-4})$alkyl (especially methyl), or $(C_{3-6})$cycloalkyl (especially cyclopropyl)];
—$SO_2$—$R^8$ wherein $R^8$ represents $(C_{1-5})$alkyl, or —$NR^{81}R^{82}$, wherein $R^{81}$ and $R^{82}$ independently represent hydrogen or $(C_{1-4})$alkyl;
—$(CH_2)_m$—$NR^9R^{10}$; wherein
  m represents the integer 0 or 1; and
  $R^9$ and $R^{10}$ together with the nitrogen to which they are attached to form a 4- to 7-membered ring optionally containing an oxygen ring atom or a group —$NR^{11}$— wherein $R^{11}$ represents $(C_{1-4})$alkyl, and wherein said ring is optionally substituted with one or two fluorine substituents (notably such ring is morpholin-4-yl, 3,3-difluoro-azetidin-1-yl, or 1-methyl-piperazin-4-yl);
$(C_{1-4})$alkyl;
$(C_{3-6})$cycloalkyl;
$(C_{1-3})$fluoroalkyl;
halogen;
cyano; or
5-membered heteroaryl (notably oxazolyl, especially oxazol-2-yl).

15) A further embodiment relates to compounds according to any one of embodiments 1) to 13), wherein $R^3$ represents phenyl, or 5- or 6-membered heteroaryl (especially pyridinyl or pyrimidinyl), wherein said aryl or heteroaryl independently is mono-, di-, or tri-substituted (especially mono- or di-substituted), wherein the substituents are independently selected from:

—$NR^4$—$SO_2$—Y—$R^5$, wherein
  $R^4$ represents hydrogen or methyl; Y represents a direct bond; and $R^5$ represents $(C_{1-4})$alkyl (especially methyl), or $(C_{3-6})$cycloalkyl (especially cyclopropyl); or
  $R^4$ represents hydrogen; Y represents —$NR^Y$— wherein $R^Y$ represents $(C_{1-3})$alkyl; and $R^5$ represents $(C_{1-4})$alkyl (especially $R^4$ represents hydrogen, Y represents —$N(CH_3)$— and $R^5$ represents $(C_{1-4})$alkyl); or
  $R^4$ and $R^5$ together with the nitrogen and the —$SO_2$—Y-group to which they are attached to form a 5-, 6-, or 7-membered ring, wherein Y represents a direct bond or —$NR^Y$— wherein $R^Y$ represents $(C_{1-3})$alkyl (especially such ring is 5-methyl-1,1-dioxido-1,2,5-thiadiazolidin-2-yl or 1,1-dioxidoisothiazolidin-2-yl);
—CO—$NR^6R^7$, wherein $R^6$ and $R^7$ independently represent hydrogen, $(C_{1-4})$alkyl, or $(C_{3-6})$cycloalkyl [especially one of $R^6$ and $R^7$ represents hydrogen or methyl, and the other of $R^6$ and $R^7$ represents $(C_{1-4})$alkyl (especially methyl), or $(C_{3-6})$cycloalkyl (especially cyclopropyl)];
—$SO_2$—$R^8$ wherein $R^8$ represents methyl or dimethylamino;
—$(CH_2)_m$—$NR^9R^{10}$; wherein
  m represents the integer 0 or 1; and
  $R^9$ and $R^{10}$ together with the nitrogen to which they are attached to form a 4-, 5-, or 6-membered ring optionally containing an oxygen ring atom or a group —$NR^{11}$— wherein $R^{11}$ represents $(C_{1-4})$alkyl, and wherein said ring is optionally substituted with one or two fluorine substituents (notably such ring is morpholin-4-yl, 3,3-difluoro-azetidin-1-yl, or 1-methyl-piperazin-4-yl);
$(C_{1-4})$alkyl;
$(C_{3-6})$cycloalkyl;
$(C_{1-4})$alkoxy;
$(C_{1-3})$fluoroalkyl;
halogen;
cyano; or
5-membered heteroaryl (notably oxazolyl, especially oxazol-2-yl).

16) A further embodiment relates to compounds according to any one of embodiments 1) to 13), wherein
$R^3$ represents 4-chloro-2-ethyl-phenyl, 2-ethyl-4-fluoro-phenyl, 4-chloro-2-cyano-phenyl, 2-chloro-4-trifluoromethyl-phenyl, 2-chloro-4-(dimethylcarbamoyl)-phenyl, 2-chloro-4-(morpholin-4-yl)-phenyl, or 2-chloro-4-(morpholin-4-yl-methyl)-phenyl;
or $R^3$ represents 2-ethyl-6-methyl-pyridin-3-yl, 2-chloro-6-cyano-pyridin-3-yl, 2-chloro-6-cyclopropyl-pyridin-3-yl, 2-ethyl-6-cyclopropyl-pyridin-3-yl, 2-chloro-6-trifluoromethyl-pyridin-3-yl, 2-chloro-6-oxazol-2-yl-pyridin-3-yl, 2-chloro-6-(3,3-difluoro-azetidin-1-yl)-pyridin-3-yl, 2-chloro-6-(morpholin-4-yl)-pyridin-3-yl, 2-chloro-6-(4-methyl-piperazin-1-yl)-pyridin-3-yl, 2-chloro-5-fluoro-pyridin-3-yl, 2-chloro-pyridin-3-yl, 2-trifluoromethyl-pyridin-3-yl, 2-chloro-4-ethyl-pyrimidin-5-yl, 2-chloro-6-(methyl-carbamoyl)-pyridin-3-yl, 2-chloro-6-(dimethyl-carbamoyl)-pyridin-3-yl, 2-chloro-6-(ethyl-(methyl)-carbamoyl)-pyridin-3-yl, 2-chloro-6-(cyclopropyl-carbamoyl)-pyridin-3-yl, 2-chloro-6-(cyclopropyl-(methyl)-carbamoyl)-pyridin-3-yl, 6-(cyclopropyl-carbamoyl)-2-ethyl-pyridin-3-yl, 2-chloro-6-(isopropyl-(methyl)-carbamoyl)-pyridin-3-yl, 2-chloro-6-(methylsulfonamido)-pyridin-3-yl, 2-chloro-6-(N-methyl-methylsulfonamido)-pyridin-3-yl, 2-ethyl-6-(methylsulfonamido)-pyridin-3-yl, 2-methoxy-6-(methylsulfonamido)-pyridin-3-yl, 2-chloro-6-(1,1-dioxo-isothiazolidin-2-yl)-pyridin-3-yl, 6-(1,1-dioxo-isothiazolidin-2-yl)-2-ethyl-pyridin-3-yl, 2-chloro-6-(5-methyl-1,1-dioxo-[1,2,5]thiadiazolidin-2-yl)-pyridin-3-yl, 2-ethyl-6-((N,N-dimethylsulfamoyl)amino)-pyridin-3-yl, or 4-ethyl-2-(methylsulfonamido)-pyrimidin-5-yl;

or $R^3$ represents 2-chloro-6-(dimethylamino)-pyridin-3-yl, 2-chloro-6-(methylsulfonyl) pyridin-3-yl, 2-chloro-6-[(2-hydroxyethyl)-methylamino)pyridin-3-yl, 2-chloro-6-[(2-methoxyethyl)-methylamino]pyridin-3-yl, 2-chloro-6-(N,N-dimethylsulfamoyl)pyridin-3-yl, 2-chloro-6-[(2,2,2-trifluoroethyl)-methylamino]pyridin-3-yl, 6-(cyclopropyl-carbamoyl)-2-cyclopropyl-pyridin-3-yl, or 2-cyclopropyl-6-(methylsulfonamido)-pyridin-3-yl.

17) A further embodiment relates to compounds according to any one of embodiments 1) to 13), wherein $R^3$ represents a fragment

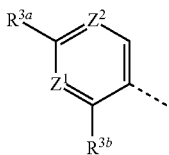

wherein
$Z^1$ and $Z^2$ independently represent CH or N;
$R^{3a}$ represents:
—$NR^4$—$SO_2$—Y—$R^5$, wherein
$R^4$ represents hydrogen or $(C_{1-3})$alkyl (especially hydrogen or methyl); Y represents a direct bond; and $R^5$ represents $(C_{1-4})$alkyl (especially methyl), or $(C_{3-6})$cycloalkyl (especially cyclopropyl); or
$R^4$ represents hydrogen or $(C_{1-3})$alkyl; Y represents —$NR^Y$— wherein $R^Y$ represents $(C_{1-3})$alkyl; and $R^5$ represents $(C_{1-4})$alkyl (especially $R^4$ represents hydrogen, Y represents —$N(CH_3)$— and $R^5$ represents $(C_{1-4})$alkyl); or
$R^4$ and $R^5$ together with the nitrogen and the —$SO_2$—Y-group to which they are attached to form a 5-, 6-, or 7-membered ring, wherein Y represents a direct bond or —$NR^Y$— wherein $R^Y$ represents $(C_{1-3})$alkyl (especially such ring is 5-methyl-1,1-dioxido-1,2,5-thiadiazolidin-2-yl or 1,1-dioxidoisothiazolidin-2-yl);
—CO—$NR^6R^7$, wherein $R^6$ and $R^7$ independently represent hydrogen, $(C_{1-4})$alkyl, or $(C_{3-6})$cycloalkyl [especially one of $R^6$ and $R^7$ represents hydrogen or methyl, and the other of $R^6$ and $R^7$ represents $(C_{1-4})$alkyl (especially methyl), or $(C_{3-6})$cycloalkyl (especially cyclopropyl)];
—$SO_2$—$R^8$ wherein $R^8$ represents $(C_{1-5})$alkyl, or —$NR^{81}R^{82}$, wherein $R^{81}$ and $R^{82}$ independently represent hydrogen or $(C_{1-4})$alkyl;
—$(CH_2)_m$—$NR^9R^{10}$; wherein m represents the integer 0 or 1; and $R^9$ and $R^{10}$ together with the nitrogen to which they are attached to form a 4- to 7-membered ring (especially a 6-membered ring) optionally containing an oxygen ring atom or a group —$NR^{11}$— wherein $R^{11}$ represents $(C_{1-4})$alkyl, and wherein said ring is optionally substituted with one or two fluorine substituents (notably such ring is morpholin-4-yl, 3,3-difluoro-azetidin-1-yl, or 1-methyl-piperazin-4-yl);
hydrogen;
halogen;
$(C_{1-4})$alkyl;
$(C_{3-6})$cycloalkyl;
$(C_{1-3})$fluoroalkyl;
5-membered heteroaryl (notably oxazolyl, especially oxazol-2-yl);
cyano; and
$R^{3b}$ represents $(C_{1-4})$alkyl (especially ethyl); halogen (especially chloro); $(C_{3-6})$cycloalkyl (especially cyclopropyl); or $(C_{1-3})$fluoroalkyl (especially trifluoromethyl) [Notably $R^{3b}$ represents $(C_{1-4})$alkyl (especially ethyl); or halogen (especially chloro)].

18) A further embodiment relates to compounds according to any one of embodiments 7) to 17), wherein $Z^1$ and $Z^2$ both represent CH; or $Z^1$ and $Z^2$ both represent N; or $Z^1$ represents N and $Z^2$ represents CH.

19) A further embodiment relates to compounds according to any one of embodiments 7) to 17), wherein $Z^1$ and $Z^2$ both represent CH.

20) A further embodiment relates to compounds according to any one of embodiments 7) to 17), wherein $Z^1$ and $Z^2$ both represent N; or $Z^1$ represents N and $Z^2$ represents CH.

21) A further embodiment relates to compounds according to any one of embodiments 7) to 17), wherein $Z^1$ represents N and $Z^2$ represents CH.

22) A further embodiment relates to compounds according to any one of embodiments 7) to 17), wherein $Z^1$ and $Z^2$ both represent N.

23) A further embodiment relates to compounds according to any one of embodiments 17) to 22), wherein $R^{38}$ represents:
—$NR^{41}$—$SO_2$—$R^{51}$, wherein $R^{41}$ represents hydrogen or $(C_{1-3})$alkyl (especially hydrogen or methyl); and $R^{51}$ represents $(C_{1-4})$alkyl (especially methyl), or $(C_{3-6})$cycloalkyl (especially cyclopropyl); or
—$NR^{42}$—$SO_2$—$NR^{Y2}$—$R^{52}$, wherein $R^{42}$ represents hydrogen; $R^{Y2}$ represents $(C_{1-3})$alkyl; and $R^{52}$ represents $(C_{1-4})$alkyl (especially $R^{Y2}$ represents methyl and $R^{52}$ represents $(C_{1-4})$alkyl); or
—$NR^{43}$—$SO_2$—$R^{53}$, wherein $R^{43}$ and $R^{53}$ together with the nitrogen and the —$SO_2$-group to which they are attached to form a 5-, 6-, or 7-membered ring (especially such ring is 1,1-dioxidoisothiazolidin-2-yl);
—$NR^{44}$—$SO_2$—$NR^{Y4}$—$R^{54}$, wherein $R^{44}$ and $R^{54}$ together with the nitrogen and the —$SO_2$—$NR^{Y4}$-group to which they are attached to form a 5-, 6-, or 7-membered ring, and $R^{Y4}$ represents $(C_{1-3})$alkyl (especially such ring is 5-methyl-1,1-dioxido-1,2,5-thiadiazolidin-2-yl);
—CO—$NR^6R^7$, wherein $R^6$ and $R^7$ independently represent hydrogen, $(C_{1-4})$alkyl, or $(C_{3-6})$cycloalkyl [especially one of $R^6$ and $R^7$ represents hydrogen or methyl, and the other of $R^6$ and $R^7$ represents $(C_{1-4})$alkyl (especially methyl), or $(C_{3-6})$cycloalkyl (especially cyclopropyl)];
—$(CH_2)_m$—$NR^9R^{10}$; wherein m represents the integer 0 or 1 (especially m represents 0); and $R^9$ and $R^{10}$ together with the nitrogen to which they are attached to form a 4-to 7-membered ring (especially a 4- or 6-membered ring) optionally containing an oxygen ring atom or a group —$NR^{11}$— wherein $R^{11}$ represents $(C_{1-4})$alkyl, and wherein said ring is optionally substituted with one or two fluorine substituents (notably such ring is morpholin-4-yl, 3,3-difluoro-azetidin-1-yl, or 1-methyl-piperazin-4-yl);
hydrogen;
halogen;
$(C_{1-4})$alkyl;
$(C_{3-6})$cycloalkyl;
$(C_{1-3})$fluoroalkyl;
5-membered heteroaryl (notably oxazolyl, especially oxazol-2-yl);
cyano; and R$^{3b}$ represents (C$_{1-4}$)alkyl (especially ethyl); halogen (especially chloro); (C$_{3-6}$)cycloalkyl (especially cyclopropyl); or (C$_{1-3}$)fluoroalkyl (especially trifluoromethyl) [Notably R$^{3b}$ represents (C$_{1-4}$)alkyl (especially ethyl), or halogen (especially chloro)].

24) A further embodiment relates to compounds according to any one of embodiments 17) to 22), wherein R$^{39}$ represents:
- —NR$^{41}$—SO$_2$—R$^{51}$, wherein R$^{41}$ represents hydrogen or (C$_{1-3}$)alkyl (especially hydrogen or methyl); and R$^{51}$ represents (C$_{1-4}$)alkyl, or (C$_{3-6}$)cycloalkyl (especially methyl or cyclopropyl); or
- —NR$^{42}$—SO$_2$—NR$^{Y2}$—R$^{52}$, wherein R$^{42}$ represents hydrogen; R$^{Y2}$ represents (C$_{1-3}$)alkyl; and R$^{52}$ represents (C$_{1-4}$)alkyl (especially R$^{Y2}$ represents methyl and R$^{52}$ represents (C$_{1-4}$)alkyl); or
- —NR$^{43}$—SO$_2$—R$^{53}$, wherein R$^{43}$ and R$^{53}$ together with the nitrogen and the —SO$_2$-group to which they are attached to form a 5-, 6-, or 7-membered ring (especially such ring is 1,1-dioxidoisothiazolidin-2-yl);
- —NR$^{44}$—SO$_2$—NR$^{Y4}$—R$^{54}$, wherein R$^{44}$ and R$^{54}$ together with the nitrogen and the —SO$_2$—NR$^{Y4}$-group to which they are attached to form a 5-, 6-, or 7-membered ring, and R$^{Y4}$ represents (C$_{1-3}$)alkyl (especially such ring is 5-methyl-1,1-dioxido-1,2,5-thiadiazolidin-2-yl);
- —CO—NR$^6$R$^7$, wherein R$^6$ and R$^7$ independently represent hydrogen, (C$_{1-4}$)alkyl, or (C$_{3-6}$)cycloalkyl [especially one of R$^6$ and R$^7$ represents hydrogen or methyl, and the other of R$^6$ and R$^7$ represents (C$_{1-4}$)alkyl (especially methyl), or (C$_{3-6}$)cycloalkyl (especially cyclopropyl)];
- —(CH$_2$)$_m$—NR$^9$R$^{10}$; wherein m represents the integer 0 or 1 (especially m represents 0); and R$^9$ and R$^{10}$ together with the nitrogen to which they are attached to form a 4, 5-, 6-, or 7-membered ring (especially a 4- or 6-membered ring) optionally containing an oxygen ring atom or a group —NR$^{11}$— wherein R$^{11}$ represents (C$_{1-4}$)alkyl, and wherein said ring is optionally substituted with one or two fluorine substituents (notably such ring is morpholin-4-yl, 3,3-difluoro-azetidin-1-yl, or 1-methyl-piperazin-4-yl);
- (C$_{3-6}$)cycloalkyl;
- 5-membered heteroaryl (notably oxazolyl, especially oxazol-2-yl); and R$^{3b}$ represents (C$_{1-4}$)alkyl (especially ethyl), or halogen (especially chloro).

25) A further embodiment relates to compounds according to any one of embodiments 17) to 22), wherein R$^{3a}$ represents:
- —NR$^{41}$—SO$_2$—R$^{51}$, wherein R$^{41}$ represents hydrogen; and R$^{51}$ represents (C$_{1-4}$)alkyl (especially methyl), or (C$_{3-6}$)cycloalkyl (especially cyclopropyl); or
- —NR$^{43}$—SO$_2$—R$^{53}$, wherein R$^{43}$ and R$^{53}$ together with the nitrogen and the —SO$_2$-group to which they are attached to form a 5-membered ring (especially such ring is 1,1-dioxidoisothiazolidin-2-yl);
- —CO—NR$^6$R$^7$, wherein R$^6$ and R$^7$ independently represent hydrogen, (C$_{1-4}$)alkyl, or (C$_{3-6}$)cycloalkyl (especially one of R$^6$ and R$^7$ represents hydrogen, and the other of R$^6$ and R$^7$ represents methyl or cyclopropyl); and R$^{3b}$ represents (C$_{1-4}$)alkyl (especially ethyl), or halogen (especially chloro).

26) A further embodiment relates to compounds according to any one of embodiments 1) to 13), wherein
R$^3$ represents 2-chloro-4-(dimethylcarbamoyl)-phenyl; or
R$^3$ represents 2-chloro-6-(methyl-carbamoyl)-pyridin-3-yl, 2-chloro-6-(dimethyl-carbamoyl)-pyridin-3-yl, 2-chloro-6-(ethyl-(methyl)-carbamoyl)-pyridin-3-yl, 2-chloro-6-(cyclopropyl-carbamoyl)-pyridin-3-yl, 2-chloro-6-(cyclopropyl-(methyl)-carbamoyl)-pyridin-3-yl, 6-(cyclopropyl-carbamoyl)-2-ethyl-pyridin-3-yl, 2-chloro-6-(isopropyl-(methyl)-carbamoyl)-pyridin-3-yl, 2-chloro-6-(methylsulfonamido)-pyridin-3-yl, 2-chloro-6-(N-methyl-methylsulfonamido)-pyridin-3-yl, 2-ethyl-6-(methylsulfonamido)-pyridin-3-yl, 2-methoxy-6-(methylsulfonamido)-pyridin-3-yl, 2-chloro-6-(1,1-dioxo-isothiazolidin-2-yl)-pyridin-3-yl, 6-(1,1-dioxo-isothiazolidin-2-yl)-2-ethyl-pyridin-3-yl, 2-chloro-6-(5-methyl-1,1-dioxo-[1,2,5]thiadiazolidin-2-yl)-pyridin-3-yl, 4-ethyl-2-(methylsulfonamido)-pyrimidin-5-yl, or 2-ethyl-6-((N,N-dimethylsulfamoyl)amino)-pyridin-3-yl.

27) The invention, thus, relates to compounds of the formula (I) as defined in embodiment 1), or to such compounds further limited by the characteristics of any one of embodiments 2) to 26), under consideration of their respective dependencies; to pharmaceutically acceptable salts thereof; and to the use of such compounds as medicaments especially in the treatment of diseases or disorders characterized by an altered rate of the tryptophan-serotonin metabolism. Especially the following embodiments relating to the compounds of formula (I) are thus possible and intended and herewith specifically disclosed in individualized form:

1, 2+1, 3+1, 3+2+1, 5+1, 5+2+1, 5+3+1, 5+3+2+1, 6+1, 6+2+1, 6+3+1, 6+3+2+1, 8+1, 8+2+1, 8+3+1, 8+3+2+1, 8+5+1, 8+5+2+1, 8+5+3+1, 8+5+3+2+1, 8+6+1, 8+6+2+1, 8+6+3+1, 8+6+3+2+1, 11+1, 11+2+1, 11+3+1, 11+3+2+1, 11+5+1, 11+5+2+1, 11+5+3+1, 11+5+3+2+1, 11+6+1, 11+6+2+1, 11+6+3+1, 11+6+3+2+1, 12+1, 12+2+1, 12+3+1, 12+3+2+1, 12+5+1, 12+5+2+1, 12+5+3+1, 12+5+3+2+1, 12+6+1, 12+6+2+1, 12+6+3+1, 12+6+3+2+1, 13+1, 13+2+1, 13+3+1, 13+3+2+1, 13+5+1, 13+5+2+1, 13+5+3+1, 13+5+3+2+1, 13+6+1, 13+6+2+1, 13+6+3+1, 13+6+3+2+1, 16+1, 16+2+1, 16+3+1, 16+3+2+1, 16+5+1, 16+5+2+1, 16+5+3+1, 16+5+3+2+1, 16+6+1, 16+6+2+1, 16+6+3+1, 16+6+3+2+1, 16+13+1, 16+13+2+1, 16+13+3+1, 16+13+3+2+1, 16+13+5+1, 16+13+5+2+1, 16+13+5+3+1, 16+13+5+3+2+1, 16+13+6+1, 16+13+6+2+1, 16+13+6+3+1, 16+13+6+3+2+1, 17+1, 17+2+1, 17+3+1, 17+3+2+1, 17+5+1, 17+5+2+1, 17+5+3+1, 17+5+3+2+1, 17+6+1, 17+6+2+1, 17+6+3+1, 17+6+3+2+1, 17+8+1, 17+8+2+1, 17+8+3+1, 17+8+3+2+1, 17+8+5+1, 17+8+5+2+1, 17+8+5+3+1, 17+8+5+3+2+1, 17+8+6+1, 17+8+6+2+1, 17+8+6+3+1, 17+8+6+3+2+1, 17+11+1, 17+11+2+1, 17+11+3+1, 17+11+3+2+1, 17+11+5+1, 17+11+5+2+1, 17+11+5+3+1, 17+11+5+3+2+1, 17+11+6+1, 17+11+6+2+1, 17+11+6+3+1, 17+11+6+3+2+1, 17+12+1, 17+12+2+1, 17+12+3+1, 17+12+3+2+1, 17+12+5+1, 17+12+5+2+1, 17+12+5+3+1, 17+12+5+3+2+1, 17+12+6+1, 17+12+6+2+1, 17+12+6+3+1, 17+12+6+3+2+1, 18+17+1, 18+17+2+1, 18+17+3+1, 18+17+3+2+1, 18+17+5+1, 18+17+5+2+1, 18+17+5+3+1, 18+17+5+3+2+1, 18+17+6+1, 18+17+6+2+1, 18+17+6+3+1, 18+17+6+3+2+1, 18+17+8+1, 18+17+8+2+1, 18+17+8+3+1, 18+17+8+3+2+1, 18+17+8+5+1, 18+17+8+5+2+1, 18+17+8+5+3+1, 18+17+8+5+3+2+1, 18+17+8+6+1, 18+17+8+6+2+1, 18+17+8+6+3+1, 18+17+8+6+3+2+1, 18+17+11+1, 18+17+11+2+1, 18+17+11+3+1, 18+17+11+3+2+1, 18+17+11+5+1, 18+17+11+5+2+1, 18+17+11+5+3+1, 18+17+11+6+1, 18+17+11+6+2+1, 18+17+11+6+3+1, 18+17+11+6+3+2+1, 18+17+12+1, 18+17+12+2+1, 18+17+12+3+1, 18+17+12+3+2+1,

18+17+12+5+1, 18+17+12+5+2+1, 18+17+12+5+3+1, 18+17+12+5+3+2+1, 18+17+12+6+1, 18+17+12+6+2+1, 18+17+12+6+3+1, 18+17+12+6+3+2+1, 21+17+1, 21+17+2+1, 21+17+3+1, 21+17+3+2+1, 21+17+5+1, 21+17+5+2+1, 21+17+5+3+1, 21+17+5+3+2+1, 21+17+6+1, 21+17+6+2+1, 21+17+6+3+1, 21+17+6+3+2+1, 21+17+8+1, 21+17+8+2+1, 21+17+8+3+1, 21+17+8+3+2+1, 21+17+8+5+1, 21+17+8+5+2+1, 21+17+8+5+3+1, 21+17+8+5+3+2+1, 21+17+8+6+1, 21+17+8+6+2+1, 21+17+8+6+3+1, 21+17+8+6+3+2+1, 21+17+11+1, 21+17+11+2+1, 21+17+11+3+1, 21+17+11+3+2+1, 21+17+11+5+1, 21+17+11+5+2+1, 21+17+11+5+3+1, 21+17+11+5+3+2+1, 21+17+11+6+1, 21+17+11+6+2+1, 21+17+11+6+3+1, 21+17+11+6+3+2+1, 21+17+12+1, 21+17+12+2+1, 21+17+12+3+1, 21+17+12+3+2+1, 21+17+12+5+1, 21+17+12+5+2+1, 21+17+12+5+3+1, 21+17+12+5+3+2+1, 21+17+12+6+1, 21+17+12+6+2+1, 21+17+12+6+3+1, 21+17+12+6+3+2+1, 24+17+1, 24+17+2+1, 24+17+3+1, 24+17+3+2+1, 24+17+5+1, 24+17+5+2+1, 24+17+5+3+1, 24+17+5+3+2+1, 24+17+6+1, 24+17+6+2+1, 24+17+6+3+1, 24+17+6+3+2+1, 24+17+8+1, 24+17+8+2+1, 24+17+8+3+1, 24+17+8+3+2+1, 24+17+8+5+1, 24+17+8+5+2+1, 24+17+8+5+3+1, 24+17+8+5+3+2+1, 24+17+8+6+1, 24+17+8+6+2+1, 24+17+8+6+3+1, 24+17+8+6+3+2+1, 24+17+11+1, 24+17+11+2+1, 24+17+11+3+1, 24+17+11+3+2+1, 24+17+11+5+1, 24+17+11+5+2+1, 24+17+11+5+3+1, 24+17+11+5+3+2+1, 24+17+11+6+1, 24+17+11+6+2+1, 24+17+11+6+3+1, 24+17+11+6+3+2+1, 24+17+12+1, 24+17+12+2+1, 24+17+12+3+1, 24+17+12+3+2+1, 24+17+12+5+1, 24+17+12+5+2+1, 24+17+12+5+3+1, 24+17+12+5+3+2+1, 24+17+12+6+1, 24+17+12+6+2+1, 24+17+12+6+3+1, 24+17+12+6+3+2+1, 24+18+17+1, 24+18+17+2+1, 24+18+17+3+1, 24+18+17+3+2+1, 24+18+17+5+1, 24+18+17+5+2+1, 24+18+17+5+3+1, 24+18+17+5+3+2+1, 24+18+17+6+1, 24+18+17+6+2+1, 24+18+17+6+3+1, 24+18+17+6+3+2+1, 24+18+17+8+1, 24+18+17+8+2+1, 24+18+17+8+3+1, 24+18+17+8+3+2+1, 24+18+17+8+5+1, 24+18+17+8+5+2+1, 24+18+17+8+5+3+1, 24+18+17+8+5+3+2+1, 24+18+17+8+6+1, 24+18+17+8+6+2+1, 24+18+17+8+6+3+1, 24+18+17+8+6+3+2+1, 24+18+17+11+1, 24+18+17+11+2+1, 24+18+17+11+3+1, 24+18+17+11+3+2+1, 24+18+17+11+5+1, 24+18+17+11+5+2+1, 24+18+17+11+5+3+1, 24+18+17+11+5+3+2+1, 24+18+17+11+6+1, 24+18+17+11+6+2+1, 24+18+17+11+6+3+1, 24+18+17+11+6+3+2+1, 24+18+17+12+1, 24+18+17+12+2+1, 24+18+17+12+3+1, 24+18+17+12+3+2+1, 24+18+17+12+5+1, 24+18+17+12+5+2+1, 24+18+17+12+5+3+1, 24+18+17+12+5+3+2+1, 24+18+17+12+6+1, 24+18+17+12+6+2+1, 24+18+17+12+6+3+1, 24+18+17+12+6+3+2+1, 24+21+17+1, 24+21+17+2+1, 24+21+17+3+1, 24+21+17+3+2+1, 24+21+17+5+1, 24+21+17+5+2+1, 24+21+17+5+3+1, 24+21+17+5+3+2+1, 24+21+17+6+1, 24+21+17+6+2+1, 24+21+17+6+3+1, 24+21+17+6+3+2+1, 24+21+17+8+1, 24+21+17+8+2+1, 24+21+17+8+3+1, 24+21+17+8+3+2+1, 24+21+17+8+5+1, 24+21+17+8+5+2+1, 24+21+17+8+5+3+1, 24+21+17+8+5+3+2+1, 24+21+17+8+6+1, 24+21+17+8+6+2+1, 24+21+17+8+6+3+1, 24+21+17+8+6+3+2+1, 24+21+17+11+1, 24+21+17+11+2+1, 24+21+17+11+3+1, 24+21+17+11+3+2+1, 24+21+17+11+5+1, 24+21+17+11+5+2+1, 24+21+17+11+5+3+1, 24+21+17+11+5+3+2+1, 24+21+17+11+6+1, 24+21+17+11+6+2+1, 24+21+17+11+6+3+1, 24+21+17+11+6+3+2+1, 24+21+17+12+1, 24+21+17+12+2+1, 24+21+17+12+3+1, 24+21+17+12+3+2+1, 24+21+17+12+5+1, 24+21+17+12+5+2+1, 24+21+17+12+5+3+1, 24+21+17+12+5+3+2+1, 24+21+17+12+6+1, 24+21+17+12+6+2+1, 24+21+17+12+6+3+1, 24+21+17+12+6+3+2+1, 24+22, 25+17+1, 25+17+2+1, 25+17+3+1, 25+17+3+2+1, 25+17+5+1, 25+17+5+2+1, 25+17+5+3+1, 25+17+5+3+2+1, 25+17+6+1, 25+17+6+2+1, 25+17+6+3+1, 25+17+6+3+2+1, 25+17+8+1, 25+17+8+2+1, 25+17+8+3+1, 25+17+8+3+2+1, 25+17+8+5+1, 25+17+8+5+2+1, 25+17+8+5+3+1, 25+17+8+5+3+2+1, 25+17+8+6+1, 25+17+8+6+2+1, 25+17+8+6+3+1, 25+17+8+6+3+2+1, 25+17+11+1, 25+17+11+2+1, 25+17+11+3+1, 25+17+11+3+2+1, 25+17+11+5+1, 25+17+11+5+2+1, 25+17+11+5+3+1, 25+17+11+5+3+2+1, 25+17+11+6+1, 25+17+11+6+2+1, 25+17+11+6+3+1, 25+17+11+6+3+2+1, 25+17+12+1, 25+17+12+2+1, 25+17+12+3+1, 25+17+12+3+2+1, 25+17+12+5+1, 25+17+12+5+2+1, 25+17+12+5+3+1, 25+17+12+5+3+2+1, 25+17+12+6+1, 25+17+12+6+2+1, 25+17+12+6+3+1, 25+17+12+6+3+2+1, 25+18+17+1, 25+18+17+2+1, 25+18+17+3+1, 25+18+17+3+2+1, 25+18+17+5+1, 25+18+17+5+2+1, 25+18+17+5+3+1, 25+18+17+5+3+2+1, 25+18+17+6+1, 25+18+17+6+2+1, 25+18+17+6+3+1, 25+18+17+6+3+2+1, 25+18+17+8+1, 25+18+17+8+2+1, 25+18+17+8+3+1, 25+18+17+8+3+2+1, 25+18+17+8+5+1, 25+18+17+8+5+2+1, 25+18+17+8+5+3+1, 25+18+17+8+5+3+2+1, 25+18+17+8+6+1, 25+18+17+8+6+2+1, 25+18+17+8+6+3+1, 25+18+17+8+6+3+2+1, 25+18+17+11+1, 25+18+17+11+2+1, 25+18+17+11+3+1, 25+18+17+11+3+2+1, 25+18+17+11+5+1, 25+18+17+11+5+2+1, 25+18+17+11+5+3+1, 25+18+17+11+5+3+2+1, 25+18+17+11+6+1, 25+18+17+11+6+2+1, 25+18+17+11+6+3+1, 25+18+17+11+6+3+2+1, 25+18+17+12+1, 25+18+17+12+2+1, 25+18+17+12+3+1, 25+18+17+12+3+2+1, 25+18+17+12+5+1, 25+18+17+12+5+2+1, 25+18+17+12+5+3+1, 25+18+17+12+5+3+2+1, 25+18+17+12+6+1, 25+18+17+12+6+2+1, 25+18+17+12+6+3+1, 25+18+17+12+6+3+2+1, 25+21+17+1, 25+21+17+2+1, 25+21+17+3+1, 25+21+17+3+2+1, 25+21+17+5+1, 25+21+17+5+2+1, 25+21+17+5+3+1, 25+21+17+5+3+2+1, 25+21+17+6+1, 25+21+17+6+2+1, 25+21+17+6+3+1, 25+21+17+6+3+2+1, 25+21+17+8+1, 25+21+17+8+2+1, 25+21+17+8+3+1, 25+21+17+8+3+2+1, 25+21+17+8+5+1, 25+21+17+8+5+2+1, 25+21+17+8+5+3+1, 25+21+17+8+5+3+2+1, 25+21+17+8+6+1, 25+21+17+8+6+2+1, 25+21+17+8+6+3+1, 25+21+17+8+6+3+2+1, 25+21+17+11+1, 25+21+17+11+2+1, 25+21+17+11+3+1, 25+21+17+11+3+2+1, 25+21+17+11+5+1, 25+21+17+11+5+2+1, 25+21+17+11+5+3+1, 25+21+17+11+5+3+2+1, 25+21+17+11+6+1, 25+21+17+11+6+2+1, 25+21+17+11+6+3+1, 25+21+17+11+6+3+2+1, 25+21+17+12+1, 25+21+17+12+2+1, 25+21+17+12+3+1, 25+21+17+12+3+2+1, 25+21+17+12+5+1, 25+21+17+12+5+2+1, 25+21+17+12+5+3+1, 25+21+17+12+5+3+2+1, 25+21+17+12+6+1, 25+21+17+12+6+2+1, 25+21+17+12+6+3+1, 25+21+17+12+6+3+2+1, 25+22, 26+1, 26+2+1, 26+3+1, 26+3+2+1, 26+5+1, 26+5+2+1, 26+5+3+1, 26+5+3+2+1, 26+6+1, 26+6+2+1, 26+6+3+1, 26+6+3+2+1, 26+13+1, 26+13+2+1, 26+13+3+1, 26+13+3+2+1, 26+13+5+1, 26+13+5+2+1, 26+13+5+3+1, 26+13+5+3+2+1, 26+13+6+1, 26+13+6+2+1, 26+13+6+3+1, 26+13+6+3+2+1.

In the list above, the numbers refer to the embodiments according to their numbering provided hereinabove whereas "+" indicates the dependency from another embodiment. The different individualized embodiments are separated by commas. In other words, "26+13+1" for example refers to embodiment 26) depending on embodiment 13), depending on embodiment 1), i.e. embodiment "26+13+1" corresponds to the compounds of embodiment 1) further limited by the features of the embodiments 13) and 26).

28) In a third aspect, the invention relates to compounds of Formula (I) according to embodiment 1), which are also compounds of Formula (II):

Formula (II)

wherein
X represents —CH$_2$—, —CH$_2$—CH$_2$—, —S—, *—CH$_2$—O—, or *—CH$_2$—NR$^x$— wherein R$^x$ represents hydrogen, —CO—CH$_3$, —CH$_2$-cyclopropyl, cyclopropyl, or —CO—O-tert-butyl; wherein the asterisks indicate the bond attached to the imidazole ring;

Z$^2$ represents N or CH;

R$^2$ represents phenyl, wherein said phenyl is mono-, di-, or tri-substituted, wherein the substituents are independently selected from:
  (C$_{1-4}$)alkyl;
  (C$_{3-6}$)cycloalkyl;
  (C$_{1-3}$)fluoroalkyl;
  halogen;
  hydroxy-(C$_{1-4}$)alkyl;
  (C$_{1-3}$)alkoxy-(C$_{1-4}$)alkyl;
  hydroxy-(C$_{2-4}$)alkoxy;
  (C$_{1-3}$)alkoxy-(C$_{2-4}$)alkoxy;
  —CO—(C$_{1-4}$)alkoxy; or
  cyano;

or R$^2$ represents 5- or 6-membered heteroaryl (notably pyridinyl, thiazolyl, thiophenyl, oxadiazolyl), wherein said heteroaryl is mono-, or di-substituted, wherein the substituents are independently selected from:
  (C$_{1-4}$)alkyl;
  (C$_{3-6}$)cycloalkyl;
  (C$_{1-3}$)fluoroalkyl;
  halogen;
  —NR$^{21}$R$^{22}$; wherein R$^{21}$ and R$^{22}$ independently represent (C$_{1-4}$)alkyl;
  —CO—NR$^{23}$R$^{24}$, wherein R$^{23}$ and R$^{24}$ independently represent hydrogen or (C$_{1-4}$)alkyl;
  —NR$^{25}$—CO—NR$^{26}$R$^{26}$, wherein R$^{25}$, R$^{26}$ and R$^{27}$ independently represent hydrogen or (C$_{1-4}$)alkyl (especially one of R$^{26}$ and R$^{27}$ represents (C$_{1-4}$)alkyl, and the remaining of R$^{25}$, R$^{26}$ and R$^{27}$ represent hydrogen);
  —CO—(C$_{1-4}$)alkoxy; or
  phenyl;

R$^{3a}$ represents:
  —NR$^{41}$—SO$_2$—R$^{51}$, wherein R$^{41}$ represents hydrogen or (C$_{1-3}$)alkyl; and R$^{51}$ represents (C$_{1-4}$)alkyl, or (C$_{3-6}$)cycloalkyl (especially methyl or cyclopropyl); or
  —NR$^{42}$—SO$_2$—NR$^{Y2}$—R$^{52}$, wherein R$^{42}$ represents hydrogen; R$^{Y2}$ represents (C$_{1-3}$)alkyl; and R$^{52}$ represents (C$_{1-4}$)alkyl (especially R$^{Y2}$ represents methyl and R$^{52}$ represents (C$_{1-4}$)alkyl); or
  —NR$^{43}$—SO$_2$—R$^{53}$, wherein R$^{43}$ and R$^{53}$ together with the nitrogen and the —SO$_2$-group to which they are attached to form a 5-membered ring (especially such ring is 1,1-dioxidoisothiazolidin-2-yl);
  —NR$^{44}$—SO$_2$—NR$^{Y4}$—R$^{54}$, wherein R$^{44}$ and R$^{54}$ together with the nitrogen and the —SO$_2$—NR$^{Y4}$-group to which they are attached to form a 5-membered ring, and R$^{Y4}$ represents (C$_{1-3}$)alkyl (especially such ring is 5-methyl-1,1-dioxido-1,2,5-thiadiazolidin-2-yl);
  —CO—NR$^6$R$^7$, wherein R$^6$ and R$^7$ independently represent hydrogen, (C$_{1-4}$)alkyl, or (C$_{3-6}$)cycloalkyl [especially one of R$^6$ and R$^7$ represents hydrogen or methyl, and the other of R$^6$ and R$^7$ represents (C$_{1-4}$)alkyl (especially methyl), or (C$_{3-6}$)cycloalkyl (especially cyclopropyl)];
  —SO$_2$—R$^8$ wherein R$^8$ represents (C$_{1-5}$)alkyl, or —NR$^{81}$R$^{82}$, wherein R$^{81}$ and R$^{82}$ independently represent (C$_{1-4}$)alkyl;
  —NR$^9$R$^{10}$; wherein R$^9$ and R$^{10}$ together with the nitrogen to which they are attached to form a 4-, 5-, 6-, or 7-membered ring (especially a 4- or 6-membered ring) optionally containing an oxygen ring atom or a group —NR$^{11}$— wherein R$^{11}$ represents (C$_{1-4}$)alkyl, and wherein said ring is optionally substituted with one or two fluorine substituents (notably such ring is morpholin-4-yl, 3,3-difluoro-azetidin-1-yl, or 1-methyl-piperazin-4-yl);
  (C$_{3-6}$)cycloalkyl;
  5-membered heteroaryl (notably oxazolyl, especially oxazol-2-yl); and R$^{3b}$ represents (C$_{1-4}$)alkyl (especially ethyl); halogen (especially chloro); or (C$_{3-6}$)cycloalkyl (especially cyclopropyl); [Notably R$^{3b}$ represents (C$_{1-4}$)alkyl (especially methyl or ethyl); or halogen (especially fluoro or chloro)];

wherein the characteristics disclosed in embodiments 2), 5) to 7), 12), 13), 21), 22), 25), and 26) above are intended to apply mutatis mutandis also to the compounds formula (II) according to embodiment 28); wherein especially the following embodiments are thus possible and intended and herewith specifically disclosed in individualized form:

28, 2+28, 5+2+28, 5+28, 6+2+28, 6+28, 12+2+28, 12+5+2+28, 12+5+28, 12+6+2+28, 12+6+28, 12+28, 13+2+28, 13+5+2+28, 13+5+28, 13+6+2+28, 13+6+28, 13+28, 21+2+28, 21+5+2+28, 21+5+28, 21+6+2+28, 21+6+28, 21+28, 25+2+28, 25+5+2+28, 25+5+28, 25+6+2+28, 25+6+28, 25+21+2+28, 25+21+5+2+28, 25+21+5+28, 25+21+6+2+28, 25+21+6+28, 25+21+28, 25+28, 26+2+28, 26+5+2+28, 26+5+28, 26+6+2+28, 26+6+28, 26+21+2+28, 26+21+5+2+28, 26+21+5+28, 26+21+6+2+28, 26+21+6+28, 26+21+28, 26+28.

In the list above, the numbers refer to the embodiments according to their numbering provided hereinabove whereas "+" indicates the dependency from another embodiment. The different individualized embodiments are separated by commas. In other words, "13+5+28" for example refers to embodiment 28) depending on embodiment 13), depending on embodiment 5), i.e. embodiment "13+5+28" corresponds to the compounds of embodiment 1) which are also compounds of formula (II) according to embodiment 28), further limited by the features of the embodiments 5) and 13).

29) In a fourth aspect, the invention relates to compounds of Formula (I) according to embodiment 1), which are also compounds of Formula (III):

Formula (III)

wherein
X represents —CH$_2$—, —CH$_2$—CH$_2$—, —S—, *—CH$_2$—O—, or *—CH$_2$—NR$^x$— wherein R$^x$ represents hydrogen, —CO—CH$_3$, —CH$_2$-cyclopropyl, cyclopropyl, or —CO—O-tert-butyl; wherein the asterisks indicate the bond attached to the imidazole ring;

$Z^2$ represents N or CH;

$R^2$ represents phenyl, wherein said phenyl is mono-, di-, or tri-substituted, wherein the substituents are independently selected from:
  methyl;
  cyclopropyl;
  trifluoromethyl;
  halogen;
  methoxy;
  trifluoromethoxy;
  cyano;
  methoxymethyl;
  methoxycarbonyl;
  2-hydroxy-ethoxy;
  2-hydroxypropan-2-yl;
  2-methoxy-ethoxy; or
  2-methoxypropan-2-yl;
  or $R^2$ represents 5- or 6-membered heteroaryl (notably pyridinyl, thiazolyl, thiophenyl, oxadiazolyl), wherein said heteroaryl is mono-, or di-substituted, wherein the substituents are independently selected from:
  $(C_{1-3})$alkyl;
  cyclopropyl;
  trifluoromethyl;
  halogen;
  dimethylamino;
  —CO—$NR^{23}R^{24}$, wherein $R^{23}$ and $R^{24}$ independently represent hydrogen, methyl, or cyclopropyl;
  —$NR^{25}$—CO—$NR^{26}R^{26}$, wherein one of $R^{26}$ and $R^{27}$ represents methyl, and the remaining of $R^{25}$, $R^{26}$ and $R^{27}$ represent hydrogen; or
  phenyl;

$R^{3a}$ represents:
  —$NR^{41}$—$SO_2$—$R^{51}$, wherein $R^{41}$ represents hydrogen or methyl; and $R^{51}$ represents methyl or cyclopropyl; or
  —$NR^{42}$—$SO_2$—$NR^{Y2}$—$R^{52}$, wherein $R^{42}$ represents hydrogen; $R^{Y2}$ represents $(C_{1-3})$alkyl; and $R^{52}$ represents $(C_{1-3})$alkyl (especially $R^{Y2}$ represents methyl, and $R^{52}$ represents methyl); or
  —$NR^{43}$—$SO_2$—$R^{53}$, wherein $R^{43}$ and $R^{53}$ together with the nitrogen and the —$SO_2$-group to which they are attached to form a 5-, 6-, or 7-membered ring (especially such ring is 1,1-dioxidoisothiazolidin-2-yl);
  —$NR^{44}$—$SO_2$—$NR^{Y4}$—$R^{54}$, wherein $R^{44}$ and $R^{54}$ together with the nitrogen and the —$SO_2$—$NR^{Y4}$-group to which they are attached to form a 5-, 6-, or 7-membered ring, and $R^{Y4}$ represents $(C_{1-3})$alkyl (especially such ring is 5-methyl-1,1-dioxido-1,2,5-thiadiazolidin-2-yl);
  —CO—$NR^6R^7$, wherein $R^6$ and $R^7$ independently represent hydrogen, $(C_{1-4})$alkyl, or $(C_{3-6})$cycloalkyl (especially one of $R^6$ and $R^7$ represents hydrogen or methyl, and the other of $R^6$ and $R^7$ represents methyl or cyclopropyl);
  —$SO_2$—$R^8$ wherein $R^8$ represents methyl or dimethylamino;
  —$NR^9R^{10}$; wherein $R^9$ and $R^{10}$ together with the nitrogen to which they are attached to form a 4-, 5-, 6-, or 7-membered ring (especially a 4- or 6-membered ring) optionally containing an oxygen ring atom or a group —$NR^{11}$— wherein $R^{11}$ represents $(C_{1-3})$alkyl, and wherein said ring is optionally substituted with one or two fluorine substituents (notably such ring is morpholin-4-yl, 3,3-difluoro-azetidin-1-yl, or 1-methyl-piperazin-4-yl);
  cyclopropyl;
  5-membered heteroaryl (notably oxazolyl, especially oxazol-2-yl); and $R^{3b}$ represents $(C_{1-3})$alkyl (especially ethyl); halogen (especially chloro); or cyclopropyl; [Notably $R^{3b}$ represents $(C_{1-4})$alkyl (especially ethyl); or halogen (especially chloro)] wherein the characteristics disclosed in embodiments 2), 5) to 7), 13), 21), and 26) above are intended to apply mutatis mutandis also to the compounds formula (III) according to embodiment 29); wherein especially the following embodiments are thus possible and intended and herewith specifically disclosed in individualized form:

29, 2+29, 5+2+29, 5+29, 6+2+29, 6+29, 13+2+29, 13+5+2+29, 13+5+29, 13+6+2+29, 13+6+29, 13+29, 21+2+29, 21+5+2+29, 21+5+29, 21+6+2+29, 21+6+29, 21+29, 26+2+29, 26+5+2+29, 26+5+29, 26+6+2+29, 26+6+29, 26+21+2+29, 26+21+5+2+29, 26+21+5+29, 26+21+6+2+29, 26+21+6+29, 26+21+29, 26+29.

In the list above, the numbers refer to the embodiments according to their numbering provided hereinabove whereas "+" indicates the dependency from another embodiment. The different individualized embodiments are separated by commas. In other words, "13+5+29" for example refers to embodiment 29) depending on embodiment 13), depending on embodiment 5), i.e. embodiment "13+5+29" corresponds to the compounds of embodiment 1) which are also compounds of formula (III) according to embodiment 29), further limited by the features of the embodiments 5) and 13).

30) Examples of compounds of Formula (I) according to embodiment 1) are selected from the group consisting of:
6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N,N-dimethylpicolinamide;
1-(1-(4-chloro-2-fluorophenyl)-3,4,6,7,8,9-hexahydro-imidazo[1,2-a:5,4-c']dipyridin-2(1H)-yl)-2-((2-chloro-6-(1,1-dioxidoisothiazolidin-2-yl)pyridin-3-yl)oxy)-ethanone;
N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-ethylpyridin-2-yl)methanesulfonamide;
5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropyl-6-ethylpicolinamide;
N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-methoxypyridin-2-yl)methanesulfonamide;
1-(1-(4-chloro-2-fluorophenyl)-3,4,6,7,8,9-hexahydroimidazo[1,2-a:5,4-c']dipyridin-2(1H)-yl)-2-((2-chloro-6-cyclopropylpyridin-3-yl)oxy)ethanone;
1-(1-(4-chloro-2-fluorophenyl)-3,4,6,7,8,9-hexahydroimidazo[1,2-a:5,4-c']dipyridin-2(1H)-yl)-2-((2-ethyl-6-methylpyridin-3-yl)oxy)ethanone;
(S)-6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropyl picolinamide;
(S)-N-(6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide;
(S)-N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-ethylpyridin-2-yl)methanesulfonamide;
1-(1-(4-chloro-2-fluorophenyl)-3,4,6,7,8,9-hexahydro-imidazo[1,2-a:5,4-c']dipyridin-2(1H)-yl)-2-((2-chloro-6-morpholinopyridin-3-yl)oxy)ethanone;
N-(6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide;

6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropyl-N-methyl picolinamide;
1-(1-(4-chloro-2-fluorophenyl)-3,4,6,7,8,9-hexahydro-imidazo[1,2-a:5,4-c']dipyridin-2(1H)-yl)-2-((2-chloro-6-(oxazol-2-yl)pyridin-3-yl)oxy)ethanone;
6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropyl picolinamide;
6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-ethyl-N-methylpicolinamide;
6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-isopropyl-N-methylpicolinamide;
N-(6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)pyridin-2-yl)-N-methylmethanesulfonamide;
N-(6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide;
3-chloro-4-(2-(1-(2,4-dimethylthiazol-5-yl)-3,4,6,7,8,9-hexahydroimidazo[1,2-a:5,4-c']dipyridin-2(1H)-yl)-2-oxoethoxy)benzonitrile;
2-(2-chloro-4-(trifluoromethyl)phenoxy)-1-(1-(2,4-dimethylthiazol-5-yl)-3,4,6,7,8,9-hexahydroimi-dazo[1,2-a:5,4-c']dipyridin-2(1H)-yl)ethanone;
N-(6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)pyridin-2-yl)-N-methylmethanesulfonamide;
N-(5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpyridin-2-yl)methanesulfonamide;
2-((2-chloro-6-(1,1-dioxidoisothiazolidin-2-yl)pyridin-3-yl)oxy)-1-(1-(2,4-dimethylthiazol-5-yl)-3,4,6,7,8,9-hexahydroimidazo[1,2-a:5,4-c']dipyridin-2(1H)-yl)ethanone;
N-cyclopropyl-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpicolinamide;
(R)—N-(5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpyridin-2-yl)methanesulfonamide;
(R)—N-cyclopropyl-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpicolinamide;
N-(5-(2-(1-(2,4-dimethylthiazol-5-yl)-3,4,6,7,8,9-hexahydroimidazo[1,2-a:5,4-c']dipyridin-2(1H)-yl)-2-oxoethoxy)-4-ethylpyrimidin-2-yl)methanesulfonamide;
6-chloro-N-cyclopropyl-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-N-methylpicolinamide;
2-((2-chloro-6-(oxazol-2-yl)pyridin-3-yl)oxy)-1-(1-(2,4-dimethylthiazol-5-yl)-3,4,6,7,8,9-hexahydroimi-dazo[1,2-a:5,4-c']dipyridin-2(1H)-yl)ethanone;
6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-N-methylpicolinamide;
6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-N,N-dimethylpicolinamide;
6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)picolinonitrile;
2-((2-chloro-6-(trifluoromethyl)pyridin-3-yl)oxy)-1-(1-(2,4-dimethylthiazol-5-yl)-3,4,6,7,8,9-hexahydroimi-dazo[1,2-a:5,4-c']dipyridin-2(1H)yl)ethanone;
2-((2-chloro-6-cyclopropylpyridin-3-yl)oxy)-1-(1-(2,4-dimethylthiazol-5-yl)-3,4,6,7,8,9-hexahydroimi-dazo[1,2-a:5,4-c']dipyridin-2(1H)-yl)ethanone;
2-((2-chloro-6-(4-methylpiperazin-1-yl)pyridin-3-yl)oxy)-1-(1-(2,4-dimethylthiazol-5-yl)-3,4,6,7,8,9-hexahydroimidazo[1,2-a:5,4-c']dipyridin-2(1H)-yl)ethanone;
N-(6-chloro-5-(2-(1-(2-ethyl-4-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide;
N-(6-chloro-5-(2-(1-(2-isopropyl-4-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide;
N-(6-ethyl-5-(2-(1-(4-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide207;
2-((6-(1,1-dioxidoisothiazoli132din-2-yl)-2-ethylpyridin-3-yl)oxy)-1-(1-(4-methylthiazol-5-yl)-3,4,6,7,8,9-hexahydroimidazo[1,2-a:5,4-c']dipyridin-2(1H)-yl)ethanone;
N-(6-ethyl-5-(2-(1-(3-fluorothiophen-2-yl)-3,4,6,7,8,9-hexahydroimidazo[1,2-a:5,4-c']dipyridin-2(1H)-yl)-2-oxoethoxy)pyridin-2-yl)methanesulfonamide;
N-cyclopropyl-6-ethyl-5-(2-(1-(3-fluorothiophen-2-yl)-3,4,6,7,8,9-hexahydroimidazo[1,2-a:5,4-c']dipyridin-2(1H)-yl)-2-oxoethoxy)picolinamide;
N-(6-ethyl-5-(2-(1-(2-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide;
2-((6-(1,1-dioxidoisothiazolidin-2-yl)-2-ethylpyridin-3-yl)oxy)-1-(1-(2-methylthiazol-5-yl)-3,4,6,7,8,9-hexahydroimidazo[1,2-a:5,4-c']dipyridin-2(1H)-yl)ethanone;
N-(6-ethyl-5-(2-oxo-2-(1-(2-phenylthiazol-5-yl)-3,4,6,7,8,9-hexahydroimidazo[1,2-a:5,4-c']dipyridin-2(1H)-yl)ethoxy)pyridin-2-yl)methanesulfonamide;
N-(6-ethyl-5-(2-oxo-2-(1-(3-phenyl-1,2, 4-oxadiazol-5-yl)-3,4,6,7,8,9-hexahydroimidazo[1,2-a:5,4-c']dipyridin-2(1H)-yl)ethoxy)pyridin-2-yl)methanesulfonamide;
N-(6-chloro-5-(2-(1-(4-methyl-2-(trifluoromethyl)thiazol-5-yl)-3,4,6,7,8,9-hexahydroimidazo[1,2-a:5, 4-c']dipyridin-2(1H)-yl)-2-oxoethoxy)pyridin-2-yl)methanesulfonamide;
N-(6-chloro-5-(2-(1-(5-fluoro-3-methylpyridin-2-yl)-3, 4,6,7,8,9-hexahydroimidazo[1,2-a:5,4-c']dipyridin-2(1H)-yl)-2-oxoethoxy)pyridin-2-yl)methanesulfonamide;
N-(6-chloro-5-(2-(1-(2-fluoro-4-methylphenyl)-3,4,6,7,8,9-hexahydroimidazo[1,2-a:5,4-c']dipyridin-2(1H)-yl)-2-oxoethoxy)pyridin-2-yl)methanesulfonamide;
2-((2-chloro-6-(oxazol-2-yl)pyridin-3-yl)oxy)-1-(1-(2-fluoro-4-methylphenyl)-3, 4,6,7,8,9-hexahydroimi-dazo[1,2-a:5,4-c']dipyridin-2(1H)-yl)ethanone;
6-chloro-N-cyclopropyl-5-(2-(1-(2-fluoro-4-methyl-phenyl)-3,4,6,7,8,9-hexahydroimidazo[1,2-a:5,4-c']dipyridin-2(1H)-yl)-2-oxoethoxy)-N-methylpicolinamide;
N-(6-chloro-5-(2-(1-(5-cyclopropyl-3-fluoropyridin-2-yl)-3,4,6,7,8,9-hexahydroimidazo[1,2-a:5,4-c']dipyridin-2(1H)-yl)-2-oxoethoxy)pyridin-2-yl)methanesulfonamide;
N-cyclopropyl-5-(2-(1-(5-cyclopropyl-3-fluoropyridin-2-yl)-3, 4,6,7,8,9-hexahydroimidazo[1,2-a:5,4-c']dipyridin-2(1H)-yl)-2-oxoethoxy)-6-ethylpicolinamide;
(R)—N-cyclopropyl-5-(2-(1-(5-cyclopropyl-3-fluoropyridin-2-yl)-3, 4,6,7,8,9-hexahydroimidazo[1,2-a:5, 4-c']dipyridin-2(1H)-yl)-2-oxoethoxy)-6-ethylpicolinamide;
6-chloro-5-(2-(1-(5-(dimethylcarbamoyl)-3-fluoro-thiophen-2-yl)-3,4,6,7,8,9-hexahydroimidazo[1,2-a:5,4-c']dipyridin-2(1H)-yl)-2-oxoethoxy)-N,N-dimethyl-picolinamide;

5-(2-(2-((2-ethyl-6-(methylsulfonamido)pyridin-3-yl)oxy) acetyl)-1,2,3,4,6,7,8,9-octahydroimidazo[1,2-a:5,4-c'] dipyridin-1H)-4-fluoro-N,N-dimethylthiophene-2-carboxamide;

Ethyl 2-(2-(2-((2-chloro-6-(methylsulfonamido)pyridin-3-yl)oxy)acetyl)-1,2,3,4,6,7,8,9-octahydroimidazo[1, 2-a:5, 4-c']dipyridin-1-yl)thiazole-4-carboxylate;

N-(6-chloro-5-(2-(1-(3-fluoro-5-methylpyridin-2-yl)-3,4,6, 7,8,9-hexahydroimidazo[1,2-a:5,4-c']dipyridin-2(1H)-yl)-2-oxoethoxy)pyridin-2-yl)methanesulfonamide;

2-((2-chloro-6-(oxazol-2-yl)pyridin-3-yl)oxy)-1-(1-(3-fluoro-5-methylpyridin-2-yl)-3,4,6,7,8,9-hexahydroimidazo[1,2-a:5,4-c']dipyridin-2(1H)-yl)ethanone;

6-chloro-N-cyclopropyl-5-(2-(1-(3-fluoro-5-methyl-pyridin-2-yl)-3,4,6,7,8,9-hexahydroimidazo[1,2-a:5,4-c'] dipyridin-2(1H)-yl)-2-oxoethoxy)-N-methyl-picolinamide;

6-chloro-5-(2-(1-(3-fluoro-5-methylpyridin-2-yl)-3,4,6,7,8, 9-hexahydroimidazo[1,2-a:5,4-c']dipyridin-2(1H)-yl)-2-oxoethoxy)-N,N-dimethylpicolinamide;

2-((2-chloro-6-(1,1-dioxidoisothiazolidin-2-yl)pyridin-3-yl) oxy)-1-(1-(3-fluoro-5-methylpyridin-2-yl)-3,4,6,7,8,9-hexahydroimidazo[1,2-a:5,4-c']dipyridin-2(1H)-yl)ethanone;

N-(6-chloro-5-(2-(1-(3-fluoro-5-methylpyridin-2-yl)-3,4,6, 7,8,9-hexahydroimidazo[1,2-a:5,4-c']dipyridin-2(1H)-yl)-2-oxoethoxy)pyridin-2-yl)-N-methylmethanesulfonamide;

N-cyclopropyl-6-ethyl-5-(2-(1-(3-fluoro-5-methylpyridin-2-yl)-3,4,6,7,8,9-hexahydroimidazo[1,2-a:5,4-c']dipyridin-2(1H)-yl)-2-oxoethoxy)picolinamide;

2-(2-(2-((2-chloro-6-(methylsulfonamido)pyridin-3-yl)oxy) acetyl)-1,2,3,4,6,7,8,9-octahydroimidazo[1,2-a:5,4-c'] dipyridin-1-yl)-N-methylthiazole-4-carboxamide;

6-chloro-N-cyclopropyl-5-(2-(1-(4-cyclopropyl-2-fluorophenyl)-3,4,6,7,8,9-hexahydroimidazo[1,2-a:5,4-c'] dipyridin-2(1H)-yl)-2-oxoethoxy)-N-methylpicolinamide;

2-((2-chloro-6-(oxazol-2-yl)pyridin-3-yl)oxy)-1-(1-(4-cyclopropyl-2-fluorophenyl)-3,4,6,7,8,9-hexahydroimidazo[1,2-a:5,4-c']dipyridin-2(1H)-yl)ethanone;

N-(6-chloro-5-(2-(1-(4-cyclopropyl-2-fluorophenyl)-3,4,6, 7,8,9-hexahydroimidazo[1,2-a:5,4-c']dipyridin-2(1H)-yl)-2-oxoethoxy)pyridin-2-yl)methanesulfonamide;

6-chloro-5-(2-(1-(4-cyclopropyl-2-fluorophenyl)-3,4,6,7,8, 9-hexahydroimidazo[1,2-a:5,4-c']dipyridin-2(1H)-yl)-2-oxoethoxy)-N,N-dimethylpicolinamide;

6-chloro-N-cyclopropyl-5-(2-(1-(4-cyclopropyl-2-fluorophenyl)-3,4,6,7,8,9-hexahydroimidazo[1,2-a:5,4-c'] dipyridin-2(1H)-yl)-2-oxoethoxy)picolinamide;

(S)-6-chloro-N-cyclopropyl-5-(2-(1-(4-cyclopropyl-2-fluorophenyl)-3,4,6,7,8,9-hexahydroimidazo[1,2-a:5,4-c'] dipyridin-2(1H)-yl)-2-oxoethoxy)picolinamide;

N-(5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)-4-ethylpyrimidin-2-yl)methanesulfonamide;

2-((2-chloro-6-(oxazol-2-yl)pyridin-3-yl)oxy)-1-(1-(2,3-difluoro-4-methylphenyl)-3,4,6,7,8,9-hexahydroimida-zo [1,2-a:5,4-c']dipyridin-2(1H)-yl)ethanone;

N-cyclopropyl-5-(2-(1-(2,3-difluoro-4-methylphenyl)-3,4, 6,7,8,9-hexahydroimidazo[1,2-a:5,4-c']dipyridin-2(1H)-yl)-2-oxoethoxy)-6-ethylpicolinamide;

N-(6-chloro-5-(2-(1-(2,3-difluoro-4-methylphenyl)-3,4,6,7, 8,9-hexahydroimidazo[1,2-a:5,4-c']dipyridin-2(1H)-yl)-2-oxoethoxy)pyridin-2-yl)methanesulfonamide;

6-chloro-N-cyclopropyl-5-(2-(1-(2,3-difluoro-4-methylphenyl)-3,4,6,7,8,9-hexahydroimidazo[1,2-a:5,4-c'] dipyridin-2(1H)-yl)-2-oxoethoxy)-N-methylpicolinamide;

2-((2-chloro-6-(4-methylpiperazin-1-yl)pyridin-3-yl)oxy)-1-(1-(2,3-difluoro-4-methylphenyl)-3,4,6,7,8,9-hexahydroimidazo[1,2-a:5,4-c']dipyridin-2(1H)-yl)ethanone;

2-(2-chloro-4-(trifluoromethyl)phenoxy)-1-(1-(2,3-difluoro-4-methylphenyl)-3,4,6,7,8,9-hexahydroimidazo[1, 2-a:5,4-c']dipyridin-2(1H)-yl)ethanone;

2-((2-chloro-6-(1,1-dioxidoisothiazolidin-2-yl)pyridin-3-yl) oxy)-1-(1-(2,3-difluoro-4-methylphenyl)-3,4,6,7,8,9-hexahydroimidazo[1,2-a:5,4-c']dipyridin-2(1H)-yl)ethanone;

N-(5-(2-(1-(2,3-difluoro-4-methylphenyl)-3,4,6,7,8,9-hexahydroimidazo[1,2-a:5,4-c']dipyridin-2(1H)-yl)-2-oxoethoxy)-6-ethylpyridin-2-yl)methanesulfonamide;

6-chloro-N-cyclopropyl-5-(2-(1-(2,3-difluoro-4-methylphenyl)-3,4,6,7,8,9-hexahydroimidazo[1,2-a:5,4-c']dipyridin-2(1H)-yl)-2-oxoethoxy)picolinamide;

N-(5-(2-(1-(2,3-difluoro-4-methylphenyl)-3,4,6,7,8,9-hexahydroimidazo[1,2-a:5,4-c']dipyridin-2(1H)-yl)-2-oxoethoxy)-4-ethylpyrimidin-2-yl)methanesulfonamide;

N-(6-chloro-5-(2-(1-(4-chloro-2-fluorophenyl)-3,4,7,8-tetrahydro-1H-pyrrolo[2',1':2,3]imidazo[4,5-c]pyridin-2 (6H)-yl)-2-oxoethoxy)pyridin-2-yl)methanesulfonamide;

N-(5-(2-(1-(4-chloro-2-fluorophenyl)-3,4,7,8-tetrahydro-1H-pyrrolo[2',1':2,3]imidazo[4,5-c]pyridin-2(6H)-yl)-2-oxoethoxy)-6-ethylpyridin-2-yl)methanesulfonamide;

1-(1-(4-chloro-2-fluorophenyl)-3,4,7,8-tetrahydro-1H-pyrrolo[2',1':2,3]imidazo[4,5-c]pyridin-2(6H)-yl)-2-((6-(1, 1-dioxidoisothiazolidin-2-yl)-2-ethylpyridin-3-yl)oxy) ethanone;

N-(6-chloro-5-(2-(1-(2-fluoro-4-methylphenyl)-3,4,7,8-tetrahydro-1H-pyrrolo[2',1':2,3]imidazo[4,5-c]pyridin-2 (6H)-yl)-2-oxoethoxy)pyridin-2-yl)methanesulfonamide;

N-(5-(2-(1-(2,3-difluoro-4-methylphenyl)-3,4,7,8-tetrahydro-1H-pyrrolo[2',1':2,3]imidazo[4,5-c]pyridin-2(6H)-yl)-2-oxoethoxy)-6-ethylpyridin-2-yl)methanesulfonamide;

1-(1-(2,4-dimethylthiazol-5-yl)-3,4,7,8-tetrahydro-1H-pyrrolo[2',1':2,3]imidazo[4,5-c]pyridin-2(6H)-yl)-2-((6-(1, 1-dioxidoisothiazolidin-2-yl)-2-ethylpyridin-3-yl)oxy) ethanone;

(R)—N-(5-(2-(1-(2,4-dimethylthiazol-5-yl)-3,4,7,8-tetrahydro-1H-pyrrolo[2',1':2,3]imidazo[4,5-c]pyridin-2(6H)-yl)-2-oxoethoxy)-6-ethylpyridin-2-yl)methanesulfonamide;

(R)—N-cyclopropyl-5-(2-(1-(2,4-dimethylthiazol-5-yl)-3,4, 7,8-tetrahydro-1H-pyrrolo[2',1':2,3]imidazo[4,5-c]pyridin-2(6H)-yl)-2-oxoethoxy)-6-ethylpicolinamide;

(R)-1-(1-(2,4-dimethylthiazol-5-yl)-3,4,7,8-tetrahydro-1H-pyrrolo[2',1':2,3]imidazo[4,5-c]pyridin-2(6H)-yl)-2-((6-(1,1-dioxidoisothiazolidin-2-yl)-2-ethylpyridin-3-yl)oxy) ethanone;

N-(6-chloro-5-(2-(1-(4-chloro-2-fluorophenyl)-3,4,7,8,9, 10-hexahydro-1H-pyrido[4',3':4,5]imidazo[1,2-a]azepin-2(6H)-yl)-2-oxoethoxy)pyridin-2-yl)methanesulfonamide;

N-(6-chloro-5-(2-(1-(2-fluoro-4-methylphenyl)-3,4,7,8,9, 10-hexahydro-1H-pyrido[4',3':4,5]imidazo-[1,2-a]azepin-2(6H)-yl)-2-oxoethoxy)pyridin-2-yl)methanesulfonamide;

N-(6-chloro-5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)pyridin-2-yl)methanesulfonamide;

N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-4-ethylpyrimidin-2-yl)methanesulfonamide;

1-(5-(4-chloro-2-fluorophenyl)-2,3,7,8-tetrahydrothiazolo[2',3':2,3]imidazo[4,5-c]pyridin-6(5H)-yl)-2-((2-chloro-4-ethyl pyrimidin-5-yl)oxy)ethanone;

6-chloro-5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-N-cyclopropylpicolinamide;

1-(5-(4-chloro-2-fluorophenyl)-2,3,7,8-tetrahydrothiazolo[2',3':2,3]imidazo[4,5-c]pyridin-6(5H)-yl)-2-((2-chloro-6-cyclopropylpyridin-3-yl)oxy)ethanone;

1-(5-(4-chloro-2-fluorophenyl)-2,3,7,8-tetrahydrothiazolo[2',3':2,3]imidazo[4,5-c]pyridin-6(5H)-yl)-2-((6-cyclopropyl-2-ethylpyridin-3-yl)oxy)ethanone;

(S)-N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

(S)-1-(5-(4-chloro-2-fluorophenyl)-2,3,7,8-tetrahydrothiazolo[2',3':2,3]imidazo[4,5-c]pyridin-6(5H)-yl)-2-((2-chloro-6-(1,1-dioxidoisothiazolidin-2-yl)pyridin-3-yl)oxy)ethanone;

1-(5-(4-chloro-2-fluorophenyl)-2,3,7,8-tetrahydrothiazolo[2',3':2,3]imidazo[4,5-c]pyridin-6(5H)-yl)-2-((2-chloro-6-(1,1-dioxidoisothiazolidin-2-yl)pyridin-3-yl)oxy)ethanone;

N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

N-(6-chloro-5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)pyridin-2-yl)-N-methylmethanesulfonamide;

1-(5-(4-chloro-2-fluorophenyl)-2,3,7,8-tetrahydrothiazolo[2',3':2,3]imidazo[4,5-c]pyridin-6(5H)-yl)-2-((2-chloro-6-(5-methyl-1,1-dioxido-1,2,5-thiadiazolidin-2-yl)pyridin-3-yl)oxy)ethanone;

1-(5-(4-chloro-2-fluorophenyl)-2,3,7,8-tetrahydrothiazolo[2',3':2,3]imidazo[4,5-c]pyridin-6(5H)-yl)-2-((6-(1,1-dioxidoisothiazolidin-2-yl)-2-ethylpyridin-3-yl)oxy)ethanone;

N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)-N',N'-dimethyl-sulfamide;

1-(5-(4-chloro-2-fluorophenyl)-2,3,7,8-tetrahydrothiazolo[2',3':2,3]imidazo[4,5-c]pyridin-6(5H)-yl)-2-((2-ethyl-6-methylpyridin-3-yl)oxy)ethanone;

5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-N-cyclopropyl-6-ethylpicolinamide;

N-cyclopropyl-5-(2-(5-(5-cyclopropyl-3-fluoropyridin-2-yl)-2,3,7,8-tetrahydrothiazolo[2',3':2,3]imidazo[4,5-c]pyridin-6(5H)-yl)-2-oxoethoxy)-6-ethylpicolinamide;

N-(5-(2-(5-(5-cyclopropyl-3-fluoropyridin-2-yl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

(R)—N-cyclopropyl-5-(2-(5-(5-cyclopropyl-3-fluoropyridin-2-yl)-2,3,7,8-tetrahydrothiazolo[2',3':2,3]imidazo[4,5-c]pyridin-6(5H)-yl)-2-oxoethoxy)-6-ethylpicolinamide;

N-(5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

N-(6-chloro-5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)pyridin-2-yl)methanesulfonamide;

6-chloro-N-cyclopropyl-5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)picolinamide;

N-(5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)-4-ethylpyrimidin-2-yl)methanesulfonamide;

N-(5-(2-(5-(2,3-difluoro-4-methylphenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

6-chloro-N-cyclopropyl-5-(2-(5-(2,3-difluoro-4-methylphenyl)-2,3,7,8-tetrahydrothiazolo[2',3':2,3]imidazo[4,5-c]pyridin-6(5H)-yl)-2-oxoethoxy)picolinamide;

N-(5-(2-(5-(2,4-dimethylthiazol-5-yl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

1-(5-(2,4-dimethylthiazol-5-yl)-2,3,7,8-tetrahydrothiazolo[2',3':2,3]imidazo[4,5-c]pyridin-6(5H)-yl)-2-((6-(1,1-dioxidoisothiazolidin-2-yl)-2-ethylpyridin-3-yl)oxy)ethanone;

N-cyclopropyl-5-(2-(5-(2,4-dimethylthiazol-5-yl)-2,3,7,8-tetrahydrothiazolo[2',3':2,3]imidazo[4,5-c]pyridin-6(5H)-yl)-2-oxoethoxy)-6-ethylpicolinamide;

6-chloro-5-(2-(5-(3-fluorothiophen-2-yl)-2,3,7,8-tetrahydrothiazolo[2',3':2,3]imidazo[4,5-c]pyridin-6(5H)-yl)-2-oxoethoxy)-N,N-dimethylpicolinamide;

N-(6-chloro-5-(2-(5-(3-fluorothiophen-2-yl)-2,3,7,8-tetrahydrothiazolo[2',3':2,3]imidazo[4,5-c]pyridin-6(5H)-yl)-2-oxoethoxy)pyridin-2-yl)methanesulfonamide;

N-(6-ethyl-5-(2-(5-(3-fluorothiophen-2-yl)-2,3,7,8-tetrahydrothiazolo[2',3':2,3]imidazo[4,5-c]pyridin-6(5H)-yl)-2-oxoethoxy)pyridin-2-yl)methanesulfonamide;

N-(5-(2-(5-(2,5-difluoro-4-methylphenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

1-(7-acetyl-1-(4-chloro-2-fluorophenyl)-3,4,6,7,8,9-hexahydropyrido[4',3':4,5]imidazo[1,2-a]pyrazin-2(1H)-yl)-2-((2-chloro-6-(3,3-difluoroazetidin-1-yl)pyridin-3-yl)oxy)ethanone;

5-(2-(7-acetyl-1-(4-chloro-2-fluorophenyl)-3,4,6,7,8,9-hexahydropyrido[4',3':4,5]imidazo[1,2-a]pyrazin-2(1H)-yl)-2-oxoethoxy)-6-chloro-N-methylpicolinamide;

5-(2-(7-acetyl-1-(4-chloro-2-fluorophenyl)-3,4,6,7,8,9-hexahydropyrido[4',3':4,5]imidazo[1,2-a]pyrazin-2(1H)-yl)-2-oxoethoxy)-6-chloro-N,N-dimethylpicolinamide;

6-chloro-5-(2-(1-(4-chloro-2-fluorophenyl)-7-cyclopropyl-3,4,6,7,8,9-hexahydropyrido[4',3':4,5]imidazo[1,2-a]pyrazin-2(1H)-yl)-2-oxoethoxy)-N,N-dimethylpicolinamide;

1-(7-acetyl-1-(3-fluoropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

1-(4-(7-acetyl-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)thiazol-2-yl)-3-ethylurea;

tert-butyl 2-(2-(2-chloro-4-(morpholinomethyl)phenoxy)acetyl)-1-(2-fluoro-4-methylphenyl)-1,2,3,4,8,9-hexahydropyrido[4',3':4,5]imidazo[1,2-a]pyrazine-7(6H)-carboxylate;

2-(2-chloro-4-(morpholinomethyl)phenoxy)-1-(1-(2-fluoro-4-methyl phenyl)-3,4,6,7,8,9-hexahydropyrido[4',3':4,5]imidazo[1,2-a]pyrazin-2(1H)-yl)ethanone;

1-(7-acetyl-1-(2-fluoro-4-methylphenyl)-3,4,6,7,8,9-hexahydropyrido[4',3':4,5]imidazo[1,2-a]pyrazin-2(1H)-yl)-2-(2-chloro-4-(morpholinomethyl)phenoxy)ethanone;

1-(7-acetyl-1-(3-fluorothiophen-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

5-(2-(7-acetyl-1-(3-fluorothiophen-2-yl)-3,4,6,7,8,9-hexahydropyrido[4',3':4,5]imidazo[1,2-a]pyrazin-2(1H)-yl)-2-oxoethoxy)-6-chloro-N,N-dimethylpicolinamide;

tert-butyl 2-(2-((2-chloro-6-morpholinopyridin-3-yl)oxy)acetyl)-1-(4-(cyanocarbamoyl)thiophen-2-yl)-1,2,3,4,8,9-hexahydropyrido[4',3':4,5]imidazo[1, 2-a]pyrazine-7(6H)-carboxylate;

1-(7-acetyl-1-(5-chloropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

1-(7-acetyl-1-(4-chloropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

1-(7-acetyl-1-(2,4-dimethylthiazol-5-yl)-3,4,6,7,8,9-hexahydropyrido[4',3':4,5]imidazo[1,2-a]pyrazin-2(1H)-yl)-2-((2-chloro-6-(oxazol-2-yl)pyridin-3-yl)oxy)ethanone;

tert-butyl 1-(4-cyclopropyl-2-fluorophenyl)-2-(2-((2-ethyl-6-methylpyridin-3-yl)oxy)acetyl)-1,2,3,4,8,9-hexahydropyrido[4',3':4,5]imidazo[1, 2-a]pyrazine-7(6H)-carboxylate;

1-(1-(4-cyclopropyl-2-fluorophenyl)-3,4,6,7,8,9-hexahydropyrido[4',3':4,5]imidazo[1,2-a]pyrazin-2(1H)-yl)-2-((2-(trifluoromethyl)pyridin-3-yl)oxy)ethanone;

6-chloro-5-(2-(1-(4-cyclopropyl-2-fluorophenyl)-3,4,6,7,8,9-hexahydropyrido[4',3':4,5]imidazo[1,2-a]pyrazin-2(1H)-yl)-2-oxoethoxy)picolinonitrile;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloro-6-(3,3-difluoroazetidin-1-yl)pyridin-3-yl)oxy)ethanone;

5-(2-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-oxoethoxy)-6-chloro-N,N-dimethylpicolinamide;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloropyridin-3-yl)oxy)ethanone;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-(trifluoromethyl)pyridin-3-yl)oxy)ethanone;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloro-5-fluoropyridin-3-yl)oxy)ethanone;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-ethyl-6-methylpyridin-3-yl)oxy)ethanone;

tert-butyl 2-(2-(2-chloro-4-morpholinophenoxy)acetyl)-1-(4-cyclopropyl-2-fluorophenyl)-1,2,3,4,8,9-hexahydropyrido[4',3':4,5]imidazo[1, 2-a]pyrazine-7(6H)-carboxylate;

1-(1-(4-cyclopropyl-2-fluorophenyl)-3,4,6,7,8,9-hexahydropyrido[4',3':4,5]imidazo[1,2-a]pyrazin-2(1H)-yl)-2-((2-ethyl-6-methylpyridin-3-yl)oxy)ethanone;

2-(2-chloro-4-morpholinophenoxy)-1-(1-(4-cyclopropyl-2-fluorophenyl)-3,4,6,7,8,9-hexahydropyrido[4',3':4,5]imidazo[1,2-a]pyrazin-2(1H)-yl)ethanone;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-(2-chloro-4-morpholinophenoxy)ethanone;

1-(1-(4-cyclopropyl-2-fluorophenyl)-7-(cyclopropylmethyl)-3,4,6,7,8,9-hexahydropyrido[4',3':4,5]imida-zo[1,2-a]pyrazin-2(1H)-yl)-2-((2-ethyl-6-methylpyridin-3-yl)oxy)ethanone;

2-(2-chloro-4-morpholinophenoxy)-1-(1-(4-cyclopropyl-2-fluorophenyl)-7-(cyclopropylmethyl)-3,4,6,7,8,9-hexahydropyrido[4',3':4,5]imidazo[1,2-a]pyrazin-2(1H)-yl)ethanone;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

3-chloro-4-(2-(1-(4-cyclopropyl-2-fluorophenyl)-3,4,6,7,8,9-hexahydropyrido[4',3':4,5]imidazo[1,2-a]pyrazin-2(1H)-yl)-2-oxoethoxy)benzonitrile;

5-(2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)-N,N-dimethylthiophene-3-carboxamide;

5-(7-acetyl-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)-N,N-dimethylthiophene-3-carboxamide;

tert-butyl 2-(2-((2-chloro-6-morpholinopyridin-3-yl)oxy)acetyl)-1-(5-cyclopropyl-3-fluoropyridin-2-yl)-1,2,3,4,8,9-hexahydropyrido[4',3':4,5]imidazo[1,2-a]pyrazine-7(6H)-carboxylate;

1-(1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-(trifluoromethyl)pyridin-3-yl)oxy)ethanone;

2-((2-chloro-6-morpholinopyridin-3-yl)oxy)-1-(1-(5-cyclopropyl-3-fluoropyridin-2-yl)-3,4,6,7,8,9-hexahydropyrido[4',3':4,5]imidazo[1,2-a]pyrazin-2(1H)-yl)ethanone;

1-(1-(5-cyclopropyl-3-fluoropyridin-2-yl)-3,4,6,7,8,9-hexahydropyrido[4',3':4,5]imidazo[1,2-a]pyrazin-2(1H)-yl)-2-(2-ethyl-4-fluorophenoxy)ethanone;

2-(4-chloro-2-ethylphenoxy)-1-(1-(5-cyclopropyl-3-fluoropyridin-2-yl)-3,4,6,7,8,9-hexahydropyrido[4',3':4,5]imidazo[1,2-a]pyrazin-2(1H)-yl)ethanone;

1-(7-acetyl-1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

1-(7-acetyl-1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-chloro-5-fluoropyridin-3-yl)oxy)ethanone;

1-(7-acetyl-1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-fluoro-6-morpholinopyridin-3-yl)oxy)ethanone;

1-(7-acetyl-1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-chloro-5-fluoro-6-morpholinopyridin-3-yl)oxy)ethanone;

methyl 5-(7-acetyl-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)thiophene-3-carboxylate;

2-((2-chloro-6-morpholinopyridin-3-yl)oxy)-1-(1-(2-(dimethylamino)thiazol-5-yl)-3,4,6,7,8,9-hexahydropyrido[4',3':4,5]imidazo[1,2-a]pyrazin-2(1H)-yl)ethanone;

1-(7-acetyl-1-(2-(dimethyl amino)thiazol-5-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

5-(2-(7-acetyl-1-(5-(dimethylcarbamoyl)-3-fluorothiophen-2-yl)-3,4,6,7,8,9-hexahydropyrido[1,2-a]pyrazin-2(1H)-yl)-2-oxoethoxy)-6-chloro-N,N-dimethylpicolinamide;

5-(7-acetyl-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)-4-fluoro-N,N-dimethylthiophene-2-carboxamide;

1-(7-acetyl-1-(3-fluoro-5-methylpyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

1-(7-acetyl-1-(3-fluoro-5-methylpyridin-2-yl)-3,4,6,7,8,9-hexahydropyrido[4',3':4,5]imidazo[1,2-a]pyrazin-2(1H)-yl)-2-((2-chloro-6-(3,3-difluoroazetidin-1-yl)pyridin-3-yl)oxy)ethanone;

1-(7-acetyl-1-(5-chloro-3-fluoropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

1-(6-(4-chloro-2-fluorophenyl)-3,4,8,9-tetrahydro-1H-pyrido[4',3':4,5]imidazo[2,1-c][1,4]oxazin-7(6H)-yl)-2-((2-chloro-6-morpholinopyridin-3-yl)oxy)ethanone;

N-(6-chloro-5-(2-(6-(4-chloro-2-fluorophenyl)-3,4,8,9-tetrahydro-1H-pyrido[4',3':4,5]imidazo[2,1-c][1,4]oxazin-7(6H)-yl)-2-oxoethoxy)pyridin-2-yl)methanesulfonamide;

2-((2-chloro-6-morpholinopyridin-3-yl)oxy)-1-(6-(4-cyclopropyl-2-fluorophenyl)-3,4,8,9-tetrahydro-1H-pyrido[4',3':4,5]imidazo[2,1-c][1,4]oxazin-7(6H)-yl)ethanone;

3-chloro-4-(2-(6-(4-cyclopropyl-2-fluorophenyl)-3,4,8,9-tetrahydro-1H-pyrido[4',3':4,5]imidazo[2,1-c][1,4]oxazin-7(6H)-yl)-2-oxoethoxy)-N,N-dimethylbenzamide;

6-chloro-5-(2-(6-(4-cyclopropyl-2-fluorophenyl)-3,4,8,9-tetrahydro-1H-pyrido[4',3':4,5]imidazo[2,1-c][1,4]oxazin-7(6H)-yl)-2-oxoethoxy)-N,N-dimethylpicolinamide;

6-chloro-5-(2-(6-(5-(dimethylcarbamoyl)-3-fluoro-thiophen-2-yl)-3,4,8,9-tetrahydro-1H-pyrido[4',3':4,5]imidazo[2,1-c][1,4]oxazin-7(6H)-yl)-2-oxoethoxy)-N,N-dimethylpicolinamide;

N-(6-chloro-5-(2-(6-(5-chloro-3-fluoropyridin-2-yl)-3,4,8,9-tetrahydro-1H-pyrido[4',3':4,5]imidazo[2,1-c][1,4]oxazin-7(6H)-yl)-2-oxoethoxy)pyridin-2-yl)methanesulfonamide;

6-chloro-5-(2-(6-(5-chloro-3-fluoropyridin-2-yl)-3,4,8,9-tetrahydro-1H-pyrido[4',3':4,5]imidazo[2,1-c][1,4]oxazin-7(6H)-yl)-2-oxoethoxy)-N,N-dimethylpicolinamide;

6-chloro-5-(2-(6-(2-fluoro-4-methylphenyl)-3,4,8,9-tetrahydro-1H-pyrido[4',3':4,5]imidazo[2,1-c][1,4]oxazin-7(6H)-yl)-2-oxoethoxy)-N,N-dimethylpicolinamide;

2-((2-chloro-6-morpholinopyridin-3-yl)oxy)-1-(6-(3-fluorothiophen-2-yl)-3,4,8,9-tetrahydro-1H-pyrido[4',3':4,5]imidazo[2,1-c][1,4]oxazin-7(6H)-yl)ethanone;

6-chloro-5-(2-(6-(3-fluorothiophen-2-yl)-3,4,8,9-tetrahydro-1H-pyrido[4',3':4,5]imidazo[2,1-c][1,4]oxazin-7(6H)-yl)-2-oxoethoxy)-N,N-dimethylpicolinamide; and N-(6-chloro-5-(2-(6-(3-fluorothiophen-2-yl)-3,4,8,9-tetrahydro-1H-pyrido[4',3':4,5]imidazo[2,1-c][1,4]oxazin-7(6H)-yl)-2-oxoethoxy)pyridin-2-yl)methanesulfonamide.

31) In addition to the compounds of embodiment 30), further examples of compounds of Formula (I) according to embodiment 1) are selected from the group consisting of:

N-(6-chloro-5-(1-(1-(4-chloro-2-fluorophenyl)-1,2,3,4,6,7,8,9-octahydroimidazo[1,2-a:5,4-c']dipyridine-2-carbonyl)cyclopropoxy)pyridin-2-yl)methanesulfonamide;

N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-cyclopropylpyridin-2-yl)methanesulfonamide;

1-(1-(4-chloro-2-fluorophenyl)-3,4,6,7,8,9-hexahydroimidazo[1,2-a:5,4-c']dipyridin-2(1H)-yl)-2-((2-chloro-6-(dimethylamino)pyridin-3-yl)oxy)ethan-1-one;

5-(2-(1-(4-chloro-2-fluorophenyl)-3,4,6,7,8,9-hexahydroimidazo[1,2-a:5,4-c']dipyridin-2(1H)-yl)-2-oxoethoxy)-N,6-dicyclopropylpicolinamide;

1-(1-(4-chloro-2-fluorophenyl)-3,4,6,7,8,9-hexahydroimidazo[1,2-a:5,4-c']dipyridin-2(1H)-yl)-2-((2-chloro-6-(methyl(2,2,2-trifluoroethyl)amino)pyridin-3-yl)oxy)ethan-1-one;

1-(1-(4-chloro-2-fluorophenyl)-3,4,6,7,8,9-hexahydroimidazo[1,2-a:5,4-c']dipyridin-2(1H)-yl)-2-((2-chloro-6-(2-methoxyethyl)(methyl)amino)pyridin-3-yl)oxy)ethan-1-one;

6-chloro-5-((1-(1-(4-chloro-2-fluorophenyl)-3,4,6,7,8,9-hexahydroimidazo[1,2-a:5,4-c']dipyridin-2(1H)-yl)-2-methyl-1-oxopropan-2-yl)oxy)-N,N-dimethylpicolinamide;

6-chloro-5-(1-(1-(4-chloro-2-fluorophenyl)-1,2,3,4,6,7,8,9-octahydroimidazo[1,2-a:5,4-c']dipyridine-2-carbonyl)cyclopropoxy)-N,N-dimethylpicolinamide;

1-(1-(4-chloro-2-fluorophenyl)-3,4,6,7,8,9-hexahydroimidazo[1,2-a:5,4-c']dipyridin-2(1H)-yl)-2-((2-chloro-6-(methylsulfonyl)pyridin-3-yl)oxy)ethan-1-one;

6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N,N-dimethylpyridine-2-sulfonamide;

1-(1-(4-chloro-2-fluorophenyl)-3,4,6,7,8,9-hexahydroimidazo[1,2-a:5,4-c']dipyridin-2(1H)-yl)-2-((2-chloro-6-(2-hydroxyethyl)(methyl)amino)pyridin-3-yl)oxy)ethan-1-one;

1-(1-(2,4-dimethylthiazol-5-yl)-3,4,6,7,8,9-hexahydroimidazo[1,2-a:5,4-c']dipyridin-2(1H)-yl)-2-((6-(1,1-dioxidoisothiazolidin-2-yl)-2-ethylpyridin-3-yl)oxy)ethan-1-one;

6-chloro-N-cyclopropyl-5-(2-(1-(2-fluoro-4-(trifluoromethoxy)phenyl)-3,4,6,7,8,9-hexahydroimidazo[1,2-a:5,4-c']dipyridin-2(1H)-yl)-2-oxoethoxy)picolinamide;

N-(6-chloro-5-(2-(1-(2-fluoro-4-(trifluoromethoxy)phenyl)-3,4,6,7,8,9-hexahydroimidazo[1,2-a:5,4-c']dipyridin-2(1H)-yl)-2-oxoethoxy)pyridin-2-yl)methanesulfonamide;

6-chloro-N-cyclopropyl-5-(2-(1-(2-fluoro-4-methoxyphenyl)-3,4,6,7,8,9-hexahydroimidazo[1,2-a:5,4-c']dipyridin-2(1H)-yl)-2-oxoethoxy)picolinamide;

N-(6-chloro-5-(2-(1-(2-fluoro-4-methoxyphenyl)-3,4,6,7,8,9-hexahydroimidazo[1,2-a:5,4-c']dipyridin-2(1H)-yl)-2-oxoethoxy)pyridin-2-yl)methanesulfonamide;

N-(6-chloro-5-(2-(1-(4-cyano-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide;

6-chloro-5-(2-(1-(4-cyano-2-fluorophenyl)-3,4,6,7,8,9-hexahydroimidazo[1,2-a:5,4-c']dipyridin-2(1H)-yl)-2-oxoethoxy)-N-cyclopropyl picolinamide;

methyl-4-(2-(2-((2-chloro-6-(methylsulfonamido)pyridin-3-yl)oxy)acetyl)-1,2,3,4,6,7,8,9-octahydroimidazo[1,2-a:5,4-c']dipyridin-1-yl)-3-fluorobenzoate;

methyl (R)-4-(2-(2-((2-chloro-6-(cyclopropylcarbamoyl)pyridin-3-yl)oxy)acetyl)-1,2,3,4,6,7,8,9-octahydroimidazo[1,2-a:5,4-c']dipyridin-1-yl)-3-fluorobenzoate;

6-chloro-N-cyclopropyl-5-(2-(1-(2-fluoro-4-(2-hydroxypropan-2-yl)phenyl)-3,4,6,7,8,9-hexahydroimidazo[1,2-a:5,4-c']dipyridin-2(1H)-yl)-2-oxoethoxy)picolinamide;

N-(6-chloro-5-(2-(1-(2-fluoro-4-(2-hydroxypropan-2-yl)phenyl)-3,4,6,7,8,9-hexahydroimidazo[1,2-a:5,4-c']dipyridin-2(1H)-yl)-2-oxoethoxy)pyridin-2-yl)methanesulfonamide;

6-chloro-N-cyclopropyl-5-(2-(1-(2-fluoro-4-(2-methoxypropan-2-yl)phenyl)-3,4,6,7,8,9-hexahydroimidazo[1,2-a:5,4-c']dipyridin-2(1H)-yl)-2-oxoethoxy)picolinamide;

N-(6-chloro-5-(2-(1-(2-fluoro-4-(2-methoxypropan-2-yl)phenyl)-3,4,6,7,8,9-hexahydroimidazo[1,2-a:5,4-c']dipyridin-2(1H)-yl)-2-oxoethoxy)pyridin-2-yl)methanesulfonamide;

6-chloro-N-cyclopropyl-5-(2-(1-(2-fluoro-4-(methoxymethyl)phenyl)-3,4,6,7,8,9-hexahydroimidazo[1,2-a:5,4-c']dipyridin-2(1H)-yl)-2-oxoethoxy)picolinamide;

N-(6-chloro-5-(2-(1-(2-fluoro-4-(methoxymethyl)phenyl)-3,4,6,7,8,9-hexahydroimidazo[1,2-a:5,4-c']dipyridin-2(1H)-yl)-2-oxoethoxy)pyridin-2-yl)methanesulfonamide;

6-chloro-N-cyclopropyl-5-(2-(1-(2-fluoro-4-(2-methoxyethoxy)phenyl)-3,4,6,7,8,9-hexahydroimidazo[1, 2-a:5, 4-c']dipyridin-2(1H)-yl)-2-oxoethoxy)picolinamide;

N-(6-chloro-5-(2-(1-(2-fluoro-4-(2-methoxyethoxy)phenyl)-3,4,6,7,8,9-hexahydroimidazo[1,2-a:5,4-c']dipyridin-2(1H)-yl)-2-oxoethoxy)pyridin-2-yl)methanesulfonamide;

6-chloro-N-cyclopropyl-5-(2-(1-(2-fluoro-4-(2-hydroxyethoxy)phenyl)-3,4,6,7,8,9-hexahydroimidazo[1, 2-a:5,4-c']dipyridin-2(1H)-yl)-2-oxoethoxy)picolinamide; and N-(6-chloro-5-(2-(1-(2-fluoro-4-(2-hydroxyethoxy)phenyl)-3,4,6,7,8,9-hexahydroimidazo[1,2-a:5,4-c']dipyridin-2(1H)-yl)-2-oxoethoxy)pyridin-2-yl)methanesulfonamide.

32) A further aspect of the present invention relates to the process for the preparation of the compounds of formula (I) as outlined herein below in scheme 2. A particular aspect relates to novel compounds of the formula (IV):

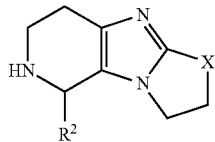

Formula (IV)

wherein said compounds of formula (IV) preferably have the absolute configuration depicted in Formula $(I_E)$/embodiment 2); and wherein $R^2$ is as defined for the compounds of formula (I) in any one of embodiments 1), 8) to 13); or 28) or 29) [especially $R^2$ is as defined in embodiment 12)]; and X is as defined in any one of embodiments 1), 3) to 7)); or 27) or 29) [especially X is as defined in embodiment 5)].

These compounds are novel intermediates suitable for the preparation of the compounds of formula (I), respectively, the compounds of formula (II) and/or (III). Such preparation process comprises acylation of the compound of formula (IV) with acid derivatives of structure 2 {wherein $R^{1a}$ and $R^{1b}$ are as defined for the compounds of formula (I) in any one of embodiments 1), 3), or 28) or 29) [especially $R^{1a}$ and $R^{1b}$ are as defined in embodiment 3)]; and $R^3$ is as defined for the compounds of formula (I) in any one of embodiments 1), 14) to 26); or 28) or 29) [especially $R^3$ is as defined in embodiment 25)]}; and wherein such acylation is effected using for example the corresponding acid chloride or an active ester of the respective acid derivative, or an the in situ activation method.

The compounds of compounds of formula (I) and (II) as defined in any one of embodiments 1) to 31) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject in need thereof a pharmaceutically active amount of a compound of formula (I) as defined in any one of embodiments 1) to 31). The invention thus also relates to a method of reducing the level of peripheral serotonin in a subject in need thereof, comprising administering to said subject a pharmaceutically active amount of a compound of formula (I) as defined in any one of embodiments 1) to 31).

In a preferred embodiment of the invention, the administered amount of such a compound of formula (I) as defined in any one of embodiments 1) to 31) is comprised between 1 mg and 1000 mg per day, particularly between 5 mg and 500 mg per day, more particularly between 10 mg and 400 mg per day.

For avoidance of any doubt, if compounds are described as being useful for the prevention or treatment of certain diseases, such compounds are likewise suitable for use in the preparation of a medicament for the prevention or treatment of said diseases.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of 25° C.

The compounds according to formula (I) are useful for the prevention or treatment of diseases or disorders characterized by an altered rate of the tryptophan-serotonin metabolism.

The term "disease or disorder characterized by an altered rate of the tryptophan-serotonin metabolism" refers to a neurological or peripheral disease or disorder characterized by an altered rate of the tryptophan-serotonin metabolism, wherein the rate limiting step of said tryptophan-serotonin metabolism is the hydroxylation of L-Tryp catalyzed by TPH and where an inhibitor of a TPH enzyme is required.

Examples of such diseases or disorders characterized by an altered rate of the tryptophan-serotonin metabolism are preferably peripheral diseases or disorders where the rate limiting step of said tryptophan-serotonin metabolism is the hydroxylation of L-Tryp catalyzed by TPH1 and where an inhibitor of a TPH1 is required. Particular examples are lung disease including interstitial lung disease (such as lung fibrosis), chronic obstructive pulmonary disease (COPD), pulmonary embolism, pulmonary hypertension including pulmonary arterial hypertension, radiation pneumonitis (including that giving rise to or contributing to pulmonary hypertension), asthma, and adult respiratory distress syndrome (ARDS); osteoporosis; gastrointestinal disorders including inflammatory bowel disease, postinfectious irritable bowel syndrome, coeliac disease, idiopathic constipation, and irritable bowel syndrome; ulcerative colitis; carcinoid syndrome; myxomatous valve disease; thrombosis; sleep disorders; pain; type 1 and type 2 diabetes; immune disorders; liver disease (including (viral-induced) hepatitis fibrosis, transplantation, regeneration); acute and chronic hypertension; cancer including breast cancer, prostate cancer, and neuroendocrine tumors with elevated serotonin secretion (e.g carcinoid tumors); subarachnoid hemorrhage; abdominal migraine; CREST syndrome (calcinosis, Raynaud's phenomenon, esophageal dysfunction, sclerodactyly, telangiectasia); Gilbert's syndrome; nausea; serotonin syndrome; functional anorectal disorders; functional bloating; and inflammatory diseases including multiple sclerosis and systemic sclerosis. Notably examples are lung fibrosis; pulmonary hypertension including pulmonary arterial hypertension; asthma; osteoporosis; ulcerative colitis; irritable bowel syndrome; carcinoid syndrome; cancer including breast cancer, prostate cancer, and neuroendocrine tumors with elevated serotonin secretion (e.g carcinoid tumors); and inflammatory diseases including multiple sclerosis and systemic sclerosis.

Further examples of such diseases or disorders characterized by an altered rate of the tryptophan-serotonin metabolism are neurological health disorders where the rate limiting step of said tryptophan-serotonin metabolism is the hydroxylation of L-Tryp catalyzed by TPH2 and where an inhibitor of a TPH2 is required. Particular examples are depression; anxiety including generalized anxiety disorder and social phobia; emetic disorders; migraine; substance abuse; attention deficit disorder (ADD); attention deficit hyperactivity disorder (ADHD); bipolar disorder; suicidal behavior; behavioral disorder; schizophrenia; Parkinson's disease; Huntigton's disease; autism; dyskinesia; eating disorders; type 2 diabetes; pain; Alzheimer's disease; sexual dysfunction; and brain tumors.

Preparation of Compounds of Formula (I)
General Preparation Routes:

The present compounds can be prepared by well known literature methods, by the methods given below, by the methods given in the experimental part or by analogous methods. Optimum reaction conditions may vary with the particular reactants or solvents used, but such conditions can be determined by a person skilled in the art by routine optimisation procedures. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. In some cases the order of carrying out the following reaction schemes, and/or reaction steps, may be varied to facilitate the reaction or to avoid unwanted reaction products. In the general sequence of reactions outlined below, the generic groups X, $R^{1a}$, $R^{1b}$, $R^2$, and $R^3$ are as defined for formula (I). In some instances the generic groups X, $R^2$, and $R^3$ may be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into pharmaceutically acceptable salts thereof in a manner known per se.

The compounds of the formula (I) may be prepared by the coupling of the amine of the structure 1 with the acid of the structure 2. Intermediate compounds of structure 2, 3 and 4 or their precursors are either commercially available or are prepared according to procedures known to a person skilled in the art or in analogy to the methods described in the experimental section below.

Compounds of structure 1 can be acylated with acid derivatives of structure 2 as depicted in scheme 2; for example using the corresponding acid chlorides or active estersin presence of a base like TEA or DIPEA in DCM, or using an the in situ activation method such as a well known amide-coupling reagent such as COMU, TBTU, HATU, EDC, DCC or PyBOP and a base like DIPEA or TEA in a solvent such as DCM, MeCN or DMF to deliver the compounds of Formula (I).

Scheme 2: Synthesis of compounds of Formula (I)

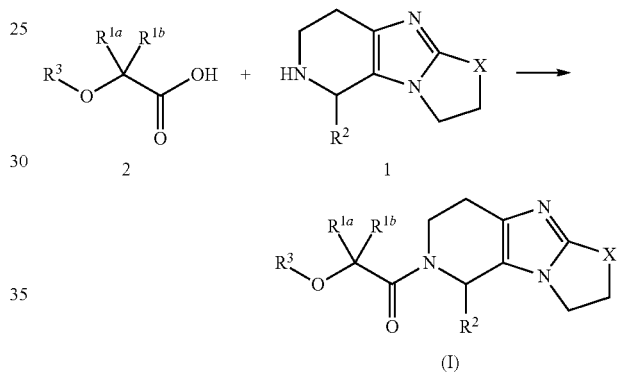

Alternatively, the desired residues $R^2$ and/or $R^3$ may also be introduced in later steps that follow the amide coupling of the appropriate precursor amine of structure 1 with the appropriate acid derivatives of structure 2.

In case in a compound of Formula (I) X represents —$CH_2$—$NR^x$—, such compound of Structure 5 can be prepared in a two-step procedure from a compound of Structure 6 (scheme 3).

Scheme 3: Synthesis of compounds of Structure 5

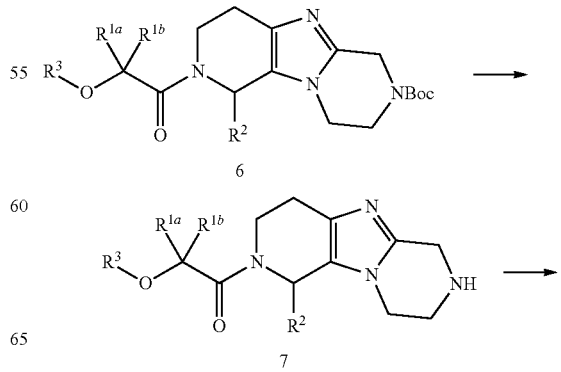

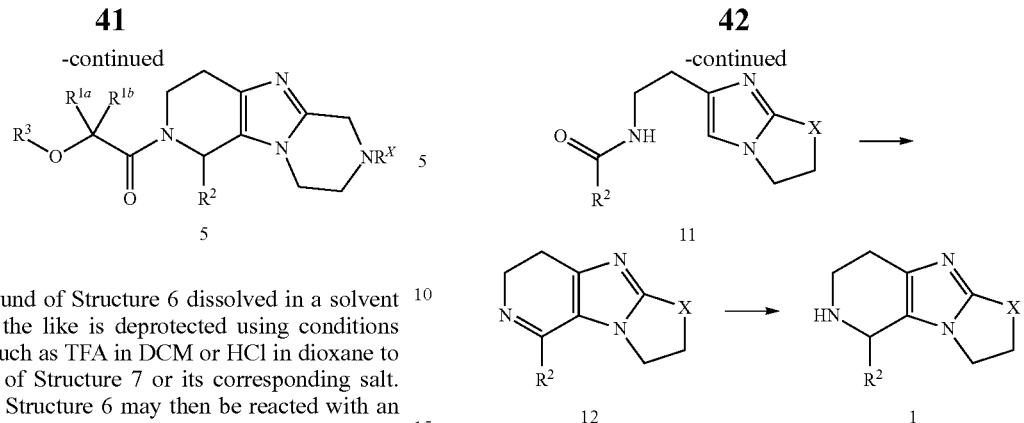

Hence a compound of Structure 6 dissolved in a solvent such as DCM or the like is deprotected using conditions known in the art such as TFA in DCM or HCl in dioxane to give a compound of Structure 7 or its corresponding salt. The compound of Structure 6 may then be reacted with an reagent of type $R^x$-LG wherein LG represents a leaving group such as Cl, Br, I, OMs, OTf or the like in an alkylation reaction well known by a person skilled in the art. Alternatively, a compound of Structure 7 can also be reacted in a reductive amination reaction under standard conditions, e.g. with an aldehyde or a ketone of type $R^{X1}R^{X2}c=O$ (or with their precursors, like acetals) in a solvent such as MeOH, EtOH and a reducing agent such as $NaBH_4$, $NaBH(OAc)_3$, $NaBH_3CN$ or the like at room temperature. In this case a compound of Structure 5 wherein Rx corresponds to $R^{X1}R^{X2}CH$ is obtained. Compounds of formula (I) wherein X represent $—CH_2—NR^X—$ wherein $R^X$ represents $R^{X3}CO$ can be made from a compound of Structure 7 according to procedures known to a person skilled in the art. In a typical reaction procedure, a compound of Structure 7 is dissolved in a solvent such as DCM, THF or water is reacted with an activated carboxylic acid derivative such as an acid chloride $R^{X3}COCl$ and a base such as NaOH, $K_2CO_3$, TEA or DIPEA at 0° C. to room temperature.

Preparation of Compounds of Structure 1

Scheme 4: Pictet-Spengler reaction

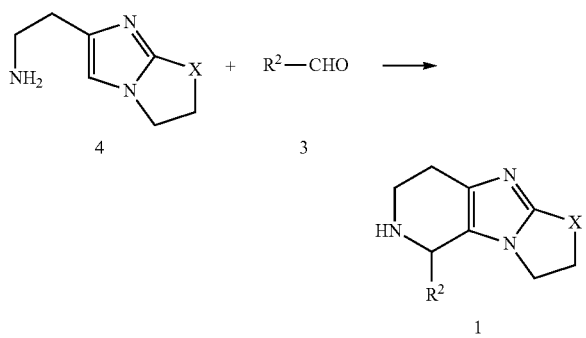

Compounds of the Structure 1 can be prepared by a reaction of amines of the Structure 4 with an aldehyde of the Structure 3 under acidic or basic conditions (Pictet-Spengler reaction, scheme 4) in a solvent such THF, toluene or the like.

Scheme 5: Synthesis of compounds of Structure 1

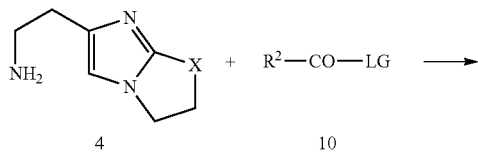

Alternatively, compounds of Structure 1 can by prepared using the three-step procedure depicted in scheme 5. In a typical reaction procedure, a compound of Structure 4 is dissolved in a solvent such as DCM, THF or water is reacted with an activated acid derivative of structure 10 (LG represents a leaving group) and a base such as NaOH, $K_2CO_3$, TEA or DIPEA at 0° C. to room temperature, according to procedures well known in the art. Subsequently, the amide of Structure 11 is cyclized with $POCl_3$, $COCl_2$, $ZnCl_2$ or the like in DCM, toluene or the like to deliver the imine of Structure 12, which may be reduced using a reducing agent such as $NaBH_4$, $NaBH(OAc)_3$, $NaBH_3CN$ or hydrogen in presence of a suitable catalyst. Conditions such as hydrogenation or transfer hydrogenation in presence of a chiral catalyst may allow for an enantiospecific reduction of the compounds of structure 12 to the appropriate enantiomerically enriched compounds of structure 1.

Preparation of Compounds of Structure 2

Acids of structure 2 may be prepared via alkylation reaction of the corresponding alcohol with halogen-acetic acid ester derivatives and subsequent hydrolysis of the ester to the acid. Under acidic or basic conditions. Alternatively, compounds of the Structure 2 may be prepared by alkylation of the corresponding alcohol under Mitsunobu reaction condition using hydroxyacetic acid derivatives in the presence of diethyl azodicarboxylate and the like in a solvent like toluene, DCM, THF and the like and subsequent hydrolysis of the ester to the acid under acidic or basic conditions.

Preparation of Compounds of Structure 3

Aldehydes of structure 3 may be prepared by an oxidation of the corresponding alcohol derivatives, or by a reduction of the corresponding carbocylic acids or their derivatives thereof like esters, nitriles and the like. Aldehydes of structure 3 may also be prepared from corresponding halogen-precursors via halogen-metal exchange like nBuli and the like and subsequent formylation with DMF and the like.

Preparation of Compounds of Structure 4

Amines of structure 4 or their precursors are either commercially available or can prepared according to procedures known to a person skilled in the art or in analogy to the methods described in the experimental part below.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min.

EXPERIMENTAL SECTION

Abbrevations (as used herein and in the description above):
aq. aqueous
Bu butyl (such as in nBuLi=n-butyl lithium)
CC column chromatography on silica gel
conc. Concentrated
DCC 1,3-dicyclohexylcarbodiimide
DCM dichloromethane
DIPEA N-ethyldiisopropylamine
DMF dimethylformamide
DMSO dimethylsulfoxide
DTT dithiothreitol
EA ethyl acetate
E. coli. Escherichia coli
Eq equivalent
Et ethyl
EtOH ethanol
FC flash chromatography
h hour(s)
HATU 2-(1H-7-Azabenzotriazol-1-yl)-1,1,3,3-tetramethyl uronium hexafluorophosphate methanaminium
HOBt 1-hydroxybenzotriazole, hydrate
LAH lithium aluminium hydride
LC liquid chromatography
M molarity [mol L$^{-1}$]
Me methyl
MeCN acetonitrile
MeOH methanol
MS mass spectroscopy
min. minute(s)
N normality
org. organic
Pd/C palladium on carbon
Ph phenyl
PTSA p-Toluenesulfonic acid
rt room temperature
Sat. Saturated
TBME tert-butylmethylether
TBTU O-benzotriazol-1-yl-N,N,N',N'-tetramethyluronium tetrafluoroborate
tBu tert-butyl=tertiary butyl
TFA trifluoroacetic acid
THF tetrahydrofuran
TMSCl trimethylsilyl chloride
Tris tris(hydroxymethyl)aminomethane
$t_R$ retention time
I. Chemistry The following examples illustrate the preparation of biologically active compounds of the invention but do not at all limit the scope thereof. If not explicitly indicated otherwise, all compounds are prepared in racemic form.

General: All temperatures are stated in degrees Celsius (° C.). Unless otherwise indicated, the reactions take place at RT under an nitrogen atmosphere and are run in a flame dried round-bottomed flask equipped with a magnetic stir bar.

Characterization Methods Used:
The LC-MS and GC-MS retention times have been obtained using the following elution conditions:

A) LC-MS (A):
Zorbax SB-Aq, 3.5 μm, 4.6×50 mm column thermostated at 40° C. The two elution solvents were as follows: solvent A=water+0.04% TFA; solvent B=acetonitrile. The eluent flow rate was 4.5 mL/min and the characteristics of the eluting mixture proportion in function of the time t from start of the elution are summarized in the table below (a linear gradient being used between two consecutive time points):

|  | t (min) | | | | | |
| --- | --- | --- | --- | --- | --- | --- |
|  | 0 | 0.08 | 1.07 | 1.57 | 1.67 | 1.70 |
| Solvent A (%) | 95 | 95 | 5 | 5 | 95 | 95 |
| Solvent B (%) | 5 | 5 | 95 | 95 | 5 | 5 |

B) LC-MS (B):
Waters Atlantis T3, 5 μm, 4.6×30 mm column thermostated at 40° C. The two elution solvents were as follows: solvent A=water+0.04% TFA; solvent B=acetonitrile. The eluent flow rate was 4.5 mL/min and the characteristics of the eluting mixture proportion in function of the time t from start of the elution are summarized in the table below (a linear gradient being used between two consecutive time points):

|  | t (min) | | | | | |
| --- | --- | --- | --- | --- | --- | --- |
|  | 0 | 0.08 | 1.07 | 1.57 | 1.67 | 1.70 |
| Solvent A (%) | 95 | 95 | 5 | 5 | 95 | 95 |
| Solvent B (%) | 5 | 5 | 95 | 95 | 5 | 5 |

C) GC-MS:
Zebron ZB-5 MS, 15 m×0.25 mm ID, 0.25 um film, 2.0 ml/min. The carrier gas is Helium and the chemical ionization occurs with $CH_4$ as reagent gas. Temp. gradient: 60-300° C. from 0 to 4.0 min and 300° C. isotherm from 4.0 to 5.0 min.

D) Non-Chiral Preparative Methods Used:
The purifications by preparative LC-MS have been performed using the conditions described hereafter.

I) Preparative LC-MS:
A X-Bridge column (Waters C18, 10 μm OBD, 30×75 mm) was used. The two elution solvents were as follows: solvent A=water+0.5% $NH_4OH$; solvent B=acetonitrile. The eluent flow rate was 75 mL/min. The elution was done using an appropriate gradient of the solvent B in the solvent A as shown in the following tables (a linear gradient being used between two consecutive time points):

|  | t (min) | | | | | |
| --- | --- | --- | --- | --- | --- | --- |
|  | 0 | 0.01 | 4.0 | 6.0 | 6.2 | 6.6 |
| Solvent A (%) | 90 | 90 | 5 | 5 | 90 | 90 |
| Solvent B (%) | 10 | 10 | 95 | 95 | 10 | 10 |
| Solvent A (%) | 80 | 80 | 5 | 5 | 80 | 80 |
| Solvent B (%) | 20 | 20 | 95 | 95 | 20 | 20 |

E) Chiral Preparative LC-MS Methods Used:
The separation of selected enantiomers has been performed using chiral column chromatography using the conditions described hereafter.

Chiral Preparative LC-MS (I):
ChiralPack IC, 5 μm, 20×250 mm was used. The two elution solvents were as follows: solvent A=heptane; solvent B=0.1% diethylamine in EtOH. The eluent flow rate was 16 mL/min. The elution was done using 10% of the solvent A and 90% of the solvent B.

Chiral Preparative LC-MS (II):

ChiralPack AS-H, 5 μm, 20×250 mm was used. The two elution solvents were as follows: solvent A=heptane; solvent B=0.1% diethylamine in EtOH. The eluent flow rate was 16 mL/min. The elution was done using 80% of the solvent A and 20% of the solvent B.

Chiral Preparative LC-MS (III):

ChiralPack IC, 5 μm, 20×250 mm was used. The two elution solvents were as follows: solvent A=heptane; solvent B=0.1% diethylamine in EtOH. The eluent flow rate was 19 mL/min. The elution was done using 10% of the solvent A and 90% of the solvent B.

Chiral Preparative LC-MS (IV):

ChiralPack IC, 5 μm, 20×250 mm was used. The two elution solvents were as follows: solvent A=heptane; solvent B=0.1% diethylamine in EtOH/DCM (50:50). The eluent flow rate was 20 mL/min. The elution was done using 10% of the solvent A and 90% of the solvent B.

Chiral Preparative LC-MS (V):

ChiralPack IC, 5 μm, 20×250 mm was used. The two elution solvents were as follows: solvent A=DCM; solvent B=0.1% diethylamine in EtOH. The eluent flow rate was 16 mL/min. The elution was done using 90% of the solvent A and 10% of the solvent B.

Chiral Preparative LC-MS (VI):

ChiralPack IA, 5 μm, 20×250 mm was used. The two elution solvents were as follows: solvent A=MeCN; solvent B=DCM/EtOH (1:1). The eluent flow rate was 23 mL/min. The elution was done using 70% of the solvent A and 30% of the solvent B.

Chiral Preparative LC-MS (VII):

ChiralPack IC, 5 μm, 20×250 mm was used. The two elution solvents were as follows: solvent A=MeCN; solvent B=0.1% diethylamine in EtOH/DCM (50:50). The eluent flow rate was 19 mL/min. The elution was done using 40% of the solvent A and 60% of the solvent B.

Preparation of the Compounds of Structure 1
Method A

All intermediates of the structure 1 have been prepared in analogy to the following procedure from the corresponding amine and aldehyde:

1-(4-Chloro-2-fluorophenyl)-1,2,3,4,6,7,8,9-octahydroimidazo[1,2-a:5,4-c']dipyridine A solution of 2-(5,6,7,8-tetrahydroimidazo[1,2-a]pyridin-2-yl)ethanamine (100 mg), 4-chloro-2-fluorobenzaldehyde (96 mg) and TFA (10 μl) in toluene (5 ml) was stirred at 80° C. for 15 h. The mixture was diluted with 1N aq. NaOH and EA, the layers were separated and the aq. phase was extracted with EA. The combined org. layers were washed with sat. aq. NaCl, dried over MgSO$_4$, filtrated off and evaporated in vacuo. The crude was purified by CC (Büchi Sepacore, 2 g cartridge, solvent A: DCM, solvent B: 7N NH$_3$ in MeOH, gradient in % B: 0 to 1, flow rate: 6 ml/min) to afford 178 mg of 1-(4-chloro-2-fluorophenyl)-1,2,3,4,6,7,8,9-octahydroimidazo[1,2-a:5,4-c']dipyridine as yellow solid. LC-MS (A) t$_R$=0.41 min; [M+H]$^+$: 305.88.

Preparation of the Compounds of Formula (I)
Method B

If not explicitly stated otherwise, all compounds of formula (I) have been prepared in analogy to the following procedure from the corresponding amine and acid:

Example 1.1.1

6-Chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N,N-dimethylpicolinamide To a solution of 2-((2-chloro-6-(dimethylcarbamoyl)pyridin-3-yl)oxy)acetic acid (TFA salt) (25 mg) in DMF (1 ml) was added TBTU (23 mg). The mixture was stirred for 30 min. The 1-(4-chloro-2-fluorophenyl)-1,2,3,4,6,7,8,9-octahydroimidazo[1,2-a:5,4-c]dipyridine (21 mg) and DIPEA (46 μl) were added and the mixture was stirred for 2 h. The crude was purified by preparative LC-MS to afford 26 mg of orange oil. LC-MS (A): t$_R$=0.67 min; [M+H]$^+$: 545.62.
Preparation of the Compounds of Structure 7
Method C Example 5.2.4

2-(2-Chloro-4-morpholinophenoxy)-1-(1-(4-cyclopropyl-2-fluorophenyl)-3,4,6,7,8,9-hexahydropyrido[4',3':4,5]imidazo[1,2-a]pyrazin-2(1H)-yl)ethan-1-one To a solution of tert-butyl-2-(2-(2-chloro-4-morpholinophenoxy)acetyl)-1-(4-cyclopropyl-2-fluorophenyl)-1,3,4,6,8,9-hexahydropyrido[4',3':4,5]imidazo[1,2-a]pyrazine-7(2H)-carboxylate (168 mg) in DCM (15 ml) was added TFA (1.5 ml) at 0° C. and the reaction was stirred 4 h at rt. The mixture was diluted with aq. sat. NaHCO$_3$, the layers were separated and the aq. phase was extracted with DCM. The combined org. layers were washed with sat. aq. NaCl, dried over MgSO$_4$, filtrated off and evaporated in vacuo. The crude was purified by CC (Büchi Sepacore, 10 g cartridge, solvent A: DCM, solvent B: 7N NH$_3$ in MeOH, gradient in % B: 1 to 3, flow rate: 15 ml/min) to afford 112 mg of colourless solid. LC-MS (A) t$_R$=0.68 min; [M+H]$^+$: 566.09.
Preparation of the Compounds of Structure 5
Method D Example 5.2.5

1-(7-Acetyl-1-(4-cyclopropyl-2-fluorophenyl)-3,4,6,7,8,9-hexahydropyrido[4',3':4,5]imidazo[1,2-a]pyrazin-2(1H)-yl)-2-(2-chloro-4-morpholinophenoxy)ethan-1-one To a solution of 2-(2-chloro-4-morpholinophenoxy)-1-(1-(4-cyclopropyl-2-fluorophenyl)-3,4,6,7,8,9-hexahydropyrido[4',3':4,5]imidazo[1,2-a]pyrazin-2(1H)-yl)ethan-1-one (25 mg) in DCM (2 ml) was added at 0° C. acetic acid anhydride (10 μl) and DIPEA (13 μl) and the reaction was stirred 15 h at rt. The mixture was diluted with aq. sat. NaHCO$_3$, the layers were separated and the aq. phase was extracted with DCM. The combined org. layers were washed with sat. aq. NaCl, dried over MgSO$_4$, filtrated off and evaporated in vacuo. The crude was purified by preparative LC-MS to afford 19 mg of colourless solid. LC-MS (A) t$_R$=0.73 min; [M+H]$^+$: 608.15.
Method E Example 5.2.7

2-(2-Chloro-4-morpholinophenoxy)-1-(1-(4-cyclopropyl-2-fluorophenyl)-7-(cyclopropylmethyl)-3,4,6,7,8,9-hexahydropyrido[4',3':4,5]imidazo[1,2-a]pyrazin-2(1H)-yl)ethan-1-one To a solution of 2-(2-chloro-4-morpholinophenoxy)-1-(1-(4-cyclopropyl-2-fluorophenyl)-3,4,6,7,8,9-hexahydropyrido[4',3':4,5]imidazo[1,2-a]pyrazin-2(1H)-yl)ethan-1-one (25 mg) and cyclopropanecarbaldehyde (3.5 μl) in DCM (2 ml) was added at rt acetic acid (3 μl) and sodium triacetoxyborohydride (34 mg) and the reaction was stirred 20 h at rt. The mixture was diluted with 1N aq. NaOH and the solvents were evaporated in vacuo. The crude was purified by preparative LC-MS to afford 14 mg of colourless solid. LC-MS (A) $t_R$=0.78 min; [M+H]$^+$: 620.12.

Following examples were synthesized starting from the appropriate acid derivative and amine following the method B. LC-MS data are listed in table 1. The LC-MS conditions used were LC-MS (A).

TABLE 1

| Example | Name | $t_R$ | [M + H]$^+$ | IC$_{50}$ |
|---|---|---|---|---|
| 1.1.1 | 6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N,N-dimethylpicolinamide | 0.67 | 545.62 | 15 |
| 1.1.2 | 1-(1-(4-chloro-2-fluorophenyl)-3,4,6,7,8,9-hexahydro-imidazo[1,2-a:5,4-c']dipyridin-2(1H)-yl)-2-((2-chloro-6-morpholinopyridin-3-yl)oxy)ethanone | 0.74 | 559.86 | 7 |
| 1.1.3 | N-(6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide | 0.69 | 567.70 | 26 |
| 1.1.4 | 6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropyl-N-methylpicolinamide | 0.72 | 572.23 | 29 |
| 1.1.5 | 1-(1-(4-chloro-2-fluorophenyl)-3,4,6,7,8,9-hexahydro-imidazo[1,2-a:5,4-c']dipyridin-2(1H)-yl)-2-((2-chloro-6-(oxazol-2-yl)pyridin-3-yl)oxy)ethanone | 0.72 | 542.18 | 21 |
| 1.1.6 | 6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropylpicolinamide | 0.72 | 558.01 | 19 |
| 1.1.7 | 6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-ethyl-N-methylpicolinamide | 0.71 | 560.95 | 25 |
| 1.1.8 | 6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-isopropyl-N-methylpicolinamide | 0.73 | 573.95 | 55 |
| 1.1.9 | N-(6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)pyridin-2-yl)-N-methylmethanesulfonamide | 0.74 | 581.83 | 25 |
| 1.1.10 | 1-(1-(4-chloro-2-fluorophenyl)-3,4,6,7,8,9-hexahydro-imidazo[1,2-a:5,4-c']dipyridin-2(1H)-yl)-2-((2-chloro-6-(1,1-dioxidoisothiazolidin-2-yl)pyridin-3-yl)oxy)-ethanone | 0.73 | 593.74 | 17 |
| 1.1.11 | N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-ethylpyridin-2-yl)methanesulfonamide | 0.68 | 561.84 | 8 |
| 1.1.12 | 5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropyl-6-ethylpicolinamide | 0.75 | 551.92 | 9 |
| 1.1.13 | N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-methoxypyridin-2-yl)methanesulfonamide | 0.65 | 563.99 | 347 |
| 1.1.14 | 1-(1-(4-chloro-2-fluorophenyl)-3,4,6,7,8,9-hexahydroimidazo[1,2-a:5,4-c']dipyridin-2(1H)-yl)-2-((2-chloro-6-cyclopropylpyridin-3-yl)oxy)ethanone | 0.77 | 515.05 | 16 |
| 1.1.15 | 1-(1-(4-chloro-2-fluorophenyl)-3,4,6,7,8,9-hexahydroimidazo[1,2-a:5,4-c']dipyridin-2(1H)-yl)-2-((2-ethyl-6-methylpyridin-3-yl)oxy)ethanone | 0.55 | 483.10 | 39 |
| 1.1.16 | (S)-6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropylpicolinamide [a] | 0.71 | 557.81 | 12 |
| 1.1.17 | (S)-N-(6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide [b] | 0.69 | 567.93 | 23 |
| 1.1.18 | (S)-N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-ethylpyridin-2-yl)methanesulfonamide [a] | 0.69 | 561.80 | 8 |
| 1.1.19 | N-(6-chloro-5-(1-(1-(4-chloro-2-fluorophenyl)-1,2,3,4,6,7,8,9-octahydroimidazo[1,2-a:5,4-c']dipyridine-2-carbonyl)cyclopropoxy)pyridin-2-yl)methanesulfonamide | 0.71 | 593.79 | 58 |
| 1.1.20 | N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-cyclopropylpyridin-2-yl)methanesulfonamide | 0.72 | 574.04 | 21 |
| 1.1.21 | 1-(1-(4-chloro-2-fluorophenyl)-3,4,6,7,8,9-hexahydroimidazo[1,2-a:5,4-c']dipyridin-2(1H)-yl)-2-((2-chloro-6-(dimethylamino)pyridin-3-yl)oxy)ethan-1-one | 0.77 | 518.04 | 13 |
| 1.1.22 | 5-(2-(1-(4-chloro-2-fluorophenyl)-3,4,6,7,8,9-hexahydroimidazo[1,2-a:5,4-c']dipyridin-2(1H)-yl)-2-oxoethoxy)-N,6-dicyclopropylpicolinamide | 0.75 | 564.17 | 10 |
| 1.1.23 | 1-(1-(4-chloro-2-fluorophenyl)-3,4,6,7,8,9-hexahydroimidazo[1,2-a:5,4-c']dipyridin-2(1H)-yl)-2-((2-chloro-6-(methyl(2,2,2-trifluoroethyl)amino)pyridin-3-yl)oxy)ethan-1-one | 0.81 | 586.16 | 9 |

TABLE 1-continued

| Example | Name | $t_R$ | $[M + H]^+$ | $IC_{50}$ |
|---|---|---|---|---|
| 1.1.24 | 1-(1-(4-chloro-2-fluorophenyl)-3,4,6,7,8,9-hexahydroimidazo[1,2-a:5,4-c']dipyridin-2(1H)-yl)-2-((2-chloro-6-((2-methoxyethyl)(methyl)amino)pyridin-3-yl)oxy)ethan-1-one | 0.77 | 561.95 | 62 |
| 1.1.25 | 6-chloro-5-((1-(1-(4-chloro-2-fluorophenyl)-3,4,6,7,8,9-hexahydroimidazo[1,2-a:5,4-c']dipyridin-2(1H)-yl)-2-methyl-1-oxopropan-2-yl)oxy)-N,N-dimethylpicolinamide | 0.72 | 574.07 | 146 |
| 1.1.26 | 6-chloro-5-(1-(1-(4-chloro-2-fluorophenyl)-1,2,3,4,6,7,8,9-octahydroimidazo[1,2-a:5,4-c']dipyridine-2-carbonyl)cyclopropoxy)-N,N-dimethylpicolinamide | 0.71 | 572.06 | 51 |
| 1.1.28 | 1-(1-(4-chloro-2-fluorophenyl)-3,4,6,7,8,9-hexahydroimidazo[1,2-a:5,4-c']dipyridin-2(1H)-yl)-2-((2-chloro-6-(methylsulfonyl)pyridin-3-yl)oxy)ethan-1-one | 0.70 | 553.01 | 90 |
| 1.1.29 | 6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N,N-dimethylpyridine-2-sulfonamide | 0.74 | 582.00 | 129 |
| 1.2.1 | N-(6-chloro-5-(2-(1-(2-fluoro-4-methylphenyl)-3,4,6,7,8,9-hexahydroimidazo[1,2-a:5,4-c']dipyridin-2(1H)-yl)-2-oxoethoxy)pyridin-2-yl)methanesulfonamide | 0.68 | 548.21 | 41 |
| 1.2.2 | 2-((2-chloro-6-(oxazol-2-yl)pyridin-3-yl)oxy)-1-(1-(2-fluoro-4-methylphenyl)-3,4,6,7,8,9-hexahydroimi-dazo[1,2-a:5,4-c']dipyridin-2(1H)-yl)ethanone | 0.71 | 522.21 | 11 |
| 1.2.3 | 6-chloro-N-cyclopropyl-5-(2-(1-(2-fluoro-4-methyl-phenyl)-3,4,6,7,8,9-hexahydroimidazo[1,2-a:5,4-c']dipyridin-2(1H)-yl)-2-oxoethoxy)-N-methylpicolinamide | 0.71 | 552.27 | 22 |
| 1.3.1 | N-(6-chloro-5-(2-(1-(5-cyclopropyl-3-fluoropyridin-2-yl)-3,4,6,7,8,9-hexahydroimidazo[1,2-a:5,4-c']dipyridin-2(1H)-yl)-2-oxoethoxy)pyridin-2-yl)methanesulfonamide | 0.66 | 575.26 | 63 |
| 1.3.2 | N-cyclopropyl-5-(2-(1-(5-cyclopropyl-3-fluoropyridin-2-yl)-3,4,6,7,8,9-hexahydroimidazo[1,2-a:5,4-c']dipyridin-2(1H)-yl)-2-oxoethoxy)-6-ethylpicolinamide | 0.72 | 559.00 | 7 |
| 1.3.3 | (R)-N-cyclopropyl-5-(2-(1-(5-cyclopropyl-3-fluoropyridin-2-yl)-3,4,6,7,8,9-hexahydroimidazo[1,2-a:5,4-c']dipyridin-2(1H)-yl)-2-oxoethoxy)-6-ethylpicolinamide $^{g)}$ | 0.72 | 558.92 | 7 |
| 1.4.1 | 6-chloro-5-(2-(1-(5-(dimethylcarbamoyl)-3-fluoro-thiophen-2-yl)-3,4,6,7,8,9-hexahydroimidazo[1,2-a:5,4-c']dipyridin-2(1H)-yl)-2-oxoethoxy)-N,N-dimethyl-picolinamide | 0.60 | 589.26 | 55 |
| 1.4.2 | 5-(2-(2-((2-ethyl-6-(methylsulfonamido)pyridin-3-yl)oxy)acetyl)-1,2,3,4,6,7,8,9-octahydroimidazo[1,2-a:5,4-c']dipyridin-1-yl)-4-fluoro-N,N-dimethylthiophene-2-carboxamide | 0.61 | 604.91 | 38 |
| 1.5.1 | Ethyl 2-(2-((2-chloro-6-(methylsulfonamido)pyridin-3-yl)oxy)acetyl)-1,2,3,4,6,7,8,9-octahydroimidazo[1,2-a:5,4-c']dipyridin-1-yl)thiazole-4-carboxylate | 0.64 | 595.12 | 558 |
| 1.6.1 | N-(6-chloro-5-(2-(1-(3-fluoro-5-methylpyridin-2-yl)-3,4,6,7,8,9-hexahydroimidazo[1,2-a:5,4-c']dipyridin-2(1H)-yl)-2-oxoethoxy)pyridin-2-yl)methanesulfonamide | 0.62 | 549.22 | 58 |
| 1.6.2 | 2-((2-chloro-6-(oxazol-2-yl)pyridin-3-yl)oxy)-1-(1-(3-fluoro-5-methylpyridin-2-yl)-3,4,6,7,8,9-hexahydroimidazo[1,2-a:5,4-c']dipyridin-2(1H)-yl)ethanone | 0.65 | 523.22 | 41 |
| 1.6.3 | 6-chloro-N-cyclopropyl-5-(2-(1-(3-fluoro-5-methyl-pyridin-2-yl)-3,4,6,7,8,9-hexahydroimidazo[1,2-a:5,4-c']dipyridin-2(1H)-yl)-2-oxoethoxy)-N-methyl-picolinamide | 0.65 | 552.96 | 114 |
| 1.6.4 | 6-chloro-5-(2-(1-(3-fluoro-5-methylpyridin-2-yl)-3,4,6,7,8,9-hexahydroimidazo[1,2-a:5,4-c']dipyridin-2(1H)-yl)-2-oxoethoxy)-N,N-dimethylpicolinamide | 0.61 | 527.30 | 33 |
| 1.6.5 | 2-((2-chloro-6-(1,1-dioxidoisothiazolidin-2-yl)pyridin-3-yl)oxy)-1-(1-(3-fluoro-5-methylpyridin-2-yl)-3,4,6,7,8,9-hexahydroimidazo[1,2-a:5,4-c']dipyridin-2(1H)-yl)ethanone | 0.66 | 574.97 | 16 |
| 1.6.6 | N-(6-chloro-5-(2-(1-(3-fluoro-5-methylpyridin-2-yl)-3,4,6,7,8,9-hexahydroimidazo[1,2-a:5,4-c']dipyridin-2(1H)-yl)-2-oxoethoxy)pyridin-2-yl)-N-methylmethanesulfonamide | 0.67 | 562.98 | 44 |
| 1.6.7 | N-cyclopropyl-6-ethyl-5-(2-(1-(3-fluoro-5-methylpyridin-2-yl)-3,4,6,7,8,9-hexahydroimidazo[1,2-a:5,4-c']dipyridin-2(1H)-yl)-2-oxoethoxy)picolinamide | 0.69 | 533.12 | 8 |
| 1.8.1 | 6-chloro-N-cyclopropyl-5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)-N-methylpicolinamide | 0.74 | 578.10 | 20 |
| 1.8.2 | 2-((2-chloro-6-(oxazol-2-yl)pyridin-3-yl)oxy)-1-(1-(4-cyclopropyl-2-fluorophenyl)-3,4,6,7,8,9-hexahydroimi-dazo[1,2-a:5,4-c']dipyridin-2(1H)-yl)ethanone | 0.74 | 548.25 | 17 |
| 1.8.3 | N-(6-chloro-5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide | 0.71 | 574.32 | 22 |
| 1.8.4 | 6-chloro-5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)-N,N-dimethylpicolinamide | 0.70 | 552.40 | 11 |
| 1.8.5 | 6-chloro-N-cyclopropyl-5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)picolinamide | 0.75 | 564.11 | 24 |

TABLE 1-continued

| Example | Name | $t_R$ | $[M + H]^+$ | $IC_{50}$ |
|---|---|---|---|---|
| 1.8.6 | (S)-6-chloro-N-cyclopropyl-5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)picolinamide [c] | 0.74 | 563.91 | 9 |
| 1.8.7 | N-(5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)-4-ethylpyrimidin-2-yl)methanesulfonamide | 0.69 | 569.06 | 54 |
| 1.9.1 | 2-((2-chloro-6-(oxazol-2-yl)pyridin-3-yl)oxy)-1-(1-(2,3-difluoro-4-methylphenyl)-3,4,6,7,8,9-hexahydroimida-zo[1,2-a:5,4-c']dipyridin-2(1H)-yl)ethanone | 0.71 | 539.92 | 20 |
| 1.9.2 | N-(6-chloro-5-(2-(1-(2,3-difluoro-4-methylphenyl)-3,4,6,7,8,9-hexahydroimidazo[1,2-a:5,4-c']dipyridin-2(1H)-yl)-2-oxoethoxy)pyridin-2-yl)methanesulfonamide | 0.69 | 565.86 | 26 |
| 1.9.3 | 6-chloro-N-cyclopropyl-5-(2-(1-(2,3-difluoro-4-methyl-phenyl)-3,4,6,7,8,9-hexahydroimidazo[1,2-a:5,4-c']di-pyridin-2(1H)-yl)-2-oxoethoxy)-N-methylpicolinamide | 0.71 | 569.91 | 27 |
| 1.9.4 | 2-((2-chloro-6-(4-methylpiperazin-1-yl)pyridin-3-yl)oxy)-1-(1-(2,3-difluoro-4-methylphenyl)-3,4,6,7,8,9-hexahydroimidazo[1,2-a:5,4-c']dipyridin-2(1H)-yl)ethanone | 0.58 | 570.95 | 18 |
| 1.9.5 | 2-(2-chloro-4-(trifluoromethyl)phenoxy)-1-(1-(2,3-difluoro-4-methylphenyl)-3,4,6,7,8,9-hexahydroimidazo[1,2-a:5,4-c']dipyridin-2(1H)-yl)ethanone | 0.82 | 539.89 | 87 |
| 1.9.6 | 2-((2-chloro-6-(1,1-dioxidoisothiazolidin-2-yl)pyridin-3-yl)oxy)-1-(1-(2,3-difluoro-4-methylphenyl)-3,4,6,7,8,9-hexahydroimidazo[1,2-a:5,4-c']dipyridin-2(1H)-yl)ethanone | 0.71 | 592.14 | 9 |
| 1.9.7 | N-(5-(2-(1-(2,3-difluoro-4-methylphenyl)-3,4,6,7,8,9-hexahydroimidazo[1,2-a:5,4-c']dipyridin-2(1H)-yl)-2-oxoethoxy)-6-ethylpyridin-2-yl)methanesulfonamide | 0.70 | 560.12 | 8 |
| 1.9.8 | 6-chloro-N-cyclopropyl-5-(2-(1-(2,3-difluoro-4-methylphenyl)-3,4,6,7,8,9-hexahydroimidazo[1,2-a:5,4-c']dipyridin-2(1H)-yl)-2-oxoethoxy)picolinamide | 0.73 | 556.10 | 16 |
| 1.9.9 | N-(5-(2-(1-(2,3-difluoro-4-methylphenyl)-3,4,6,7,8,9-hexahydroimidazo[1,2-a:5,4-c']dipyridin-2(1H)-yl)-2-oxoethoxy)-4-ethylpyrimidin-2-yl)methanesulfonamide | 0.67 | 560.98 | 58 |
| 1.9.10 | N-cyclopropyl-5-(2-(1-(2,3-difluoro-4-methylphenyl)-3,4,6,7,8,9-hexahydroimidazo[1,2-a:5,4-c']dipyridin-2(1H)-yl)-2-oxoethoxy)-6-ethylpicolinamide | 0.74 | 549.98 | 9 |
| 1.10.1 | N-(6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide | 0.59 | 551.35 | 12 |
| 1.10.2 | 6-chloro-N-cyclopropyl-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-N-methylpicolinamide | 0.62 | 554.96 | 82 |
| 1.10.3 | 2-((2-chloro-6-(oxazol-2-yl)pyridin-3-yl)oxy)-1-(1-(2,4-dimethylthiazol-5-yl)-3,4,6,7,8,9-hexahydroimi-dazo[1,2-a:5,4-c']dipyridin-2(1H)-yl)ethanone | 0.62 | 525.22 | 16 |
| 1.10.4 | 6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-N-methylpicolinamide | 0.60 | 515.18 | 36 |
| 1.10.5 | 6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-N,N-dimethylpicolinamide | 0.58 | 530.10 | 85 |
| 1.10.6 | 6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)picolinonitrile | 0.64 | 483.16 | 77 |
| 1.10.7 | 2-((2-chloro-6-(trifluoromethyl)pyridin-3-yl)oxy)-1-(1-(2,4-dimethylthiazol-5-yl)-3,4,6,7,8,9-hexahydroimi-dazo[1,2-a:5,4-c']dipyridin-2(1H)-yl)ethanone | 0.70 | 526.18 | 177 |
| 1.10.8 | 2-((2-chloro-6-cyclopropylpyridin-3-yl)oxy)-1-(1-(2,4-dimethylthiazol-5-yl)-3,4,6,7,8,9-hexahydroimi-dazo[1,2-a:5,4-c']dipyridin-2(1H)-yl)ethanone | 0.68 | 498.01 | 33 |
| 1.10.9 | 2-((2-chloro-6-(4-methylpiperazin-1-yl)pyridin-3-yl)oxy)-1-(1-(2,4-dimethylthiazol-5-yl)-3,4,6,7,8,9-hexahydroimidazo[1,2-a:5,4-c']dipyridin-2(1H)-yl)ethanone | 0.51 | 556.34 | 17 |
| 1.10.10 | 3-chloro-4-(2-(1-(2,4-dimethylthiazol-5-yl)-3,4,6,7,8,9-hexahydroimidazo[1,2-a:5,4-c']dipyridin-2(1H)-yl)-2-oxoethoxy)benzonitrile | 0.66 | 481.96 | 207 |
| 1.10.11 | 2-(2-chloro-4-(trifluoromethyl)phenoxy)-1-(1-(2,4-dimethylthiazol-5-yl)-3,4,6,7,8,9-hexahydroimi-dazo[1,2-a:5,4-c']dipyridin-2(1H)-yl)ethanone | 0.74 | 525.19 | 132 |
| 1.10.12 | N-(6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)pyridin-2-yl)-N-methylmethanesulfonamide | 0.64 | 564.89 | 20 |
| 1.10.13 | N-(5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpyridin-2-yl)methanesulfonamide | 0.59 | 544.86 | 8 |
| 1.10.14 | 2-((2-chloro-6-(1,1-dioxidoisothiazolidin-2-yl)pyridin-3-yl)oxy)-1-(1-(2,4-dimethylthiazol-5-yl)-3,4,6,7,8,9-hexahydroimidazo[1,2-a:5,4-c']dipyridin-2(1H)-yl)ethanone | 0.63 | 576.87 | 14 |

TABLE 1-continued

| Example | Name | $t_R$ | $[M + H]^+$ | $IC_{50}$ |
|---|---|---|---|---|
| 1.10.15 | N-cyclopropyl-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpicolinamide | 0.66 | 534.93 | 8 |
| 1.10.16 | (R)-N-(5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpyridin-2-yl)methanesulfonamide [d] | 0.60 | 544.96 | 6 |
| 1.10.17 | (R)-N-cyclopropyl-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpicolinamide [d] | 0.64 | 535.11 | 5 |
| 1.10.18 | N-(5-(2-(1-(2,4-dimethylthiazol-5-yl)-3,4,6,7,8,9-hexahydroimidazo[1,2-a:5,4-c']dipyridin-2(1H)-yl)-2-oxoethoxy)-4-ethylpyrimidin-2-yl)methanesulfonamide | 0.58 | 545.75 | 121 |
| 1.10.19 | 1-(1-(2,4-dimethylthiazol-5-yl)-3,4,6,7,8,9-hexahydroimidazo[1,2-a:5,4-c']dipyridin-2(1H)-yl)-2-((6-(1,1-dioxidoisothiazolidin-2-yl)-2-ethylpyridin-3-yl)oxy)ethan-1-one | 0.65 | 570.91 | 11 |
| 1.11.1 | N-(6-chloro-5-(2-(1-(2-ethyl-4-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide | 0.60 | 564.92 | 49 |
| 1.12.1 | N-(6-chloro-5-(2-(1-(2-isopropyl-4-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide | 0.63 | 578.94 | 819 |
| 1.13.1 | N-(6-ethyl-5-(2-(1-(4-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide207 | 0.58 | 530.89 | 44 |
| 1.13.2 | 2-((6-(1,1-dioxidoisothiazoli132din-2-yl)-2-ethylpyridin-3-yl)oxy)-1-(1-(4-methylthiazol-5-yl)-3,4,6,7,8,9-hexahydroimidazo[1,2-a:5,4-c']dipyridin-2(1H)-yl)ethanone | 0.64 | 556.97 | 15 |
| 1.14.1 | N-(6-ethyl-5-(2-(1-(3-fluorothiophen-2-yl)-3,4,6,7,8,9-hexahydroimidazo[1,2-a:5,4-c']dipyridin-2(1H)-yl)-2-oxoethoxy)pyridin-2-yl)methanesulfonamide | 0.64 | 533.89 | 16 |
| 1.14.2 | N-cyclopropyl-6-ethyl-5-(2-(1-(3-fluorothiophen-2-yl)-3,4,6,7,8,9-hexahydroimidazo[1,2-a:5,4-c']dipyridin-2(1H)-yl)-2-oxoethoxy)picolinamide | 0.70 | 523.94 | 12 |
| 1.15.1 | N-(6-ethyl-5-(2-(1-(2-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide | 0.59 | 530.90 | 36 |
| 1.15.2 | 2-((6-(1,1-dioxidoisothiazolidin-2-yl)-2-ethylpyridin-3-yl)oxy)-1-(1-(2-methylthiazol-5-yl)-3,4,6,7,8,9-hexahydroimidazo[1,2-a:5,4-c']dipyridin-2(1H)-yl)ethanone | 0.64 | 556.92 | 27 |
| 1.16.1 | N-(6-ethyl-5-(2-oxo-2-(1-(2-phenylthiazol-5-yl)-3,4,6,7,8,9-hexahydroimidazo[1,2-a:5,4-c']dipyridin-2(1H)-yl)ethoxy)pyridin-2-yl)methanesulfonamide | 0.69 | 592.90 | 225 |
| 1.17.1 | N-(6-ethyl-5-(2-oxo-2-(1-(3-phenyl-1,2,4-oxadiazol-5-yl)-3,4,6,7,8,9-hexahydroimidazo[1,2-a:5,4-c']dipyridin-2(1H)-yl)ethoxy)pyridin-2-yl)methanesulfonamide | 0.70 | 577.82 | 79 |
| 1.18.1 | N-(6-chloro-5-(2-(1-(4-methyl-2-(trifluoromethyl)thiazol-5-yl)-3,4,6,7,8,9-hexahydroimidazo[1,2-a:5,4-c']dipyridin-2(1H)-yl)-2-oxoethoxy)pyridin-2-yl)methanesulfonamide | 0.67 | 604.92 | 126 |
| 1.19.1 | N-(6-chloro-5-(2-(1-(5-fluoro-3-methylpyridin-2-yl)-3,4,6,7,8,9-hexahydroimidazo[1,2-a:5,4-c']dipyridin-2(1H)-yl)-2-oxoethoxy)pyridin-2-yl)methanesulfonamide | 0.63 | 549.02 | 113 |
| 1.20.1 | 6-chloro-N-cyclopropyl-5-(2-(1-(2-fluoro-4-(trifluoromethoxy)phenyl)-3,4,6,7,8,9-hexahydroimidazo[1,2-a:5,4-c']dipyridin-2(1H)-yl)-2-oxoethoxy)picolinamide | 0.76 | 607.99 | 26 |
| 1.20.2 | N-(6-chloro-5-(2-(1-(2-fluoro-4-(trifluoromethoxy)phenyl)-3,4,6,7,8,9-hexahydroimidazo[1,2-a:5,4-c']dipyridin-2(1H)-yl)-2-oxoethoxy)pyridin-2-yl)methanesulfonamide | 0.73 | 617.91 | 37 |
| 1.21.1 | 6-chloro-N-cyclopropyl-5-(2-(1-(2-fluoro-4-methoxyphenyl)-3,4,6,7,8,9-hexahydroimidazo[1,2-a:5,4-c']dipyridin-2(1H)-yl)-2-oxoethoxy)picolinamide | 0.70 | 554.10 | 18 |
| 1.21.2 | N-(6-chloro-5-(2-(1-(2-fluoro-4-methoxyphenyl)-3,4,6,7,8,9-hexahydroimidazo[1,2-a:5,4-c']dipyridin-2(1H)-yl)-2-oxoethoxy)pyridin-2-yl)methanesulfonamide | 0.66 | 564.02 | 78 |
| 1.22.1 | N-(6-chloro-5-(2-(1-(4-cyano-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide | 0.64 | 559.03 | 48 |
| 1.22.2 | 6-chloro-5-(2-(1-(4-cyano-2-fluorophenyl)-3,4,6,7,8,9-hexahydroimidazo[1,2-a:5,4-c']dipyridin-2(1H)-yl)-2-oxoethoxy)-N-cyclopropylpicolinamide | 0.67 | 549.20 | 28 |
| 1.23.1 | methyl-4-(2-(2-((6-chloro-6-(methylsulfonamido)pyridin-3-yl)oxy)acetyl)-1,2,3,4,6,7,8,9-octahydroimidazo[1,2-a:5,4-c']dipyridin-1-yl)-3-fluorobenzoate | 0.66 | 592.01 | 21 |
| 1.23.2 | methyl (R)-4-(2-(2-((6-chloro-6-(cyclopropylcarbamoyl)pyridin-3-yl)oxy)acetyl)-1,2,3,4,6,7,8,9-octahydroimidazo[1,2-a:5,4-c']dipyridin-1-yl)-3-fluorobenzoate | 0.70 | 582.06 | 56 |
| 1.24.1 | 6-chloro-N-cyclopropyl-5-(2-(1-(2-fluoro-4-(2-hydroxypropan-2-yl)phenyl)-3,4,6,7,8,9-hexahydroimidazo[1,2-a:5,4-c']dipyridin-2(1H)-yl)-2-oxoethoxy)picolinamide | 0.65 | 582.18 | 68 |

TABLE 1-continued

| Example | Name | $t_R$ | $[M + H]^+$ | $IC_{50}$ |
|---|---|---|---|---|
| 1.24.2 | N-(6-chloro-5-(2-(1-(2-fluoro-4-(2-hydroxypropan-2-yl)phenyl)-3,4,6,7,8,9-hexahydroimidazo[1,2-a:5,4-c']dipyridin-2(1H)-yl)-2-oxoethoxy)pyridin-2-yl)methanesulfonamide | 0.61 | 592.15 | 131 |
| 1.25.1 | 6-chloro-N-cyclopropyl-5-(2-(1-(2-fluoro-4-(2-methoxypropan-2-yl)phenyl)-3,4,6,7,8,9-hexahydroimidazo[1,2-a:5,4-c']dipyridin-2(1H)-yl)-2-oxoethoxy)picolinamide | 0.71 | 596.23 | 68 |
| 1.25.2 | N-(6-chloro-5-(2-(1-(2-fluoro-4-(2-methoxypropan-2-yl)phenyl)-3,4,6,7,8,9-hexahydroimidazo[1,2-a:5,4-c']dipyridin-2(1H)-yl)-2-oxoethoxy)pyridin-2-yl)methanesulfonamide | 0.67 | 606.15 | 303 |
| 1.26.1 | 6-chloro-N-cyclopropyl-5-(2-(1-(2-fluoro-4-(methoxymethyl)phenyl)-3,4,6,7,8,9-hexahydroimidazo[1,2-a:5,4-c']dipyridin-2(1H)-yl)-2-oxoethoxy)picolinamide | 0.69 | 568.16 | 19 |
| 1.26.2 | N-(6-chloro-5-(2-(1-(2-fluoro-4-(methoxymethyl)phenyl)-3,4,6,7,8,9-hexahydroimidazo[1,2-a:5,4-c']dipyridin-2(1H)-yl)-2-oxoethoxy)pyridin-2-yl)methanesulfonamide | 0.65 | 578.29 | 25 |
| 1.27.1 | 6-chloro-N-cyclopropyl-5-(2-(1-(2-fluoro-4-(2-methoxyethoxy)phenyl)-3,4,6,7,8,9-hexahydroimidazo[1,2-a:5,4-c']dipyridin-2(1H)-yl)-2-oxoethoxy)picolinamide | 0.69 | 598.19 | 60 |
| 1.27.2 | N-(6-chloro-5-(2-(1-(2-fluoro-4-(2-methoxyethoxy)phenyl)-3,4,6,7,8,9-hexahydroimidazo[1,2-a:5,4-c']dipyridin-2(1H)-yl)-2-oxoethoxy)pyridin-2-yl)methanesulfonamide | 0.65 | 608.15 | 34 |
| 1.28.1 | 6-chloro-N-cyclopropyl-5-(2-(1-(2-fluoro-4-(2-hydroxyethoxy)phenyl)-3,4,6,7,8,9-hexahydroimidazo[1,2-a:5,4-c']dipyridin-2(1H)-yl)-2-oxoethoxy)picolinamide | 0.63 | 584.08 | 54 |
| 1.28.2 | N-(6-chloro-5-(2-(1-(2-fluoro-4-(2-hydroxyethoxy)phenyl)-3,4,6,7,8,9-hexahydroimidazo[1,2-a:5,4-c']dipyridin-2(1H)-yl)-2-oxoethoxy)pyridin-2-yl)methanesulfonamide | 0.59 | 594.25 | 21 |
| 2.1.1 | N-(6-chloro-5-(2-(1-(4-chloro-2-fluorophenyl)-3,4,7,8-tetrahydro-1H-pyrrolo[2',1':2,3]imidazo[4,5-c]pyridin-2(6H)-yl)-2-oxoethoxy)pyridin-2-yl)methanesulfonamide | 0.67 | 553.76 | 13 |
| 2.1.2 | N-(5-(2-(1-(4-chloro-2-fluorophenyl)-3,4,7,8-tetrahydro-1H-pyrrolo[2',1':2,3]imidazo[4,5-c]pyridin-2(6H)-yl)-2-oxoethoxy)-6-ethylpyridin-2-yl)methanesulfonamide | 0.67 | 547.90 | 13 |
| 2.1.3 | 1-(1-(4-chloro-2-fluorophenyl)-3,4,7,8-tetrahydro-1H-pyrrolo[2',1':2,3]imidazo[4,5-c]pyridin-2(6H)-yl)-2-((6-(1,1-dioxidoisothiazolidin-2-yl)-2-ethylpyridin-3-yl)oxy)ethanone | 0.72 | 573.92 | 8 |
| 2.2.1 | N-(6-chloro-5-(2-(1-(2-fluoro-4-methylphenyl)-3,4,7,8-tetrahydro-1H-pyrrolo[2',1':2,3]imidazo[4,5-c]pyridin-2(6H)-yl)-2-oxoethoxy)pyridin-2-yl)methanesulfonamide | 0.66 | 533.97 | 15 |
| 2.3.1 | N-(5-(2-(1-(2,3-difluoro-4-methylphenyl)-3,4,7,8-tetrahydro-1H-pyrrolo[2',1':2,3]imidazo[4,5-c]pyridin-2(6H)-yl)-2-oxoethoxy)-6-ethylpyridin-2-yl)methanesulfonamide | 0.67 | 545.82 | 8 |
| 2.4.1 | 1-(1-(2,4-dimethylthiazol-5-yl)-3,4,7,8-tetrahydro-1H-pyrrolo[2',1':2,3]imidazo[4,5-c]pyridin-2(6H)-yl)-2-((6-(1,1-dioxidoisothiazolidin-2-yl)-2-ethylpyridin-3-yl)oxy)ethanone | 0.62 | 556.92 | 8 |
| 2.4.2 | (R)-N-(5-(2-(1-(2,4-dimethylthiazol-5-yl)-3,4,7,8-tetrahydro-1H-pyrrolo[2',1':2,3]imidazo[4,5-c]pyridin-2(6H)-yl)-2-oxoethoxy)-6-ethylpyridin-2-yl)methanesulfonamide [d] | 0.57 | 530.87 | 7 |
| 2.4.3 | (R)-N-cyclopropyl-5-(2-(1-(2,4-dimethylthiazol-5-yl)-3,4,7,8-tetrahydro-1H-pyrrolo[2',1':2,3]imidazo[4,5-c]pyridin-2(6H)-yl)-2-oxoethoxy)-6-ethylpicolinamide [d] | 0.64 | 520.94 | 9 |
| 2.4.4 | (R)-1-(1-(2,4-dimethylthiazol-5-yl)-3,4,7,8-tetrahydro-1H-pyrrolo[2',1':2,3]imidazo[4,5-c]pyridin-2(6H)-yl)-2-((6-(1,1-dioxidoisothiazolidin-2-yl)-2-ethylpyridin-3-yl)oxy)ethanone [d] | 0.61 | 557.04 | 7 |
| 3.1.1 | N-(6-chloro-5-(2-(1-(4-chloro-2-fluorophenyl)-3,4,7,8,9,10-hexahydro-1H-pyrido[4',3':4,5]imidazo[1,2-a]azepin-2(6H)-yl)-2-oxoethoxy)pyridin-2-yl)methanesulfonamide | 0.70 | 582.08 | 26 |
| 3.2.1 | N-(6-chloro-5-(2-(1-(2-fluoro-4-methylphenyl)-3,4,7,8,9,10-hexahydro-1H-pyrido[4',3':4,5]imidazo-[1,2-a]azepin-2(6H)-yl)-2-oxoethoxy)pyridin-2-yl)methanesulfonamide | 0.69 | 561.95 | 21 |
| 4.1.1 | N-(6-chloro-5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)pyridin-2-yl)methanesulfonamide | 0.68 | 571.80 | 19 |
| 4.1.2 | 1-(5-(4-chloro-2-fluorophenyl)-2,3,7,8-tetrahydrothiazolo[2',3':2,3]imidazo[4,5-c]pyridin-6(5H)-yl)-2-((2-chloro-6-(1,1-dioxidoisothiazolidin-2-yl)pyridin-3-yl)oxy)ethanone | 0.72 | 597.84 | 7 |
| 4.1.3 | N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide | 0.69 | 565.92 | 16 |
| 4.1.4 | N-(6-chloro-5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)pyridin-2-yl)-N-methylmethanesulfonamide | 0.74 | 586.02 | 16 |
| 4.1.5 | 1-(5-(4-chloro-2-fluorophenyl)-2,3,7,8-tetrahydrothiazolo[2',3':2,3]imidazo[4,5-c]pyridin-6(5H)-yl)-2-((2-chloro-6-(5-methyl-1,1-dioxido-1,2,5-thiadiazolidin-2-yl)pyridin-3-yl)oxy)ethanone | 0.74 | 612.82 | 12 |

TABLE 1-continued

| Example | Name | $t_R$ | $[M + H]^+$ | $IC_{50}$ |
|---|---|---|---|---|
| 4.1.6 | 1-(5-(4-chloro-2-fluorophenyl)-2,3,7,8-tetrahydrothiazolo[2',3':2,3]imidazo[4,5-c]pyridin-6(5H)-yl)-2-((6-(1,1-dioxidoisothiazolidin-2-yl)-2-ethylpyridin-3-yl)oxy)ethanone | 0.74 | 591.98 | 12 |
| 4.1.7 | N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)-N',N'-dimethyl-sulfamide | 0.72 | 594.76 | 76 |
| 4.1.8 | 1-(5-(4-chloro-2-fluorophenyl)-2,3,7,8-tetrahydrothiazolo[2',3':2,3]imidazo[4,5-c]pyridin-6(5H)-yl)-2-((2-ethyl-6-methylpyridin-3-yl)oxy)ethanone | 0.56 | 487.05 | 28 |
| 4.1.9 | 5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-N-cyclopropyl-6-ethylpicolinamide | 0.73 | 555.88 | 31 |
| 4.1.10 | N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-4-ethylpyrimidin-2-yl)methanesulfonamide | 0.67 | 566.96 | 67 |
| 4.1.11 | 1-(5-(4-chloro-2-fluorophenyl)-2,3,7,8-tetrahydrothiazolo[2',3':2,3]imidazo[4,5-c]pyridin-6(5H)-yl)-2-((2-chloro-4-ethylpyrimidin-5-yl)oxy)ethanone | 0.73 | 508.02 | 185 |
| 4.1.12 | 6-chloro-5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-N-cyclopropylpicolinamide | 0.72 | 561.85 | 9 |
| 4.1.13 | 1-(5-(4-chloro-2-fluorophenyl)-2,3,7,8-tetrahydrothiazolo[2',3':2,3]imidazo[4,5-c]pyridin-6(5H)-yl)-2-((2-chloro-6-cyclopropylpyridin-3-yl)oxy)ethanone | 0.77 | 519.00 | 11 |
| 4.1.14 | 1-(5-(4-chloro-2-fluorophenyl)-2,3,7,8-tetrahydrothiazolo[2',3':2,3]imidazo[4,5-c]pyridin-6(5H)-yl)-2-((6-cyclopropyl-2-ethylpyridin-3-yl)oxy)ethanone | 0.59 | 512.84 | 16 |
| 4.1.15 | (S)-N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide [e] | 0.68 | 565.89 | 6 |
| 4.1.16 | (S)-1-(5-(4-chloro-2-fluorophenyl)-2,3,7,8-tetrahydrothiazolo[2',3':2,3]imidazo[4,5-c]pyridin-6(5H)-yl)-2-((2-chloro-6-(1,1-dioxidoisothiazolidin-2-yl)pyridin-3-yl)oxy)ethanone [e] | 0.72 | 599.81 | 6 |
| 4.2.1 | N-cyclopropyl-5-(2-(5-(5-cyclopropyl-3-fluoropyridin-2-yl)-2,3,7,8-tetrahydrothiazolo[2',3':2,3]imidazo[4,5-c]pyridin-6(5H)-yl)-2-oxoethoxy)-6-ethylpicolinamide | 0.71 | 562.92 | 8 |
| 4.2.2 | N-(5-(2-(5-(5-cyclopropyl-3-fluoropyridin-2-yl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide | 0.65 | 572.88 | 8 |
| 4.2.3 | (R)-N-cyclopropyl-5-(2-(5-(5-cyclopropyl-3-fluoropyridin-2-yl)-2,3,7,8-tetrahydrothiazolo[2',3':2,3]imidazo[4,5-c]pyridin-6(5H)-yl)-2-oxoethoxy)-6-ethylpicolinamide [f] | 0.72 | 562.89 | 16 |
| 4.3.1 | N-(5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide | 0.71 | 571.80 | 6 |
| 4.3.2 | N-(6-chloro-5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)pyridin-2-yl)methanesulfonamide | 0.70 | 577.75 | 10 |
| 4.3.3 | 6-chloro-N-cyclopropyl-5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)picolinamide | 0.74 | 568.01 | 14 |
| 4.3.4 | N-(5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)-4-ethylpyrimidin-2-yl)methanesulfonamide | 0.69 | 572.97 | 25 |
| 4.4.1 | N-(5-(2-(5-(2,3-difluoro-4-methylphenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide | 0.69 | 563.91 | 6 |
| 4.4.2 | 6-chloro-N-cyclopropyl-5-(2-(5-(2,3-difluoro-4-methylphenyl)-2,3,7,8-tetrahydrothiazolo[2',3':2,3]imidazo[4,5-c]pyridin-6(5H)-yl)-2-oxoethoxy)picolinamide | 0.72 | 560.02 | 15 |
| 4.5.1 | N-(5-(2-(5-(2,4-dimethylthiazol-5-yl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide | 0.59 | 548.99 | 16 |
| 4.5.2 | 1-(5-(2,4-dimethylthiazol-5-yl)-2,3,7,8-tetrahydrothiazolo[2',3':2,3]imidazo[4,5-c]pyridin-6(5H)-yl)-2-((6-(1,1-dioxidoisothiazolidin-2-yl)-2-ethylpyridin-3-yl)oxy)ethanone | 0.65 | 574.77 | 10 |
| 4.5.3 | N-cyclopropyl-5-(2-(5-(2,4-dimethylthiazol-5-yl)-2,3,7,8-tetrahydrothiazolo[2',3':2,3]imidazo[4,5-c]pyridin-6(5H)-yl)-2-oxoethoxy)-6-ethylpicolinamide | 0.66 | 538.87 | 6 |
| 4.6.1 | 6-chloro-5-(2-(5-(3-fluorothiophen-2-yl)-2,3,7,8-tetrahydrothiazolo[2',3':2,3]imidazo[4,5-c]pyridin-6(5H)-yl)-2-oxoethoxy)-N,N-dimethylpicolinamide | 0.62 | 521.78 | 28 |
| 4.6.2 | N-(6-chloro-5-(2-(5-(3-fluorothiophen-2-yl)-2,3,7,8-tetrahydrothiazolo[2',3':2,3]imidazo[4,5-c]pyridin-6(5H)-yl)-2-oxoethoxy)pyridin-2-yl)methanesulfonamide | 0.63 | 543.84 | 58 |
| 4.6.3 | N-(6-ethyl-5-(2-(5-(3-fluorothiophen-2-yl)-2,3,7,8-tetrahydrothiazolo[2',3':2,3]imidazo[4,5-c]pyridin-6(5H)-yl)-2-oxoethoxy)pyridin-2-yl)methanesulfonamide | 0.63 | 537.85 | 19 |

TABLE 1-continued

| Example | Name | $t_R$ | $[M + H]^+$ | $IC_{50}$ |
|---|---|---|---|---|
| 4.7.1 | N-(5-(2-(5-(2,5-difluoro-4-methylphenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide | 0.69 | 564.03 | 6 |
| 5.1.1 | 1-(7-acetyl-1-(4-chloro-2-fluorophenyl)-3,4,6,7,8,9-hexahydropyrido[4',3':4,5]imida-zo[1,2-a]pyrazin-2(1H)-yl)-2-((2-chloro-6-(3,3-difluoroazetidin-1-yl)pyridin-3-yl)oxy)ethanone | 0.75 | 610.97 | 7 |
| 5.1.2 | 5-(2-(7-acetyl-1-(4-chloro-2-fluorophenyl)-3,4,6,7,8,9-hexahydropyrido[4',3':4,5]imida-zo[1,2-a]pyrazin-2(1H)-yl)-2-oxoethoxy)-6-chloro-N-methylpicolinamide | 0.66 | 574.99 | 13 |
| 5.1.3 | 5-(2-(7-acetyl-1-(4-chloro-2-fluorophenyl)-3,4,6,7,8,9-hexahydropyrido[4',3':4,5]imidazo[1,2-a]pyrazin-2(1H)-yl)-2-oxoethoxy)-6-chloro-N,N-dimethylpicolinamide | 0.64 | 589.00 | 11 |
| 5.1.4 | 6-chloro-5-(2-(1-(4-chloro-2-fluorophenyl)-7-cyclopropyl-3,4,6,7,8,9-hexahydropyrido[4',3':4,5]imidazo[1,2-a]pyrazin-2(1H)-yl)-2-oxoethoxy)-N,N-dimethylpicolinamide | 0.70 | 586.96 | 41 |
| 5.2.1 | tert-butyl 1-(4-cyclopropyl-2-fluorophenyl)-2-(2-((2-ethyl-6-methylpyridin-3-yl)oxy)acetyl)-1,2,3,4,8,9-hexahydropyrido[4',3':4,5]imidazo[1,2-a]pyrazine-7(6H)-carboxylate | 0.66 | 590.22 | 74 |
| 5.2.2 | tert-butyl 2-(2-((2-chloro-4-morpholinophenoxy)acetyl)-1-(4-cyclopropyl-2-fluorophenyl)-1,2,3,4,8,9-hexahydropyrido[4',3':4,5]imidazo[1,2-a]pyrazine-7(6H)-carboxylate | 0.83 | 666.24 | 121 |
| 5.2.3 | 1-(1-(4-cyclopropyl-2-fluorophenyl)-3,4,6,7,8,9-hexahydropyrido[4',3':4,5]imidazo[1,2-a]pyrazin-2(1H)-yl)-2-((2-ethyl-6-methylpyridin-3-yl)oxy)ethanone | 0.52 | 490.20 | 54 |
| 5.2.4 | 2-(2-chloro-4-morpholinophenoxy)-1-(1-(4-cyclopropyl-2-fluorophenyl)-3,4,6,7,8,9-hexahydropyrido[4',3':4,5]imidazo[1,2-a]pyrazin-2(1H)-yl)ethanone | 0.68 | 566.09 | 24 |
| 5.2.5 | 1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-(2-chloro-4-morpholinophenoxy)ethanone | 0.73 | 608.15 | 7 |
| 5.2.6 | 1-(1-(4-cyclopropyl-2-fluorophenyl)-7-(cyclopropyl-methyl)-3,4,6,7,8,9-hexahydropyrido[4',3':4,5]imida-zo[1,2-a]pyrazin-2(1H)-yl)-2-((2-ethyl-6-methylpyridin-3-yl)oxy)ethanone | 0.59 | 544.07 | 16 |
| 5.2.7 | 2-(2-chloro-4-morpholinophenoxy)-1-(1-(4-cyclopropyl-2-fluorophenyl)-7-(cyclopropylmethyl)-3,4,6,7,8,9-hexahydropyrido[4',3':4,5]imidazo[1,2-a]pyrazin-2(1H)-yl)ethanone | 0.78 | 620.12 | 8 |
| 5.2.8 | 1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone | 0.73 | 609.42 | 5 |
| 5.2.9 | 3-chloro-4-(2-(1-(4-cyclopropyl-2-fluorophenyl)-3,4,6,7,8,9-hexahydropyrido[4',3':4,5]imidazo[1,2-a]pyrazin-2(1H)-yl)-2-oxoethoxy)benzonitrile | 0.69 | 506.51 | 92 |
| 5.2.10 | 1-(1-(4-cyclopropyl-2-fluorophenyl)-3,4,6,7,8,9-hexahydropyrido[4',3':4,5]imidazo[1,2-a]pyrazin-2(1H)-yl)-2-((2-(trifluoromethyl)pyridin-3-yl)oxy)ethanone | 0.65 | 516.51 | 50 |
| 5.2.11 | 6-chloro-5-(2-(1-(4-cyclopropyl-2-fluorophenyl)-3,4,6,7,8,9-hexahydropyrido[4',3':4,5]imidazo[1,2-a]pyrazin-2(1H)-yl)-2-oxoethoxy)picolinonitrile | 0.67 | 507.51 | 108 |
| 5.2.12 | 1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloro-6-(3,3-difluoroazetidin-1-yl)pyridin-3-yl)oxy)ethanone | 0.76 | 615.07 | 6 |
| 5.2.13 | 5-(2-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-oxoethoxy)-6-chloro-N,N-dimethylpicolinamide | 0.66 | 595.09 | 4 |
| 5.2.14 | 1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloropyridin-3-yl)oxy)ethanone | 0.67 | 523.87 | 28 |
| 5.2.15 | 1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-(trifluoromethyl)pyridin-3-yl)oxy)ethanone | 0.71 | 558.04 | 10 |
| 5.2.16 | 1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloro-5-fluoropyridin-3-yl)oxy)ethanone | 0.71 | 541.97 | 25 |
| 5.2.17 | 1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-ethyl-6-methylpyridin-3-yl)oxy)ethanone | 0.56 | 532.17 | 11 |
| 5.4.1 | tert-butyl 2-(2-((2-chloro-6-morpholinopyridin-3-yl)oxy)acetyl)-1-(5-cyclopropyl-3-fluoropyridin-2-yl)-1,2,3,4,8,9-hexahydropyrido[4',3':4,5]imidazo[1,2-a]pyrazine-7(6H)-carboxylate | 0.79 | 668.71 | 77 |
| 5.4.2 | 1-(1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-(trifluoromethyl)pyridin-3-yl)oxy)ethanone | 0.61 | 517.49 | 456 |
| 5.4.3 | 2-((2-chloro-6-morpholinopyridin-3-yl)oxy)-1-(1-(5-cyclopropyl-3-fluoropyridin-2-yl)-3,4,6,7,8,9-hexahydropyrido[4',3':4,5]imidazo[1,2-a]pyrazin-2(1H)-yl)ethanone | 0.63 | 268.51 | 20 |
| 5.4.4 | 1-(1-(5-cyclopropyl-3-fluoropyridin-2-yl)-3,4,6,7,8,9-hexahydropyrido[4',3':4,5]imidazo[1,2-a]pyrazin-2(1H)-yl)-2-(2-ethyl-4-fluorophenoxy)ethanone | 0.69 | 494.57 | 329 |

TABLE 1-continued

| Example | Name | $t_R$ | $[M + H]^+$ | $IC_{50}$ |
|---|---|---|---|---|
| 5.4.5 | 2-(4-chloro-2-ethylphenoxy)-1-(1-(5-cyclopropyl-3-fluoropyridin-2-yl)-3,4,6,7,8,9-hexahydropyrido[4',3':4,5]imidazo[1,2-a]pyrazin-2(1H)-yl)ethanone | 0.72 | 510.51 | 143 |
| 5.4.6 | 1-(7-acetyl-1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone | 0.69 | 610.16 | 9 |
| 5.4.7 | 1-(7-acetyl-1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-chloro-5-fluoropyridin-3-yl)oxy)ethanone | 0.66 | 542.96 | 431 |
| 5.4.8 | 1-(7-acetyl-1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-fluoro-6-morpholinopyridin-3-yl)oxy)ethanone | 0.66 | 593.95 | 91 |
| 5.4.9 | 1-(7-acetyl-1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-chloro-5-fluoro-6-morpholinopyridin-3-yl)oxy)ethanone | 0.71 | 628.05 | 15 |
| 5.5.1 | methyl 5-(7-acetyl-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)thiophene-3-carboxylate | 0.67 | 615.67 | 5 |
| 5.6.1 | 2-((2-chloro-6-morpholinopyridin-3-yl)oxy)-1-(1-(2-(dimethylamino)thiazol-5-yl)-3,4,6,7,8,9-hexahydropyrido[4',3':4,5]imidazo[1,2-a]pyrazin-2(1H)-yl)ethanone | 0.54 | 559.47 | 415 |
| 5.6.2 | 1-(7-acetyl-1-(2-(dimethylamino)thiazol-5-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone | 0.57 | 601.60 | 37 |
| 5.7.1 | 5-(2-(7-acetyl-1-(5-(dimethylcarbamoyl)-3-fluorothiophen-2-yl)-3,4,6,7,8,9-hexahydropyrido[4',3':4,5]imidazo[1,2-a]pyrazin-2(1H)-yl)-2-oxoethoxy)-6-chloro-N,N-dimethylpicolinamide | 0.57 | 631.96 | 27 |
| 5.7.2 | 5-(7-acetyl-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)-4-fluoro-N,N-dimethylthiophene-2-carboxamide | 0.64 | 645.95 | 6 |
| 5.8.1 | 1-(7-acetyl-1-(3-fluoro-5-methylpyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone | 0.65 | 584.06 | 11 |
| 5.8.2 | 1-(7-acetyl-1-(3-fluoro-5-methylpyridin-2-yl)-3,4,6,7,8,9-hexahydropyrido[4',3':4,5]imidazo[1,2-a]pyrazin-2(1H)-yl)-2-((2-chloro-6-(3,3-difluoroazetidin-1-yl)pyridin-3-yl)oxy)ethanone | 0.68 | 590.04 | 51 |
| 5.9.1 | 1-(7-acetyl-1-(5-chloro-3-fluoropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone | 0.67 | 604.23 | 8 |
| 5.10.1 | 1-(7-acetyl-1-(3-fluoropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone | 0.62 | 570.02 | 14 |
| 5.11.1 | 1-(4-(7-acetyl-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)thiazol-2-yl)-3-ethylurea | 0.63 | 644.07 | 100 |
| 5.12.1 | tert-butyl 2-(2-(2-chloro-4-(morpholinomethyl)phenoxy)acetyl)-1-(2-fluoro-4-methylphenyl)-1,2,3,4,8,9-hexahydropyrido[4',3':4,5]imidazo[1,2-a]pyrazine-7(6H)-carboxylate | 0.66 | 654.18 | 310 |
| 5.12.2 | 2-(2-chloro-4-(morpholinomethyl)phenoxy)-1-(1-(2-fluoro-4-methylphenyl)-3,4,6,7,8,9-hexahydropyrido[4',3':4,5]imidazo[1,2-a]pyrazin-2(1H)-yl)ethanone | 0.52 | 554.09 | 52 |
| 5.12.3 | 1-(7-acetyl-1-(2-fluoro-4-methylphenyl)-3,4,6,7,8,9-hexahydropyrido[4',3':4,5]imidazo[1,2-a]pyrazin-2(1H)-yl)-2-(2-chloro-4-(morpholinomethyl)phenoxy)ethanone | 0.55 | 596.21 | 15 |
| 5.13.1 | 1-(7-acetyl-1-(3-fluorothiophen-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone | 0.66 | 574.97 | 6 |
| 5.13.2 | 5-(2-(7-acetyl-1-(3-fluorothiophen-2-yl)-3,4,6,7,8,9-hexahydropyrido[4',3':4,5]imidazo[1,2-a]pyrazin-2(1H)-yl)-2-oxoethoxy)-6-chloro-N,N-dimethylpicolinamide | 0.58 | 560.79 | 24 |
| 5.15.1 | 1-(7-acetyl-1-(5-chloropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone | 0.67 | 586.03 | 11 |
| 5.16.1 | 1-(7-acetyl-1-(4-chloropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone | 0.66 | 585.99 | 48 |
| 5.17.1 | 1-(7-acetyl-1-(2,4-dimethylthiazol-5-yl)-3,4,6,7,8,9-hexahydropyrido[4',3':4,5]imidazo[1,2-a]pyrazin-2(1H)-yl)-2-((2-chloro-6-(oxazol-2-yl)pyridin-3-yl)oxy)ethanone | 0.58 | 568.21 | 27 |
| 6.1.1 | 1-(6-(4-chloro-2-fluorophenyl)-3,4,8,9-tetrahydro-1H-pyrido[4',3':4,5]imidazo[2,1-c][1,4]oxazin-7(6H)-yl)-2-((2-chloro-6-morpholinopyridin-3-yl)oxy)ethanone | 0.72 | 561.51 | 4 |
| 6.1.2 | N-(6-chloro-5-(2-(6-(4-chloro-2-fluorophenyl)-3,4,8,9-tetrahydro-1H-pyrido[4',3':4,5]imidazo[2,1-c][1,4]oxazin-7(6H)-yl)-2-oxoethoxy)pyridin-2-yl)methanesulfonamide | 0.66 | 569.83 | 18 |
| 6.2.1 | 2-((2-chloro-6-morpholinopyridin-3-yl)oxy)-1-(6-(4-cyclopropyl-2-fluorophenyl)-3,4,8,9-tetrahydro-1H-pyrido[4',3':4,5]imidazo[2,1-c][1,4]oxazin-7(6H)-yl)ethanone | 0.74 | 568.02 | 4 |

TABLE 1-continued

| Example | Name | $t_R$ | $[M + H]^+$ | $IC_{50}$ |
|---|---|---|---|---|
| 6.2.2 | 3-chloro-4-(2-(6-(4-cyclopropyl-2-fluorophenyl)-3,4,8,9-tetrahydro-1H-pyrido[4',3':4,5]imidazo[2,1-c][1,4]oxazin-7(6H)-yl)-2-oxoethoxy)-N,N-dimethylbenzamide | 0.70 | 552.92 | 13 |
| 6.2.3 | 6-chloro-5-(2-(6-(4-cyclopropyl-2-fluorophenyl)-3,4,8,9-tetrahydro-1H-pyrido[4',3':4,5]imidazo[2,1-c][1,4]oxazin-7(6H)-yl)-2-oxoethoxy)-N,N-dimethylpicolinamide | 0.67 | 553.91 | 3 |
| 6.3.1 | 6-chloro-5-(2-(6-(5-(dimethylcarbamoyl)-3-fluoro-thiophen-2-yl)-3,4,8,9-tetrahydro-1H-pyrido[4',3':4,5]imidazo[2,1-c][1,4]oxazin-7(6H)-yl)-2-oxoethoxy)-N,N-dimethylpicolinamide | 0.57 | 590.95 | 37 |
| 6.4.1 | N-(6-chloro-5-(2-(6-(5-chloro-3-fluoropyridin-2-yl)-3,4,8,9-tetrahydro-1H-pyrido[4',3':4,5]imidazo[2,1-c][1,4]oxazin-7(6H)-yl)-2-oxoethoxy)pyridin-2-yl)methanesulfonamide | 0.61 | 572.83 | 143 |
| 6.4.2 | 6-chloro-5-(2-(6-(5-chloro-3-fluoropyridin-2-yl)-3,4,8,9-tetrahydro-1H-pyrido[4',3':4,5]imidazo[2,1-c][1,4]oxazin-7(6H)-yl)-2-oxoethoxy)-N,N-dimethylpicolinamide | 0.60 | 548.91 | 76 |
| 6.5.1 | 6-chloro-5-(2-(6-(2-fluoro-4-methylphenyl)-3,4,8,9-tetrahydro-1H-pyrido[4',3':4,5]imidazo[2,1-c][1,4]oxazin-7(6H)-yl)-2-oxoethoxy)-N,N-dimethylpicolinamide | 0.64 | 527.94 | 7 |
| 6.6.1 | 2-((2-chloro-6-morpholinopyridin-3-yl)oxy)-1-(6-(3-fluorothiophen-2-yl)-3,4,8,9-tetrahydro-1H-pyrido[4',3':4,5]imidazo[2,1-c][1,4]oxazin-7(6H)-yl)ethanone | 0.67 | 533.84 | 8 |
| 6.6.2 | 6-chloro-5-(2-(6-(3-fluorothiophen-2-yl)-3,4,8,9-tetrahydro-1H-pyrido[4',3':4,5]imidazo[2,1-c][1,4]oxazin-7(6H)-yl)-2-oxoethoxy)-N,N-dimethylpicolinamide | 0.59 | 519.85 | 29 |
| 6.6.3 | N-(6-chloro-5-(2-(6-(3-fluorothiophen-2-yl)-3,4,8,9-tetrahydro-1H-pyrido[4',3':4,5]imidazo[2,1-c][1,4]oxazin-7(6H)-yl)-2-oxoethoxy)pyridin-2-yl)methanesulfonamide | 0.61 | 541.83 | 160 |

[a] prepared from the corresponding enantiomeric pure amine of the structure 1, which has been isolated by chiral separation of the corresponding racemic mixture by the chiral preparative LC-MS (I);
[b] isolated by chiral separation of the corresponding racemic mixture (example 1.1.3) by the chiral preparative LC-MS (VI);
[c] prepared from the corresponding enantiomerically pure amine of the structure 1, which has been isolated by chiral separation of the corresponding racemic mixture by the preparative LC-MS (IV);
[d] prepared from the corresponding enantiomerically pure amine of the structure 1, which has been isolated by chiral separation of the corresponding racemic mixture by the preparative LC-MS (III);
[e] prepared from the corresponding enantiomerically pure amine of the structure 1, which has been isolated by chiral separation of the corresponding racemic mixture by the preparative LC-MS (V);
[f] prepared from the corresponding enantiomerically pure amine of the structure 1, which has been isolated by chiral separation of the corresponding racemic mixture by the preparative LC-MS (II);
[g] prepared from the corresponding enantiomerically pure amine of the structure 1, which has been isolated by chiral separation of the corresponding racemic mixture by the preparative LC-MS (VII);

Synthesis of Aldehydes of the Structure 3

Aldehyde 1: 4-Chloro-2-fluorobenzaldehyde (4-Chloro-2-fluorophenyl)methanol

To a solution of 4-chloro-2-fluorobenzoic acid (300 mg) in THF (15 ml) was added at 0° C. LiAlH$_4$ (130 mg). The suspension was stirred at 0° C. for 16 h. The reaction mixture was diluted with EA and aq. solution of potassium sodium tartrate and stirred for 1 h at rt. The layers were separated and the org. phase was further washed with water. The combined org. layers were dried over MgSO$_4$, filtrated off and evaporated in vacuo. The crude was purified by CC (Büchi Sepacore, 5 g cartridge, solvent A: DCM, solvent B: 3N ammonia in MeOH, gradient in % B: 0 to 5, flow rate: 6.0 ml/min) to afford 224 mg of colourless oil. LC-MS: (A) $t_R$=0.68 min; [M+H]$^+$: not visible.

4-Chloro-2-fluorobenzaldehyde

To a solution of (4-chloro-2-fluorophenyl)methanol (222 mg) in MeCN (20 ml) was added MnO$_2$ (480 mg). The mixture was stirred for 24 h. The mixture was filtered over celite, the org. layer was dried over MgSO$_4$ and evaporated in vacuo. The crude aldehyde was used without purification in the next step. LC-MS: (A) $t_R$=0.76 min; [M+H]$^+$: not visible.

Aldehyde 2: 5-Cyclopropyl-3-fluoropicolinaldehyde

This aldehyde has been prepared from (5-cyclopropyl-3-fluoropyridin-2-yl)methanol according to the procedure described for aldehyde 1 (2.step). LC-MS (A): $t_R$=0.68 min; [M+H]$^+$: 166.25.

Aldehyde 3: N,N-Diethyl-4-fluoro-5-formylthiophene-2-carboxamide 2-(3-Fluorothiophen-2-yl)-1,3-dioxane To a solution of 3-fluorothiophene-2-carbaldehyde (7.3 g) in dioxane (80 ml) were added 1,3-propandiol (36.5 ml), molecular sieve 4A (20 g) and PTSA (3.84 g). The reaction mixture was stirred at rt overnight. The mixture was filtrated off and evaporated in vacuo. The residue was diluted with sat. aq. Na$_2$CO$_3$ and EA, the layers were separated and the aq. phase was extracted with EA. The combined org. layers were washed with sat. aq. NaCl, dried over MgSO$_4$, filtrated off and evaporated in vacuo. The crude was purified by CC (Flash Master, 50 g cartridge, solvent A: Heptane, solvent B: EA, gradient in % B: 20, flow rate: 30 ml/min) to afford 6.95 g of yellow oil. GC-MS: $t_R$=2.20 min; [M+H]$^+$: 190.20.

5-(1,3-Dioxan-2-yl)-4-fluorothiophene-2-carboxylic acid

To a solution of 2-(3-fluorothiophen-2-yl)-1,3-dioxane (500 mg) in THF (13 ml) was added at −78° C. tBuLi 1.7M in pentane (2.34 ml). The mixture was stirred at −40° C. for 1 h. The solution was added under nitrogen via a syringe into freshly crushed dry ice. The reaction mixture was stirred at −40° C. for 1 h and at rt overnight. The mixture was diluted with EA and 2N aq. HCl to maintain acidic pH. The layers were separated and the aq. phase was washed with EA. The combined org. layers were dried over MgSO$_4$, filtrated off and evaporated in vacuo. The crude was purified by preparative LC-MS (I) to afford 352 mg of white solid. LC-MS (A): $t_R$=0.66 min; [M+H]$^+$: not visible.

5-(1,3-Dioxan-2-yl)-4-fluoro-N,N-dimethylthiophene-2-carboxamide

To a solution of 5-(1,3-dioxan-2-yl)-4-fluorothiophene-2-carboxylic acid (100 mg) in DMF (2 ml) was added TBTU (145 mg). The mixture was stirred at rt for 30 min. Dimethylamine (1.1 ml, 2M in THF) and DIPEA (0.2 ml) were added and the reaction mixture was stirred at rt overnight. TBTU (870 mg) was added and the reaction mixture was stirred at rt for 3 h. The mixture was diluted with EA and water, the layers were separated and the aq. phase was washed with EA. The combined org. layers were washed with sat. aq. NaCl, dried over MgSO$_4$, filtrated off and evaporated in vacuo. The crude was purified by CC (Büchi Sepacore, 5 g cartridge, solvent A: Heptane, solvent B: EA, gradient in % B: 5 to 20, flow rate: 10 ml/min) to afford 77 mg of a colourless oil. LC-MS (A): $t_R$=0.67 min; [M+H]$^+$: 260.05.

4-Fluoro-5-formyl-N,N-dimethylthiophene-2-carboxamide

To a solution of 5-(1,3-dioxan-2-yl)-4-fluoro-N,N-dimethylthiophene-2-carboxamide (75 mg) in THF (2 ml) was added at 0° C. 1N aq. HCl (0.78 ml). The reaction mixture was stirred at rt overnight. The mixture was diluted with sat aq. NaHCO$_3$ and EA, the layers were separated and the aq. phase was washed with EA. The combined org. layers were dried over MgSO$_4$, filtrated off and evaporated in vacuo. The crude (374 mg of a colourless solid) was used without purification in the next step. LC-MS (A): $t_R$=0.59 min; [M+H]$^+$: 202.19.

Aldehyde 4: Ethyl 2-formylthiazole-4-carboxylate 2,2-Diethoxyethanethioamide

To a solution of diethoxyacetonitrile (10.8 ml) in EtOH (455 ml) was added ammonium sulfide (330 ml). The reaction mixture was stirred at 50° C. for 4 h. The mixture was diluted with water and EA, the layers were separated and the aq. phase was washed with EA. The combined org. layers were dried over Na$_2$SO$_4$, filtrated off and evaporated in vacuo. The crude compound (11.01 g of a beige solid) was used without purification in the next step. LC-MS (B): $t_R$=0.53 min; [M+H]$^+$: not visible.

Ethyl 2-(diethoxymethyl)thiazole-4-carboxylate

To a solution of 2,2-diethoxyethanethioamide (9 g) in EtOH (90 ml) were added molecular sieve 3Å (22 g) and ethylbromopyruvate (6.8 ml). The reaction mixture was stirred under reflux for 6.5 h. The mixture was evaporated in vacuo and the residue was diluted with EA. The molecular sieve was filtrated off and washed with EA. The org. layer was washed with NaHCO$_3$, dried over MgSO$_4$, filtrated off and evaporated in vacuo. The crude compound (14.3 g of a brown oil) was used without purification in the next step. LC-MS (B): $t_R$=0.82 min; [M+H]$^+$: 260.12.

Ethyl 2-formylthiazole-4-carboxylate

To a solution of ethyl 2-(diethoxymethyl)thiazole-4-carboxylate (1 g) in acetone (70 ml) was added 1M aq. HCl (9.2 ml). The reaction mixture was stirred under reflux for 4 h. The mixture was evaporated in vacuo, the residue was diluted with EA and sat. aq. NaHCO$_3$. The layers were separated, the aq. layer was washed with EA and the combined org. layers were washed with sat. aq. NaCl, dried over MgSO$_4$, filtrated off and evaporated in vacuo. The crude compound (715 mg of a yellow solid) was used without purification in the next step. LC-MS (A): $t_R$=0.63 min; [M+H]$^+$: not visible.

Aldehyde 5: 3-Fluoro-5-methylpicolinaldehyde

This aldehyde has been prepared from (3-fluoro-5-methylpyridin-2-yl)methanol according to the procedure described for aldehyde 1 (2.step). LC-MS (A): $t_R$=0.55 min; [M+H]$^+$: 140.06.

Aldehyde 6: 4-Cyclopropyl-2-fluorobenzaldehyde

Methyl 4-bromo-2-fluorobenzoate

A solution of 4-bromo-2-fluorobenzoyl chloride (15 ml) in MeOH (200 ml) was stirred at rt for 18 h. The reaction mixture was evaporated in vacuo. The residue was diluted with DCM and sat. aq. NaHCO$_3$. The layers were separated, the aq. layer was extracted with DCM, the combined org. layers were dried over MgSO$_4$, filtrated off and evaporated in vacuo. The crude (25 g of a white solid) was used without purification in the next step. LC-MS (A): $t_R$=0.84 min; [M+H]$^+$: not visible.

Methyl 4-cyclopropyl-2-fluorobenzoate

To a solution of methyl 4-bromo-2-fluorobenzoate (25 g) in THF (500 ml) were added potassium cyclopropyltrifluoroborate (15.9 g), cesium carbonate (105 g) and water (50 ml). The solution was degassed under argon and (1,1'-bis(diphenylphosphino)ferrocene) dichloropalladium (II) dichloromethane adduct (8.8 g) was finally added. The reaction mixture was stirred at 70° C. overnight. The mixture was diluted with water and TBME, the layers were separated. The aq. layer was extracted with TBME and the combined org. layers were washed with sat. aq. NaCl, dried over MgSO$_4$, filtrated off and evaporated in vacuo. The crude was purified by CC (Büchi Sepacore, 350 g cartridge, solvent A: Heptane, solvent B: EA, gradient in % B: 1 to 20, flow rate: 100 ml/min) to afford 19.2 g of yellow oil. LC-MS (A): $t_R$=0.87 min; [M+H]$^+$: 195.45.

4-Cyclopropyl-2-fluorobenzaldehyde

This aldehyde has been prepared from methyl 4-cyclopropyl-2-fluorobenzoate according to the reduction/oxidation procedure described for aldehyde 1. LC-MS (A): $t_R$=0.83 min; [M+H]$^+$: not visible.

Aldehyde 7: 3-Fluorothiophene-2-carbaldehyde

This aldehyde has been prepared from 3-fluoro-2-thiophenecarboxylic acid according to the reduction/oxidation procedures described for aldehyde 1. LC-MS (A): $t_R$=0.59 min; [M+H]$^+$: not visible.

Aldehyde 8: 2-Ethyl-4-methylthiazole-5-carbaldehyde

This aldehyde has been prepared from (2-ethyl-4-methylthiazol-5-yl)methanol according to the procedure described for aldehyde 1 (2.step). LC-MS (A): $t_R$=0.64 min; [M+H]$^+$: 156.11.

Aldehyde 9: 2-Methylthiazole-5-carbaldehyde

This aldehyde has been prepared from (2-methylthiazol-5-yl)methanol according to the procedure described for aldehyde 1 (2.step). LC-MS (A): $t_R$=0.50 min; [M+H]$^+$: 128.34.

Aldehyde 10: 2,5-Difluoro-4-methylbenzaldehyde

To a solution of 1-bromo-2,5-difluoro-4-methylbenzene (500 mg) in THF (3 ml) was added at −78° C. nBuLi 1.6M in hexanes (1. ml). The mixture was stirred at −78° C. for 15 min. DMF (0.205 ml) was added dropwise and the reaction mixture was stirred for 10 min. The mixture was diluted with sat. aq. NH$_4$Cl and TBME, the layers were separated and the aq. phase was extracted with TBME. The combined org. layers were dried over MgSO$_4$, filtrated off and evaporated in vacuo. The crude was purified by CC (Büchi Sepacore, 20 g cartridge, solvent A: Heptane, solvent B: EA, gradient in % B: 0 to 3, flow rate: 20 ml/min) to afford 50 mg of a yellow oil. LC-MS (A): $t_R$=0.79 min; [M+H]$^+$: not visible.

Aldehyde 11: 5-Fluoro-3-methylpicolinaldehyde

This aldehyde has been prepared from (5-fluoro-3-methylpyridin-2-yl)methanol according to the procedure described for aldehyde 1 (2.step). LC-MS (A): $t_R$=0.62 min; [M+H]$^+$: 140.37.

Aldehyde 12: 4-methyl-2-(trifluoromethyl)thiazole-5-carbaldehyde

This aldehyde has been prepared from (4-methyl-2-(trifluoromethyl)thiazol-5-yl)methanol according to the procedure described for aldehyde 1 (2.step). LC-MS (A): $t_R$=0.77 min; [M+H]$^+$: not visible.

Aldehyde 13: 2-Isopropyl-4-methylthiazole-5-carbaldehyde

Methyl 2-isopropyl-4-methylthiazole-5-carboxylate

To a solution of 2-isopropyl-4-methylthiazole-5-carboxylic acid (500 mg) in MeOH (10 ml) was added (trimethylsilyl)diazomethane 2M in diethyl ether (4.1 ml). The reaction mixture was stirred at rt for 5 h. The mixture was evaporated in vacuo. The crude compound (393 mg of a yellow oil) was used without purification in the next step. LC-MS (A): $t_R$=0.81 min; [M+H]$^+$: 200.21.

2-Isopropyl-4-methylthiazole-5-carbaldehyde

This aldehyde has been prepared from methyl 2-isopropyl-4-methylthiazole-5-carboxylate according to the reduction/oxidation procedure described for aldehyde 1. LC-MS (A): $t_R$=0.71 min; [M+H]$^+$: 170.23.

Aldehyde 14: 1-Ethyl-3-(2-formylthiazol-4-yl)urea

Ethyl 4-(3-ethylureido)thiazole-2-carboxylate

To a solution of ethyl 2-amino-1,3-thiazole-4-carboxylate (1 g) in DMF (28 mL) were added ethylisocyanate (1.24 g) and DIPEA (1 mL). The reaction mixture was stirred at rt overnight. The reaction mixture was evaporated in vacuo, diluted with water and DCM, the layers were separated and the aq. phase was washed with DCM. The combined org. layers were washed with sat. aq. NaCl, dried over MgSaidried over MgSO$_4$, filtrated off and evaporated in vacuo. The crude was purified by CC (Büchi Sepacore, 25 g cartridge, solvent A: DCM, solvent B: MeOH, gradient in % B: 0 to 5, flow rate: 35 ml/min) to afford 1.4 g of a yellow solid. LC-MS (A): $t_R$=0.65 min; [M+H]$^+$: 244.83.

1-Ethyl-3-(4-formylthiazol-2-yl)urea

To a solution of ethyl 4-(3-ethylureido)thiazole-2-carboxylate (1.4 g) in THF (800 mL) was added LAH (368 mg). The reaction mixture was stirred at 0° C. for 1 h 30. Water was added, followed by 20% aq. NaOH and finally water. The mixture was stirred at rt for 30 min and filtrated over celite. The solution was evaporated in vacuo. The crude was purified by CC (Büchi Sepacore, 20 g cartridge, solvent A: Heptane, solvent B: EA, gradient in % B: 2 to 15, flow rate: 15 ml/min) to afford 248 mg of a yellow solid. LC-MS (A): $t_R$=0.52 min; [M+H]$^+$: 200.11.

Aldehyde 15: 5-Chloro-3-fluoropicolinaldehyde

Methyl 5-chloro-3-fluoropicolinate

This compound has been from prepared 5-chloro-3-fluoropicolinic acid according to the procedure described for aldehyde 13 (1.step). LC-MS (A): $t_R$=0.64 min; [M+H]$^+$: 190.19.

(5-Chloro-3-fluoropyridin-2-yl)methanol

To a solution of methyl 5-chloro-3-fluoropicolinate (1.05 g) in THF (25 ml) was added at 0° C. lithium borohydride 2M in THF (5.6 ml). The reaction mixture was stirred at 0° C. for 1 h. The mixture was diluted with sat. aq. NaHCO$_3$ and EA, the layers were separated and the aq. phase was washed with EA. The combined org. layers were washed with sat. aq. NaCl, dried over MgSO$_4$, filtrated off and evaporated in vacuo. The crude was purified by CC (Büchi Sepacore, 50 g cartridge, solvent A: DCM, solvent B: MeOH, gradient in % B: 0 to 5, flow rate: 30 ml/min) to afford 2.70 g of a yellow solid. LC-MS (A): $t_R$=0.50 min; [M+H]$^+$: 161.95.

5-Chloro-3-fluoropicolinaldehyde

This aldehyde has been prepared from (5-chloro-3-fluoropyridin-2-yl)methanol according to the procedure described for aldehyde 1 (2.step). LC-MS (A): $t_R$=0.59 min; [M+H]$^+$: not visible.

Aldehyde 16: Methyl 5-formylthiophene-3-carboxylate

Methyl 5-(1,3-dioxolan-2-yl)thiophene-3-carboxylate

To a solution of 2-(4-bromothien-2-yl)-1,3-dioxolane (5 g) in diethyl ether (200 ml) was added at −78° C. nBuLi 1.6M in hexanes (16 ml) under nitrogen. The mixture was stirred at −78° C. for 15 min. Methyl chloroformate (16.6 ml) was added dropwise and the reaction mixture was stirred at −78° C. for 1 h under nitrogen. The mixture was diluted with sat. aq. NH$_4$Cl and EA, the layers were separated and the aq. phase was extracted with EA. The combined org. layers were dried over MgSO$_4$, filtrated off and evaporated in vacuo. The crude was purified by CC (Büchi Sepacore, 50 g cartridge, solvent A: Heptane, solvent B: EA, gradient in % B: 0 to 5, flow rate: 30 ml/min) to afford 2.89 g of a colourless oil. LC-MS (A): $t_R$=0.72 min; [M+H]$^+$: 214.85.

Methyl 5-form ylthiophene-3-carboxylate

To a solution of methyl 5-(1,3-dioxolan-2-yl)thiophene-3-carboxylate (1 g) in THF (20 ml) was added at 0° C. 1N aq. HCl (12.7 ml). The reaction mixture was stirred at rt for 4 h. The mixture was diluted with 1N aq. NaOH and EA, the layers were separated and the aq. phase was washed with EA. The combined org. layers were dried over MgSO$_4$, filtrated off and evaporated in vacuo. The crude (732 mg of a colourless solid) was used without purification in the next step. LC-MS (A): $t_R$=0.66 min; [M+H]$^+$: not visible.

Aldehyde 17: 2-(Dimethylamino)thiazole-5-carbaldehyde

To a solution of 2-bromothiazole-5-carbaldehyde (2 g) in DMF (20 ml) was added at 2M Me$_2$NH in THF (6.8 ml) and K$_2$CO$_3$ (4.3 g). The reaction mixture was stirred at rt for 1.5 h. After filtration was the mixture diluted with sat. aq. NH$_4$Cl and EA, the layers were separated and the aq. phase was extracted with EA. The combined org. layers were dried over MgSO$_4$, filtrated off and evaporated in vacuo. The crude was purified by CC (Büchi Sepacore, 20 g cartridge, solvent A: Heptane, solvent B: EA, gradient in % B: 1 to 10, flow rate: 20 ml/min) to afford 1.42 g of a yellowish solid. LC-MS (A): $t_R$=0.54 min; [M+H]$^+$: 157.22.

Aldehyde 18: 2-Fluoro-4-(2-hydroxypropan-2-yl)benzaldehyde

Methyl 4-(dimethoxymethyl)-3-fluorobenzoate

A solution of methyl 3-fluoro-4-formylbenzoate (1.0 g), trimethylorthoformate (4.0 ml) and PTSA (9 mg) in MeOH (10 ml) was stirred under reflux for 3 h. The solvent was evaporated in vacuo. The crude was dissolved in DCM and washed with sat. aq. NaCl. The org. layer was dried over MgSO$_4$, filtrated off and evaporated in vacuo. The crude (1.26 g of a yellowish oil) was used in the next step without purification. LC-MS (A): $t_R$=0.82 min; [M+H]$^+$: not visible.

2-(4-(Dimethoxymethyl)-3-fluorophenyl)propan-2-ol

To a solution of methyl 4-(dimethoxymethyl)-3-fluorobenzoate (400 mg) was at −78° C. added methylmagnesium bromide 3M in Et$_2$O (730 ml) and the mixture was stirred at rt for 4 h. The reaction mixture was diluted with rochelle salt, EA and water. The layers were separated and the water phase was extracted with EA. The combined org. layers were dried over MgSO$_4$, filtrated off and evaporated in vacuo. The crude was purified by CC (Büchi Sepacore, 5 g cartridge, solvent A: Heptane, solvent B: EA, gradient in % B: 5 to 15, flow rate: 10 ml/min) to afford 330 mg of a yellowish oil. LC-MS (A): $t_R$=0.71 min; [M+H]$^+$: not visible.

2-Fluoro-4-(2-hydroxypropan-2-yl)benzaldehyde

To a solution 2-(4-(dimethoxymethyl)-3-fluorophenyl)propan-2-ol (330 mg) in THF (15 ml) was added at 0° C. 2N aq. HCl (2.2 ml). The reaction mixture was stirred at rt for 1 h. The solvent was evaporated in vacuo and the crude was dissolved in DCM. The solution was washed with sat. aq. NaCl, dried over MgSO$_4$, filtrated off and evaporated in vacuo. The crude (250 mg of a yellow oil) was used without purification in the next step. LC-MS (A) $t_R$=0.66 min; [M+H]$^+$: not visible.

Aldehyde 19: 2-Fluoro-4-(2-methoxypropan-2-yl)benzaldehyde

1-(Dimethoxymethyl)-2-fluoro-4-(2-methoxypropan-2-yl)benzene

To a solution of 2-(4-(dimethoxymethyl)-3-fluorophenyl)propan-2-ol (330 mg) in THF (10 ml) was added at 0° C. NaH (76 mg). The reaction mixture was stirred at rt for 30 min. Iodomethane (0.185 ml) was added and the reaction mixture was stirred at rt overnight. The mixture was diluted with sat. aq. NH$_4$Cl and EA. The layers were separated and the aq. phase was washed with EA. The combined org. layers were washed with sat. aq. NaCl, dried over MgSO$_4$, filtrated off and evaporated in vacuo. The crude was purified by CC (Büchi Sepacore, 10 g cartridge, solvent A: Heptane, solvent B: EA, gradient in % B: 1 to 12, flow rate: 15 ml/min) to afford 254 mg of a colourless solid. LC-MS (A): $t_R$=0.85 min; [M+H]$^+$: not visible.

2-Fluoro-4-(2-methoxypropan-2-yl)benzaldehyde

This compound has been prepared from 1-(dimethoxymethyl)-2-fluoro-4-(2-methoxypropan-2-yl)benzene according to the procedure described for aldehyde 18 (3. step). LC-MS (A): $t_R$=0.80 min; [M+H]$^+$: not visible.

Aldehyde 20: 2-Fluoro-4-(methoxymethyl)benzaldehyde

(4-(Dimethoxymethyl)-3-fluorophenyl)methano/This

This compound has been prepared from 2-(4-(dimethoxymethyl)-3-fluorophenyl)propan-2-ol according to the procedure described for aldehyde 1 (1. step). LC-MS (A): $t_R$=0.62 min; [M+H]$^+$: not visible.

1-(Dimethoxymethyl)-2-fluoro-4-(methoxymethyl)benzene

This compound has been prepared from (4-(dimethoxymethyl)-3-fluorophenyl)methanol according to the procedure described for aldehyde 19 (1. step) using DMF instead of THF as a solvent. LC-MS (A): $t_R$=0.78 min; [M+H]$^+$: not visible.

2-Fluoro-4-(methoxymethyl)benzaldehyde

This compound has been prepared from 1-(dimethoxymethyl)-2-fluoro-4-(methoxymethyl)penzene according to the procedure described for aldehyde 18 (3. step). LC-MS (A): $t_R$=0.71 min; [M+H]$^+$: not visible

Aldehyde 21: 2-Fluoro-4-(2-methoxyethoxy)benzaldehyde

A solution of 2-fluoro-4-hydroxybenzaldehyde (200 mg), K$_2$CO$_3$ (592 mg) and 1-bromo-2-methoxyethane in DMF (5 ml) was stirred at 60° C. for 2 h. The reaction mixture was diluted at rt with DCM and water. The layers were separated and the water phase was extracted with DCM. The combined org. layers were dried over MgSO$_4$, filtrated off and evaporated in vacuo. The crude brown oil (330 mg) was used in the next step without purification LC-MS (A): $t_R$=0.72 min; [M+H]$^+$: 199.15.

Synthesis of Amines of the Structure 4

Amine 1: 2-(6,8-Dihydro-5H-imidazo[2,1-c][1,4]oxazin-2-yl)ethanamine

(E)-2-(2-Nitrovinyl)-6,8-dihydro-5H-imidazo[2,1-c][1,4]oxazine

A solution of 6,8-dihydro-5H-imidazo[2,1-c][1,4]oxazine-2-carbaldehyde (2.5 g) and ammoniumacetate (760 mg) in nitromethane (22 ml) was stirred at 100° C. for 1 h. The reaction mixture was evaporated in vacuo. The residue was diluted with sat. aq. NaCl and EA, the layers were separated and the aq. phase was extracted with EA. The combined org. layers were dried over MgSO$_4$, filtrated off and evaporated in vacuo. The crude was used in the next step without further purification. LC-MS (A): $t_R$=0.49 min; [M+H]$^+$: 196.25.

2-(6, 8-Dihydro-5H-imidazo[2, 1-c][1, 4]oxazin-2-yl)ethanamine

TMSCl (15.1 ml) was added at rt to the solution of lithium borohydride (2M in THF, 30 ml). After 30 min a solution of (E)-2-(2-nitrovinyl)-6,8-dihydro-5H-imidazo[2,1-c][1,4]oxazine (2.92 g) in THF (115 ml) was added at rt dropwise and the mixture was stirred at rt overnight. Methanol (15 ml) was added at 0° C. and the mixture was stirred at rt for 4 h. The reaction mixture was evaporated in vacuo and the crude was purified by CC (Büchi Sepacore, 50 g cartridge, solvent A: DCM, solvent B: 7N ammonia in MeOH, gradient in % B: 0 to 10, flow rate: 30 ml/min) to afford 1.35 g of an orange oil. LC-MS: (A) $t_R$=0.14 min; [M+H]$^+$: 168.01.

Amine 2: Tert-butyl 2-(2-aminoethyl)-5,6-dihydroimidazo[1,2-a]pyrazine-7(8H)-carboxylate

7-Tert-butyl 2-ethyl 5,6-dihydroimidazo[1,2-a]pyrazine-2,7(8H)-dicarboxylate A solution of ethyl 5,6,7,8-tetrahydroimidazo[1,2-a]pyrazine-2-carboxylate dihydrochloride (1 g), di-tert-butyl dicarbonate (1.63 g) and DIPEA (1.92 ml) in DCM (50 ml) was stirred at rt for 20 min. The reaction mixture was washed with water and with sat. aq. NaCl. The org. layer was dried over MgSO$_4$, filtrated off and evaporated in vacuo. The crude was used in the next step without further purification. LC-MS (A): $t_R$=0.65 min; [M+H]$^+$: 296.39.

Tert-butyl 2-(hydroxymethyl)-5,6-dihydroimidazo[1,2-a]pyrazine-7(8H)-carboxylate This compound has been prepared from 7-tert-butyl 2-ethyl 5,6-dihydroimidazo[1,2-a]pyrazine-2,7(8H)-dicarboxylate according to the procedure described for the aldehyde 1 (1.step). LC-MS (A): $t_R$=0.47 min; [M+H]$^+$: 254.32.

Tert-butyl 2-formyl-5,6-dihydroimidazo[1,2-a]pyrazine-7(8H)-carboxylate

This compound has been prepared from tert-butyl 2-(hydroxymethyl)-5,6-dihydroimidazo[1,2-a]pyrazine-7(8H)-carboxylate according to the procedure described for the aldehyde 1 (2.step). LC-MS (A): $t_R$=0.59 min; [M+H]$^+$: 252.31.

Tert-butyl 2-(2-aminoethyl)-5,6-dihydroimidazo[1,2-a]pyrazine-7(8H)-carboxylate This compound has been prepared from tert-butyl 2-formyl-5,6-dihydroimidazo[1,2-a]pyrazine-7(8H)-carboxylate according to the procedures described for the amine 1. LC-MS (A): $t_R$=0.41 min; [M+H]$^+$: 267.11.

Synthesis of Acids of the Structure 2

Acid 1: 2-((2-Chloro-6-morpholinopyridin-3-yl)oxy)acetic acid

2-Chloro-6-iodo-3-(methoxymethoxy)pyridine

To a solution of 2-chloro-6-iodo-3-pyridinol (5 g) in DCM (100 ml) were added at 0° C. DIPEA (5 ml) and chloromethyl methyl ether (1.7 ml). The reaction mixture was stirred at 0° C. for 1 h. The mixture was washed with 1M aq. KHSO$_4$. The layers were separated, the aq. phase was washed with DCM and the combined org. layers were washed with sat. aq. NaCl, dried over MgSO$_4$, filtrated off and evaporated in vacuo. The crude was purified by CC (Büchi Sepacore, 50 g cartridge, solvent A: Heptane, solvent B: EA, gradient in % B: 0 to 2, flow rate: 15 ml/min) to afford 5.52 g of a colourless oil. LC-MS (A): $t_R$=0.83 min; [M+H]$^+$: 299.99.

4-(6-Chloro-5-(methoxymethoxy)pyridin-2-yl)morpholine

To a solution of 2-chloro-6-iodo-3-(methoxymethoxy)pyridine (5.95 g) in DMSO (100 ml) were added morpholine (8.57 ml), copper iodide (3.71 g), L-proline (4.04 g) and potassium carbonate (6.19 g). The mixture was stirred at 80° C. for 1 h. The reaction mixture was diluted with sat. aq. NaCl and EA. The layers were separated, the aq. phase was washed with EA and the combined org. layers were dried over MgSO$_4$, filtrated off and evaporated in vacuo. The crude was purified by CC (Büchi Sepacore, 50 g cartridge, solvent A: Heptane, solvent B: EA, gradient in % B: 2 to 5, flow rate: 30 ml/min) to afford 4.14 g of a colourless oil. LC-MS (A): $t_R$=0.80 min; [M+H]$^+$: 258.90.

2-Chloro-6-morpholinopyridin-3-ol dihydrochloride

To a solution of 4-(6-chloro-5-(methoxymethoxy)pyridin-2-yl)morpholine (1080 mg) in EA (18 ml) and MeOH (6 ml)

was added a solution of HCl 4M in dioxane (2.2 ml) and the mixture was stirred at rt overnight. The mixture was evaporated in vacuo and the crude (1.3 g) was used in the next step without purification LC-MS (A): $t_R$=0.62 min; [M+H]$^+$: 215.15.

Tert-butyl 2-((2-chloro-6-morpholinopyridin-3-yl)oxy)acetate

To a solution of 2-chloro-6-morpholinopyridin-3-ol dihydrochloride (1.3 g) in DMF (15 ml) was added NaH (493 mg) portionwise at 0° C. After 30 min tert-butyl bromoacetate (0.94 ml) was added and the mixture was stirred at 80° C. for 6 h. The reaction mixture was diluted with EA and sat. aq. NH$_4$Cl. The layers were separated and the org. phase was washed with sat. aq. NaCl. The combined org. layers were dried over MgSO$_4$, filtrated off and evaporated in vacuo. The crude was purified by CC (Büchi Sepacore, 20 g cartridge, solvent A: Heptane, solvent B: EA, gradient in % B: 1 to 5, flow rate: 15 ml/min) to afford 1.43 g of a yellow solid. LC-MS (A): $t_R$=0.91 min; [M+H]$^+$: 328.97.

2-((2-Chloro-6-morpholinopyridin-3-yl)oxy)acetic acid

To a solution of tert-butyl 2-((2-chloro-6-morpholinopyridin-3-yl)oxy)acetate (1.43 g) in DCM (25 ml) was added TFA (5.4 ml) at 0° C. and the reaction was stirred overnight at rt. The mixture was evaporated in vacuo. The crude product was washed with Et$_2$O. The crude product (978 mg of a white solid) was used in the next step without purification. LC-MS (A): $t_R$=0.66 min; [M+H]$^+$: 273.04.

Acid 2: 2-((2-Chloro-6-(methylsulfonamido)pyridin-3-yl)oxy)acetic acid

Tert-butyl 2-((2-chloro-6-iodopyridin-3-yl)oxy)acetate

This ester has been prepared from 2-chloro-6-iodo-3-pyridinol according to the procedure described for acid 1 (4.step). LC-MS (A): $t_R$=0.94 min; [M+H]$^+$: 369.66.

Tert-butyl 2-((2-chloro-6-(methylsulfonamido)pyridin-3-yl)oxy)acetate

To a solution of tert-butyl 2-((2-chloro-6-iodopyridin-3-yl)oxy)acetate (7.07 g) in DMF (150 ml) were added methansulfonamide (1.80 g), copper iodide (550 mg), (trans)-N,N'-dimethyl-1,2-cyclohexanediamine (0.90 ml) and potassium carbonate (5.3 g). The reaction mixture was stirred at 100° C. for 1 h 45. The reaction mixture was diluted with EA and sat. aq. NH$_4$Cl. The layers were separated, the aq. phase was washed with EA and the combined org. layers were washed with sat. aq. NaCl, dried over Na$_2$SO$_4$, filtrated off and evaporated in vacuo. The crude was purified by CC (Büchi Sepacore, 100 g cartridge, solvent A: Heptane, solvent B: EA, gradient in % B: 2 to 25, flow rate: 40 ml/min) to afford 3.01 g of a white solid. LC-MS (A): $t_R$=0.81 min; [M+H]$^+$: 337.04.

2-((2-Chloro-6-(methylsulfonamido)pyridin-3-yl)oxy)acetic acid

This acid has been prepared from tert-butyl 2-((2-chloro-6-(methylsulfonamido)pyridin-3-yl)oxy)acetate according to the procedure described for acid 1 (5.step). LC-MS (A): $t_R$=0.53 min; [M+H]$^+$: 281.06.

Acid 3: 2-((2-Chloro-6-(trifluoromethyl)pyridin-3-yl)oxy)acetic acid

Tert-butyl 2-((2-chloro-6-(trifluoromethyl)pyridin-3-yl)oxy)acetate

This ester has been prepared from 2-chloro-6-(trifluoromethyl)pyridin-3-ol according to the procedure described for acid 1 (4.step). LC-MS (A): $t_R$=0.95 min; [M+H]$^+$: 312.15.

2-((2-Chloro-6-(trifluoromethyl)pyridin-3-yl)oxy)acetic acid

This acid has been prepared from tert-butyl 2-((2-chloro-6-(trifluoromethyl)pyridin-3-yl)oxy)acetate according to the procedure described for acid 1 (5.step). LC-MS (A): $t_R$=0.72 min; [M+H]$^+$: 256.01.

Acid 4: 2-((2-Chloro-6-cyanopyridin-3-yl)oxy)acetic acid

6-Chloro-5-(methoxymethoxy)picolinic acid

To a solution of 2-chloro-6-iodo-3-(methoxymethoxy)pyridine (5.85 g) in toluene (80 ml) under nitrogen was added at −78° C. nBuLi 1.6M in hexanes (16 ml) under nitrogen. The mixture was stirred at −78° C. for 30 min. The reaction mixture was poured into CO$_2$ (solid). After the addition, 1M aq. NaOH (30 ml) was added and the aq. layer was extracted with Et$_2$O. The layers were separated, the aq. phase was acidified at 0° C. with 2N aq. HCl until pH 1 and washed with DCM. The org. layer was dried over MgSO$_4$, filtrated off and evaporated in vacuo. The crude (3.73 g of a beige solid) was used in the next step without purification. LC-MS (A): $t_R$=0.58 min; [M+H]$^+$: 217.98.

6-Chloro-5-(methoxymethoxy)picolinamide

To a solution of 6-chloro-5-(methoxymethoxy)picolinic acid (3.6 g) in THF (80 ml) were added at 0° C. triethylamine (6 ml) and methylchloroformate (3 ml). The mixture was stirred at 0° C. for 30 min. Ammonium hydroxide 25% in water (20 ml) was added and the reaction mixture was stirred at rt for 10 min. The reaction mixture was diluted with EA and water. The layers were separated, the org. phase was washed with sat. aq. NaCl, dried over MgSO$_4$, filtrated off and evaporated in vacuo. The crude was purified by CC (Büchi Sepacore, 50 g cartridge, solvent A: DCM, solvent B: MeOH, gradient in % B: 1 to 3, flow rate: 35 ml/min) to afford 2.4 g of a white solid. LC-MS (A): $t_R$=0.63 min; [M+H]$^+$: 217.03.

6-Chloro-5-(methoxymethoxy)picolinonitrile

To a solution of 6-chloro-5-(methoxymethoxy)picolinamide (2.4 g) in DCM (100 ml) was added Burgess reagent (6 g). The reaction mixture was stirred at rt for 3 h. The reaction mixture was diluted with DCM and sat. aq. NaHCO$_3$. The layers were separated, the org. phase was washed with water and sat. aq. NaCl, dried over MgSO$_4$, filtrated off and evaporated in vacuo. The crude was purified by CC (Büchi Sepacore, 50 g cartridge, solvent A: Heptane, solvent B: EA, gradient in % B: 1 to 20, flow rate: 30 ml/min) to afford 1.72 g of a colourless oil. LC-MS (A): $t_R$=0.76 min; [M+H]$^+$: not visible.

6-Chloro-5-hydroxypicolinonitrile hydrochloride

This alcohol has been prepared from 6-chloro-5-(methoxymethoxy)picolinonitrile according to the procedure described for acid 1 (3.step). LC-MS (A): $t_R$=0.60 min; [M+H]$^+$: not visible.

Tert-butyl 2-((2-chloro-6-cyanopyridin-3-yl)oxy)acetate

This ester has been prepared from 6-chloro-5-hydroxypicolinonitrile hydrochloride according to the procedure described for acid 1 (4.step). LC-MS (A): $t_R$=0.89 min; [M+H]$^+$: not visible.

2-((2-Chloro-6-cyanopyridin-3-yl)oxy)acetic acid

This acid has been prepared from tert-butyl 2-((2-chloro-6-cyanopyridin-3-yl)oxy)acetate according to the procedure described for acid 1 (5.step). LC-MS (A): $t_R$=0.59 min; [M+H]$^+$: not visible.

Acid 5: 2-((2-Chloro-6-(dimethylcarbamoyl)pyridin-3-yl)oxy)acetic acid

6-Chloro-5-(methoxymethoxy)-N,N-dimethylpicolinamide

To a solution of 6-chloro-5-(methoxymethoxy)picolinic acid (213 mg) in DMF (5 ml) were added TBTU (330 mg), dimethylamine 2M in THF (0.46 ml) and DIPEA (0.5 ml). The reaction mixture was stirred at rt for 15 min. The reaction mixture was diluted with EA and sat. aq. NH$_4$Cl. The layers were separated, the aq. phase was washed with EA, the combined org. layers were washed with sat. aq. NaCl, dried over MgSO$_4$, filtrated off and evaporated in vacuo. The crude was purified by CC (Büchi Sepacore, 5 g cartridge, solvent A: Heptane, solvent B: EA, gradient in % B: 1 to 35, flow rate: 10 ml/min) to afford 220 mg of a yellow solid. LC-MS (A): $t_R$=0.64 min; [M+H]$^+$: 245.08.

6-Chloro-5-hydroxy-N,N-dimethylpicolinamide hydrochloride

This alcohol has been prepared from 6-chloro-5-(methoxymethoxy)-N,N-dimethyl-picolinamide according to the procedure described for acid 1 (3.step). LC-MS (A): $t_R$=0.50 min; [M+H]$^+$: 201.10.

Tert-butyl 2-((2-chloro-6-(dimethylcarbamoyl)pyridin-3-yl)oxy)acetate

This ester has been prepared from 6-chloro-5-hydroxy-N,N-dimethylpicolinamide hydrochloride according to the procedure described for acid 1 (4.step). LC-MS (A): $t_R$=0.80 min; [M+H]$^+$: 315.09.

2-((2-Chloro-6-(dimethylcarbamoyl)pyridin-3-yl)oxy)acetic acid

This acid has been prepared from tert-butyl 2-((2-chloro-6-(dimethylcarbamoyl) pyridin-3-yl)oxy)acetate according to the procedure described for acid 1 (5.step). LC-MS (A): $t_R$=0.51 min; [M+H]$^+$: 258.96.

Acid 6: 2-(2-Chloro-4-cyanophenoxy)acetic acid

3-Chloro-4-hydroxybenzonitrile

To a solution of 3-chloro-4-methoxybenzonitrile (4.25 g) in DCM (85 ml) was added a −78° C. dropwise 1M BBr$_3$ in DCM (50.7 ml). The reaction mixture was stirred at −78° C. for 10 min and at rt overnight. The mixture was then stirred at 40° C. for 4.5 d and additional BBr$_3$ sol. (26 ml) was added on the first, second and third day, respectively. The reaction mixture was carefully quenched with water, the solid precipitate was filtrated off. The layers were separated, the aq. phase was washed with DCM and the combined org. layers were dried over MgSO$_4$, filtrated off and evaporated in vacuo. The crude was purified by CC (Büchi Sepacore, 50 g cartridge, solvent A: Heptane, solvent B: EA, gradient in % B: 0 to 40, flow rate: 30 ml/min) to afford 3.17 g of a brown oil. LC-MS (A): $t_R$=0.68 min; [M+H]$^+$: not visible.

Methyl 2-(2-chloro-4-cyanophenoxy)acetate

To a solution of 3-chloro-4-hydroxybenzonitrile (500 mg) in THF (10 ml) was added NaH (156 mg) portionwise at 0° C. After 30 min methyl bromoacetate (0.45 ml) was added and the mixture was stirred overnight at 80° C. The reaction mixture was diluted with EA and sat. aq. NH$_4$Cl. The layers were separated and the org. phase was washed with sat. aq. NaCl. The combined org. layers were dried over MgSO$_4$, filtrated off and evaporated in vacuo. The crude was purified by CC (Büchi Sepacore, 20 g cartridge, solvent A: Heptane, solvent B: EA, gradient in % B: 1 to 8, flow rate: 17 ml/min) to afford 1683 mg of a yellow solid. LC-MS (A): $t_R$=0.79 min; [M+H]$^+$: not visible.

2-(2-Chloro-4-cyanophenoxy)acetic acid

To a solution of methyl 2-(2-chloro-4-cyanophenoxy)acetate (680 mg) in MeOH (25 ml) was added 1M aq. NaOH (7 ml). The reaction mixture was stirred at rt for 48 h. The MeOH was evaporated in vacuo and DCM (20 ml) was added. 1M aq. HCl (10 ml) was added at 0° C. The layers were separated and the aq. phase was washed with DCM. The combined org. layers were dried over MgSO$_4$, filtrated off and evaporated in vacuo. The crude (432 mg of a white solis) was used in the next step without purification. LC-MS (A): $t_R$=0.67 min; [M+H]$^+$: not visible.

Acid 7: 2-(2-Chloro-4-(trifluoromethyl)phenoxy)acetic acid

This compound was prepared from 2-chloro-4-(trifluoromethyl)phenol according to the procedures described for acid 6 (step 2-3). LC-MS (A): $t_R$=0.74 min; [M+H]$^+$: not visible.

Acid 8: 2-((2-Chloro-6-(methylcarbamoyl)pyridin-3-yl)oxy)acetic acid

This compound was prepared from 6-chloro-5-(methoxymethoxy)picolinic acid according to the procedures described for acid 5 using methylamine instead of dimethylamine for the amide coupling. LC-MS (A): $t_R$=0.53 min; [M+H]$^+$: 318.19.

Acid 9: 2-((2-Chloro-6-(oxazol-2-yl)pyridin-3-yl)oxy)acetic acid

2-(6-Chloro-5-(methoxymethoxy)pyridin-2-yl)oxazole

To a solution of 2-chloro-6-iodo-3-(methoxymethoxy) pyridine (1 g) in DMF (10 ml) were added 2-(tri-n-butylstannyl)oxazole (2.4 g) and tetrakis(triphenylphosphine)palladium (0) (20 mg). The mixture was stirred at 120° C. for 1 h. The solvent was evaporated in vacuo and the remaining crude was purified by CC (Büchi Sepacore, 20 g cartridge, solvent A: Heptane, solvent B: EA, gradient in % B: 1 to 20, flow rate: 20 ml/min) to afford 420 mg of a white solid. LC-MS (A): $t_R$=0.74 min; [M+H]$^+$: 240.96.

2-((2-Chloro-6-(oxazol-2-yl)pyridin-3-yl)oxy)acetic acid

This acid has been prepared from 2-(6-chloro-5-(methoxymethoxy)pyridin-2-yl)oxazole according to the procedures described for acid 1 (3 to 5.step). LC-MS (A): $t_R$=0.59 min; [M+H]$^+$: 255.14.

Acid 10: 2-((2-chloro-6-(cyclopropyl(methyl)carbamoyl)pyridin-3-yl)oxy)acetic acid

6-Chloro-N-cyclopropyl-5-(methoxymethoxy)-N-methylpicolinamide

This compound has been prepared from 6-chloro-5-(methoxymethoxy)picolinic acid according to procedures described for acid 5 (1.step to 4.step) using N-methylcyclopropanamine instead of dimethylamine in the amide coupling. LC-MS (A): $t_R$=0.59 min; [M+H]$^+$: 285.15.

Acid 11: 2-((2-Chloro-6-(N-methylmethylsulfonamido)pyridin-3-yl)oxy)acetic acid This compound has been prepared from tert-butyl 2-((2-chloro-6-iodopyridin-3-yl)oxy)acetate according to the procedures described for acid 2 (2.step to 3.step) using N-methylmethanesulfonamide instead of methanesulfonamide in the Ullmann coupling. LC-MS (A): $t_R$=0.63 min; [M+H]$^+$: 295.06.

Acid 12: 2-((2-Chloro-6-(N-methylmethylsulfonamido)pyridin-3-yl)oxy)acetic acid

Tert-butyl 2((2-ethyl-6-(methylsulfonamido)pyridin-3-yl)oxy)acetate

To solution of tert-butyl 2-((2-chloro-6-(methylsulfonamido)pyridin-3-yl)oxy)acetate (192 mg) in dioxane (8 ml) was added at rt diethylzinc 1M in hexanes (0.855 ml), (1,1'-bis(diphenylphosphino) ferrocene) dichloropalladium (II) dichloromethane adduct (15 mg) and the mixture was stirred at 85° C. for 1.5 h. The reaction mixture was diluted with water and EA. The layers were separated, the aq. phase was washed with EA and the combined org. layers were washed with sat. aq. NaCl, dried over MgSO$_4$, filtrated off and evaporated in vacuo. The crude was purified by preparative LC-MS to afford 180 mg of a white solid. LC-MS (A): $t_R$=0.83 min; [M+H]$^+$: 331.26.

2-((2-Chloro-6-(N-methylmethylsulfonamido)pyridin-3-yl)oxy)acetic acid

This acid has been prepared from tert-butyl 2-((2-ethyl-6-(methylsulfonamido)pyridin-3-yl)oxy)acetate according to the procedures described for acid 1 (5.step). LC-MS (A): $t_R$=0.55 min; [M+H]$^+$: 275.01.

Acid 13: 2 2-((2-Chloro-6-(1,1-dioxidoisothiazolidin-2-yl)pyridin-3-yl)oxy)acetic acid This compound has been prepared from tert-butyl 2-((2-chloro-6-iodopyridin-3-yl)oxy)acetate according to the procedures described for acid 2 (2.step to 3.step) using isothiazolidine 1,1-dioxide instead of methanesulfonamide in the Ullmann coupling. LC-MS (A): $t_R$=0.61 min; [M+H]$^+$: 307.01.

Acid 14: 2-((2-Chloro-6-(4-methylpiperazin-1-yl)pyridin-3-yl)oxy)acetic acid This compound has been prepared from tert-butyl 2-((2-chloro-6-iodopyridin-3-yl)oxy)acetate according to the procedures described for acid 2 (2.step to 3.step) using 1-methylpiperazine instead of methanesulfonamide in the Ullmann coupling. LC-MS (A): $t_R$=0.45 min; [M+H]$^+$: 286.11.

Acid 15: 2-((2-Chloro-6-(cyclopropylcarbamoyl)pyridin-3-yl)oxy)acetic acid

This compound has been prepared from 6-chloro-5-(methoxymethoxy)picolinic acid according to the procedures described for acid 5 using cyclopropylamine instead of dimethylamine in the amide coupling. LC-MS (A): $t_R$=0.61 min; [M+H]$^+$: 271.16.

Acid 16: 2-((2-Chloro-6-(ethyl(methyl)carbamoyl)pyridin-3-yl)oxy)acetic acid This compound has been prepared from 6-chloro-5-(methoxymethoxy)picolinic acid according to the procedures described for acid 5 using ethylmethylamine instead of dimethylamine in the amide coupling. LC-MS (A): $t_R$=0.58 min; [M+H]$^+$: 273.13.

Acid 17: 2-((2-Chloro-6-(isopropyl(methyl)carbamoyl)pyridin-3-yl)oxy)acetic acid This compound has been prepared from 6-chloro-5-(methoxymethoxy)picolinic acid according to procedures described for acid 5 using isopropylmethylamine instead of dimethylamine in the amide coupling. LC-MS (A): $t_R$=0.62 min; [M+H]$^+$: 287.14.

Acid 18: 2-((2-Chloro-6-cyclopropylpyridin-3-yl)oxy)acetic acid

Tert-butyl 2-((2-chloro-6-cyclopropylpyridin-3-yl)oxy)acetate

A solution of tert-butyl 2-((2-chloro-6-iodopyridin-3-yl)oxy)acetate (250 mg), cyclopropylboronic acid (116 mg), palladium(II)acetate (23 mg), tricyclohexylphosphine (57 mg) and K$_2$PO$_4$.H$_2$O (234 mg) in toluene (7 ml) was stirred in a sealed tube at 90° C. for 48 h. The mixture was filtrated over celite, the solid was washed with EA and the combined org. layers were washed with sat. aq. NaCl, dried over MgSO$_4$, filtrated off and evaporated in vacuo. The crude was purified by CC (Büchi Sepacore, 10 g cartridge, solvent A: Heptane, solvent B: EA, gradient in % B: 0 to 3, flow rate:

2-((2-Chloro-6-cyclopropylpyridin-3-yl)oxy)acetic acid

This acid has been prepared from tert-butyl 2-((2-chloro-6-cyclopropylpyridin-3-yl)oxy)acetate according to the procedure described for acid 1 (5.step). LC-MS (A): $t_R$=0.69 min; [M+H]$^+$: 228.14.

Acid 19: 2-((2-Chloro-6-(5-methyl-1,1-dioxido-1,2,5-thiadiazolidin-2-yl)pyridin-3-yl)-oxy)acetic acid This acid has been prepared from tert-butyl 2-((2-chloro-6-iodopyridin-3-yl)oxy)acetate according to the procedure described for acid 2 (2 and 3.step) using 2-methyl-1,2,5-thiadiazolidine 1,1-dioxide instead of methysulfonamide in the Ulmann coupling. LC-MS (A): $t_R$=0.65 min; [M+H]$^+$: 321.84.

Acid 20: 2-((6-(1,1-Dioxidoisothiazolidin-2-yl)-2-ethylpyridin-3-yl)oxy)acetic acid This compound has been prepared from acid 13 according to procedures described for acid 12 (1.step). LC-MS (A): $t_R$=0.65 min; [M+H]$^+$: 301.26.

Acid 21: 2-((6-((N,N-Dimethylsulfamoyl)amino)-2-ethylpyridin-3-yl)oxy)acetic acid

Tert-butyl 2-((2-chloro-6-((N,N-dimethylsulfamoyl)amino)pyridin-3-yl)oxy)acetate This compound has been prepared from tert-butyl 2-((2-chloro-6-iodopyridin-3-yl)oxy)acetate according to procedures described for acid 2 (2.step) using N,N-dimethylsulfamide instead of methansulfonamide LC-MS (A): $t_R$=0.87 min; [M+H]$^+$: 366.23.

Tert-butyl 2-((6-((N,N-dimethylsulfamoyl)amino)-2-ethylpyridin-3-yl)oxy)acetate This compound has been prepared from tert-butyl 2-((2-chloro-6-((N,N-dimethylsulfamoyl)amino)pyridin-3-yl)oxy)acetate according to procedures described for acid 12 (1.step). LC-MS (A): $t_R$=0.87 min; [M+H]$^+$: 360.04.

2-((6-((N,N-Dimethylsulfamoyl)amino)-2-ethylpyridin-3-yl)oxy)acetic acid

This compound has been prepared from tert-butyl 2-((6-((N,N-dimethylsulfamoyl)amino)-2-ethylpyridin-3-yl)oxy)acetate according to procedures described for acid 1 (5.step). LC-MS (A): $t_R$=0.62 min; [M+H]$^+$: 304.10.

Acid 22: 2((6-(Cyclopropylcarbamoyl)-2-ethylpyridin-3-yl)oxy)acetic acid

Tert-butyl 2((6-(cyclopropylcarbamoyl)-2-ethylpyridin-3-yl)oxy)acetate

This compound has been prepared from tert-butyl 2-((2-chloro-6-(cyclopropylcarbamoyl)pyridin-3-yl)oxy)acetate (see synthesis of the acid 15) according to procedures described for acid 12 (1.step). LC-MS (A): $t_R$=0.91 min; [M+H]$^+$: 320.12.

2((6-(Cyclopropylcarbamoyl)-2-ethylpyridin-3-yl)oxy)acetic acid

This compound has been prepared from tert-butyl 2-((6-(cyclopropylcarbamoyl)-2-ethylpyridin-3-yl)oxy)acetate according to the procedure described for acid 1 (5.step). LC-MS (A): $t_R$=0.67 min; [M+H]$^+$: 265.14.

Acid 23: 2-((2-Methoxy-6-(methylsulfonamido)pyridin-3-yl)oxy)acetic acid

6-iodo-2-methoxy-3-(methoxymethoxy)pyridine

A solution of 2-chloro-6-iodo-3-(methoxymethoxy)pyridine (400 mg) and sodium methoxide (97 mg) in DMSO (12 ml) was stirred at 90° C. for 1.5 h. The reaction mixture was diluted with sat. aq. NH$_4$Cl and EA. The layers were separated, the aq. phase was washed with EA and the combined org. layers were washed with sat. aq. NaCl, dried over MgSO$_4$, filtrated off and evaporated in vacuo. The crude was purified by CC (Büchi Sepacore, 10 g cartridge, solvent A: Heptane, solvent B: EA, gradient in % B: 2 to 12, flow rate: 15 ml/min) to afford 323 mg of a yellow oil. LC-MS (A): $t_R$=0.85 min; [M+H]$^+$: 295.93.

6-Iodo-2-methoxypyridin-3-ol

This compound has been prepared from 6-iodo-2-methoxy-3-(methoxymethoxy)pyridine according to procedures described for acid 1 (2.step). LC-MS (A): $t_R$=0.72 min; [M+H]$^+$: 251.97.

2-((2-Methoxy-6-(methylsulfonamido)pyridin-3-yl)oxy)acetic acid

This compound has been prepared from 6-iodo-2-methoxypyridin-3-ol according to the procedures described for acid 2 (steps 1-3). LC-MS (A): $t_R$=0.49 min; [M+H]$^+$: 277.04.

Acid 24: ((2-Ethyl-6-methylpyridin-3-yl)oxy)acetic acid

This compound has been prepared from 2-ethyl-3-hydroxy-6-methylpyridine according to the procedures described for acid 1 (steps 4-5). LC-MS (A): $t_R$=0.36 min; [M+H]$^+$: 196.13.

Acid 25: 2((4-Ethyl-2-(methylsulfonamido)pyrimidin-5-yl)oxy)acetic acid

2-Chloro-4-ethyl-5-methoxypyrimidine

To a solution of 2,4-dichloro-5-methoxypyrimidine (4 g) and iron(III) acetylacetonate (790 mg) in THF (40 ml) was added at 0° dropwise ethylmagnesium chloride 2M in Et$_2$O (13 ml). The mixture was stirred at rt overnight. The reaction mixture was diluted with TBME, water and aq. 1N HCl. The layers were separated, the aq. phase was washed with TBME and the combined org. layers were washed with sat. aq. NaHCO$_3$, water and sat. aq. NaCl, dried over MgSO$_4$, filtrated off over Whatman filter and evaporated in vacuo. The crude was purified by CC (Büchi Sepacore, 50 g cartridge, solvent A: Heptane, solvent B: EA, gradient in % B: 1 to 8, flow rate: 30 ml/min) to afford 2.8 mg of a colourless solid. LC-MS (A): $t_R$=0.72 min; [M+H]$^+$: 173.02.

2-Chloro-4-ethylpyrimidin-5-ol

This compound has been prepared from 2-chloro-4-ethyl-5-methoxypyrimidine according to procedures described for acid 6 (1.step). LC-MS (A): $t_R$=0.59 min; [M+H]$^+$: 159.06.

Tert-butyl 2-((2-chloro-4-ethylpyrimidin-5-yl)oxy) acetate

This compound has been prepared from 2-chloro-4-ethylpyrimidin-5-ol according to procedures described for acid 1 (4.step). LC-MS (A): $t_R$=0.89 min; [M+H]$^+$: 273.11.

Tert-butyl 2((4-ethyl-2-(methylthio)pyrimidin-5-yl)oxy)acetate

A solution of tert-butyl 2-((2-chloro-4-ethylpyrimidin-5-yl)oxy)acetate (391 mg) and sodium thiomethoxide (160 mg) in THF (10 ml) was stirred at 60° C. for 24 h. The reaction mixture was diluted with sat. aq. NH$_4$Cl and EA. The layers were separated, the aq. phase was washed with EA and the combined org. layers were washed with sat. aq. NaCl, dried over MgSO$_4$, filtrated off and evaporated in vacuo. The crude was purified by CC (Büchi Sepacore, 5 g cartridge, solvent A: Heptane, solvent B: EA, gradient in % B: 2 to 20, flow rate: 10 ml/min) to afford 273 mg of a yellow oil. LC-MS (A): $t_R$=0.93 min; [M+H]$^+$: 285.10.

Tert-butyl 2-((4-ethyl-2-(methylsulfonyl)pyrimidin-5-yl)oxy)acetate

A solution of tert-butyl 2-((4-ethyl-2-(methylthio)pyrimidin-5-yl)oxy)acetate (270 mg) and peracetic acid (39% in acetic acid) (0.5 ml) in DCM (20 ml) was stirred at rt for 4 h. Additional peracetic acid sol. (0.5 ml) was added after the first and third hour, respectively. The reaction mixture was diluted with sat. aq. NaHCO$_3$ and DCM. The layers were separated, the aq. phase was washed with DCM and the combined org. layers were washed with sat. aq. NaCl, dried over MgSO$_4$, filtrated off and evaporated in vacuo. The crude colourless solid (261 mg) was used in the next step without purification. LC-MS (A): $t_R$=0.81 min; [M+H]$^+$: 317.06.

Tert-butyl 2((4-ethyl-2-(methylsulfonamido)pyrimidin-5-yl)oxy)acetate

A solution of tert-butyl 2-((4-ethyl-2-(methylsulfonyl) pyrimidin-5-yl)oxy)acetate (300 mg) and methanesulfonamide potassium salt (380 mg) in DMSO (15 ml) was stirred in a microwave at 100° C. for 1 h. The reaction mixture was diluted with sat. aq. NaHCO$_3$ and EA. The layers were separated, the aq. phase was washed with EA and the combined org. layers were washed with sat. aq. NaCl, dried over MgSO$_4$, filtrated off and evaporated in vacuo. The crude was purified by CC (Büchi Sepacore, 10 g cartridge, solvent A: Heptane, solvent B: EA, gradient in % B: 0 to 30, flow rate: 10 ml/min) to afford 58 mg of a colourless solid. LC-MS (A): $t_R$=0.80 min; [M+H]$^+$: 332.06.

2((4-Ethyl-2-(methylsulfonamido)pyrimidin-5-yl)oxy)acetic acid

This compound has been prepared from tert-butyl 2-((4-ethyl-2-(methylsul-fonamido)pyrimidin-5-yl)oxy)acetate according to the procedures described for acid 1 (5.step). LC-MS (A): $t_R$=0.51 min; [M+H]$^+$: 276.06.

Acid 26: 2-((2-Chloro-4-ethylpyrimidin-5-yl)oxy)acetic acid

This compound has been prepared from tert-butyl 2-((2-chloro-4-ethylpyrimidin-5-yl)oxy)acetate (for the synthesis see acid 25) according to procedures described for acid 1 (5.step). LC-MS (A): $t_R$=0.59 min; [M+H]$^+$: 217.04.

Acid 27: 2((6-Cyclopropyl-2-ethylpyridin-3-yl)oxy)acetic acid

This compound has been prepared from tert-butyl 2-((2-chloro-6-cyclopropylpyridin-3-yl)oxy)acetate (for the synthesis see acid 18) according to the procedures described for acid 12 (steps 1-2). LC-MS (A): $t_R$=0.44 min; [M+H]$^+$: 222.17.

Acid 28: 2-(2-Chloro-4-(morpholinomethyl)phenoxy)acetic acid

Tert-butyl 2-(2-chloro-4-formylphenoxy)acetate

To a solution of 3-chlor-4-hydroxybenzaldehyde (12.84 g) in MeCN was added NaI (1.23 g) and K$_2$CO$_3$ (12.47 g). The mixture was stirred at 80° C. for 45 min. Tert-butyl bromoacetate (8 g) was added dropwise and the mixture was stirred at 80° C. for 15 h. The reaction mixture was diluted at rt with water and DCM. The layers were separated, the aq. phase was washed with EA and the combined org. layers were dried over Na$_2$SO$_4$, filtrated off and evaporated in vacuo. The crude was used without further purification in the next step. LC-MS (A): $t_R$=0.91 min; [M+H]$^+$: not visible.

Tert-butyl 2-(2-chloro-4-(morpholinomethyl)phenoxy)acetate

To a solution of tert-butyl 2-(2-chloro-4-formylphenoxy) acetate (4.5 g) and morpholine (2.5 ml) in MeCN (45 ml) was added at 0° C. sodium triacetoxyborohydrid (7.4 g) and the reaction mixture was stirred at rt overnight. The reaction mixture was diluted with aq. 1N NaOH and EA. The layers were separated, the aq. phase was washed with DCM and the combined org. layers were washed with sat. aq. NaCl, dried over MgSO$_4$, filtrated off and evaporated in vacuo. The crude was purified by FC (A: EA, solvent B: heptane, ratio A:B=50:50) to afford 5.3 g of an colourless oil. LC-MS (A): $t_R$=0.46 min; [M+H]$^+$: 342.16.

2-(2-Chloro-4-(morpholinomethyl)phenoxy)acetic acid

This acid was prepared from tert-butyl 2-(2-chloro-4-(morpholinomethyl)phenoxy)acetate according to the procedure described for acid 1 (5.step). LC-MS (A): $t_R$=0.44 min; [M+H]$^+$: 286.15.

Acid 29: 2-(2-Chloro-4-morpholinophenoxy)acetic acid

This compound has been prepared from 4-bromo-chlorophenol according to the procedures described for acid 1 (steps 1-5). LC-MS (A): $t_R$=0.63 min; [M+H]$^+$: 272.02

Acid 30: 2-(2-Ethyl-4-fluorophenoxy)acetic acid

This compound has been prepared from 2-ethyl-4-fluorophenol according to the procedures described for acid 1 (steps 4-5). LC-MS (A): $t_R$=0.77 min; [M+H]$^+$: not visible.

Acid 31: 2-((2-Chloro-5-fluoropyridin-3-yl)oxy)acetic acid

This compound has been prepared from 2-chloro-5-fluoropyridin-3-ol according to procedures described for acid 1 (steps 4-5).). LC-MS (A): $t_R$=0.88 min; [M+H]$^+$: 262.10.

Acid 32: 2-((2-(Trifluoromethyl)pyridin-3-yl)oxy)acetic acid 2-(Trifluoromethyl)pyridin-3-ol To a solution of 1.6M nBuLi in hexane (0.94 ml) in THF (2.7 ml) was added at −78° C. 2,2,6,6-tetramethylpiperidin (0.28 ml) followed by 2-trifluoromethylpyridine (0.14 ml). The reaction was stirred at −78° C. for 17 h. Trimethylborate (0.32 ml) was added and the reaction was stirred at −78° c. for 2 h. Peracetic acid was added (0.39 ml, 39% solution in AcOH) and the reaction mixture was allowed to warm to 0° C. under stirring for 3 h. The reaction mixture was diluted with sat. aq. Na$_2$SO$_3$ and DCM. The layers were separated, the aq. phase was washed with EA and the combined org. layers were dried over MgSO$_4$, filtrated off and evaporated in vacuo. The crude was purified by FC (A: DCM, solvent B: MeOH, gradient in % B: 2) to afford 114 mg of an orange oil. LC-MS (A): $t_R$=0.46 min; [M+H]$^+$: 164.20.

2((2-(Trifluoromethyl)pyridin-3-yl)oxy)acetic acid

This compound was prepared from 2-(trifluoromethyl)pyridin-3-ol according to the procedures described for acid 1 (steps 4-5). LC-MS (A): $t_R$=0.49 min; [M+H]$^+$: 221.98.

Acid 33: 2-((2-Fluoro-6-morpholinopyridin-3-yl)oxy)acetic acid

2-Fluoro-6-iodopyridin-3-ol

To a solution of 2-fluoro-3-hydroxypyridine (500 mg) in water (22 ml) were added K$_2$CO$_3$ (599 mg) and iodine (660 mg). The reaction mixture was stirred at rt overnight. A solution of sat. aq. sodium thiosulfate was added, then 2N aq. HCl and the mixture was extracted with EA. The layers were separated, the org. layer was dried over MgSO$_4$, filtrated off and evaporated in vacuo. The crude was purified by CC (Büchi Sepacore, 20 g cartridge, solvent A: Heptane, solvent B: EA, gradient in % B: 10, flow rate: 15 ml/min) to afford 220 mg of a yellow solid. GC-MS (A): $t_R$=2.13 min; [M+H]$^+$: 239.90.

2-((2-Fluoro-6-morpholinopyridin-3-yl)oxy)acetic acid

This acid has been prepared from 2-fluoro-6-iodopyridin-3-ol according to the procedures described for acid 2 (step 1-3) using morpholine instead of methansulfonamide in the Ullmann coupling. LC-MS (A): $t_R$=0.62 min; [M+H]$^+$: 257.16.

Acid 34: 2-((6-(3,3-Difluoroazetidin-1-yl)-2-chloropyridin-3-yl)oxy)acetic acid This compound has been prepared from tert-butyl 2-((2-chloro-6-iodopyridin-3-yl)oxy)acetate (for the synthesis see acid 2) according to the procedures described for acid 2 (step 2-3) using 3,3-difluoroazetidine instead of methanesulfonamide in the Ullmann coupling. LC-MS (A): $t_R$=0.61 min; [M+H]$^+$: 307.01.

Acid 35: 2-((2-Chloropyridin-3-yl)oxy)acetic acid

This compound was prepared from 2-chloropyridin-3-ol according to the procedures described for acid 6 (step 2-3). LC-MS (A): $t_R$=0.50 min; [M+H]$^+$: 188.18.

Acid 36: 2-((2-Chloro-5-fluoro-6-morpholinopyridin-3-yl)oxy)acetic acid 2-Chloro-5-fluoro-6-iodopyridin-3-ol A solution of 2-chloro-5-fluoropyridin-3-ol (500 mg), K$_2$CO$_3$ (937 mg) and iodine (886 mg) in water (17 ml) was stirred at rt overnight. A solution of sat. aq. sodium thiosulfate was added followed by 2N aq. HCl and the mixture was extracted with EA. The layers were separated, the org. layer was dried over MgSO$_4$, filtrated off and evaporated in vacuo. The crude (992 mg) was used in the next step without further purification.

Tert-butyl 2-((2-chloro-5-fluoro-6-iodopyridin-3-yl)oxy)acetate

This ester has been prepared from 2-chloro-5-fluoro-6-iodopyridin-3-ol according to the procedure described for acid 1 (4. step). LC-MS (A): $t_R$=0.96 min; [M+H]$^+$: 387.89.

Tert-butyl 2-((2-chloro-5-fluoro-6-morpholinopyridin-3-yl)oxy)acetate

This compound has been prepared from tert-butyl 2-((2-chloro-5-fluoro-6-iodopyridin-3-yl)oxy)acetate according to the procedure described for acid 1 (2. step). LC-MS (A): $t_R$=0.94 min; [M+H]$^+$: 347.06.

2-((2-Chloro-5-fluoro-6-morpholinopyridin-3-yl)oxy)acetic acid

This acid has been prepared from tert-butyl 2-((2-chloro-5-fluoro-6-morpholinopyridin-3-yl)oxy)acetate according to the procedure described for acid 1 (5.step). LC-MS (A): $t_R$=0.70 min; [M+H]$^+$: 291.06.

Acid 37: 2-(2-Chloro-4-(dimethylcarbamoyl)phenoxy)acetic acid

3-Chloro-4-hydroxy-N, N-dimethylbenzamide

A solution of 3-chloro-4-hydroxybenzoic acid (1 g), DCC (1.4 g), HOBt (0.92 g) and dimethylamine (5.8 ml, 2M in THF) in DMF (12 ml) was stirred at r overnight. The reaction mixture was diluted with sat. aq. NH$_4$Cl and EA. The reaction mixture was filtrated off and evaporated in vacuo and the crude was crystalized from EA to afford 0.82 g of a colourless solid. LC-MS (A): $t_R$=0.57 min; [M+H]$^+$: 200.22.

2-(2-Chloro-4-(dimethylcarbamoyl)phenoxy)acetic acid

This acid has been prepared from 3-chloro-4-hydroxy-N,N-dimethylbenzamide according to procedure described for acid 1 (steps 4-5). LC-MS (A): $t_R$=0.58 min; [M+H]$^+$: 257.89

Acid 38: 2((2-Cyclopropyl-6-(methylsulfonamido)pyridin-3-yl)oxy)acetic acid

Tert-butyl 2((2-cyclopropyl-6-(methylsulfonamido)pyridin-3-yl)oxy)acetate

A mixture of tert-butyl 2-((2-chloro-6-(methylsulfonamido)pyridin-3-yl)oxy)acetate (for the synthesis see acid 2) (100 mg), cyclopropylboronic acid (175 mg), tetrakis(trphenylphosphine)palladium (102 mg) and K$_2$CO$_3$ (62 mg) in dioxane (6 ml) was stirred at 120° C. for 3 days. The mixture was filtered off and the solvent was evaporated in vacuo. The crude was purified by preparative LC-MS (I) and by CC (Büchi Sepacore, 5 g cartridge, solvent A: Heptane, solvent B: EA, gradient in % B: 1 to 25, flow rate: 10 ml/min) to afford 50 mg of a yellowish solid. LC-MS (A): $t_R$=0.86 min; [M+H]$^+$: 343.10.

2((2-Cyclopropyl-6-(methylsulfonamido)pyridin-3-yl)oxy)acetic acid

This compound has been prepared from tert-butyl 2-((2-cyclopropyl-6-(methylsulfonamido)pyridin-3-yl)oxy)acetate according to the procedure described for acid 1 (5.step). LC-MS (A): $t_R$=0.62 min; [M+H]$^+$: 287.10.

Acid 39: 2-((2-Chloro-6-(dimethylamino)pyridin-3-yl)oxy)acetic acid

This acid has been prepared according to the synthesis described for acid 1 using dimethylamine instead of morpholine in the Ullmann coupling. LC-MS (A): $t_R$=0.67 min; [M+H]$^+$: 231.25.

Acid 40: 2-((2-Cyclopropyl-6-(cyclopropylcarbamoyl)pyridin-3-yl)oxy)acetic acid 3-(Benzyloxy)-2-chloro-6-iodopyridine A mixture of 2-chloro-6-iodopyridin-3-ol (40.4 g), K$_2$CO$_3$ (33 g) and benzyl bromide (20 ml) in DMF (320 ml) was stirred at 60° C. for 2 h. The mixture was diluted at rt with EA and aq. sat. NH$_4$Cl. The layers were separated and the aq. phase was washed twice with EA. The combined org. layers were washed with aq. sat. NaCl, dried over MgSO$_4$, filtrated off and evaporated in vacuo. The crude was stirred with mixture of heptane/EA (95/5) at rt for 10 min and filtrated off to afford 43.2 g of a colourless solid. LC-MS (A): $t_R$=0.97 min; [M+H]$^+$: 345.79.

5-(Benzyloxy)-6-chloropicolinic acid

This compound has been prepared from 3-(benzyloxy)-2-chloro-6-iodopyridine according to the procedure described for acid 4 (2.step). LC-MS (A): $t_R$=0.77 min; [M+H]$^+$: 263.99.

5-(Benzyloxy)-6-chloro-N-cyclopropylpicolinamide

This compound has been prepared from 5-(benzyloxy)-6-chloropicolinic acid according to procedures described for acid 5 (1.step) using cyclopropylamine instead of dimethylamine in the amide coupling. LC-MS (A): $t_R$=0.90 min; [M+H]$^+$: 302.99.

6-Chloro-N-cyclopropyl-5-hydroxypicolinamide

A mixture of 5-(benzyloxy)-6-chloro-N-cyclopropylpicolinamide (13.67 g) and Pd/C (1.37 g) in MeOH (600 ml) was stirred under hydrogen (1 bar) at rt for 20 min. The mixture was filtrated off and the solvent was evaporated in vacuo. The crude was triturated (3×) with DCM/MeOH (99.5/0.5) to afford 7.5 g of colourless solid. (LC-MS (A): $t_R$=0.62 min; [M+H]$^+$: 213.07.

N,6-Dicyclopropyl-5-hydroxypicolinamide

This compound has been prepared from 6-chloro-N-cyclopropyl-5-hydroxypicolinamide according to the procedure described for acid 38 (1.step). LC-MS (A): $t_R$=0.70 min; [M+H]$^+$: 219.13.

2-((2-Cyclopropyl-6-(cyclopropylcarbamoyl)pyridin-3-yl)oxy)acetic acid

This compound has been prepared from N,6-dicyclopropyl-5-hydroxypicolinamide according to the procedures described for acid 1 (step 4 and 5). LC-MS (A): $t_R$=0.70 min; [M+H]$^+$: 277.13.

Acid 41: 2-((2-Chloro-6-(methyl(2,2,2-trifluoroethyl)amino)pyridin-3-yl)oxy)acetic acid

6-Chloro-5-(methoxymethoxy)-N-methylpyridin-2-amine

A solution of 2-chloro-6-iodo-3-(methoxymethoxy)pyridine (1 g) in methylamine 40% in water (35 ml) and copper (106 mg) was stirred at 100° C. for 1 h45. The reaction mixture was diluted with EA. The layers were separated, the aq. phase was washed with EA and the combined org. layers were dried over Na$_2$SO$_4$, filtrated off and evaporated in vacuo. The crude was recrystallized in EA and a few drops of heptane to afford 400 mg of a brown solid. LC-MS (A): $t_R$=0.69 min; [M+H]$^+$: 203.20.

N-(6-Chloro-5-(methoxymethoxy)pyridin-2-yl)-2,2,2-trifluoro-N-methylacetamide To a solution of 6-chloro-5-(methoxymethoxy)-N-methylpyridin-2-amine (61 mg) in DCM (3 ml) were added trifluoroacetic anhydride (63 μl) and DIPEA (103 μl). The mixture was stirred at 0° C. for 1 h and at rt for 1.5 h. The mixture was diluted with DCM and 1N aq. HCl. The layers were separated, the org. phase was washed with water and sat. aq. NaCl. The combined org. layers were dried over MgSO$_4$, filtrated off and evaporated in vacuo. The crude was purified by CC (Flash Master, 2 g cartridge, solvent A: Heptane, solvent B: EA, gradient in % B: 0 to 5, flow rate: 6 ml/min) to afford 76 mg of a yellow oil. LC-MS (A): $t_R$=0.84 min; [M+H]$^+$: 299.03.

2-Chloro-6-(methyl(2,2,2-trifluoroethyl)amino)pyridin-3-ol

To a solution of N-(6-chloro-5-(methoxymethoxy)pyridin-2-yl)-2,2,2-trifluoro-N-methyl acetamide (80 mg) in THF (1.5 ml) was added borane-methyl sulfide complex (2M in THF, 1.34 ml). The reaction mixture was stirred at 50° C. overnight. The mixture was evaporated in vacuo, the residue was diluted with EA and 1N aq. NaOH. The layers were separated and the aq. phase was washed with EA. The combined org. layers were dried over $Na_2SO_4$, filtrated off and evaporated in vacuo. The crude alcohol (72 mg) was used in the next step without purification. LC-MS (A): $t_R$=0.80 min; $[M+H]^+$: 240.98.

Tert-butyl 2-((2-chloro-6-(methyl(2,2,2-trifluoroethyl)amino)pyridin-3-yl)oxy)acetate This ester has been prepared from 2-chloro-6-(methyl(2,2,2-trifluoroethyl)amino)pyridin-3-ol according to the procedure described for acid 1 (4.step). LC-MS (A): $t_R$=0.99 min; $[M+H]^+$: 354.91.

2-((2-Chloro-6-(methyl(2,2,2-trifluoroethyl)amino)pyridin-3-yl)oxy)acetic acid

This acid has been prepared from tert-butyl 2-((2-chloro-6-(methyl(2,2,2-trifluoroethyl)amino)pyridin-3-yl)oxy)acetate according to the procedure described for acid 1 (5.step). LC-MS (A): $t_R$=0.80 min; $[M+H]^+$: 299.08.

Acid 42: 2-((2-Chloro-6-((2-methoxyethyl)(methyl)amino)pyridin-3-yl)oxy)acetic acid Tert-butyl 2-((2-chloro-6-(2-methoxyethyl)(methyl)amino)pyridin-3-yl)oxy)acetate This compound has been prepared from tert-butyl 2-((2-chloro-6-iodopyridin-3-yl)oxy)acetate (see synthesis of acid 2, 1.step) according to the procedure described for acid 1 (2.step) using 2-methoxy-N-methylethan-1-amine instead of morpholine. LC-MS (A): $t_R$=0.94 min; $[M+H]^+$: 331.18.

2-((2-Chloro-6-(2-methoxyethyl)(methyl)amino)pyridin-3-yl)oxy)acetic acid

This acid has been prepared from tert-butyl 2-((2-chloro-6-((2-methoxyethyl)(methyhamino)pyridin-3-yl)oxy)acetate according to the procedure described for acid 1 (5.step). LC-MS (A): $t_R$=0.70 min; $[M+H]^+$: 275.09.

Acid 43: 2-((2-Chloro-6-(methylsulfonyl)pyridin-3-yl)oxy)acetic acid

Tert-butyl 2-((2-chloro-6-(methylsulfonyl)pyridin-3-yl)oxy)acetate

A mixture of tert-butyl 2-((2-chloro-6-iodopyridin-3-yl)oxy)acetate (see synthesis of acid 2, 1.step) (100 mg), sodium methanesulfinate (33 mg) and CuI (155 mg) in DMSO (5 ml) was stirred at 100° C. for 30 min. The mixture was diluted at rt with EA and aq. sat. $NH_4Cl$. The layers were separated and the aq. phase was washed twice with EA. The combined org. layers were washed with aq. sat. NaCl, dried over $MgSO_4$, filtrated off and evaporated in vacuo. The crude was purified by CC (solvent A: Heptane, solvent B: EA, gradient in % B: 5 to 100) to afford 70 mg of a colourless solid. LC-MS (A): $t_R$=0.82 min; $[M+H]^+$: 322.05.

2-((2-Chloro-6-(methylsulfonyl)pyridin-3-yl)oxy)acetic acid

This compound has been prepared from tert-butyl 2-((2-chloro-6-(methylsulfonyl) pyridin-3-yl)oxy)acetate according to the procedure described for acid 1 (5.step). LC-MS (A): $t_R$=0.51 min; $[M+H]^+$: 265.39.

Acid 44: 2-((2-Chloro-6-(N,N-dimethylsulfamoyl)pyridin-3-yl)oxy)acetic acid

Methyl 3-((5-(2-(tert-butoxy)-2-oxoethoxy)-6-chloropyridin-2-yl)sulfonyl)propanoate This compound has been prepared from tert-butyl 2-((2-chloro-6-iodopyridin-3-yl)oxy)acetate (see synthesis of acid 2) and sodium 3-methoxy-3-oxopropane-1-sulfinate according to the procedure described for acid 43 (1.step). LC-MS (A): $t_R$=0.86 min; $[M+H]^+$: 394.12.

Tert-butyl 2-((2-chloro-6-(N,N-dimethylsulfamoyl)pyridin-3-yl)oxy)acetate

A mixture of methyl 3-((5-(2-(tert-butoxy)-2-oxoethoxy)-6-chloropyridin-2-yl)sulfonyl)propanoate (100 mg) and 0.5M sodium methanolate in MeOH (0.5 ml) was stirred at rt for 15 min. The solvent was evaporated in vacuo and the crude was dissolved in THF (4 ml). ChloraminT trihydrate (116 mg) was added and the mixture was stirred at rt for 15 min. Dimethylethylamine in methanol (33%-solution, 0.46 ml) was added and the mixture was stirred at rt for 19 h. The mixture was diluted at rt with EA and aq. sat. $NH_4Cl$. The layers were separated and the aq. phase was washed twice with EA. The combined org. layers were washed with aq. sat. NaCl, dried over $MgSO_4$, filtrated off and evaporated in vacuo. The crude was purified by preparative LC-MS (I) to afford 53 mg of a yellowish solid. LC-MS (A): $t_R$=0.89 min; $[M+H]^+$: 351.07.

2-((2-Chloro-6-(N,N-dimethylsulfamoyl)pyridin-3-yl)oxy)acetic acid

This compound has been prepared tert-butyl 2-((2-chloro-6-(N,N-dimethylsulfamoyl)pyridin-3-yl)oxy)acetate according to the procedure described for acid 1 (5.step). LC-MS (A): $t_R$=0.63 min; $[M+H]^+$: 295.04.

Acid 45: 1-((2-Chloro-6-(((methylthio)peroxy)amino)pyridin-3-yl)oxy)cyclopropane-1-carboxylic acid Tert-butyl 4-bromo-2-((2-chloro-6-iodopyridin-3-yl)oxy)butanoate To a solution of 2-chloro-6-iodopyridin-3-ol (500 mg) in DMF (10 ml) was added at 0° C. NaH (115 mg, 60% dispersion in mineral oil) and the mixture was stirred at this temperature for 30 min. Methyl 2,4-dibromobutanoate (0.400 ml) was added and the mixture was stirred at rt for 6 h. The mixture was diluted with heptane and aq. sat. $NaHCO_3$. The layers were separated and the aq. phase was washed twice with heptane. The combined org. layers were washed with aq. sat. NaCl, dried over $MgSO_4$, filtrated off and evaporated in vacuo. The crude was purified by CC (Büchi Sepacore, 20 g cartridge, solvent A: Heptane, solvent B: EA, gradient in % B: 1 to 5, flow rate: 20 ml/min) to afford 417 mg of a colourless oil. LC-MS (A): $t_R$=1.02 min; $[M+H]^+$: 475.82.

Tert-butyl 1-((2-chloro-6-iodopyridin-3-yl)oxy)cyclopropane-1-carboxylate

To a solution of tert-butyl 4-bromo-2-((2-chloro-6-iodopyridin-3-yl)oxy)butanoate (415 mg) in THF (10 ml) was added at −20° C. potassium tert-butoxide (103 mg) and the mixture was stirred for 15 minutes. The mixture was diluted with EA and water. The layers were separated and the aq. phase was washed twice with EA. The combined org. layers were washed with aq. sat. NaCl, dried over MgSO$_4$, filtrated off and evaporated in vacuo. The crude 307 mg of a yellowish oil—was used in the next step without purification. LC-MS (A): $t_R$=0.98 min; [M+H]$^+$: 396.02.

Tert-butyl 1-((2-chloro-6-(((methylthio)peroxy)amino)pyridin-3-yl)oxy)cyclopropane-1-carboxylate This compound has been prepared from tert-butyl 1-((2-chloro-6-iodopyridin-3-yl)oxy)cyclopropane-1-carboxylate according to the procedure described for acid 2 (2.step). LC-MS (A): $t_R$=0.86 min; [M+H]$^+$: 363.11.

1-((2-Chloro-6-(((methylthio)peroxy)amino)pyridin-3-yl)oxy)cyclopropane-1-carboxylic acid This compound has been prepared from tert-butyl 1-((2-chloro-6-(((methylthio)peroxy)amino)pyridin-3-yl)oxy)cyclopropane-1-carboxylate according to the procedure described for acid 1 (5.step). LC-MS (A): $t_R$=0.63 min; [M+H]$^+$: 306.89.

Acid 46: 1-((2-Chloro-6-(dimethylcarbamoyl)pyridin-3-yl)oxy)cyclopropane-1-carboxylic acid 5-(1-Tert-butoxycarbonyl)cyclopropoxy)-6-chloropicolinic acid This compound has been prepared from tert-butyl 1-((2-chloro-6-iodopyridin-3-yl)oxy)cyclopropane-1-carboxylate (for the synthesis see acid 45, step 1 and 2) according to the procedure described for acid 4 (2.step). LC-MS (A): $t_R$=0.80 min; [M+H]$^+$: 314.02.

1-((2-Chloro-6-(dimethylcarbamoyl)pyridin-3-yl)oxy)cyclopropane-1-carboxylic acid This compound has been prepared from 5-(1-tert-butoxycarbonyl)cyclopropoxy)-6-chloropicolinic acid according to the procedures described for acid 5 (step 1 and 4). LC-MS (A): $t_R$=0.61 min; [M+H]$^+$: 285.07.

Acid 47: 2-((2-Chloro-6-(dimethylcarbamoyl)pyridin-3-yl)oxy)-2-methylpropanoic acid Tert-butyl 2-((2-chloro-6-iodopyridin-3-yl)oxy)-2-methylpropanoate This compound has been prepared from 2-chloro-6-iodopyridin-3-ol and tert-butyl 2-bromo-2-methylpropanoate according to the procedure described for acid 2 (1.step). LC-MS (A): $t_R$=1.01 min; [M+H]$^+$: 398.02.

5-((1-(Tert-butoxy)-2-methyl-1-oxopropan-2-yl)oxy)-6-chloropicolinic acid

This compound has been prepared from tert-butyl 2-((2-chloro-6-iodopyridin-3-yl)oxy)-2-methylpropanoate according to the procedure described for acid 4 (2.step). LC-MS (A): $t_R$=0.83 min; [M+H]$^+$: 316.03.

2-((2-Chloro-6-(dimethylcarbamoyl)pyridin-3-yl)oxy)-2-methylpropanoic acid

This compound has been prepared from 54(1-(tert-butoxy)-2-methyl-1-oxopropan-2-yl)oxy)-6-chloropicolinic acid according to the procedures described for acid 5 (step 1 and 4). LC-MS (A): $t_R$=0.63 min; [M+H]$^+$: 287.08.

Acid 48: 2-((2-Chloro-6-iodopyridin-3-yl)oxy)acetic acid

This acid has been prepared from tert-butyl 2-((2-chloro-6-iodopyridin-3-yl)oxy)acetate (see acid 2 (2.step) according to the procedures described for acid 1 (5.step). LC-MS (A): $t_R$=0.69 min; [M+H]$^+$: 313.82.

Following compounds were prepared by modified synthetic routes.

Example 1.1.27

1-(1-(4-chloro-2-fluorophenyl)-3,4,6,7,8,9-hexahydroimidazo[1,2-a:5,4-c']dipyridin-2(1H)-yl)-2-((2-chloro-64(2-hydroxyethyl)(methyl)amino)pyridin-3-yl)oxy)ethan-1-one 1-(1-(4-Chloro-2-fluorophenyl)-3,4,6,7,8,9-hexahydroimidazo[1,2-a:5,4-c']dipyridin-2(1H)-yl)-2-((2-chloro-6-iodopyridin-3-yl)oxy)ethan-1-one This compound has been prepared from 1-(4-chloro-2-fluorophenyl)-1,2,3,4,6,7,8,9-octahydroimidazo[1,2-a:5,4-c]dipyridine according to the method B. LC-MS (A): $t_R$=0.93 min; [M+MeCN]$^+$: 644.86.

1-(1-(4-Chloro-2-fluorophenyl)-3,4,6,7,8,9-hexahydroimidazo[1,2-a:5,4-c']dipyridin-2(1H)-yl)-2-((2-chloro-6-(2-hydroxyethyl)(methyl)amino)pyridin-3-yl)oxy)ethan-1-one This compound has been prepared from 1-(1-(4-chloro-2-fluorophenyl)-3,4,6,7,8,9-hexahydroimidazo[1,2-a:5,4-c]dipyridin-2(1H)-yl)-2-((2-chloro-6-iodopyridin-3-yl)oxy)ethan-1-one and 2-(methylamino)ethan-1-ol according to the procedure described for acid 1 (2.step). LC-MS (A): $t_R$=0.70 min; [M+MeCN]+: 548.08.

Example 1.7.1

2-(2-(2-((2-Chloro-6-(methylsulfonamido)pyridin-3-yl)oxy)acetyl)-1,2,3,4,6,7,8,9-octahydroimidazo[1,2-a:5,4-c']dipyridin-1-yl)-N-methylthiazole-4-carboxamide 2-(2-(2-((2-Chloro-6-(methylsulfonamido)pyridin-3-yl)oxy)acetyl)-1,2,3,4,6,7,8,9-octahydroimidazo[1,2-a:5,4-c']dipyridin-1-yl)thiazole-4-carboxylic acid To a solution of ethyl 2-(2-(2-((2-chloro-6-(methylsulfonamido)pyridin-3-yl)oxy)acetyl)-1,2,3,4,6,7,8,9-octahydroimidazo[1,2-a: 5,4-c]dipyridin-1-yl)thiazole-4-carboxylate (example 1.5.1) (52 mg) in EtOH (3 ml) was added 2.5M aq. NaOH (0.3 ml). The reaction mixture was stirred at rt for 1 h. The EtOH was evaporated in vacuo and DCM (10 ml) was added. 1M aq. HCl (3 ml) was added at 0° C. The layers were separated and the aq. phase was washed with DCM. The combined org. layers were dried over MgSO$_4$, filtrated off and evaporated in vacuo. The crude (78 mg of a white solid) was used in the next step without purification. LC-MS (A): $t_R$=0.56 min; [M+H]$^+$: 567.24.

2-(2-(2-((2-Chloro-6-(methylsulfonamido)pyridin-3-yl)oxy)acetyl)-1,2,3,4,6,7,8,9-octahydroimidazo[1,2-a:5,4-c']dipyridin-1-yl)-N-methylthiazole-4-carboxamide This compound has been prepared from 2-(2-(2-((2-chloro-6-(methylsulfonamido)pyridin-3-yl)oxy)acetyl)-1,2,3,4,6,7,8,9-octahydroimidazo[1,2-a:5,4-c]dipyridin-1-yl) thiazole-4-carboxylic acid and methylamine according to the Method B. LC-MS (A): $t_R$=0.59 min; [M+H]$^+$:580.06.

Example 5.3.1

5-(2-(2-((2-Chloro-6-morpholinopyridin-3-yl)oxy) acetyl)-1,2,3,4,6,7,8,9-octahydropyrido[4',3':4,5] imidazo[1,2-a]pyrazin-1-yl)-N,N-dimethylthiophene-3-carboxamide 5-(7-(Tert-butoxycarbonyl)-2-(2-(2-chloro-6-morpholinopyridin-3-yl)oxy)acetyl)-1,2,3,4,6,7,8,9-octahydropyrido[4',3':4,5]imidazo[1,2-a]pyrazin-1-yl) thiophene-3-carboxylic acid This compound has been prepared from tert-butyl 2-(2-((2-chloro-6-morpholinopyridin-3-yl)oxy)acetyl)-1-(4-(methoxycarbonyl)thiophen-2-yl)-1,3,4,6,8,9-hexahydropyrido [4',3':4,5]imidazo[1,2-a]pyrazine-7(2H)-carboxylate (intermediate in the synthesis of example 5.5.1) according to the procedure described for acid 6 (3.step). LC-MS (A): $t_R$=0.72 min; [M+H]$^+$:659.10.

Tert-butyl 2-(2-(2-chloro-6-morpholinopyridin-3-yl) oxy)acetyl)-1-(4-(dimethylcarba-moyl)thiophen-2-yl)-1,3,4,6,8,9-hexahydropyrido[4',3':4,5]imidazo[1,2-a]pyrazine-7(2H)-carboxylate This compound has been prepared from 5-(7-(tert-butoxycarbonyl)-2-(2-(2-chloro-6-morpholinopyridin-3-yl)oxy) acetyl)-1,2,3,4,6,7,8,9-octahydropyrido[4',3':4,5]imidazo[1,2-a]pyrazin-1-yl)thiophene-3-carboxylic acid and dimethylamine according to the Method B. LC-MS (A): $t_R$=0.73 min; [M+H]$^+$:686.66.

5-(2-(2-(2-Chloro-6-morpholinopyridin-3-yl)oxy) acetyl)-1,2,3,4,6,7,8,9-octahydropyrido [4',3':4,5] imidazo[1,2-a]pyrazin-1-yl)-N,N-dimethylthiophene-3-carboxamide This compound has been prepared from tert-butyl 2-(2-((2-chloro-6-morpholinopyridin-3-yl)oxy)acetyl)-1-(4-(methoxycarbonyl)thiophen-2-yl)-1,3,4,6,8,9-hexahydropyrido[4',3':4,5]imidazo[1,2-a]pyrazine-7(2H)-carboxylate according to the method C. LC-MS (A): $t_R$=0.59 min; [M+H]$^+$:586.53.

Example 5.3.2

5-(7-Acetyl-2-(2-((2-chloro-6-morpholinopyridin-3-yl)oxy)acetyl)-1,2,3,4,6,7,8,9-octahydropyrido[4',3': 4,5]imidazo[1,2-a]pyrazin-1-yl)-N,N-dimethylthiophene-3-carboxamide This compound has been prepared 5-(2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)-N,N-dimethylthiophene-3-carboxamide (example 5.3.1) according to the method D. LC-MS (A): $t_R$=0.62 min; [M+H]$^+$:628.66.

Example 5.14.1

Tert-butyl 2-(2-((2-chloro-6-morpholinopyridin-3-yl)oxy)acetyl)-1-(4-(cyanocarbamoyl)thiophen-2-yl)-1,2,3,4,8,9-hexahydropyrido[4',3':4,5]imidazo[1, 2-a]pyrazine-7(6H)-carboxylate 5-(7-(Tert-butoxycarbonyl)-2-(2-(2-chloro-6-morpholinopyridin-3-yl)oxy)acetyl)-1,2,3,4,6,7,8,9-octahydropyrido[4',3':4,5]imidazo[1,2-a]pyrazin-1-yl) thiophene-3-carboxylic acid This compound has been prepared from tert-butyl 2-(2-((2-chloro-6-morpholinopyridin-3-yl)oxy)acetyl)-1-(4-(m ethoxycarbonyl)thiophen-2-yl)-1,2,3,4,8,9-hexahydropyrido [4',3':4,5]imidazo[1,2-a]pyrazine-7(6H)-carboxylate (an intermediate in the synthesis of the example 5.5.1) according to the procedure described for acid 6 (3.step). LC-MS (A): $t_R$=0.56 min; [M+H]$^+$:567.24.

Tert-butyl 2-(2-(2-chloro-6-morpholinopyridin-3-yl) oxy)acetyl)-1-(4-(cyanocarbamoyl) thiophen-2-yl)-1,2,3,4,8,9-hexahydropyrido[4',3':4,5]imidazo[1,2-a] pyrazine-7(6H)-carboxylate A solution of 5-(7-(tert-butoxycarbonyl)-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)thiophene-3-carboxylic acid (50 mg), cyanamide (32 mg), trietylamine (0.080 ml) and HATU (45 mg) in DMF (1 ml) was stirred at r overnight. The reaction mixture was diluted with sat. aq. NH$_4$Cl and EA. The layers were separated, the aq. phase was washed with EA and the combined org. layers were washed with sat. aq. NaCl, dried over MgSO$_4$, filtrated off and evaporated in vacuo. The crude was purified by preparative LC-MS to afford 7 mg of a yellow oil. LC-MS (A): $t_R$=0.73 min; [M+H]$^+$: 683.64.

TABLE 2

| Example No | IC$_{50}$ [nM] |
| --- | --- |
| 1.1.27 | 15 |
| 1.7.1 | 844 |
| 5.3.1 | 94 |
| 5.3.2 | 35 |
| 5.14.1 | 341 |

II. Biological Assays

Inhibitory activities on tryptophan hydroxylase 1 have been measured for each example compound using the following procedure:

Biochemical In Vitro Assay Using Fluorescence Readout

To generate the enzyme, full length human TPH1 is cloned into the plasmid pET20b(+) (Novagen) and expressed in *E. coli*. The bacterial cells are ruptured by sonication on ice and the lysate is cleared by centrifugation. The resulting protein in the pellet is re-extracted and TPH1 is purified from the obtained lysate by affinity chromatography using a pterin cosubstrate analog immobilized to the resin of the column. The protein is further purified by size exclusion chromatography to remove protein aggregates. The activity of TPH1 is determined by using a fluorescence assay. The enzyme activity assay is carried out at 15° C. with atmosphere oxygen for the duration of 60 minutes in a volume of 64 µl. The reaction is carried out in a 0.1M Tris-HCl buffer, adjusted to pH 7.6, containing 1 mM DTT, 0.2 mg/ml catalase, 100 µM (±)-6-methyl-5,6,7,8-tetrahydropterine dihydrochloride, 40 µM L-tryptophan, and 40-80 nM of TPH1. The reaction is started by bringing together L-tryptophan with all the other reaction substituents and stopped by quenching with perchloric acid (HClO4). The amount of 5-hydroxy-L-tryptophan produced during the enzymatic reaction is determined by fluorescence readout. Fluorescence, as determined at 540 nm when excited at 300 nm wavelength, increases proportionally to the 5-hydroxy-L-tryptophan formed. Compounds are prepared as 10 mM stock solution in DMSO, then diluted in 384-well plates using DMSO followed by a transfer of the dilutions into the assay plate. Fluorescence is measured for each well and the fluorescence at 540 nm wavelength is compared to the fluorescence of the vehicle in place of compound. Inhibitory activities of example compounds with respect to the TPH1 protein are determined by calculating the $IC_{50}$ value (the concentration of compound needed to inhibit 50% of the enzyme activity). The calculated $IC_{50}$ values may fluctuate depending on the daily biochemical assay performance. Fluctuations of this kind are known to those skilled in the art. In the case where $IC_{50}$ values have been determined several times for the same compound, the mean is given. $IC_{50}$ values of exemplified compounds are displayed in the table 1.

The invention claimed is:

1. A compound of Formula (I)

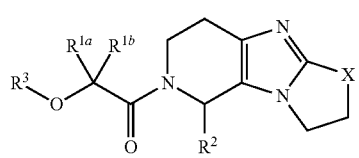

Formula (I)

wherein

X represents —$CH_2$—, —$CH_2$—$CH_2$—, —$CH_2$—$CH_2$—$CH_2$—, —S—, *—$CH_2$—O—, or *—$CH_2$—$NR^x$— wherein $R^x$ represents hydrogen, —CO—($C_{1-4}$)alkyl, —($C_{1-3}$)alkyl-($C_{3-6}$)cycloalkyl, ($C_{3-6}$)cycloalkyl, or —CO—($C_{1-4}$)alkoxy; wherein the asterisks indicate the bond attached to the imidazole ring;

$R^{1a}$ and $R^{1b}$ independently represent hydrogen, methyl, ethyl; or $R^{1a}$ and $R^{1b}$ together with the carbon atom to which they are attached to form a cyclopropyl ring;

$R^2$ represents aryl, or heteroaryl, wherein said aryl or heteroaryl independently is unsubstituted, or mono-, di-, or tri-substituted, wherein the substituents are independently selected from:

($C_{1-4}$)alkyl;
($C_{1-4}$)alkoxy;
($C_{3-6}$)cycloalkyl;
($C_{1-3}$)fluoroalkyl;
($C_{1-3}$)fluoroalkoxy;
halogen;
cyano;
—$(CH_2)_n$—$NR^{21}R^{22}$; wherein n represents the integer 0 or 1; and
$R^{21}$ and $R^{22}$ independently represent hydrogen or ($C_{1-4}$)alkyl; or
$R^{21}$ and $R^{22}$ together with the nitrogen atom to which they are attached to form a 4- to 7-membered saturated ring, wherein said ring optionally includes one ring oxygen atom;
—CO—$NR^{23}R^{24}$, wherein $R^{23}$ and $R^{24}$ independently represent hydrogen or ($C_{1-4}$)alkyl;
—CO—NH—CN;
—$NR^{25}$—CO—$NR^{26}R^{27}$, wherein $R^{25}$, $R^{26}$ and $R^{27}$ independently represent hydrogen or ($C_{1-4}$)alkyl;
—CO—($C_{1-4}$)alkoxy;
phenyl;
hydroxy-($C_{1-4}$)alkyl;
($C_{1-3}$)alkoxy-($C_{1-4}$)alkyl;
hydroxy-($C_{2-4}$)alkoxy; or
($C_{1-3}$)alkoxy-($C_{2-4}$)alkoxy;

$R^3$ represents aryl, or heteroaryl, wherein said aryl or heteroaryl independently is unsubstituted, or mono-, di-, or tri-substituted, wherein the substituents are independently selected from:

—$NR^4$—Y—$R^5$, wherein
$R^4$ represents hydrogen or ($C_{1-3}$)alkyl; Y represents a direct bond; and $R^5$ represents ($C_{1-4}$)alkyl, or ($C_{3-6}$)cycloalky; or
$R^4$ represents hydrogen or ($C_{1-3}$)alkyl; Y represents —$NR^Y$— wherein $R^Y$ represents ($C_{1-3}$)alkyl; and $R^5$ represents ($C_{1-4}$)alkyl; or
$R^4$ and $R^5$ together with the nitrogen and the —$SO_2$—Y-group to which they are attached to form a 5-, 6-, or 7-membered ring, wherein Y represents a direct bond or —$NR^Y$— wherein $R^Y$ represents ($C_{1-3}$)alkyl;
—CO—$NR^6R^7$, wherein $R^6$ and $R^7$ independently represent hydrogen, ($C_{1-4}$)alkyl, or ($C_{3-6}$)cycloalkyl;
—$SO_2$—$R^8$ wherein $R^8$ represents ($C_{1-5}$)alkyl, or —$NR^{81}R^{82}$, wherein $R^{81}$ and $R^{82}$ independently represent hydrogen or ($C_{1-4}$)alkyl;
—$(CH_2)_m$—$NR^9R^{10}$; wherein m represents the integer 0 or 1; and
$R^9$ and $R^{10}$ independently represent hydrogen, ($C_{1-4}$)alkyl, ($C_{2-3}$)fluoroalkyl, hydroxy-($C_{2-4}$)alkyl, ($C_{1-4}$)alkoxy-($C_{2-4}$)alkyl; or
$R^9$ and $R^{10}$ together with the nitrogen to which they are attached to form a 4-to 7-membered ring optionally including an oxygen ring atom or a group —$NR^{11}$— wherein
$R^{11}$ represents ($C_{1-4}$)alkyl, and wherein said ring is optionally substituted with one or two fluorine substituents;

($C_{1-4}$)alkyl;
($C_{3-6}$)cycloalkyl;
($C_{1-4}$)alkoxy;
($C_{1-3}$)fluoroalkyl;
($C_{1-3}$)fluoroalkoxy;
halogen;
cyano; or
5-membered heteroaryl;

or a pharmaceutically acceptable salt thereof.

2. The compound according to claim 1, wherein the absolute configuration of the carbon atom carrying the substituent $R^2$ is as depicted in Formula ($I_E$):

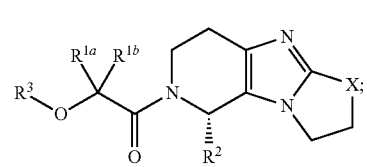

Formula ($I_E$)

or a pharmaceutically acceptable salt thereof.

3. The compound according to claim 1, wherein $R^{1a}$ and $R^{1b}$ both represent hydrogen;
or a pharmaceutically acceptable salt thereof.

4. The compound according to claim 1, wherein X represents —$CH_2$—, —$CH_2$—$CH_2$—, or —S—;
or a pharmaceutically acceptable salt thereof.

5. The compound according to claim 1, wherein X represents —$CH_2$—, —$CH_2$—$CH_2$—, or —S—;
or a pharmaceutically acceptable salt thereof.

6. The compound according to claim 1, wherein $R^2$ represents phenyl, or 5-or 6-membered heteroaryl, wherein said phenyl or heteroaryl independently is mono-, di-, or tri-substituted, wherein the substituents are independently selected from:
($C_{1-4}$)alkyl;
($C_{1-4}$)alkoxy;
($C_{3-6}$)cycloalkyl;
($C_{1-3}$)fluoroalkyl;
($C_{1-3}$)fluoroalkoxy;
halogen;
cyano;
—$NR^{21}R^{22}$; wherein
   $R^{21}$ and $R^{22}$ independently represent hydrogen or ($C_{1-4}$)alkyl; or
   $R^{21}$ and $R^{22}$ together with the nitrogen atom to which they are attached to form a 4- to 7-membered saturated ring, wherein said ring optionally contains one ring oxygen atom;
—CO—$NR^{23}R^{24}$, wherein $R^{23}$ and $R^{24}$ independently represent hydrogen or ($C_{1-4}$)alkyl;
—$NR^{25}$—CO—$NR^{26}R^{27}$, wherein $R^{25}$, $R^{26}$ and $R^{27}$ independently represent hydrogen or ($C_{1-4}$)alkyl;
—CO—($C_{1-4}$)alkoxy;
phenyl;
hydroxy-($C_{1-4}$)alkyl;
($C_{1-3}$)alkoxy-($C_{1-4}$)alkyl;
hydroxy-($C_{2-4}$)alkoxy; or
($C_{1-3}$)alkoxy-($C_{2-4}$)alkoxy;
or a pharmaceutically acceptable salt thereof.

7. The compound according to claim 1, wherein
$R^2$ represents phenyl, wherein said phenyl is mono-, di-, or tri-substituted, wherein the substituents are independently selected from:
($C_{1-4}$)alkyl;
($C_{3-6}$)cycloalkyl; or
halogen;
or $R^2$ represents 5-or 6-metnbered heteroaryl, wherein said heteroaryl is mono-, or di-substituted, wherein the substituents are independently selected from:
($C_{1-4}$)alkyl;
($C_{3-6}$)cycloalkyl;
($C_{1-3}$)fluoroalkyl; or
halogen;
or a pharmaceutically acceptable salt thereof.

8. The compound according to claim 1, wherein $R^3$ represents a fragment

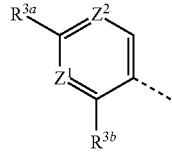

wherein
$Z^1$ and $Z^2$ independently represent CH or N;
$R^{3a}$ represents:
—$NR^4$—$SO_2$—Y—$R^5$, wherein
   $R^4$ represents hydrogen or ($C_{1-3}$)alkyl; Y represents direct bond; and $R^5$ represents ($C_{1-4}$)alkyl, or ($C_{3-6}$)cycloalkyl; or
   $R^4$ represents hydrogen or ($C_{1-3}$)alkyl; Y represents —$NR^Y$— wherein $R^Y$ represents ($C_{1-3}$)alkyl; and $R^5$ represents ($C_{1-4}$)alkyl; or
   $R^4$ and $R^5$ together with the nitrogen and the —$SO_2$—Y-group to which they are attached to form a 5-, 6-, or 7-membered ring, wherein Y represents a direct bond or —$NR^Y$— wherein $R^Y$ represents ($C_{1-3}$)alkyl;
—CO—$NR^6R^7$, wherein $R^6$ and $R^7$ independently represent hydrogen, ($C_{1-4}$)alkyl, or ($C_{3-6}$)cycloalkyl;
—$SO_2$—$R^8$ wherein $R^8$ represents ($C_{1-5}$)alkyl, or —$NR^{81}R^{82}$, wherein $R^{81}$ and $R^{82}$ independently represent hydrogen or ($C_{1-4}$)alkyl;
—$(CH_2)_m$—$NR^9R^{10}$; wherein m represents the integer 0 or 1; and $R^9$ and $R^{10}$ together with the nitrogen to which they are attached to form a 4- to 7-membered ring optionally including an oxygen ring atom or a group —$NR^{11}$— wherein $R^{11}$ represents ($C_{1-4}$)alkyl, and wherein said ring is optionally substituted with one or two fluorine substituents;
hydrogen;
halogen;
($C_{1-4}$)alkyl;
($C_{3-6}$)cycloakyl;
($C_{1-3}$)fluoroalkyl;
5-membered heteroaryl;
cyano; and
$R^{3b}$ represents ($C_{1-4}$)alkyl; halogen; ($C_{3-6}$)cycloalky; or ($C_{1-3}$)fluoroalkyl;
or a pharmaceutically acceptable salt thereof.

9. The compound according to claim 8, wherein $Z^1$ represents N and $Z^2$ represents CH;
or a pharmaceutically acceptable salt thereof.

10. The compound according to claim 8, wherein $R^{3a}$ represents:
—$NR^{41}$—$SO_2$—$R^{51}$, wherein $R^{41}$ represents hydrogen; and $R^{51}$ represents ($C_{1-4}$)alkyl or ($C_{3-6}$)cycloalkyl; or
—$NR^{43}$—$SO_2$—$R^{53}$, wherein $R^{43}$ and $R^{53}$ together with the nitrogen and the —$SO_2$-group to which they are attached to form a 5-membered ring;
—CO—$NR^6R^7$, wherein $R^6$ and $R^7$ independently represent hydrogen, ($C_{1-4}$)alkyl, or ($C_{3-6}$)cycloalkyl; and
$R^{3b}$ represents ($C_{1-4}$)alkyl or halogen;
or a pharmaceutically acceptable salt thereof.

11. The compound according to claim 1, wherein
$R^3$ represents 2-chloro-4-(dimethylcarbamoyl)-phenyl; or
$R^3$ represents 2-chloro-6-(methyl-carbamoyl)-pyridin-3-yl, 2-chloro-6-(dimethyl-carbamoyl)-pyridin-3-yl, 2-chloro-6-(ethyl-(methyl)-carbamoyl)-pyridin-3-yl, 2-chloro-6-(cyclopropyl-carbamoyl)-pyridin-3-yl, 2-chloro-6-(cyclopropyl-(methyl)-carbamoyl)-pyridin-3-yl, 6-(cyclopropyl-carbamoyl)-2-ethyl-pyridin-3-yl, 2-chloro-6-(isopropyl-(methyl)-carbamoyl)-pyridin-3-yl, 2-chloro-6-(methylsulfonamido)-pyridin-3-yl, 2-chloro-6-(N-methyl-methylsulfonamido)-pyridin-3-yl, 2-ethyl-6-(methylsulfonamido)-pyridin-3-yl, 2-methoxy-6-(methylsulfonamido)-pyridin-3-yl, 2-chloro-6-(1,1-dioxo-isothiazolidin-2-yl)-pyridin-3-yl, 6-(1,1-dioxo-isothiazolidin-2-yl)-2-ethyl-pyridin-3-yl, 2-chloro-6-(5-methyl-1,1-dioxo-[1,2,5]thiadiazolidin-2-yl)-pyridin-3-yl, 4-ethyl-2-(methylsulfonamido)-pyrimidin-5-yl, or 2-ethyl-6-(N,N-dimethylsulfamoyl)amino)-pyridin-3-yl;

or a pharmaceutically acceptable salt thereof.

12. The compound according to claim 1, wherein said compound is:

6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N,N-dimethylpicolinamide;

1-(1-(4-chloro-2-fluorophenyl)-3,4,6,7,8,9-hexahydroimidazo[1,2-a:5,4-c']dipyridin-2(1H)-yl)-2-((2-chloro-6-(1,1-dioxidoisothiazolidin-2-yl)pyridin-3-yl)oxy)-ethanone;

N-(5-(2-(1-(4-chloro-2-fluorophenyl)-3,4,6,7,8,9-hexahydroimidazo[1,2-a:5,4c']dipyridin-2(1H)-yl)-2-oxoethoxy)-6-ethylpyridin-2-yl)methanesulfonamide;

5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropyl-6-ethylpicolinamide;

N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-methoxypyridin-2-yl)methanesulfonamide;

1-(1-(4-chloro-2-fluorophenyl)-3,4,6,7,8,9-hexahydroimidazo[1,2-a:5,4-c']dipyridin-2(1H)-yl)-2-((2-chloro-6-cyclopropylpyridin-3-yl)oxy)ethanone;

1-(1-(4-chloro-2-fluorophenyl)-3,4,6,7,8,9-hexahydroimidazo[1,2-a:5,4-c']dipyridin-2(1H)-yl)-2-((2-ethyl-6-methylpyridin-3-yl)oxy)ethanone;

(S)-6-chloro-5-(2-(1-(4-chloro-2-fluoropheny)-3,4,6,7,8,9-hexahydroimidazo[1,2-a:5,4-c']dipyridin-2(1H)-yl)-2-oxoethoxy)-N-cyclopropylpicolinamide;

(S)-N-(6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide;

(S)-N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-ethylpyridin-2-yl)methanesulfonamide;

1-(1-(4-chloro-2-fluorophenyl)-3,4,6,7,8,9-hexahydroimidazo[1,2-a:5,4c']pyridin-2(1H)-yl)-2-((2-chloro-6-morpholinopyridin-3-yl)oxy)ethanone;

N-(6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide;

6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropyl-N-methylpicolinamide;

1-(1-(4-chloro-2-fluorophenyl)-3,4,6,7,8,9-hexahydroimidazo[1,2-a:5,4-c']dipyridin-2(1H)-yl)-2-((2-chloro-6-(oxazol-2-yl)pyridin-3-yl)oxy)ethanone;

6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-cyclopropylpicolinamide;

6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-ethyl-N-methylpicolinamide;

6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N-isopropyl-N-methylpicolinamide;

N-(6-chloro-5-(2-(1-(4chloro-2-fluorophenyl)-3,4,6,7,8,9-hexahydroimidazo[1,2-a:5,4-c']dipyridin-2(1H)-yl)-2-oxoethoxy)pyridin-2-yl)-N-methylmethanesulfonamide;

N-(6-chloro-5-(2-(1-(2,4-dimethylthiazol-5-yl)-3,6,7,8,9-hexahydroimidazo[1,2-a:5,4-c']dipyridin-2(1H)-yl)-2-oxoethoxy)pyridin-2-yl)methanesulfonamide;

3-chloro-4-(2-(1-(2,4-dimethylthiazol-5-yl)-3,4,6,7,8,9-hexahydroimidazo[1,2-a:5,4-c']dipyridin-2(1H)-yl)-2-oxoethoxy)benzonitrile;

2-(2-chloro-4-(trifluoromethyl)phenoxy)-1-(1-(2,4-dimethylthiazol-5-yl)-3,4,6,7,8,9-hexahydroimidazo[1,2-a:5,4-c']dipyridin-2(1H)-yl)ethanone;

N-(6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)pyridin-2-yl)-N-methylmethanesulfonamide;

N-(5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpyridin-2-yl)methanesulfonamide;

2-((2-chloro-6-(1,1-dioxidoisothiazolidin-2-yl)pyridin-3-yl)oxy)-1-(1-(2,4-dimethylthiazol-5-yl)-3,4,6,7,8,9-hexahydroimidazo[1,2-a:5,4-c']dipyridin-2(1H)-yl)ethanone;

N-cyclopropyl-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpicolinamide;

(R)-N-(5-(2-(1-(2,4-dimethyithiazol-5-yl)-3,4,6,7,8,9-hexahydroimidazo[1,2-a:5,4-c']dipyridin-2(1H)-yl)-2-oxoethoxy)-6-ethylpyridin-2-yl)methanesulfonamide;

(R)-N-cyclopropyl-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-6-ethylpicolinamide;

N-(5-(2-(1-(2,4-dimethylthiazol-5-yl)-3,4,6,7,8,9-hexahydroimidazo[1,2-a:5,4-c']dipyridin-2(1H)-yl)-2-oxoethoxy)-4-ethylpyrimidin-2-yl)methanesulfonamide;

6-chloro-N-cyclopropyl-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-N-methylpicolinamide;

2-((2-chloro-6-(oxazol-2-yl)pyridin-3-yl)oxy)-1-(1-(2,4-dimethylthiazol-5-yl)-3,4,6,7,8,9-hexahydroimidazo[1,2-a:5,4-c']dipyridin-2(1H)-yl)ethanone;

6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)-N-methylpicolinamide;

6-chloro-5-(2-(2,4-dimethylthiazol-5-yl)-3,4,6,7,8,9-hexahydroinaidazo[1,2-a:5,4-c']dipyridin-2(1H)-yl)-2-oxoethoxy)-N,N-dimethylpicolinamide;

6-chloro-5-(2-(1-(2,4-dimethylthiazol-5-yl)-3,4,6,7,8,9-hexahydroimidazo[1,2-a:5,4-c']dipyridin-2(1H)-yl)-2-oxoethoxy)picolinonitrile;

2-((2-chloro-6-(trifluoromethyl)pyridin-3-yl)oxy)-1-(1-(2,4-dimethylthiazol-5-yl)-3,4,6,7,8,9-hexahydroimidazo[1,2-a:5,4-c']dipyridin-2(1H)-yl)ethanone;

2-((2-chloro-6-cyclopropylpyridin-3-yl)oxy)-1-(1-(2,4-dimethylthiazol-5-yl)-3,4,6,7,8,9-hexahydroimidazo[1,2-a:5,4-c']dipyridin-2(1H)-yl)ethanone;

2-((2-chloro-6-(4-methylpiperazin-1-yl)pyridin-3-yl)oxy)-1-(1-(2,4-dimethylthiazol-5-yl)-3,4,6,7,8,9-hexahydroimidazo[1,2-a:5,4-c']dipyridin-2(1H)-yl)ethanone;

N-(6-chloro-5(2-(1-(2-ethyl-4-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide;

N-(6-chloro-5-(2-(1-(2-isopropyl-4-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide;

N-(6-ethyl-5-(2-(1-(4-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide;

2-((6-(1,1-dioxidoisothiazoliazolidin-2-yl)-2-ethylpyridin-3-yl)oxy)-1-(1-(4-methylthiazol-5-yl)-3,4,6,7,8,9-hexahydroimidazo[1,2-a:5,4-c']dipyridin-2(1H)-yl)ethanone;

N-(6-ethyl-5-(2-(1-(3-fluorothiophen-2-yl)-3,4,6,7,8,9-hexahydroimidazo[1,2-a:5,4-c']dipyridin-2(1H)-yl)-2-oxoethoxy)pyridin-2-yl)methanesalfonamide;

N-cyclopropyl-6-ethyl-5-(2-(1-(3-fluorothiophen-2-yl)-3,4,6,7,8,9-hexahydroimidazo[1,2-a:5,4-c']dipyridin-2(1H)-yl)-2-oxoethoxy)picolinamide;

N-(6-ethyl-5-(2-(1-(2-methylthiazol-5-yl)-3,4,6,7,8,9-hexahydroimidazo[1,2-a:5,4-c']dipyridin-2(1H)-yl)-2-oxoethoxy)pyridin-2-yl)methanesulfonamide;

2-((6-(1,1-dioxidoisothiazolidin-2-yl)-2-ethylpyridin-3-yl)oxy)-(1-(1-(2-methylthiazol-5-yl)-3,4,6,7,8,9-hexahydroimidazo[1,2-a:5,4-c']dipyridin-2(1H)-yl)ethanone;

N-(6-ethyl-5-(2-oxo-2-(1-(2-phenylthiazol-5-yl)-3,4,6,7,8,9-hexahydroimidazo[1,2-a:5,4-c']dipyridin-2(1H)-yl)ethoxy)pyridin-2-yl)methanesulfonamide;

N-(6ethyl-5-(2-oxo-2-(1-(3-phenyl-1,2,4-oxadiazol-5-yl)-3,4,6,7,8,9-hexahydroimidazo[1,2-a:5,4c']dipyridin-2(1H)-yl)ethoxy)pyridin-2-yl)methanesulfonamide;

N-(6-chloro-5-(2-(1-(4-methyl-2-(trifluoromethyl)thiazol-5-yl)-3,4,6,7,8,9-hexahydroimidazo[1,2-a:5,4-c']dipyridin-2(1H)-yl)-2-oxoethoxy)pyridin-2-yl)methanesulfonamide;

N-(6-chloro-5-(2-(1-(5fluoro-3-methylpyridin-2-yl)-3,4,6,7,8,9-hexahydroimidazo[1,2-a:5,4-c']dipyridin-2(1H)-yl)-2-oxoethoxy)pyridin-2-yl)methanesulfonamide;

N-(6-chloro-5-(2-(1-(2-fluoro-4-methylphenyl)-3,4,6,7,8,9-hexahydroimidazo[1,2-a:5,4-c']dipyridin-2(1H)-yl)-2-oxoethoxy)pyridin-2-yl)methanesulfonamide;

2-((2-chloro-6-(oxazol-2-yl)pyridin-3-yl)oxy)-1-(1-(2-fluoro-4-methylphenyl)-3,4,6,7,8,9-hexahydroimidazo[1,2-a:5,4-c']dipyridin-2(1H)-yl)ethanone;

6-chloro-N-cyclopropyl-5-(2-(1-(2-fluoro-4-methylphenyl)-3,4,6,7,8,9-hexahydroimidazo[1,2-a:5,4-c']dipyridin-2(1H)-yl)-2-oxoethoxy)-N-methylpicolinamide;

N-(6-chloro-5-(2-(1-(5-cyclopropyl-3-fluoropyridin-2-yl)-3,4,6,7,8,9-hexahydroimidazo[1,2-a:5,4c']dipyridin-2(1H)-yl)-2-oxoethoxy)pyridin-2-yl)methanesulfonamide;

N-cyclopropyl-5-(2-(1-(5-cyclopropyl-3-fluoropyridin-2-yl)-3,4,6,7,8,9-hexahydroimidazo[1,2-a:5,4-c']dipyridin-2(1H)-yl)-2-oxoethoxy)-6-ethylpicolinamide;

(R)-N-cyclopropyl-5-(2-(1-(5-cyclopropyl-3fluoropyridin-2-yl)-3,4,6,7,8,9-hexahydroimidazo[1,2-a:5,4-c']dipyridin-2(1H)-yl)-2-oxoethoxy)-6-ethylpicolinamide;

6-chloro-5-(2-(1-(5-(dimethylcarbamoyl)-3-fluorothiophen-2-yl)-3,4,6,7,8,9-hexahydroimidazo[1,2-a:5,4-']dipyridin-2(1H)-yl)-2-oxoethoxy)-N,N-dimethylpicolinamide;

5-(2-(2-((2-ethyl-6-(methylsulfonamido)pyridin-3-yl)oxy)acetyl)-1,2,3,4,6,7,8,9-octahydroimidazo[1,2-a:5,4-c']dipyridin-1-yl)-4-fluoro-N,N-dimethylthiophene-2-carboxamide;

Ethyl 2-(2-((2-chloro-6-(methylsulfonamido)pyridin-3-yl)oxy)acetyl)-1,2,3,4,6,7,8,9-octahydroimidazo[1,2-a:5,4-c']dipyridin-1-yl)thiazole-4-carboxylate;

N-(6-chloro-5-(2-(1-(3-fluoro-5-methylpyridin-2-yl)-3,4,6,7,8,9-hexahydroimidazo[1,2-a:5,4-c']dipyridin-2(1H)-yl)-2-oxoethoxy)pyridin-2-yl)methanesulfonamide;

2-((2-chloro-6-(oxazol-2-yl)pyridin-3-yl)oxy)-1-(1-(3-fluoro-5-methylpyridin-2-yl)-3,4,6,7,8,9-hexahydroimidazo[1,2-a:5,4-c']dipyridin-2(1H)-yl)ethanone;

6-chloro-N-cyclopropyl-5-(2-(1-(3-fluoro-5-methylpyridin-2-yl)-3,4,6,7,8,9-hexahydroimidazo[1,2-a:5,4-c']dipyridin-2(1H)-yl)-2-oxoethoxy)-N-methylpicolinamide;

6-chloro-5-(2-(1-(3-fluoro-5methylpyridin-2-yl)-3,4,6,7,8,9-hexahydroimidazo[1,2-a:5,4-c']dipyridin-2(1H)-yl)-2-oxoethoxy)-N,N-dimethylpicolinamide;

2((2-chloro-6-(1,1-dioxidoisothiazolidin-2-yl)pyridin-3-yl)oxy)-1-(1-(1-(3-fluoro-5-methylpyridin-2-yl)-3,4,6,7,8,9-hexahydroimidazo[1,2-a:5,4-c']dipyridin-2(1H)-yl)ethanone;

N-(6-chloro-5-(2-(1-(3-fluoro-5-methylpyridin-2-yl)-3,4,6,7,8,9-hexahydroimidazo[1,2-a:5,4-c']dipyridin-2(1H)-yl)-2-oxoethoxy)pyridin-2-yl)-N-methylmethanesulfonamide;

N-cyclopropyl-6-ethyl-5-(2-(1-(3-fluoro-5-methylpyridin-2yl)-3,4,6,7,8,9-hexahydroimidazo[1,2-a:5,4-c']dipyridin-2(1H)-yl)-2-oxoethoxy)picolinamide;

2-(2-(2-((2-chloro-6-(methylsulfonamido)pyridin-3-yl)oxy)acetyl)-1,2,3,4,6,7,8,9-octahydroimidazo[1,2-a:5,4-c']dipyridin-1-yl)-N-methylthiazole-4-carboxamide;

6-chloro-N-cyclopropyl-5-(2-(1-(4-cyclopropyl-2fluorophenyl)-3,4,6,7,8,9-hexahydroimidazo[1,2-a:5,4-c']dipyridin-2(1H)-yl)-2oxoethoxy)-N-methylpicolinamide;

2-((2-chloro-6-(oxazol-2-yl)pyridin-3-yl)oxy)-1-(1-(4-cyclopropyl-2-fluorophenyl)-3,4,6,7,8,9-hexahydroimidazo[1,2-a :5,4-c']dipyridin-2(1H)-yl)ethanone;

N-(6-chloro-5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide;

6-chloro-5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)-N,N-dimethylpicolinamide;

6-chloro-N-cyclopropyl-5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)picolinamide;

(S)-6-chloro-N-cyclopropyl-5-(2-(1-(4-cyclopropyl-2-fluorophenyl)-3,4,6,7,8,9-hexahydroimidazo[1,2-a:5,4-c']dipyridin-2(1H)-yl)-2-oxoethoxy)picolinamide;

N-(5-(2-(1-(4-cyclopropyl-2-fluorophenyl)-3,4,6,7,8,9-hexahydroimidazo[1,2-a:5,4-c']dipyridin-1H)-yl)-2-oxoethoxy)-4-ethylpyrimidin-2-yl)methanesulfonamide;

2-((2-chloro-6-(oxazol-2-yl)pyridin-3-yl)oxy)-1-(2,3-difluoro-4-methylphenyl)-3,4,6,7,8,9-hexahydroimidazo[1,2]dipyridin-2(1H)-yl)ethanone;

N-cyclopropyl-5-(2-(1-(2,3-difluoro-4-methylphenyl)-3,4,6,7,8,9-hexahydroimidazo[1,2-a:5,4-c']dipyridin-2(1H)-yl)-2-oxoethoxy)-6-methylpicolinamide;

N-(6-chloro-5-(2-(1-(2,3-difluoro-4-methylphenyl)-3,4,6,7,8,9-hexahydroimidazo[1,2-a:5,4-c']dipyridin-2(1H)-yl)-2-oxoethoxy)pyridin-2-yl)methanesulfonamide;

6-chloro-N-cyclopropyl-5-(2-(1-(2,3-difluoro-4-methylphenyl)-3,4,6,7,8,9-hexahydroimidazo[1,2-a:5,4-c']dipyridin-2(1H)-yl)-2-oxoethoxy)-N-methylpicolinamide;

2-((2-chloro-6-(4-methylpiperazin-1-yl)pyridin-3-yl)oxy)-1-(1-(2,3-difluoro-4-methylphenyl)-3,4,6,7,8,9-hexahydroimidazo[1,2-a:5,4-c']dipyridin-2(1H)-yl)ethanone;

2-(2-chloro-4-(trifluoromethyl)phenoxy)-1-(1-(2,3-difluoro-4-methylphenyl)-3,4,6,7,8,9-hexahydroimidazo[1,2-a:5,4-c']dipyridin-2(1H)-yl)ethanone;

2-((2-chloro-6-(1,1-dioxidoisothiazolidin-2-yl)pyridin-3-yl)oxy)-1-(1-(2,3-difluoro-4-methylphenyl)-3,4,6,7,8,9-hexahydroimidazo[1,2-a:5,4c']dipyridin-2(1H)-yl)ethanone;

N-(5-(2-(1-(2,3-difluoro-4-methylphenyl)-3,4,6,7,8,9-hexahydromidazo[1,2-a:5,4-c']dipyridin-2(1H)-yl)-2-oxoethoxy)-6-ethylpyridin-2-yl)methanesulfonamide;

6-chloro-N-cyclopropyl-5-(2-(1-(2,3-difluoro-4-methylphenyl)-3,4,6,7,8,9-hexahydroimidazo[1,2-a:5,4c']dipyridin-2(1H)-yl)-2-oxoethoxy)picolinamide;

N-(5-(2-(1-(2,3-difluoro-4-methylphenyl)-3,4,6,7,8,9-hexahydroimidazo[1,2-a:5,4-c']dipyridin-2(1H)-yl)-2-oxoethoxy)-4-ethylpyrimidin-2-yl)methanesulfonamide;

N-(6-chloro-5-(2-(1-(4-chloro-2-fluorophenyl)-3,4,7,8-tetrahydro-1H-pyrrolo[2',1':2,3]imidazo[4,5-c']dipyridin-2(6H)-yl)-2-oxoethoxy)pyridin-2-yl)methanesulfonamide;

N-(5-(2-(1-(4-chloro-2-fluorophenyl)-3,4,7,8-tetrahydro-H-pyrrolo[2',1':2,3]imidazo[4,5-c]pyridin-2(6H)-yl)-2-oxoethoxy)-6-ethylpyridin-2-yl)methanesulfonamide;

1-(1-(4-chloro-2-fluorophenyl)-3,4,7,8-tetrahydro-1H-pyrrolo[2',1':2,3]imidazo[4,5-c]pyridin-2(6H)-yl)-2-((6-(1,1-dioxidoisothiazoildin-2-yl)-2-ethylpyridin-3-yl)oxy)ethanone;

N-(6-chloro-5-(2-(1-(2-fluoro-4-methylphenyl)-3,4,7,8-tetrahydro-1H-pyrrolo[2',1':2,3]imidazo[4,5-c']pyridin-2(6H)-yl)-2-oxoethoxy)pyridin-2-yl)methanesulonamide;

N-(5-(2-(1-(2,3-difluoro-4-methylphenyl)-3,4,7,8-tetrahydro-1H-pyrrolo[2',1':2,3]imidazo[4,5-c']pyridin-2(6H)-yl)-2-oxoethoxy)-6-ethylpyridin-2-yl)methanesulfonamide;

1-(1-(2,4-dimethylthiazol-5-yl)-3,4,7,8-tetrahydro-1H-pyrrolo[2',1':2,3]imidazo[4,5-c']pyridin-2(6H)-yl)-2-((6-(1,1-dioxidoisothiazolidin-2-yl)-2-ethylpyridin-3-yl-)oxy)ethanone;

(R)-N-(5-(2-(1-(2,4-dimethylthiazol-5-yl)-3,4,7,8-tetrahydro-1H-pyrrolo[2',1':2,3]imidazo[4,5-c']pyridin-2(6H)-yl)-2-oxoethoxy)-6-ethylpyridin-2-yl)methanesulfonamide;

(R)-N-cyclopropyl-5-(2-(1-(2,4-dimethylthiazol-5-yl)-3,4,7,8-tetrahydro-1H-pyrrolo[2',1':2,3]imidazo[4,5-c']pyridin-2(6H)-yl)-2-oxoethoxy)-6-ethylpicolinamide;

(R)-1-(1-(2,4-dimethylthiazol-5-yl)-3,4,7,8-tetrahydro-1H-pyrrolo[2',1':2,3]imidazo[4,5-c]pyridin-2(6H)-yl)-2-((6-(1,1-dioxidoisothiazolidin-2-yl)-2-ethylpyridin-3-yl)oxy)ethanone;

N-(6-chloro-5-(2-(1-(4-chloro-2-fluorophenyl)-3,4,7,8,9,10-hexahydro-1H-pyrido[4',3':4,5]imidazo[1,2-a]azepin-2(6H)-yl)-2-oxoethoxy)pyridin-2-yl)methanesulfonamide;

N-(6-chloro-5-(2-(1-(2-fluoro-4-methylphenyl)-3,4,7,8,9,10-hexahydro-1H-pyrido[4',3':4,5]imidazo[1,2-a]azepin-2(6H)-yl)-2-oxoethoxy)pyridin-2-yl)methanesulfonamide;

N-(6-chloro-5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)pyridin-2-yl)methanesulfonamide;

N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-4-ethylpyrimidin-2-yl)methanesulfonamide;

1-(5-(4-chloro-2-fluorophenyl)-2,3,7,8-tetrahydrothiazolo[2',3':2,3]imidazo[4,5-c]pyridin-6(5H)-yl)-2-((2-chloro-4-ethylpyrimidin-5-yl)oxy)ethanone;

6-chloro-5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-N-cyclopropylpicolinamide;

1-(5-(4-chloro-2-fluorophenyl)-2,3,7,8-tetrahydrothiazolo[2',3':2,3]imidazo[4,5-c]pyridin-6(5H)-yl)-2-((2-chloro-6-cyclopropylpyridin-3-yl)oxy)ethanone;

1-(5-(4-chloro-2-fluorophenyl)-2,3,7,8-tetrahydrothiazolo[2',3':2,3]imidazo[4,5-c]pyridin-6(5H)-yl)-2-((6-cyclopropyl-2-ethylpyridin-3-yl)oxy)ethanone;

(S)-N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

(S)-1-(5-(4-chloro-2-fluorophenyl)-2,3,7,8-tetrahydrothiazolo[2',3':2,3]imidazo[4,5-c]pyridin-6(5H)-yl)-2-((2-chloro-6-(1,1-dioxidoisothiazolidin-2-yl)pyridin-3-yl)oxy)ethanone;

1-(5-(4-chloro-2-fluorophenyl)-2,3,7,8-tetrahydrothiazolo[2',3':2,3]imidazo[4,5-c]pyridin-6(5H)-yl)-2-((2-chloro-6-(1,1-dioxidoisothiazolidin-2-yl)pyridin-3-yl)oxy)ethanone;

N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

N-(6-chloro-5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)pyridin-2-yl)-N-methylmethanesulfonamide;

1-(5-(4-chloro-2-fluorophenyl)-2,3,7,8-tetrahydrothiazolo[2',3':2,3]imidazo[4,5-c]pyridin-6(5H)-yl)-2-((2-chloro-6-(5-methyl-1,1-dioxido-1,2,5-thiadiazolidin-2-yl)pyridin-3-yl)oxy)ethanone;

1-(5-(4-chloro-2-fluorophenyl)-2,3,7,8-tetrahydrothiazolo[2',3':2,3]imidazo[4,5-c]pyridin-6(5H)-yl)-2-((6-(1,1-dioxidoisothiazolidin-2-yl)-2-ethylpyridin-3-yl)oxy)ethanone;

N-(5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)-N',N'-dimethylsulfamide;

1-(5-(4-chloro-2-fluorophenyl)-2,3,7,8-tetrahydrothiazolo[2',3':2,3]imidazo[4,5-c]pyridin-6(5H)-yl)-2-((2-ethyl-6-methylpyridin-3-yl)oxy)ethanone;

5-(2-(5-(4-chloro-2-fluorophenyl)-2,3,7,8-tetrahydrothiazolo[2',3':2,3]imidazo[4,5-c]pyridin-6(5H)-yl)-2-oxoethoxy)-N-cyclopropyl-6-ethylpicolinamide;

N-cyclopropyl-5-(2-(5-(5-cyclopropyl-3-fluoropyridin-2-yl)-2,3,7,8-tetrahydrothiazolo[2',3':2,3]imidazo[4,5-c]pyridin-6(5H)-yl)-2-oxoethoxy)-6-ethylpicolinamide;

N-(5-(2-(5-(5-cyclopropyl-3-fluoropyridin-2-yl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

(R)—N-cyclopropyl-5-(2-(5-(5-cyclopropyl-3-fluoropyridin-2-yl-2,3,7,8-tetrahydrothiazolo[2',3':2,3]imidazo[4,5-c]pyridin-6(5H)-yl)-2-oxoethoxy)-6-ethylpicolinamide;

N-(5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

N-(6-chloro-5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)pyridin-2-yl)methanesulfonamide;

6-chloro-N-cyclopropyl-5-(2-(5-(4-cyclopropyl-2-fluorophenyl)-2,3,7,8-tetrahydrothiazolo[2',3':2,3]imidazo[4,5-c]pyrimidin-6(5H)-yl)-2-oxoethoxy)picolinamide;

N-(5-(2-(5-(4-cyclopropyl-2-fluorophenyl)-2,3,7,8-tetrahydrothiazolo[2',3':2,3]imidazo[4,5-c]pyridin-6(5H)-yl)-2-oxoethoxy)-4-ethylpyrimidin-2-yl)methanesulfonamide;

N-(5-(2-(5-(2,3-difluoro-4-methylphenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

6-chloro-N-cyclopropyl-5-(2-(5-(2,3-difluoro-4-methylphenyl)-2,3,7,8-tetrahydrothiazolo[2',3':2,3]imidazo[4,5-c]pyridin-6(5H)-yl)-2-oxoethoxy)picolinamide;

N-(5-(2-(5-(2,4-dimethylthiazol-5-yl)-2,3,7,8-tetrahydrotidazolo[2',3':2,3]imidazo[4,5-c]pyridin-6(5H)-yl)-2-oxoethoxy)-6-ethylpyridin-2-yl)methanesulfonamide;

1-(5-(2,4-dimethylthiazol-5-yl)-2,3,7,8-tetrahydrothiazolo[2',3':2,3]imidazo[4,5-c]pyridin-6(5H)-yl)-2-((6-(1,1-dioxoisothiazolidin-2-yl)-2-ethylpyridin-3-yl)oxy)ethanone;

N-cyclopropyl-5-(2-(5-(2,4-dimethylthiazol-5-yl)-2,3,7,8-tetrahydrothiazolo[2',3':2,3]imidazo[4,5-c]pyridin-6(5H)-yl)-2-oxoethoxy)-6-ethylpicolinamide;

6-chloro-5-(2-(5-(3-fluorothiophen-2-yl)-2,3,7,8-tetrahydrothiazolo[2',3':2,3]imidazo[4,5-c]pyridin-6(5H)-yl)-2-oxoethoxy)-N,N-dimethylpicolinamide;

N-(6-chloro-5-(2-(5-(3-fluorothiophen-2-yl)-2,3,7,8-tetrahydrothiazolo[2',3':2,3]imidazo[4,5-c]pyridin-6(5H)-yl)-2-oxoethoxy)pyridin-2-yl)methanesulfonamide;

N-(6-ethyl-5-(2-(5-(3-fluorothiophen-2-yl)-2,3,7,8-tetrahydrothiazolo[2',3':2,3]imidazo[4,5-c]pyridin-6(5H)-yl)-2-oxoethoxy)pyridin-2-yl)methanesulfonamide;

N-(5-(2-(5-(2,5-difluoro-4-methylphenyl)-2,3,7,8-tetrahydrothiazolo[2',3':2,3]imidazo[4,5-c]pyridin-6(5H)-yl)-2-oxoethoxy)-6-ethylpyridin-2-yl)methanesulfonamide;

1-(7-acetyl-1-(4-chloro-2-fluorophenyl)-3,4,6,7,8,9-hexahydropyrido[4',3':4,5]imidazo[1,2-a]pyrazin-2(1H)-yl)-2-((2-chloro-6-(3,3-difluoroazetidin-1-yl)pyridin-3-yl)oxy)ethanone;

5-(2-(7-acetyl-1-(4-chloro-2-fluorophenyl)-3,4,6,7,8,9-hexahydropyrido[4',3':4,5]imidazo[1,2-a]pyrazin-2(1H)-yl)-2-oxoethoxy)-6-chloro-N-methylpicolinamide;

5-(2-(7-acetyl-1-(4-chloro-2-fluorophenyl)-3,4,6,7,8,9-hexahydropyrido[4',3':4,5]imidazo[1,2-a]pyrazin-2(1H)-yl)-2-oxoethoxy)-6-chloro-N,N-dimethylpicolinamide;

6-chloro-5-(2-(1-(4-chloro-2-fluorophenyl)-7-cyclopropyl-3,4,6,7,8,9-hexahydropyrido[4',3':4,5]imidazo[1,2-a]pyrazin-2(1H)-yl)-2-oxoethoxy)-N,N-dimethylpicolinamide;

1-(7-acetyl-1-(3-fluoropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

1-(4-(7-acetyl-2-((2-chloro-6-morpholinopyridin-3-yl)oxy)acetyl)-1,2,3,4,6,7,8,9-octahydropyrido[4',3':4,5]imidazo[1,2-a]pyrazin-1-yl)thiazol-2-yl)-3-ethylurea;

tert-butyl 2-(2-(2-chloro-4-(morpholinomethyl)phenoxy)acetyl)-1-(2-fluoro-4-methylphenyl)-1,2,3,4,8,9-hexahydropyrido[4',3':4,5]imidazo[1,2-a]pyrazine-7(6H)-carboxylate;

2-(2-chloro-4-(morpholinomethyl)phenoxy)-1-(1-(2-fluoro-4-methylphenyl)-3,4,6,7,8,9-hexahydropyrido[4',3':4,5]imidazo[1,2-a]pyrazin-2(1H)-yl)ethanone;

1-(7-acetyl-1-(2-fluoro-4-methylphenyl)-3,4,6,7,8,9-hexahydropyrido[4',3':4,5]imidazo[1,2-a]pyrazin-2(1H)-yl)-2-(2-chloro-4-(morpholinomethyl)phenoxy)ethanone;

1-(7-acetyl-1-(3-fluorothiophen-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

5-(2-(7-acetyl-1-(3-fluorothiophen-2-yl)-3,4,6,7,8,9-hexahydropyrido[4',3':4,5]imidazo[1,2-a]pyrazin-2(1H)-yl)-2-oxoethoxyl-6-chloro-N,N-dimethylpicolinamide;

tert-butyl 2-(2-((2-chloro-6-morpholinopyridin-3-yl)oxy)acetyl)-1-(4-(cyanocarbamoyl)thiophen-2-yl)-1,2,3,4,8,9-hexahydropyrido[4',3':4,5]imidazo[1,2-a]pyrazine-7(6H)-carboxylate;

1-(7-acetyl-1-(5-chloropyridin-2-yl)-3,4,6,7,8,9-hexahydropyrido[4',3':4,5]imidazo[1,2-a]pyrazin-2(1H)-yl)-2-((2chloro-6-morpholinopyridin-3-yl)oxy)ethanone;

1-(7-acetyl-1-(4-chloropyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

1-(7-acetyl-1-(2,4-dimethylthiazol-5-yl)-3,4,6,7,8,9-hexahydroprido[4',3':4,5]imidazo[1,2-a]pyrazin-2(1H)-yl)-2-((2-chloro-6-(oxazol-2-yl)pyridin-3-yl)oxy)ethanone;

tert-butyl 1-(4-cyclopropyl-2-fluorophenyl)-2-(2-((2-ethyl-6-methylpyridin-3-yl)oxy)acetyl)-1,2,3,4,8,9-hexahydropyrido[4',3':4,5]imidazo[1,2-a]pyrazine-7(6H)-carboxylate;

1-(1-(4-cyclopropyl-2-fluorophenyl)-3,4,6,7,8,9-hexahydropyrido[4',3':4,5 ]imidazo[1,2-a]pyrazin-2(1H)-yl)-2-((2-(trifluoromethyl)pyridin-3-yl)oxy)ethanone;

6-chloro-5-(2-(1-(4-cyclopropyl-2-fluorophenyl)-3,4,6,7,8,9-hexahydropyrido[4',3':4,5]imidazo[1,2-a]pyrazin-2(1H)-yl)-2-oxoethoxy)picolinonitrile;

1-(7acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloro-6-(3,3-difluoroazetidin-1-yl)pyridin-3yl)oxy)ethanone;

5-(2-(7-acetyl-1-(4cyclopropyl-2-fluorophenyl)-3,4,6,7,8,9-hexahydropyrido[4',3':4,5]imidazo[1,2-a]pyrazin-2(1H)-yl)-2-oxoethoxy)-6-chloro-N,N-dimethylpicolinamide;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2(2-chloropyridin-3-yl)oxy)ethanone;

1-(7-acetyl-1-(4-cyclopropyl-2-fluorophenyl)-3,4,6,7,8,9-hexahydropyrido[4',3': 4,5]imidazo[1,2-a]pyrazin-2(1H)-yl)-2-((2-(trifluoromethyl)pyridin-3-yl)oxy)ethanone;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloro-5-fluoropyridin)oxy)ethanone;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-ethyl-6-methylpyridin-3-yl)oxy)ethanone;

tert-butyl 2-(2-(2-chloro-4-morpholinophenoxy)acetyl)-1-(4-cyclopropyl-2-fluorophenyl)-1,2,3,4,8,9-hexahydropyrido[4',3':4,5]imidazo[1,2-a]pyrazine-7(6H)-carboxylate;

1-(1-(4-cyclopropyl-2-fluorophenyl)-3,4,6,7,8,9-hexahydropyrido[4',3':4,5]imidazo[1,2-a]pyrazin-2(1H)-yl)-2-((2-ethyl-6-methylpyridin-3-yl)oxy)ethanone;

2-(2-chloro-4-morpholinophenoxy)-1-(1-(4-cyclopropyl-2-fluorophenyl)-3,4,6,7,8,9-hexahydropyrido[4',3':4,5]imidazo[1,2-a]pyrazin-2(1H)-yl)ethanone;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-(2-chloro-4-morpholinophenoxy)ethanone;

1-(1-(4-cyclopropyl-2-fluorophenyl)-7-(cyclopropylmethyl)-3,4,6,7,8,9-hexahydropyrido[4',3':4,5]imidazo[1,2-a]pyrazin-2(1H)-yl)-2-((2-ethyl-6-methylpyridin-3-yl)oxy)ethanone;

2-(2-chloro-4-morpholinophenoxy)-1-(1-(4-cyclopropyl-2-fluorophenyl)-7-(cyclopropylmethyl)-3,4,6,7,8,9-hexahydropyrido[4',3':4,5]imidazo[1,2-a]pyrazin-2(1H)-yl)ethanone;

1-(7-acetyl-1-(4-cyclopropyl-2-fluorophenyl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

3-chloro-4-(2-(1-(4-cyclopropyl-2-fluorophenyl)-3,4,6,7,8,9-hexahydropyrido[4',3':4,5]imidazo[1,2-a]pyrazin-2(1H)-yl)-2-oxoethoxy)benzonitrile;

5-(2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)-N,N-dimethylthiophene-3-carboxamide;

5-(7-acetyl-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)-N,N-dimethylthiophene-3-carboxamide;

tert-butyl 2-(2-((2-chloro-6-morpholinopyridin-3-yl)oxy)acetyl)-1-(5-cyclopropyl-3-fluoropyridin-2-yl)1,2,3,4,8,9-hexahydropyrido[4',3':4,5]imidazo[1,2-a]pyrazine-7(6H)-carboxylate;

-(1-(1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-(trifluoromethyl)pyridin-3-yl)oxy)ethanone;

2-((2-chloro-6-morpholinopyridin-3-yl)oxy)-1-(1-(5-cyclopropyl-3-fluoropyridin-2-yl)-3,4,6,7,8,9-hexahydropyrido[4',3':4,5]imidazo[1,2-a]pyrazin-2(1H)-yl)ethanone;

1-(1-(5-cyclopropyl-3-fluoropyridin-2-yl)-3,4,6,7,8,9-hexahydropyrido[4',3':4,5]imidazo[1,2-a]pyrazin-2(1H)-yl)-2-(2-ethyl-4-fluorophenoxy)ethanone;

2-(4-chloro-2-ethylphenoxy)-1-(1-(5-cyclopropyl-3-fluoropyridin-2-yl)-3,4,6,7,8,9-hexahydropyrido[4',3':4,5]imidazo[1,2-a]pyrazin-2(1H)-yl)ethanone;

1-(7-acetyl-1-(5-cyclopropyl-3-fluoropyridin-2-yl)-3,4,6,7,8,9-hexahydropyrido[4',3',4,5]imidazo[1,2-a]pyrazin-2(1H)-yl)-2-((2-chloro-6-morpholinopyridin-3-yl)oxy)ethanone;

1-(7-acetyl-1-(5-cyclopropyl-3-fluoropyridin-2-yl)-3,4,6,7,8,9hexahydropyrido[4',3':4,5]imidazo[1,2-a]pyrazin-2(1H)-yl)-2-((2-chloro-5-fluoropyridin-3-yl)oxy)ethanone;

1-(7-acetyl-1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-fluoro-6-morpholinopyridin-3-yl)oxy)ethanone;

1-(7-acetyl-1-(5-cyclopropyl-3-fluoropyridin-2-yl)-3,4,6,7,8,9-hexahydropyrido[4',3':4,5]imidazo[1,2-a]pyrazin-2(1H)-yl)-2-((2-chloro-5-fluoro-6-morpholinopyridin-3-yl)oxy)ethanone;

methyl 5-(7-acetyl-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)thiophene-3-carboxylate;

2-((2-chloro-6-morphoinopyridin-3-yl)oxy)-1-(1-(2-(dimethylamino)thiazol-5-yl)-3,4,6,7,8,9-hexahydropyrido[4',3':4,5 ]imidazo[1,2-a]pyrazin-2(1H)-yl)ethanone;

1-(7-acetyl-1-(2-(dimethylamino)thiazol-5-yl)-3,4,6,7,8,9-hexahydropyrido[4',3',4,5]imidazo[1,2-a]pyrazin-2(1H)-yl)-2-((2-chloro-6-morpholinopyridin-3-yl)oxy)ethanone;

5-(2-(7-acetyl-1-(5-(dimethylcarbamoyl)-3-fluorothiophen-2-yl)-3,4,6,7,8,9-hexahydropyrido[4',3':4,5]imidazo[1,2-a]pyrazin-2(1H)-yl)-2-oxoethoxy)-6-chloro-N,N-dimethylpicolinamide;

5-(7-acetyl-2-(2-((2-chloro-6-morpholinopyridin-3-yl)oxy)acetyl)-1,2,3,4,6,7,8,9-octahydropyrido[4',3':4,5]imidazo[1,2-a]pyrazin-1-yl)-4-fluoro-N,N-dimethylthiophene-2-carboxamide;

1-(7-acetyl-1-(3-fluoro-5-methylpyridin-2-yl)-3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

1-(7-acetyl-1-(3-fluoro-5-methylpyridin-2-yl)-3,4,6,7,8,9-hexahydropyrido[4',3':4,5]imidazo[1,2-a]pyrazin-2(1H)-yl)-2-((2-chloro-6-(3,3difluoroazetidin-1-yl)pyridin-3-yl)oxy)ethanone;

1-(7-acetyl-1-(5-chloro-3-fluoropyridin-2-yl) -3,4,6,7,8,9-hexahydropyrido[4',3':4,5]imidazo[1,2-a]pyrazin-2(1H)-yl)-2-((2-chloro-6-morpholinopyridin-3-yl)oxy)ethanone;

1-(6-(4-chloro-2-fluorophenyl)-3,4,8,9-tetrahydro-1H-pyrido[4',3':4,5]imidazo[2,1-c][1,4]oxazin-7(6H)-yl)-2-((2-chloro-6-morpholinopyridin-3-yl)oxy)ethanone;

N-(6-chloro-5-(2-(6-(4-chloro-2-fluorophenyl)-3,4,8,9-tetrahydro-1H-pyrido[4',3':4,5]imidazo[2,1-c][1,4]oxazin-7(6H)-yl)-2-oxoethoxy)pyridin-2-yl)methanesulfonamide;

2-((2-chloro-6-morpholinopyridin-3-yl)oxy)-1-(6-(4-cyclopropyl-2-fluorophenyl)-3,4,8,9-tetrahydro-1H-pyrido[4',3':4,5]imidazo[2,1-c][1,4]oxazin-7(6H)-yl)ethanone;

3-chloro-4-(2-(6-(4-cyclopropyl-2-fluorophenyl)-3,4,8,9-tetrahydro-1H-pyrido[4',3':4,5]imidazo[2,1-c][1,4]oxazin-7(6H)-yl)-2-oxoethoxy)-N,N-dimethylbenzamide;

6-chloro-5-(2-(6-(4-cyclopropyl-2-fluorophenyl)-3,4,8,9-tetrahydro-1H-pyrido[4',3':4,5]imidazo[2,1-c][1,4]oxazin-7(6H)-yl)-2-oxoethoxy)-N,N-dimethylpicolinamide;

6-chloro-5-(2-(6-(5-(dimethylcarbamoyl)-3-fluorothiophen-2-yl)-3,4,8,9-tetrahydro-1H-pyrido[4',3':4,5]imidazo[2,1-c][1,4]oxazin-7(6H)-yl)-2-oxoethoxy)-N,N-dimethylpicolinamide;

N-(6-chloro-5-(2-(6-(5-chloro-3-fluoropyridin-2-yl)-3,4,8,9-tetrahydro-1H-pyrido[4',3':4,5]imidazo[2,1-c][1,4]oxazin-7(6H)-yl)-2-oxoethoxy)pyridin-2-yl)methanesulfonamide;

6-chloro-5-(2-(6-(5-chloro-3-fluoropyridin-2-yl)-3,4,8,9-tetrahydro-1H-pyrido[4',3':4,5]imidazo[2,1-c][1,4]oxazin-7(6H)-yl)-2-oxoethoxy)-N,N-dimethylpicolinamide;

6-chloro-5-(2-(6-(2-fluoro-4-methylphenyl)-3,4,8,9-tetrahydro-1H-pyrido[4',3':4,5]imidazo[2,1-c][1,4]oxazin-7(6H)-yl)-2-oxoethoxy)-N,N-dimethylpicolinamide;
2-((2-chloro-6-morpholinopyridin-3-yl)oxy)-1-(6-(3-fluorothiophen-2-yl)-3,4,8,9-tetrahydro-1H-pyrido[4',3':4,5]imidazo[2,1-c][1,4]oxazin-7(6H)-yl)ethanone;
6-chloro-5-(2-(6-(3-fluorothiophen-2-yl)-3,4,8,9-tetrahydro-1H-pyrido[4',3':4,5]imidazo[2,1-c][1,4]oxazin-7(6H)-yl)-2-oxoethoxy)-N,N-dimethylpicolinamide;
N-(6-chloro-5-(2-(6-(3-fluorothiophen-2-yl)-3,4,8,9-tetrahydro-1H-pyrido[4',3':4,5]imidazo[2,1-c][1,4]oxazin-7(6H)-yl)-2-oxoethoxy)pyridin-2-yl)methanesulfonamide;
N-(6-chloro-5-(1-(1-(4-chloro-2-fluorophenyl)-1,2,3,4,6,7,8,9-octahydroimidazo[1,2-a:5,4-c']dipyridine-2-carbonyl)cyclopropoxy)pyridin-2-yl)methanesulfonamide;
N-(5-(2-(1-(4-chloro-2-fluorophenyl)-3,4,6,7,8,9-hexahydroimidazo[1,2-a:5,4-c']dipyridin-2(1H)-yl)-2-oxoethoxy)-6-cyclopropylpyridin-2-yl)methanesulfonamide;
1-(1-(4-chloro-2-fluorophenyl)-3,4,6,7,8-hexahydroimidazo[1,2-a: 5,4-c']dipyridin-2(1H)-yl)-2-((2-chloro-6-(dimethylamino)pyridin-3-yl)oxy)ethan-1-one;
5-(2-(1-(4-chloro-2-fluorophenyl)-3,4,6,7,8,9-hexahydroimidazo[1,2-a:5,4-c']dipyridin-2(1H)-yl)-2-oxoethoxy)-N,6-dicyclopropylpicolinamide;
1-(1-(4-chloro-2-fluorophenyl)-3,4,6,7,8,9-hexahydroimidazo[1,2-a:5,4-c']dipyridin-2(1H)-yl)-2-((2-chloro-6-(methyl(2,2,2-trifluoroethyl)amino)pyridin-3-yl)oxy)ethan-1-one;
1-(1-(4-chloro-2-fluorophenyl)-3,4,6,7,8,9-hexahydroimidazo[1,2-a:5,4-c']dipyridin-2(1H)-yl)-2-((2-chloro-6-((2-methoxyethyl)(methyl)amino)pyridin-3-yl)oxy)ethan-1-one;
6-chloro-5-((1-(1-(4-chloro-2-fluorophenyl)-3,4,6,7,8,9-hexahydroimidazo[1,2-a:5,4-c']dipyridin-2(1H)-yl)-2-methyl-1-oxopropan-2-yl)oxy)-N-dimethylpicolinamide;
6-chloro-5-((1-(1-(4-chloro-2-fluorophenyl)-1,2,3,4,6,7,8,9-octahydroimidazo[1,2-a:5,4-c']dipyridine-2-carbonyl)cyclopropoxy)-N,N-dimethylpicolinamide;
1-(1-(4-chloro-2-fluorophenyl)-3,4,6,7,8,9hexahydroimidazo[1,2-a:5,4-c']dipyridin-2(1H)-yl)-2-((2-chloro-6-(methylsulfonyl)pyridin-3-yl)oxy)ethan-1-one;
6-chloro-5-(2-(1-(4-chloro-2-fluorophenyl)-3,4,6,7,8,9-hexahydroimidazo[1,2-a:5,4-c']dipyridin-2(1H)-yl)-2-oxoethoxy)-N,N-dimethylpyridine-2-sulfonamide;
1-(1-(4-chloro-2-fluorophenyl)-3,4,6,7,8,9-hexahydroimidazo[1,2-a:5,4-c']dipyridin-2(1H)-yl)-2-((2-chloro-6-((2-hydroxyethyl)(methyl)amino)pyridin-3-yl)oxy)ethan-1-one;
1-(1-(2,4-dimethylthiazol-5-yl)-3,4,6,7,8,9-hexahydroimidazo[1,2-a:5,4-c']dipyridin-2(1H)-yl)-2-((6-(1,1-dioxidoisothiazolidin-2-yl)-2-ethylpyridin-3-yl)oxy)ethan-1-one;
6-chloro-N-cyclopropyl-5-(2-(1-(2-fluoro-4-(trifuoromethoxy)phenyl)-3,4,6,7,8,9-hexahydroimidazo[1,2-a:5,4-c']dipyridin-2(1H)-yl)-2-oxoethoxy)picolinamide;
N-(6-chloro-5-(2-(1-(2-fluoro-4-(trifluoromethoxy)phenyl)-3,6,7,8,9-hexahydroimidazo[1,2-a:5,4-c']dipyridin-2(1H)-yl)-2-oxoethoxy)pyridin-2-yl)methanesulfonamide;
6-chloro-N-cyclopropyl-5-(2-(1-(2-fluoro-4-methoxyphenyl)-3,4,6,7,8,9-hexahydroimidazo[1,2-a:5,4-c']dipyridin-2(1H)-yl)-2-oxoethoxy)picolinamide;
N-(6-chloro-5-(2-(1-(2-fluoro-4-methoxyphenyl)-3,4,6,7,8,9-hexahydroimidazo[1,2-a:5,4-c']dipyridin-2(1H)-yl)-2-oxoethoxy)pyridin-2-yl)methanesulfonamide;
N-(6-chloro-5-(2-(1-(4-cyano-2-fluorophenyl)-3,4,6,7,8,9-hexahydroimidazo[1,2-a:5,4-c']dipyridin-2(1H)-yl)-2-oxoethoxy)pyridin-2-yl)methanesulfonamide;
6-chloro-5-(2-(1-(4-cyano-2-fluorophenyl)-3,4,6,7,8,9-hexahydroimidazo[1,2-a:5,4-c']dipyridin-2-(1H)-yl)-2-oxoethoxy)-N-cyclopropylpicolinamide;
methyl-4-(2-(2-((2-chloro-6-(methylsulfonamido)pyridin-3-yl)oxy)acetyl)-1,2,3,4,6,7,8,9-octahydroimidazo[1,2-a:5,4-c']dipyridin-1-yl)-3-fluorobenzoate;
methyl (R)-4-(2-(2-((2-chloro-6-(cyclopropylcarbamoyl)pyridin-3-yl)oxy)acetyl)-1,2,3,4,6,7,8,9octahydroimidazo[1,2-a:5,4-c']dipyridin-1-yl)-3-fluorobenzoate;
6-chloro-N-cyclopropyl-5-(2-(1-(2-fluoro-4-(2-hydroxypropan-2-yl)phenyl)-3,4,6,7,8,9-hexahydroimidazo[1,2-a:5,4-c']dipyridin-2 (1H)-yl)-2-oxoethoxy)picolinanaide;
N-(6-chloro-5-(2-(1-(2-fluoro-4-(2-hydroxypropan-2-yl)phenyl)-3,4,6,7,8,9-hexahydroimidazo[1,2-a:5,4-c']dipyridin-2(1H)-yl)-2-oxoethoxy)pyridin-2-yl)methanesulfonamide;
6-chloro-N-cyclopropyl-5-(2-(1-(2-fluoro-4-(2-methoxypropan-2-yl)phenyl)-3,4,6,7,8,9-hexahydroimidazo[1,2-a:5,4-c']dipyridin-2(1H)-yl)-2-oxoethoxy)picolinanaide;
N-(6-chloro-5-(2-(1-(2-fluoro-4-(2-methoxypropan-2-yl)phenyl)-3,4,6,7,8,9-hexahydroimidazo[1,2-a:5,4-c']dipyridin-2(1H)-yl)-2-oxoethoxy)pyridin-2-yl)methanesulfonamide;
6-chloro-N-cyclopropyl-5-(2-(1-(2-fluoro-4-(methoxymethyl)phenyl)-3,4,6,7,8,9-hexahydroimidazo[1,2-a:5,4-c']dipyridin-2(1H)-yl)-2-oxoethoxy)picolinamide;
N-(6-chloro-5-(2-(1-(2-fluoro-4-(methoxymethyl)phenyl)-3,4,6,7,8,9-hexahydroimidazo[1,2-a:5,4-c']dipyridin-2(1H)-yl)-2-oxoethoxy)pyridin-2-yl)methanesulfonamide;
6-chloro-N-cyclopropyl-5-(2-(1-(2-fluoro-4-(2-methoxyethoxy)phenyl)-3,4,6,7,8,9-hexahydroimidazo[1,2-a:5,4-c']dipyridin-2(1H)-yl)-2-oxoethoxy)picolinamide;
N-(6-chloro-5-(2-(1-(2-fluoro-4-(2-methoxyethoxy)phenyl)-3,4,6,7,8,9-hexahydroimidazo[1,2-a:5,4-c']dipyridin-2(1H)-yl)-2-oxoethoxy)pyridin-2-yl)methanesulfonamide;
6-chloro-N-cyclopropyl-5-(2-(1-(2-fluoro-4-(2-hydroxyethoxy)phenyl)-3,4,6,7,8,9-hexahydroimidazo[1,2-a:5,4-c']dipyridin-2(1H)-yl)-2-oxoethoxy)picolinamide; or
N-(6-chloro-5-(2-(1-(2-fluoro-4-(2-hydroxyethoxy)phenyl)-3,4,6,7,8,9-hexahydroimidazo[1,2-a:5,4-c']dipyridin-2(1H)-yl)-2-oxoethoxy)pyridin-2-yl)methanesulfonamide;

or a pharmaceutically acceptable salt thereof.

13. A pharmaceutical composition comprising, as active principle, one or more compounds according to claim 1, or a pharmaceutically acceptable salt thereof, and at least one therapeutically inert excipient.

14. The compound according to claim 1, or a pharmaceutically acceptable salt thereof, wherein the compound is formulated as a medicament.

15. A process for preparing a compound of formula (I), comprising acylating a compound of formula (IV):

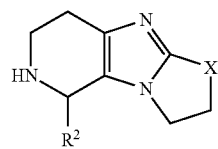
Formula (IV)
wherein $R^2$ and X are defined for the respective compound of formula (I) according to claim 1.
16. A compound of the formula (IV):
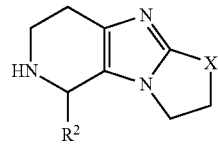
Formula (IV)
wherein $R^2$ and X are as defined for the compounds of formula (I) according to claim 1.
* * * * *